(12) United States Patent
Hirakawa et al.

(10) Patent No.: US 8,194,096 B2
(45) Date of Patent: Jun. 5, 2012

(54) IMAGE DISPLAY APPARATUS

(75) Inventors: Katsumi Hirakawa, Sagamihara (JP); Satomi Kobayashi, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 626 days.

(21) Appl. No.: 12/249,552

(22) Filed: Oct. 10, 2008

(65) Prior Publication Data

US 2009/0043157 A1 Feb. 12, 2009

Related U.S. Application Data

(63) Continuation of application No. PCT/JP2007/058066, filed on Apr. 12, 2007.

(30) Foreign Application Priority Data

Apr. 14, 2006 (JP) ................... 2006-112367
Jul. 18, 2006 (JP) ................... 2006-196095

(51) Int. Cl.
*G09G 5/00* (2006.01)
*A61B 1/00* (2006.01)
*A61B 1/04* (2006.01)
*A61B 5/05* (2006.01)
*A61B 5/103* (2006.01)

(52) U.S. Cl. ........ 345/619; 345/660; 345/661; 345/670; 600/103; 600/109; 600/117; 600/118; 600/424; 600/593

(58) Field of Classification Search .......... 600/101–183, 600/424, 593; 345/619, 660, 661, 670
See application file for complete search history.

(56) References Cited

U.S. PATENT DOCUMENTS

| | | | |
|---|---|---|---|
| 2002/0109774 A1 | 8/2002 | Meron et al. | |
| 2003/0208107 A1* | 11/2003 | Refael | 600/300 |
| 2004/0267122 A1* | 12/2004 | Nadadur et al. | 600/440 |
| 2005/0075551 A1* | 4/2005 | Horn et al. | 600/361 |
| 2006/0106318 A1* | 5/2006 | Davidson | 600/476 |
| 2006/0164511 A1 | 7/2006 | Krupnik | |
| 2006/0209185 A1 | 9/2006 | Yokoi | |
| 2006/0217593 A1* | 9/2006 | Gilad et al. | 600/160 |
| 2007/0268280 A1 | 11/2007 | Fujita et al. | |

FOREIGN PATENT DOCUMENTS

| | | |
|---|---|---|
| CN | 1694643 A | 11/2005 |
| EP | 1 946 695 A1 | 7/2008 |
| JP | 11-259630 | 9/1999 |
| JP | 2002-211049 | 7/2002 |
| JP | 2003-019111 | 1/2003 |
| JP | 2004-328188 | 11/2004 |
| JP | 2006-061469 | 3/2006 |
| JP | 2006-068534 | 3/2006 |
| WO | WO 2005/020147 A1 | 3/2005 |
| WO | WO 2005/048825 A1 | 6/2005 |

* cited by examiner

OTHER PUBLICATIONS

Extended Supplementary European Search Report dated Mar. 17, 2011.

*Primary Examiner* — Xiao M. Wu
*Assistant Examiner* — Andrew Shin
(74) *Attorney, Agent, or Firm* — Scully, Scott, Murphy & Presser, PC

(57) ABSTRACT

An image display apparatus includes a display unit that displays images contained in a plurality of image groups inside a subject picked up by a plurality of imaging devices, and a control unit that extracts a related image related to a currently displayed image currently displayed in the display unit from the plurality of image groups to make the display unit display the related image extracted.

6 Claims, 61 Drawing Sheets

| SITE | TIME DIFFERENCE ΔT |
|---|---|
| ESOPHAGUS | ΔT1 |
| STOMACH | ΔT2 |
| SMALL INTESTINE | ΔT3 |
| LARGE INTESTINE | ΔT4 |

($\Delta T1 < \Delta T2 \leqq \Delta T3 < \Delta T4$)

FIG.41
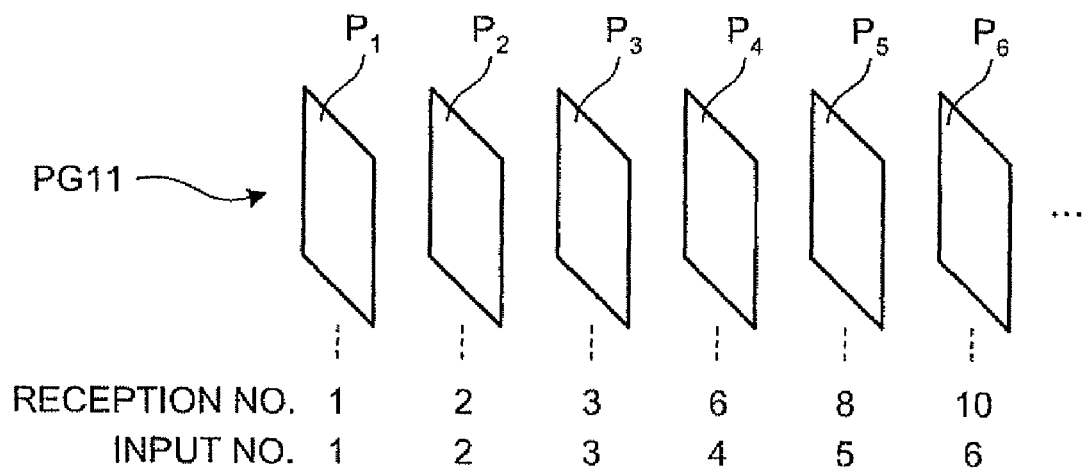
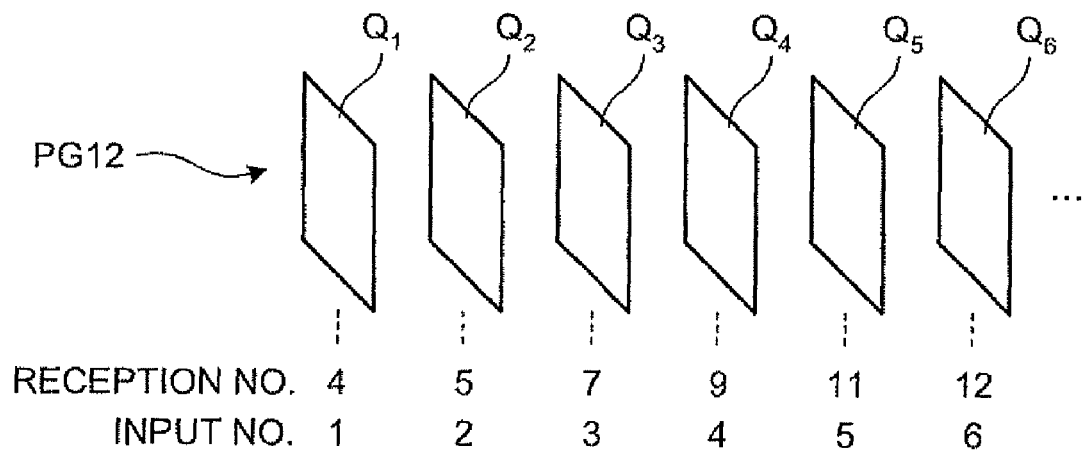

FIG.45
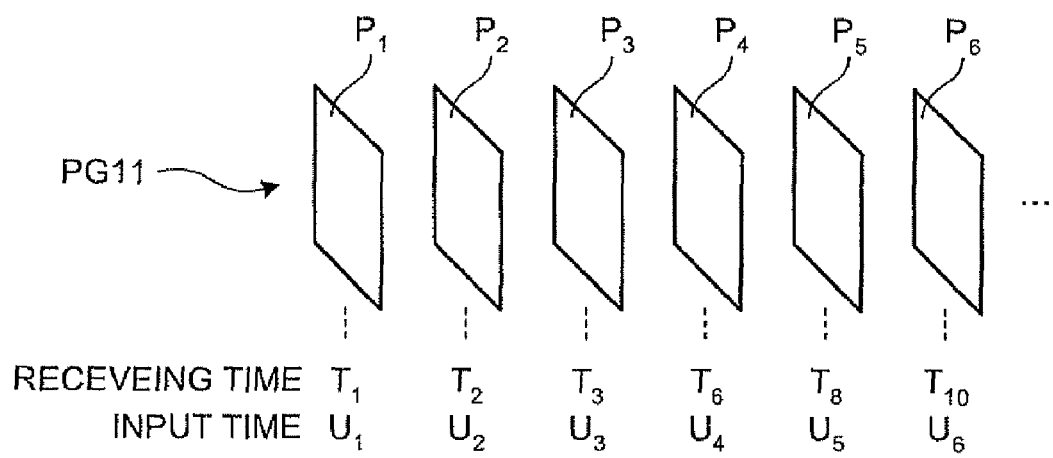
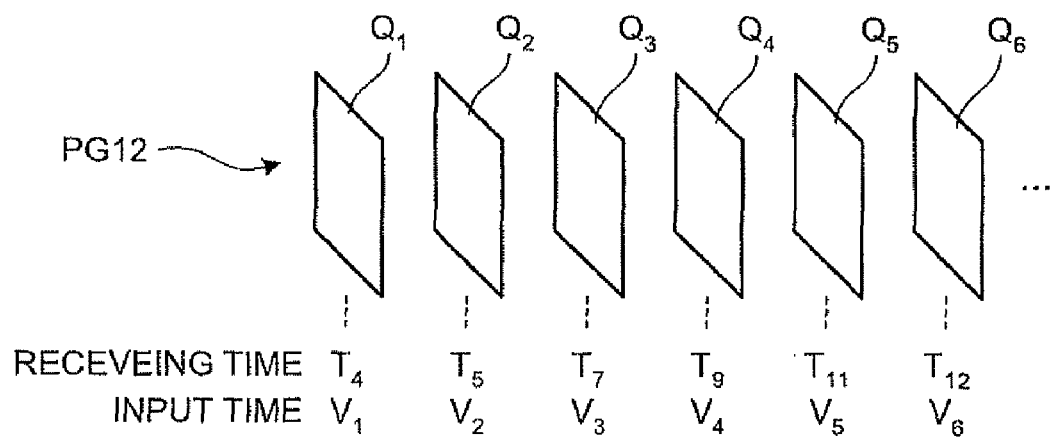

IMAGE DISPLAY APPARATUS

CROSS-REFERENCE TO RELATED APPLICATIONS

This application is a continuation of PCT international application Ser. No. PCT/JP2007/058066 filed Apr. 12, 2007, designating the United States, incorporated herein by reference, and which claims the benefit of priority from Japanese Patent Application No. 2006-112367, filed Apr. 14, 2006; and Japanese Patent Application No. 2006-196095, filed Jul. 18, 2006, the entire contents of both of which are incorporated herein by reference.

BACKGROUND OF THE INVENTION

1. Field of the Invention

The present invention relates to an image display apparatus for displaying a series of images picked up inside a subject along time series.

2. Description of the Related Art

In the field of endoscope, swallowable capsule endoscopes equipped with an imaging function and a radio communication function have been proposed and intra-subject information acquisition systems which acquire images inside a subject using such capsule endoscopes have been developed. After being swallowed through the mouth of a subject for observation (examination), a capsule endoscope moves through organs such as stomach and small intestine in accordance with peristaltic movement thereof before being naturally excreted from the subject and sequentially picks up images inside the subject at intervals of, for example 0.5 sec.

While the capsule endoscope moves inside the subject, images picked up by the capsule endoscope are sequentially transmitted to an external receiving apparatus by radio communication. The receiving apparatus has a radio communication function and a memory function and sequentially saves images received from the capsule endoscope inside the subject in a memory. By carrying such a receiving apparatus, the subject can act freely between the time when the subject swallows the capsule endoscope and the time when the capsule endoscope is naturally excreted. After the capsule endoscope is naturally excreted from the subject, a physician or a nurse can diagnose the subject by making an image display apparatus take in images accumulated in the memory of the receiving apparatus and display images of organs inside the subject (See, for example, Japanese Patent Application Laid-Open No. 2003-19111).

In such an intra-subject information acquisition system, a multiple-lens capsule endoscope equipped with a plurality of imaging devices may be used. Such a multiple-lens capsule endoscope has the plurality of imaging devices imaging mutually different directions to acquire images from a plurality of directions picked up by the plurality of imaging devices (See, for example, US Patent Application Laid-Open No. 2002/0109774 Specification). In this case, the multiple-lens capsule endoscope transmits the acquired images from the plurality of directions to a receiving apparatus by radio. The receiving apparatus sequentially accumulates images from the plurality of directions picked up by the multiple-lens capsule endoscope. An image display apparatus takes in image groups from the plurality of directions accumulated in the receiving apparatus and displays each image contained in the acquired image groups alternately in each display area of a screen (See, for example, Japanese Patent Application Laid-open No. 2006-68534). Image display apparatuses that display a large quantity of images picked up by imaging devices in each display area of the screen separately include those disclosed in Japanese Patent Application Laid-Open No. 2002-211049 and Japanese Patent Application Laid-Open No. H11-259630.

SUMMARY OF THE INVENTION

An image display apparatus according to one aspect of the present invention includes a display unit that displays images contained in a plurality of image groups inside a subject picked up by a plurality of imaging devices, and a control unit that extracts a related image related to a currently displayed image currently displayed in the display unit from the plurality of image groups to make the display unit display the related image extracted.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 is a schematic diagram showing a specific example of a window displaying GUIs for creating a report of a subject;

FIG. 16 is a schematic diagram showing a specific example of default data of time difference set for each site of the subject;

FIG. 41 is a schematic diagram illustrating processing by an image classifier to attach an input number to each image contained in each of a plurality of image groups of an inside of the subject;

FIG. 45 is a schematic diagram illustrating processing by the image classifier to associate an input time with each image contained in each of the plurality of image groups of an inside of the subject;

DETAILED DESCRIPTION OF THE PREFERRED EMBODIMENTS

Preferred embodiments of the image display apparatus according to the present invention will be described below in detail. However, the present invention is not limited by these embodiments.

Figure 1:
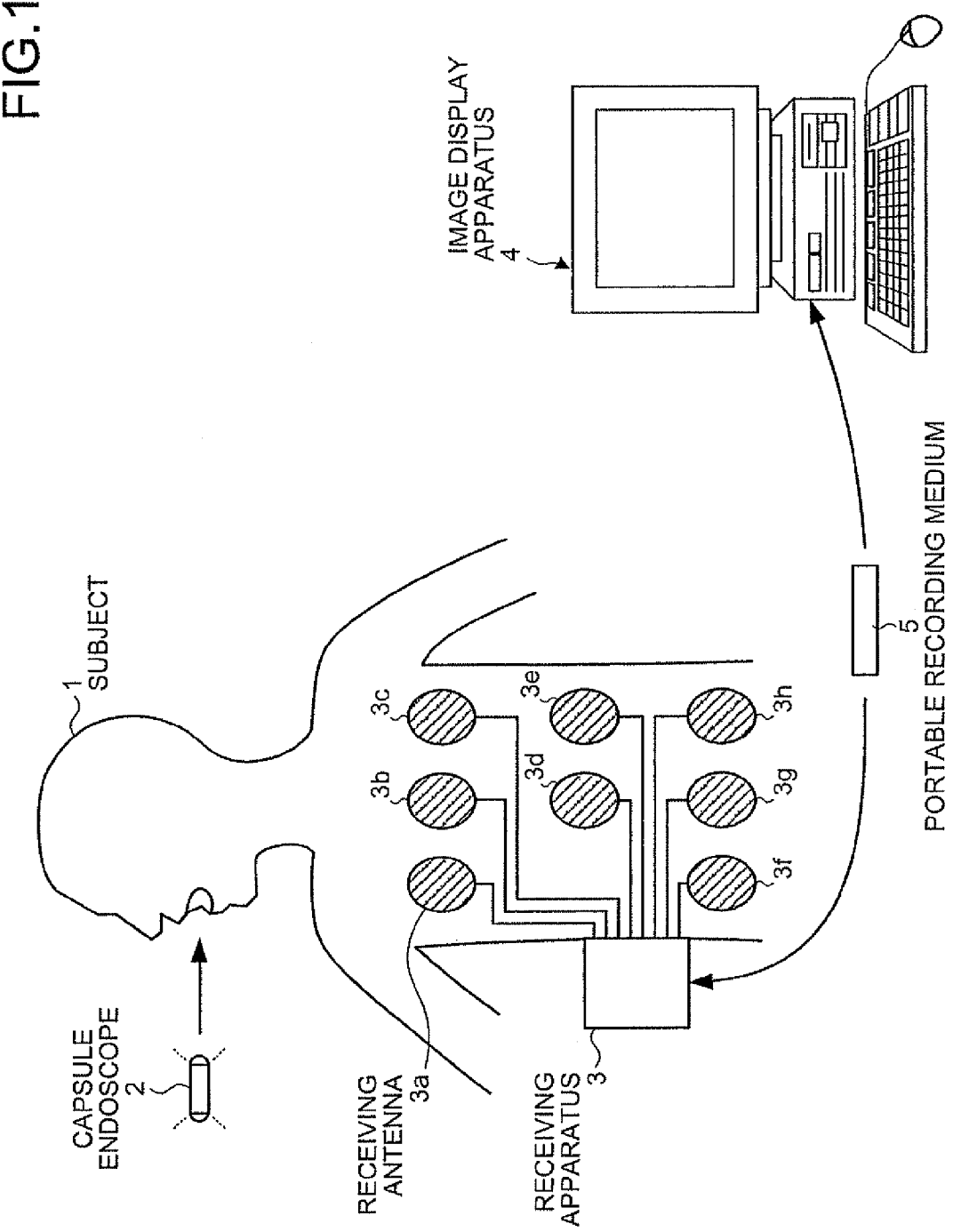
FIG. 1 is a schematic diagram exemplarily showing a configuration example of an intra-subject information acquisition system having an image display apparatus according to a first embodiment of the present invention.

FIG. 1 is a schematic diagram exemplarily showing a configuration example of an intra-subject information acquisition system having an image display apparatus according to the first embodiment of the present invention. As shown in FIG. 1, the intra-subject information acquisition system includes a capsule endoscope 2 that moves through the digestive tract of a subject 1 and picks up images inside the subject 1, a receiving apparatus 3 that receives a radio signal transmitted by the capsule endoscope 2 to accumulate images contained in the received radio signal, an image display apparatus 4 that displays images accumulated in the receiving apparatus 3, that is, images picked up by the capsule endoscope 2, and a portable recording medium 5 that serves to pass data between the receiving apparatus 3 and the image display apparatus 4.

The capsule endoscope 2 is a multiple-lens capsule endoscope equipped with a group of imaging devices which each pick up images from mutually different directions. The multiple-lens capsule endoscope 2 has an imaging function in multiple directions to sequentially pick up images from a plurality of directions inside the subject 1 along time series after being introduced into the subject 1 and a radio communication function to transmit image groups picked up from multiple directions to the outside by radio. More specifically, the capsule endoscope 2 passes through the esophagus in the subject 1 and moves through the body cavity in accordance with peristaltic movement of the lumen of digestive tract after being swallowed by the subject 1. At the same time, the capsule endoscope 2 sequentially picks up images from multiple directions inside the subject 1 at predetermined intervals, for example, at intervals of 0.5 second and then sequentially transmits images from multiple directions inside the subject 1 to the receiving apparatus 3 via predetermined electric waves.

The receiving apparatus 3 is connected, for example, to a plurality of receiving antennas 3a to 3h distributed over the body surface of the subject 1, receives a radio signal from the capsule endoscope 2 via any of the plurality of receiving antennas 3a to 3h, and acquires images from multiple directions inside the subject 1 based on the received radio signal. Further, the portable recording medium 5 is detachably inserted into the receiving apparatus 3 and, the receiving apparatus 3 sequentially stores images sequentially acquired based on the radio signal from the capsule endoscope 2, that is, images from multiple directions picked up by the capsule endoscope 2 in the portable recording medium 5. Thus, the receiving apparatus 3 accumulates groups of images (that is, a plurality of image groups classified by imaging device) picked up along time series from multiple directions inside the subject 1 by a group of imaging devices of the capsule endoscope 2 in the portable recording medium 5.

The receiving antennas 3a to 3h are realized with, for example, a loop antenna and receive a radio signal transmitted by the capsule endoscope 2. As shown in FIG. 1, the receiving antennas 3a to 3h are arranged at predetermined positions over the body surface of the subject 1, for example, at positions corresponding to the passing route (that is, the digestive tract) of the capsule endoscope 2 inside the subject 1 in a scattered manner. The receiving antennas 3a to 3h may also be arranged at predetermined positions of a jacket to be worn by the subject 1. In this case, the receiving antennas 3a to 3h are arranged at predetermined positions over the body surface of the subject 1 corresponding to the passing route of the capsule endoscope 2 inside the subject 1 when the subject 1 wears the jacket. Only one or more such receiving antennas need to be arranged for the subject 1 and the number of arranged receiving antennas is not particularly limited to eight.

The portable recording medium 5 is a recording medium that can be carried such as CompactFlash®. The portable recording medium 5 is detachable from the receiving apparatus 3 and the image display apparatus 4 and has a structure enabling output and recording of data when inserted in the receiving apparatus 3 or the image display apparatus 4. More specifically, when inserted in the receiving apparatus 3, the portable recording medium 5 sequentially stores various kinds of data such as image groups from multiple directions by the capsule endoscope 2 and imaging times acquired by the receiving apparatus 3. When inserted in the image display apparatus 4, on the other hand, the portable recording medium 5 outputs saved data such as the image groups from multiple directions by the capsule endoscope 2 to the image display apparatus 4. In this manner, the saved data in the portable recording medium 5 is taken into the image display apparatus 4. On the other hand, the image display apparatus 4 writes, for example, information concerning the subject 1 of a capsule-endoscopic examination into the portable recording medium 5. The capsule-endoscopic examination is an examination in which images picked up by the capsule endoscope 2 after being introduced into the subject 1 are observed.

The image display apparatus 4 is used to display images or the like picked up from multiple directions by the capsule endoscope 2. More specifically, the image display apparatus 4 has a configuration like a workstation that acquires various kinds of data such as images picked up from multiple directions by the capsule endoscope 2 by taking in various kinds of data accumulated in the portable recording medium 5 by the receiving apparatus 3 and displays images from multiple directions inside the subject 1 based on the acquired data. In this case, the image display apparatus 4 saves the acquired image groups from multiple directions after classifying the image groups by imaging device of capsule endoscope 2. The image display apparatus 4 has an image display function to sequentially display at least one of each image contained in one image group of image groups from multiple directions inside the subject 1 and each image contained in another image group. Further, the image display apparatus 4 has a processing function allowing a user such as physician or a nurse to diagnose the subject 1 by observing (examining) images inside the subject 1. In this case, the user sequentially makes images inside the subject 1 displayed on the image display apparatus 4 to observe (examine) sites inside the subject 1, for example, the esophagus, stomach, small intestine, and large intestine and can diagnose the subject 1 based on the observation (examination).

Figure 2:
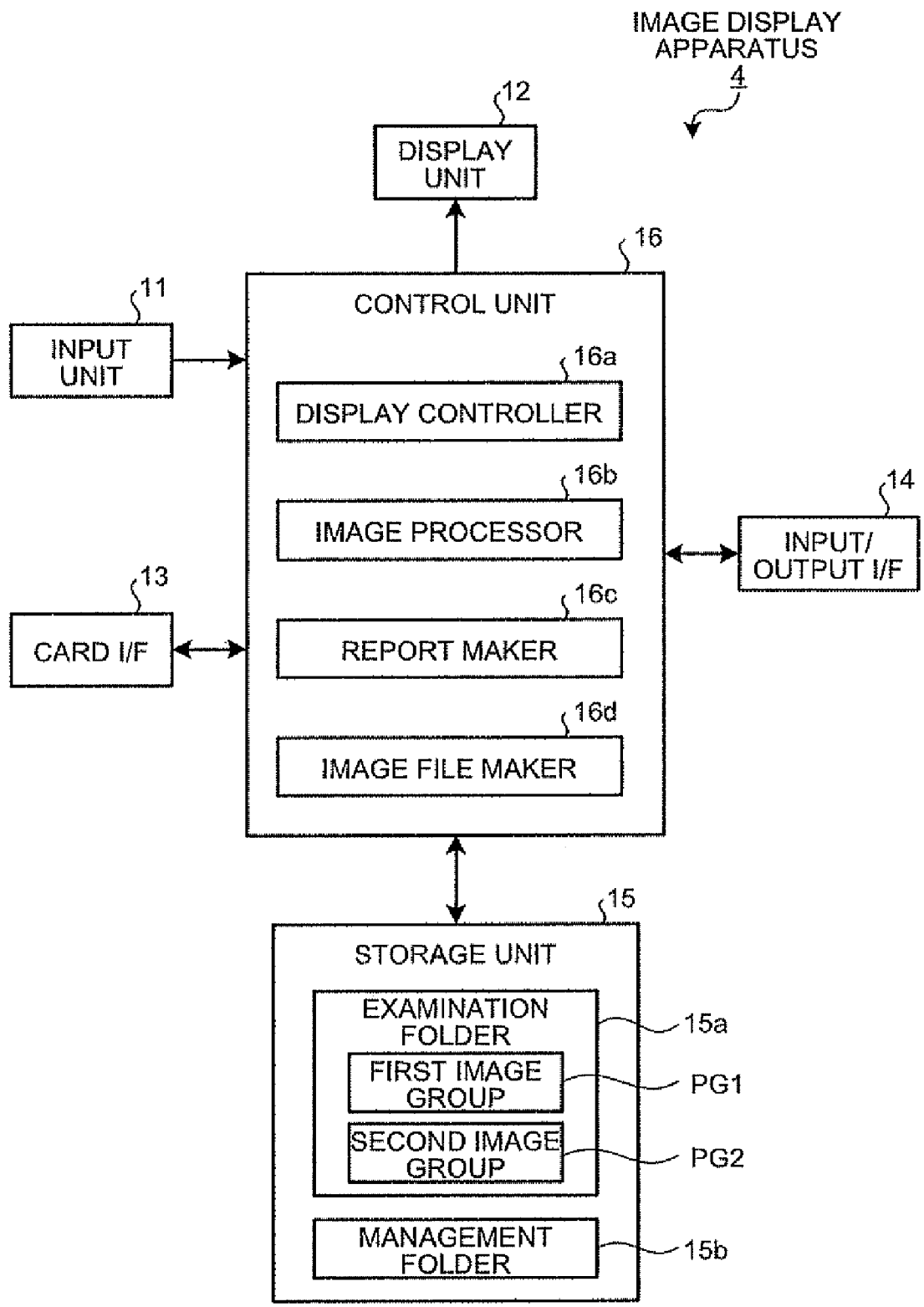
FIG. 2 is a block diagram exemplarily showing a configuration example of the image display apparatus according to the first embodiment of the present invention.

Next, the configuration of the image display apparatus 4 according to the first embodiment of the present invention will be described. FIG. 2 is a block diagram exemplarily showing a configuration example of the image display apparatus 4 according to the first embodiment of the present invention. As shown in FIG. 2, the image display apparatus 4 has an input unit 11 that inputs various kinds of information or data, a display unit 12 that displays images inside the subject 1, GUIs (Graphical User Interface) and the like in a screen, and a card interface (I/F) 13 that takes in saved data accumulated in the portable recording medium 5 such as images inside the subject 1. The image display apparatus 4 also has an input/output I/F 14 that serves for input/output of various kinds of information or data with respect to an external computer, printer or the like, or a portable recording medium, a storage unit 15 that saves various kinds of data such as images of the subject 1, and a control unit 16 that controls driving of each component of the image display apparatus 4.

The input unit 11 is realized with an input device such as a keyboard or a mouse and inputs various kinds of information or data to the control unit 16 according to user's input operations. More specifically, the input unit 11 inputs instruction information instructing the control unit 16, patient information about the subject 1, setting information for setting an image display mode of images of the subject 1 to be displayed in the display unit 12, data required for displaying images of the subject 1 in such image display mode and the like.

The patient information is registered in the receiving apparatus 3 via the portable recording medium 5, for example, to initialize the receiving apparatus 3 as a receiving apparatus for performing a capsule-endoscopic examination of the subject 1. The patient information is, for example, patient's name, sex, date of birth, patient ID and the like.

The display unit 12 is realized with various kinds of displays such as a CRT display and liquid crystal display and displays various kinds of information or data instructed to display by the control unit 16. More specifically, the display unit 12 displays various kinds of information or data required for observing and diagnosing the subject 1, for example, each image contained in two image groups among a plurality of images of subject 1 picked up by the group of imaging devices of the capsule endoscope 2. The display unit 12 also displays GUIs functioning as a setting unit for setting various image display modes to display images of the subject 1. In addition to setting various image display modes, such GUIs function as a setting unit for setting data (for example, time difference data described later) needed for displaying images of the subject 1 in set image display mode and further, function as an operation unit for operating the display of such images of the subject 1.

The card I/F 13 is used to take in saved data of the portable recording medium 5. More specifically, when the portable recording medium 5 is detachably inserted, the card I/F 13 reads saved data accumulated in the portable recording medium 5 and transfers the acquired saved data to the control unit 16. The card I/F 13 also writes information instructed by the control unit 16 to write, for example, the above patient information to the inserted portable recording medium 5.

The input/output I/F 14 inputs/outputs various kinds of data between, for example, a peripheral device such as an external computer or printer and the image display apparatus 4, or between an inserted portable recording medium and the image display apparatus 4. More specifically, the input/output I/F 14 can have a portable recording medium such as a flexible disk (FD), compact disk (CD), and DVD (Digital Versatile Disk) detachably inserted thereto and is realized with a drive or the like performing read processing or write processing of various kinds of data from/to the inserted recording medium. The input/output I/F 14 also has a structure allowing data communication with a peripheral device such as an external computer or printer via a predetermined cable or LAN. The input/output I/F 14 writes data instructed to write by the control unit 16 into a recording medium in a drive and outputs data instructed to output by the control unit 16 to a peripheral device such as an external computer or printer, The input/output I/F 14 also reads data instructed to read by the control unit 16 from a recording medium in a drive and transfers the acquired data to the control unit 16.

The storage unit 15 is realized with an information storage unit in which various kinds of information or data can be stored and from which various kinds of information or data can be read such as a RAM, EEPROM, or a hard disk and saves information or data instructed to write by the control unit 16 and transmits saved information or saved data instructed to read by the control unit 16 to the control unit 16. The storage unit 15 has an examination folder 15a for maintaining and managing an examination file of the subject 1 including image groups, patient information, and examination information (for example, the examination date and examination ID) and a management folder 15b for maintaining and managing various files such as a medical record (report) of the subject 1 generated by the processing function of the image display apparatus 4, static images, and dynamic images. In this case, the storage unit 15 saves a first image group PG1 and a second image group PG2 of image groups picked up inside the subject 1 by the group of imaging devices of the multiple-lens capsule endoscope 2 in the examination folder 15a.

The first image group PG1 and the second image group PG2 are image groups respectively picked up by two imaging devices picking up images from mutually different directions in the group of imaging devices mounted on the multiple-lens capsule endoscope 2. For example, the first image group PG1 is picked up by an imaging device for picking up images from a front direction (that is, the traveling direction in the digestive tract of the subject 1) of the capsule endoscope 2. The second image group PG2, on the other hand, is picked up by an imaging device for picking up images from a back direction (that is, the direction opposite to the traveling direction in the digestive tract of the subject 1) of the capsule endoscope 2.

As described above, the control unit 16 controls each component of the image display apparatus 4, for example, controls driving of each of the input unit 11, the display unit 12, the card I/F 13, the input/output I/F 14, and the storage unit 15 to control input/output of information with each of such components. More specifically, the control unit 16 generates an examination file obtained by creating a file in which image groups (for example, the first image group PG1 and the second image group PG2) from multiple directions of the subject 1 acquired via the portable recording medium 5, time information about imaging time of each image contained in the image groups from multiple directions, patient information of the subject 1, and examination information of the subject 1 and then saves the acquired examination file in the examination folder 15a. In this case, the control unit 16 maintains and manages each examination file saved in the examination folder 15a, for example, by subject or examination ID.

The control unit 16 has a display controller 16a, an image processor 16b, a report maker 16c, and an image file maker 16d. The display controller 16a has a plurality of image display modes and controls a display operation of the display unit 12 in accordance with the mode selected from the plurality of image display modes.

The image processor 16b performs various kinds of processing on a plurality of image groups inside the subject 1 acquired via the portable recording medium 5. More specifically, the image processor 16b performs predetermined image processing on the plurality of image groups acquired via the portable recording medium 5, classifies the plurality of image groups (that is, the image groups from multiple directions) by imaging device of the capsule endoscope 2, and saves each of the classified image groups (for example, the first image group and the second image group) in the storage unit 15. The image processor 16b also creates reduced images (for example, thumbnail images) of images displayed in the display areas of the display unit 12 based on instruction information input from the input unit 11.

The report maker 16c creates a report describing diagnosis results concerning the subject 1 and the like using various kinds of information input by the input unit 11, images of the subject 1 and the like. Based on an image group (for example, the first image group PG1 or the second image group PG2) contained in the examination file, the image file maker 16d creates an image file of desired static images or dynamic images.

Figure 3:
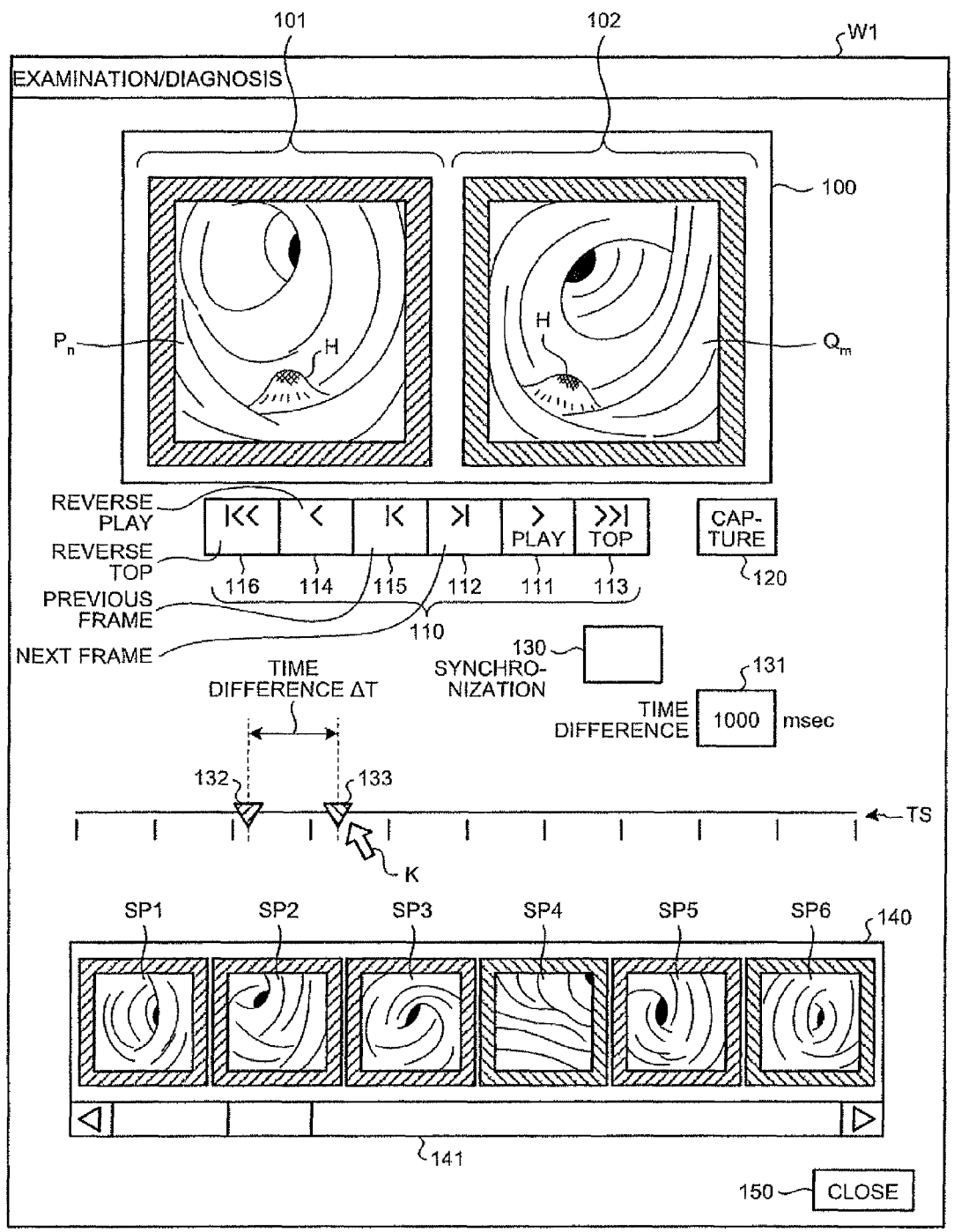
FIG. 3 is a schematic diagram exemplarily showing a specific example of various GUIs displayed in a display unit of the image display apparatus according to the first embodiment.

Next, a display screen of the display unit 12 is specifically exemplified to describe various GUIs displayed in the display unit 12 and the operation of the display controller 16a that controls the display operation of the display unit 12. FIG. 3 is a schematic diagram exemplarily showing a specific example of various GUIs displayed in the display unit 12. When predetermined login processing is performed by the control unit 16, the display controller 16a makes the display unit 12 display a window W1 shown in FIG. 3.

In the window W1, an image $P_n$ (n=0, 1, 2, 3, ... ), contained in the first image group PG1 stored in the examination folder 15a of the storage unit 15, an image $Q_m$ (m=0, 1, 2, 3, ... ), contained in the second image group PG2, and the various GUIs described above are displayed. More specifically, as shown in FIG. 3, in the window W1, a main image display area 100 in which the images $P_n$ and $Q_m$ are displayed, a display operation icon group 110 which are operation GUIs for performing various display operations of images to be displayed in the main image display area 100, and a capture icon 120, which is a GUI for instructing creation of reduced images (for example, thumbnail images) of images displayed in the main image display area 100 are formed in the window W1. In this case, the main image display area 100 has a display area 101 to sequentially display the image $P_n$, and a display area 102 to sequentially display the image $Q_m$.

Also in the window W1, a synchronization icon 130, which is a setting GUI for setting one of the plurality of image display modes held by the above-described display controller 16a, and a data setting area 131 for setting a time difference $\Delta T$ between the imaging time of the image $P_n$ and that of the image $Q_m$ displayed in the display areas 101 and 102 respectively inside the main image display area 100 are formed. Further, in the window W1, a time scale TS indicating a temporal length of the first image group PG1 and the second image group PG2 displayed in the main image display area 100 (for example, an elapsed time of the first image group PG1 and the second image group PG2 after starting imaging), a time slider 132, which is a GUI for indicating a temporal position of the image $P_n$ displayed in the display area 101 (that is, the position on the time scale TS temporally corresponding to the image $P_n$), and a time slider 133, which is a GUI for indicating a temporal position of the image $Q_m$ displayed in the display area 102 (that is, the position on the time scale TS temporally corresponding to the image $Q_m$) are formed.

Here, the time slider 132 indicates the temporal position of the image $P_n$ displayed in the display area 101 and moves on the time scale TS in the forward direction or reverse direction along time series in synchronization with switching of the image $P_n$ in the display area 101 based on control of the display controller 16a. In this case, in synchronization with the movement of the time slider 132, the display controller 16a makes the image $P_n$ corresponding to the current temporal position indicated by the time slider 132 displayed in the display area 101. The time slider 133, on the other hand, indicates the temporal position of the image $Q_m$ displayed in the display area 102 and moves on the time scale TS in the forward direction or reverse direction along time series in synchronization with switching of the image $Q_m$ in the display area 102 based on control of the display controller 16a. In this case, in synchronization with the movement of the time slider 133, the display controller 16a makes the image $Q_m$ corresponding to the current temporal position indicated by the time slider 133 displayed in the display area 102.

Like the data setting area 131 described above, the time difference $\Delta T$ between the image $P_m$ and image $Q_m$ can be set by a drag operation using the input unit 11. In this case, as shown in FIG. 3, an interval of temporal positions indicated by the time sliders 132 and 133 corresponds to the time difference $\Delta T$ between the image $P_n$ and image $Q_m$ displayed in the data setting area 131.

Therefore, the synchronization icon 130, the data setting area 131, and the time sliders 132 and 133 are GUIs functioning as a setting unit for setting a synchronous display mode in which the images $P_n$ and $Q_m$ having the time difference $\Delta T$ are displayed synchronously in the respective display areas 101 and 102 as an image display mode of the display controller 16a. The synchronization icon 130 as described above sets the synchronous display mode when a click operation using the input unit 11 is performed. More specifically, with the click operation of the synchronization icon 130 being performed once, the input unit 11 inputs setting information instructing to set the synchronous display mode to the control unit 16. In this case, the display controller 16a selects the synchronous display mode based on the setting information input by the input unit 11 from the plurality of image display modes.

If such a click operation is performed again, the synchronization icon 130 sets a normal display mode as the image display mode of the display controller 16a (in other words, cancels the synchronous display mode). More specifically, with the click operation of the synchronization icon 130 being performed again, the input unit 11 inputs setting information instructing to set the normal display mode to the control unit 16. In this case, the display controller 16a selects the normal display mode based on the setting information input by the input unit 11 from the plurality of image display modes.

The synchronous display mode as described above is an image display mode in which the image $P_n$ and the image $Q_m$ in which an object (for example, a lesion site H) common to the image $P_n$ appears are synchronously displayed in the respective display areas 101 and 102. The images $P_n$ and $Q_m$ synchronously displayed in the synchronous display mode are images in which a common object such as the lesion site H appears and are deeply associated images of mutual connection. In the synchronous display mode, the difference between imaging times of the images $P_n$ and $Q_m$ synchronously displayed in the respective display areas 101 and 102 is approximately the same as the time difference $\Delta T$ set in the data setting area 131 or by the time sliders 132 and 133. In this case, the difference between a frame number n (n=0, 1, 2, 3, ...) of the image $P_n$ in the first image group PG1 and a frame number m (m=0, 1, 2, 3, ...) of the image $Q_m$ in the second image group PG2 corresponds to the time difference $\Delta T$. If, for example, the first image group PG1 and the second image group PG2 are picked up at intervals of 0.5 sec per image, when time difference $\Delta T$ of images $P_n$ and $Q_m$ is set to 1000 msec, the difference (m−n) of frame numbers of such images $P_n$ and $Q_m$ is 2.

On the other hand, the normal display mode described above is an image display mode in which the images $P_n$ and $Q_m$ are sequentially displayed in the respective display areas 101 and 102 in the order of frame number regardless of the time difference $\Delta T$. In the normal display mode, the frame numbers n and m of the images $P_n$ and $Q_m$ displayed in the respective display areas 101 and 102 are normally the same.

As shown in FIG. 3, the window W1 also has a sub-image display area 140 to additionally display each reduced image of the images $P_n$ and $Q_m$ instructed to create by a click operation of the capture icon 120 and a scroll bar 141 for performing a scroll operation of reduced images (for example, thumbnail images) displayed in the sub-image display area 140 formed therein. More specifically, with a click operation of the capture icon 120 being performed, the input unit 11 inputs instruction information instructing to create reduced images of the images $P_n$ and $Q_m$ displayed in the respective display areas 101 and 102 to the control unit 16. In this case, each time such instruction information is input by the input unit 11, the image processor 16b creates reduced images of each of the images $P_n$ and $Q_m$. The display controller 16a saves reduced images created by the image processor 16b in the storage unit 15 and also makes the reduced images additionally displayed in the sub-image display area 140 one by one. In this manner, for example, thumbnail images SP1, SP2, SP3, and SP5 corresponding to the images displayed in the display area 101 and thumbnail images SP4 and SP6 corresponding to the images displayed in the display area 102 are displayed in the sub-image display area 140.

In addition, a cursor K for performing a click operation or drag operation of various GUIs by operating the input unit 11 and a Close icon 150 for closing the window W1 are formed in the window W1.

Here, the display operation icon group 110 displayed in the window W1 includes a play icon 111, a frame advance icon 112, a top search icon 113, a reverse play icon 114, a previous frame icon 115, and a review search icon 116. The display operation icon group 110 sets a display operation of the images $P_n$ and $Q_m$ in the respective display areas 101 and 102 by a click operation using the input unit 11. In this case, the input unit 11 performs a click operation on one of the icons of the display operation icon group 110 to input display instruction information in accordance with the icon in the display operation icon group 110 to the control unit 16. Based on the display instruction information input by the input unit 11, the display controller 16a makes the images $P_n$ and $Q_m$ sequentially displayed in the respective display areas 101 and 102.

More specifically, when a click operation of the play icon 111 is performed, the display controller 16a makes the images $P_n$ and $Q_m$ sequentially displayed in the respective display areas 101 and 102 in the forward direction of time series and, when a click operation of the frame advance icon 112 is performed, the display controller 16a each time makes the images $P_n$ and $Q_m$ sequentially displayed in the respective display areas 101 and 102 in the forward direction of time series. When a click operation of the reverse play icon 114 is performed, the display controller 16a makes the images $P_n$ and $Q_m$ sequentially displayed in the respective display areas 101 and 102 in the reverse direction of time series and, when a click operation of the previous frame icon 115 is performed, the display controller 16a each time makes the images $P_n$ and $Q_m$ sequentially displayed in the respective display areas 101 and 102 in the reverse direction of time series.

If, on the other hand, a click operation of the top search icon 113 is performed, the display controller 16a makes the image at the end of the first image group PG1 displayed in the display area 101 and the image at the end of the second image group PG2 displayed in the display area 102. If a click operation of the review search icon 116 is performed, the display controller 16a makes the image at the head of the first image group PG1 displayed in the display area 101 and the image at the head of the second image group PG2 displayed in the display area 102.

The display areas 101 and 102 are highlighted by a frame in a predetermined color or pattern when images are displayed. In this case, the time slider 132 indicating the temporal position of the image $P_n$ displayed in the display area 101 and the thumbnail images SP1, SP2, SP3, and SP5 corresponding to the image displayed in the display area 101 are highlighted in the same manner as the display area 101 is highlighted. Further, the time slider 133 indicating the temporal position of the image $Q_m$ displayed in the display area 102 and the thumbnail images SP4 and SP6 corresponding to the image displayed in the display area 102 are highlighted in the same manner as the display area 102 is highlighted. Such highlighting allows one to easily, visually recognize association of the display area 101, the time slider 132, and the thumbnail images SP1, SP2, SP3, and SP5, and also that of the display area 102, the time slider 133, and the thumbnail images SP4 and SP6.

Figure 4:
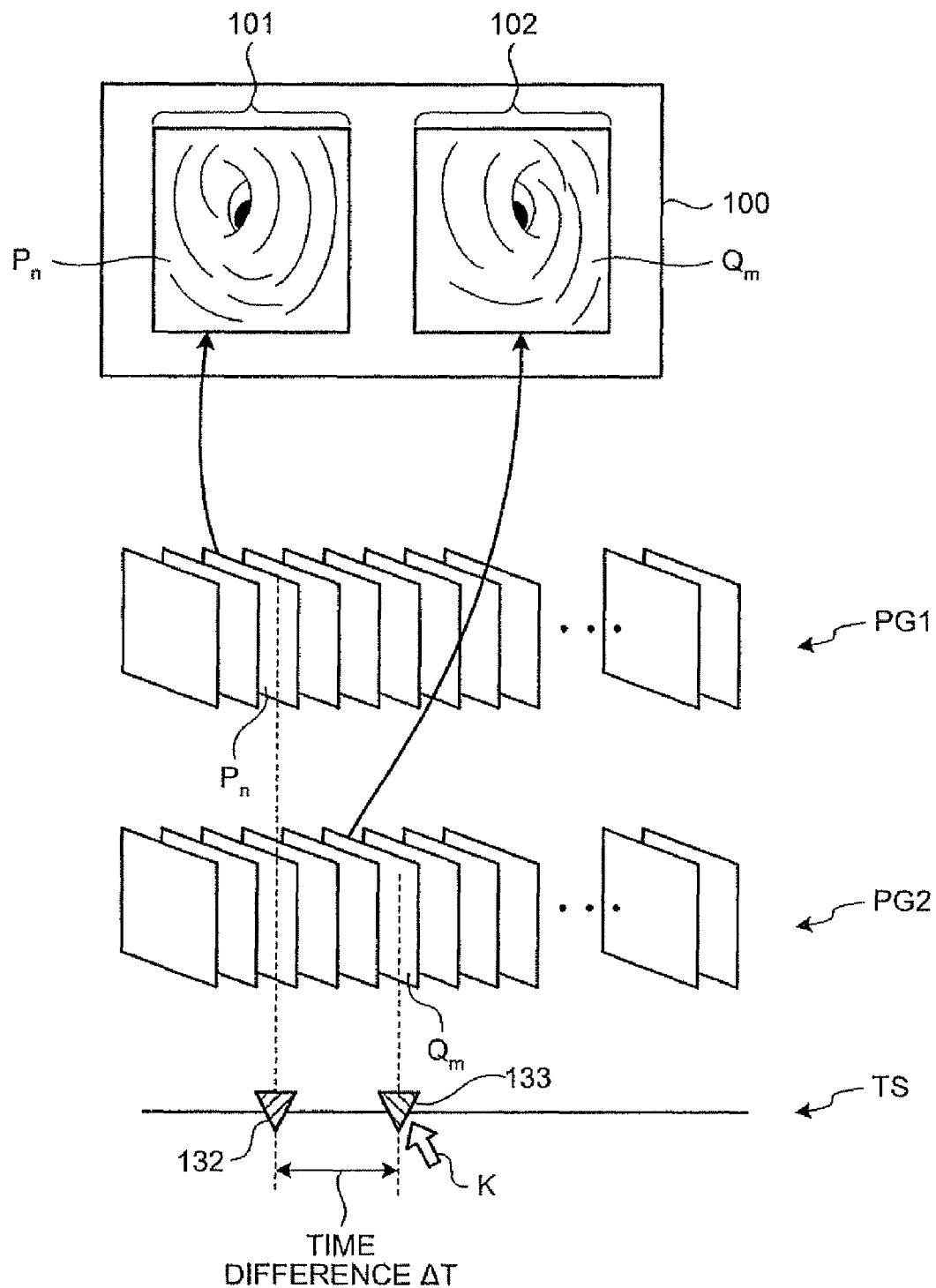
FIG. 4 is a schematic diagram illustrating a procedure for setting a time difference using a data setting area or a time slider.

Next, how to set the time difference $\Delta T$ using the data setting area 131 or the time sliders 132 and 133 will be described. FIG. 4 is a schematic diagram illustrating a procedure for setting the time difference $\Delta T$ using the data setting area 131 or the time sliders 132 and 133.

In FIG. 4, the images $P_n$ and $Q_m$ are made to be displayed in the display areas 101 and 102 of the main image display area 100, respectively. Next, if the first image group PG1 is picked up by an imaging device whose imaging field of view is directed in the forward direction of the capsule endoscope 2, a drag operation of the time slider 133 is performed using the input unit 11 while referencing to the images $P_n$ and $Q_m$ displayed in the respective display areas 101 and 102 to move the time slider 133 and to sequentially switch the image $Q_m$. By such a drag operation of the time slider 133, an image $Q_m$ in which an object common to the image $P_n$ currently displayed in the display area 101 appears is detected from the second image group PS2 and such images $P_n$ and $Q_m$ are made to be displayed in the display areas 101 and 102, respectively.

In this case, the images $P_n$ and $Q_m$ are images of a common object picked up from different directions.

In this state, the interval between the time sliders 132 and 133 corresponds to the time difference $\Delta T$ of the images $P_n$ and $Q_m$. In this manner, the time sliders 132 and 133 can set the time difference $\Delta T$ of the images $P_n$ and $Q_m$. In this case, a numeric value of the time difference $\Delta T$ set by the time sliders 132 and 133 is displayed in the data setting area 131.

Or, the time difference $\Delta T$ of the images $P_n$ and $Q_m$ may be set by performing a drag operation of the time sliders 132 and 133 so as to detect the images $P_n$ and $Q_m$ in which the lesion site H or a characteristic inner wall inside the digestive tract is picked up from different angles.

More specifically, after the images $P_n$ and $Q_m$ are made to be displayed in the display areas 101 and 102 of the main image display area 100 respectively, a drag operation of the time slider 132 is performed using the input unit 11 with reference to the image $P_n$ displayed in the display area 101 to move the time slider 132 and to sequentially switch the image $P_n$. By such a drag operation of the time slider 132, an image $P_n$ in which a characteristic object (for example, the lesion site H or a characteristic inner wall inside the digestive tract) is picked up is detected from the first image group PG1 and the image $P_n$ of such a characteristic object is made to be displayed in the display area 101.

Next, a drag operation of the time slider 133 is performed using the input unit 11 with reference to the image $Q_m$ displayed in the display area 102 to move the time slider 133 and to sequentially switch the image $Q_m$. By such a drag operation of the time slider 133, an image $Q_m$ in which the characteristic object common to the image $P_n$ appears is detected from the second image group PG2 and the image $Q_m$ of such a characteristic object is made to be displayed in the display area 102. In this case, the images $P_n$ and $Q_m$ are images of a common characteristic object picked up from different directions.

In this state, the interval between the time sliders 132 and 133 corresponds to the time difference $\Delta T$ of the images $P_n$ and $Q_m$ and, as a result, the time sliders 132 and 133 can set the time difference $\Delta T$ of the images $P_n$ and $Q_m$. Further in this case, a numeric value of the time difference $\Delta T$ set by the time sliders 132 and 133 is displayed in the data setting area 131.

The time difference $\Delta T$ of such images $P_n$ and $Q_m$ can also be set by direct input of a numerical value into the data setting area 131 by using the input unit 11. In this case, the time sliders 132 and 133 move in such a way that the interval corresponding to the time difference $\Delta T$ input in the data setting area 131 is maintained.

When the time difference $\Delta T$ is set by the data setting area 131 or the time sliders 132 and 133, the input unit 11 inputs time difference data corresponding to the time difference $\Delta T$ to the control unit 16. In this case, the control unit 16 saves the time difference data input by the input unit 11 in the storage unit 15 and maintains and manages the time difference data as the time difference $\Delta T$ of the images $P_n$ and $Q_m$ in the synchronous display mode described above. When the time difference $\Delta T$ is reset by the data setting area 131 or the time sliders 132 and 133, the control unit 16 updates the time difference data maintained and managed in the storage unit 15 to the time difference $\Delta T$ after resetting (that is, after the change).

Figure 5:
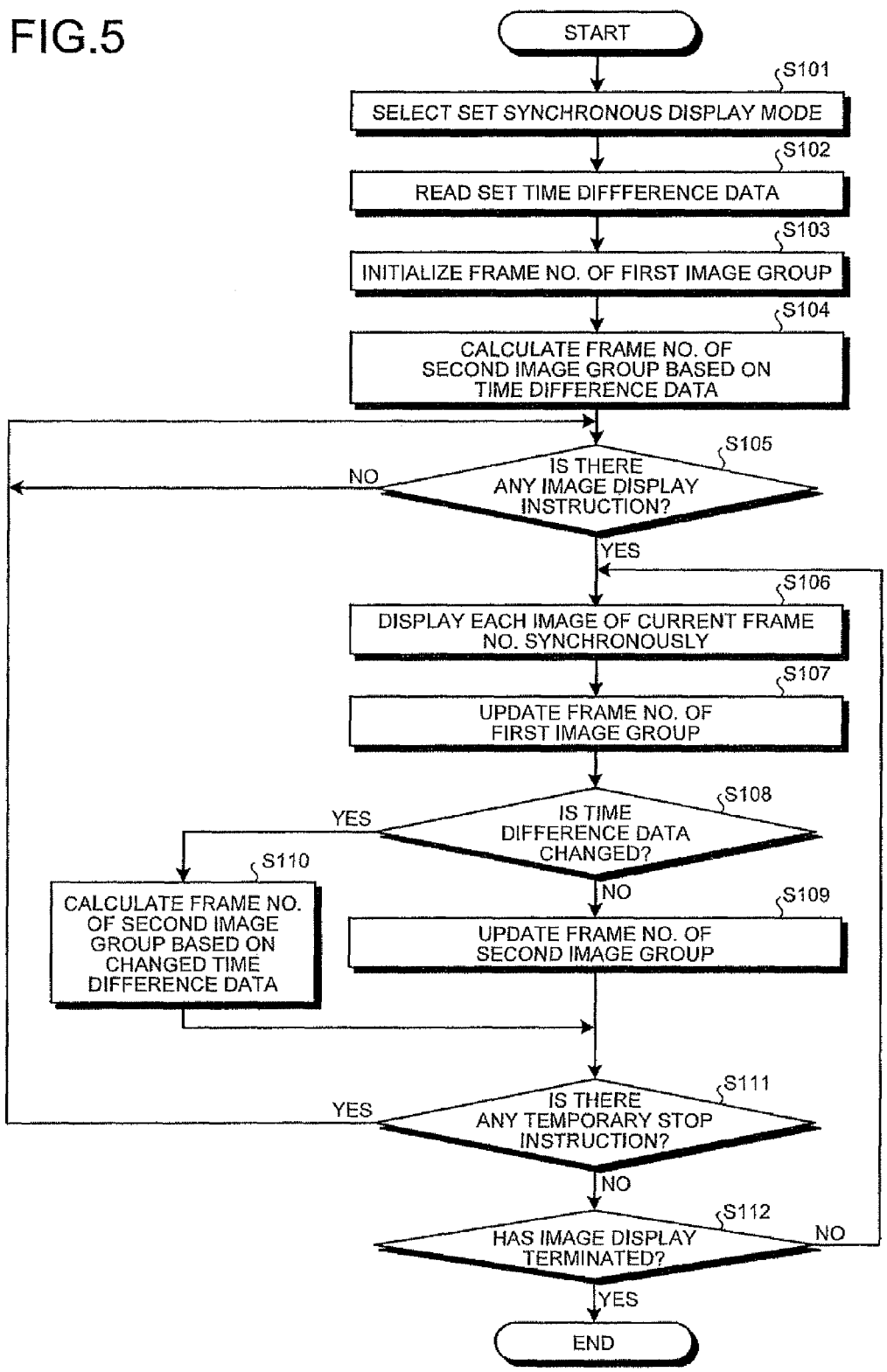
FIG. 5 is a flowchart illustrating a processing procedure by a control unit that makes images having a time difference set through the GUI synchronously displayed in respective display areas.

Next, the operation of the control unit 16 controlling the synchronous display of the images $P_n$ and $Q_m$ in the respective display areas 101 and 102 in the synchronous display mode will be described. FIG. 5 is a flowchart illustrating a processing procedure by the control unit 16 that makes the images $P_n$ and $Q_m$ having the time difference $\Delta T$ set through the GUI synchronously displayed in the respective display areas 101 and 102.

In FIG. 5, the control unit 16 first selects the synchronous display mode set by the synchronization icon 130 as the image display mode (step S101). In this case, the display controller 16a selects the synchronous display mode from the plurality of image display modes based on setting information input from the input unit 11 by a click operation of the synchronization icon 130. Thus, when the synchronous display mode is set, the control unit 16 reads out the time difference data set by the data setting area 131 or the time sliders 132 and 133 from the storage unit 15 (step S102). The display controller 16a acquires the time difference data read out in this manner as the time difference $\Delta T$ of the images $P_n$ and $Q_m$ in the synchronous display mode.

Next, the control unit 16 initializes the frame numbers of the first image group PG1 (step S103). In this case, the display controller 16a initializes the frame number n of the image to be processed for display from the first image group PG1 (for example, set n=0). Subsequently, the control unit 16 calculates the frame number m of the image to be processed for display from the second image group PG2 based on the set time difference data (step S104). In this case, the display controller 16a calculates the frame number m of the image $Q_m$ having the time difference $\Delta T$ with respect to the image $P_n$ (for example, n=0) to be displayed synchronously in the display area 101 based on the time difference data read out at step S102 described above.

Then, the control unit 16 determines whether or not any image display instruction of the images $P_n$ and $Q_m$ has been issued (step S105). More specifically, if a click operation of one of the icons (for example, the play icon 111, the frame advance icon 112, the top search icon 113, the reverse play icon 114, the previous frame icon 115, and the review search icon 116) of the display operation icon group 110 is performed, the input unit 11 inputs display instruction information corresponding to the click-operated icon to the control unit 16. If no such display instruction information has been input from the input unit 11, the control unit 16 determines that no image display instruction of the images $P_n$ and $Q_m$ has been issued (step S105, No) and repeats step S105. That is, the control unit 16 repeats step S105 until such display instruction information is input by the input unit 11.

If, on the other hand, such display instruction information has been input from the input unit 11, the control unit 26 determines that an image display instruction of the images $P_n$ and $Q_m$ has been issued based on the input display instruction information (step S105, Yes) and makes the images $P_n$ and $Q_m$ of the current frame numbers n and m synchronously displayed in the respective display areas 101 and 102 (step S106). In this case, the display controller 16a extracts the image $P_n$ of the current frame number n (n=0, 1, 2, 3, ...) from among the first image group PG1 saved in the storage unit 15 and performs control to display the extracted image $P_n$ in the display area 101. In synchronization with the display of the image $P_n$, the display controller 16a extracts the image $Q_m$ of the current frame number m (m=0, 1, 2, 3, ...) from among the second image group PG2 saved in the storage unit 15 and performs control to display the extracted image $Q_m$ in the display area 102. In this manner, the display controller 16a makes the images $P_n$ and $Q_m$ having the set time difference $\Delta T$ (that is, mutually related images) synchronously displayed in the respective display areas 101 and 102.

Here, the current frame number m is the frame number of the image $Q_m$ having the time difference $\Delta T$ with respect to the image $P_n$ made displayed in the display area 101 at step S106. Therefore, the current frame number m has a frame number difference α (α=1, 2, 3, . . . ) corresponding to the time difference ΔT with respect to the frame number n. That is, at step S106, the display controller 16a makes the images $P_n$ and $Q_m$ (m=n+α) having the frame number difference α corresponding to the set time difference ΔT displayed in the respective display areas 101 and 102.

The current frame number n at step S106 is the frame number n (n=0) initialized at step S103 or a frame number n updated at step S107 described later.

Then, the control unit 16 updates the frame number n of the first image group PG1 (step S107). In this case, the display controller 16a updates (for example, adds +1) the frame number n of the first image group PG1 to read the image $P_n$ to be displayed in the display area 101 at next step S106 from the storage unit 15.

Next, the control unit 16 determines whether or not the time difference data has been changed (reset) by the data setting area 131 or the time sliders 132 and 133 (step S108). More specifically, the input unit 11 inputs time difference data reset by the data setting area 131 or the time sliders 132 and 133 to the control unit 16. The control unit 16 determines that the time difference ΔT has not been changed if no reset time difference data has been input from the input unit 11 (step S108, No) and updates the frame number m of the second image group PG2 (step S109). In this case, the display controller 16a updates (for example, adds +1) the frame number m (m=n+α) of the second image group PG2 in accordance with the frame number n to read the image $Q_m$ to be displayed in the display area 102 in synchronization with the image $P_n$ at next step S106 from the storage unit 15.

If, on the other hand, such reset time difference data has been input from the input unit 11, the control unit 16 determines that the time difference ΔT has been changed based on the input time difference data (step S108, Yes) and updates the time difference data in the storage unit 15 to one corresponding to the time difference ΔT after being changed. Then, the control unit 16 calculates the frame number m of the second image group PG2 based on the time difference data after being changed (step S110). In this case, based on the time difference data after being changed (after resetting), the display controller 16a calculates the frame number m (m=n+β) of the image $Q_m$ having the time difference ΔT after being changed with respect to the image $P_n$ to be synchronously displayed in the display area 101 at next step S106. The frame number difference β is a frame number difference between the images $P_n$ and $Q_m$ having the time difference ΔT after being changed.

Then, the control unit 16 determines whether or not any temporary stop instruction to the control to display the images $P_n$ and $Q_m$ in the respective display areas 101 and 102 has been issued (step S111). More specifically, if display instruction information corresponding to one of the frame advance icon 112, the top search icon 113, the previous frame icon 115, and the review search icon 116 is input from the input unit 11 at step S105, the control unit 16 determines that a temporary stop instruction has been issued (step S111, Yes). In this case, the control unit 16 returns to step S105 to repeat the processing procedure of step S105 and onward.

If, on the other hand, display instruction information corresponding to one of the play icon 111 and the reverse play icon 114 is input from the input unit 11 at step S105, the control unit 16 determines that no temporary stop instruction has been issued (step S111, No). In this case, the control unit 16 determines whether or not synchronous display processing of the images $P_n$ and $Q_m$ in the synchronous display mode has terminated (step S112).

More specifically, if the frame number n updated at step S107 is equal to or greater than the number of frames in the first image group PG1, or the frame number m updated at step S109 or that calculated at step S110 is equal to or greater than the number of frames in the second image group PG2, the control unit 16 determines that synchronous display processing of the images $P_n$ and $Q_m$ in the synchronous display mode has terminated (step S112, Yes) and completes the synchronous display processing in the synchronous display mode.

If, on the other hand, the frame number n updated at step S107 is less than the number of frames in the first image group PG1, and the frame number m updated at step S109 or that calculated at step S110 is less than the number of frames in the second image group PG2, the control unit 16 determines that the synchronous display processing of the images $P_n$ and $Q_m$ in the synchronous display mode has not terminated (step S112, No) and returns to step S106. Then, the control unit 16 repeats the processing procedure of step S106 and onward.

Figure 6:
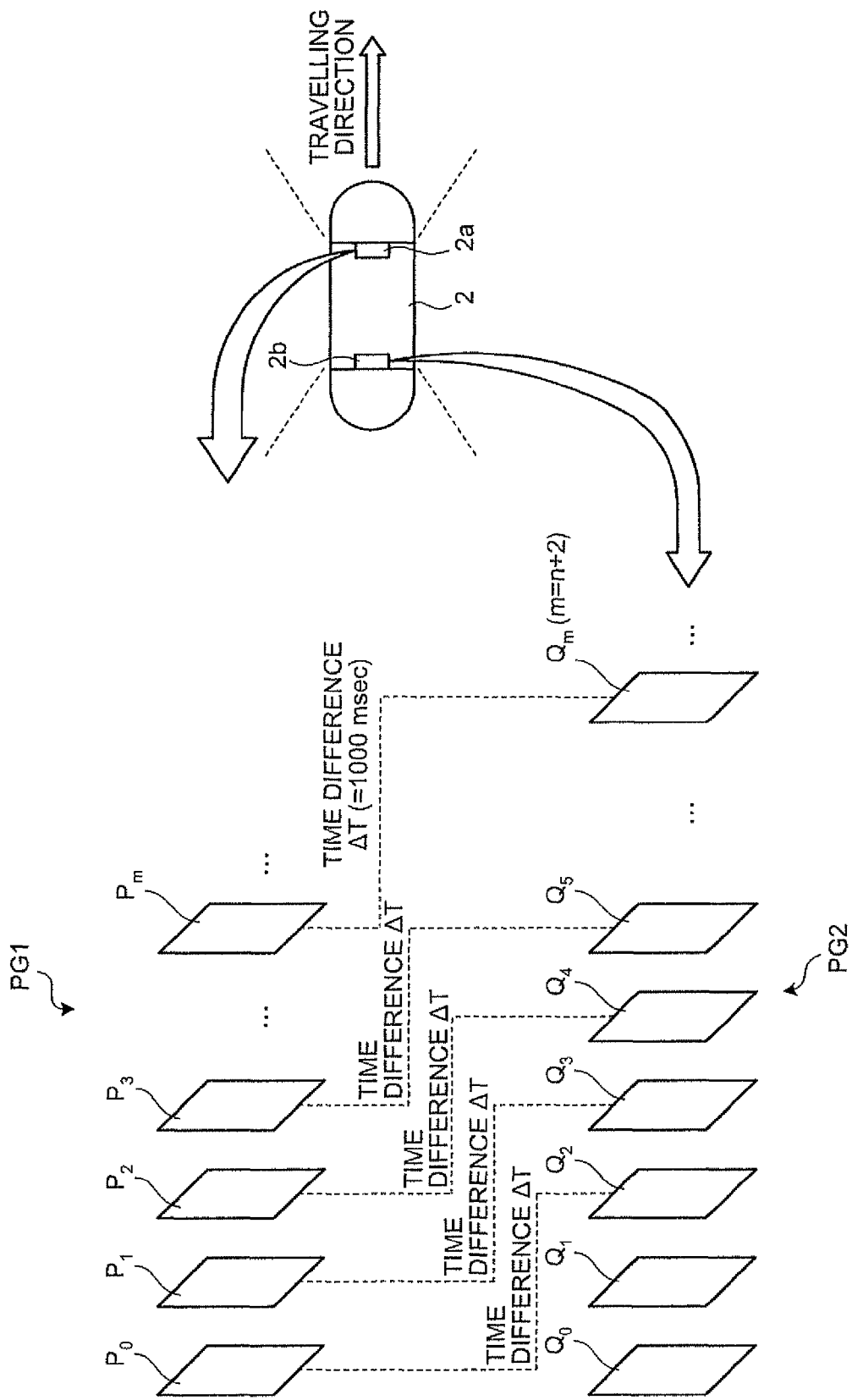
FIG. 6 is a schematic diagram illustrating a specific example of operation of the control unit that makes images having a set time difference synchronously displayed in respective display areas sequentially.

Next, a case in which the first image group PG1 and the second image group PG2 inside the subject 1 are picked up at intervals of 0.5 sec per image by a group of imaging devices of the multiple-lens capsule endoscope 2 is exemplified to specifically describe the operation of the control unit 16 controlling the sequential, synchronous display of the images $P_n$ and $Q_m$ in the respective display areas 101 and 102 in the synchronous display mode. FIG. 6 is a schematic diagram illustrating a specific example of operation of the control unit 16 that makes the images $P_n$ and $Q_m$ having the set time difference ΔT sequentially, synchronously displayed in the respective display areas 101 and 102.

In FIG. 6, the first image group PG1 is an image group picked up at intervals of, for example, 0.5 seq by an imaging device 2a having the imaging field of view in the forward direction (the traveling direction of the capsule endoscope 2) among the group of imaging devices of the multiple-lens capsule endoscope 2. The second image group PG2 is an image group picked up at intervals of, for example, 0.5 sec by an imaging device 2b having the imaging field of view in the reverse direction (the direction opposite to the traveling direction of the capsule endoscope 2) among the group of imaging devices. The control unit 16 saves image groups from multiple directions taken in via the portable recording medium 5 in the examination folder 15a of the storage unit 15. In this case, the image processor 16b forms the first image group PG1 and the second image group PG2 by classifying such image groups by imaging device of the capsule endoscope 2 and then saves the first image group PG1 and the second image group PG2 in the examination folder 15a.

Here, if the time difference ΔT is set by the data setting area 131 or the time sliders 132 and 133, and the synchronous display mode is set by the synchronization icon 130, as described above, the control unit 16 makes the images $P_n$ and $Q_m$ having the time difference ΔT synchronously displayed in the respective display areas 101 and 102. More specifically, if the time difference ΔT is set, for example, to 1000 msec, the display controller 16a makes a first image $P_0$ (frame number n=0) in the first image group PG1 picked up at intervals of 0.5 sec and an image $Q_2$ having the time difference ΔT of 1000 msec with respect to the image $P_0$ from the second image group PG2 picked up at intervals of 0.5 sec synchronously displayed respectively in the display areas 101 and 102. Then, the display controller 16a makes the display areas 101 and 102 respectively and synchronously display an image $P_1$ of the frame number n=1 and an image $Q_3$ having the time difference ΔT of 1000 msec with respect to the image $P_1$, an image $P_2$ of the frame number n=2 and an image $Q_4$ having the time difference ΔT of 1000 msec with respect to the image $P_2$, and an image $P_3$ of the frame number n=3 and an image $Q_5$ having the time difference ΔT of 1000 msec with respect to the image $P_3$.

In this manner, the display controller 16a makes an image $P_n$ of the frame number n and an image $Q_m$ (m=n+α) having the time difference ΔT of 1000 msec with respect to the image $P_n$ sequentially and synchronously displayed in the respective display areas 101 and 102. If the first image group PG1 and the second image group PG2 are each picked up at intervals of 0.5 sec per image, the frame number difference α of the images $P_n$ and $Q_m$ having the time difference ΔT of 1000 msec is 2.

If the time difference ΔT is changed (reset) by the data setting area 131 or the time sliders 132 and 133, the display controller 16a each time switches the time difference ΔT between the images $P_n$ and $Q_m$ displayed respectively in the display areas 101 and 102 to the time difference ΔT after being changed. In this case, the display controller 16a makes the images $P_n$ and $Q_m$ (m=n+β) having the frame number difference β (β: integer) corresponding to the time difference ΔT after being changed sequentially and synchronously displayed in the respective display areas 101 and 102.

Figure 7:
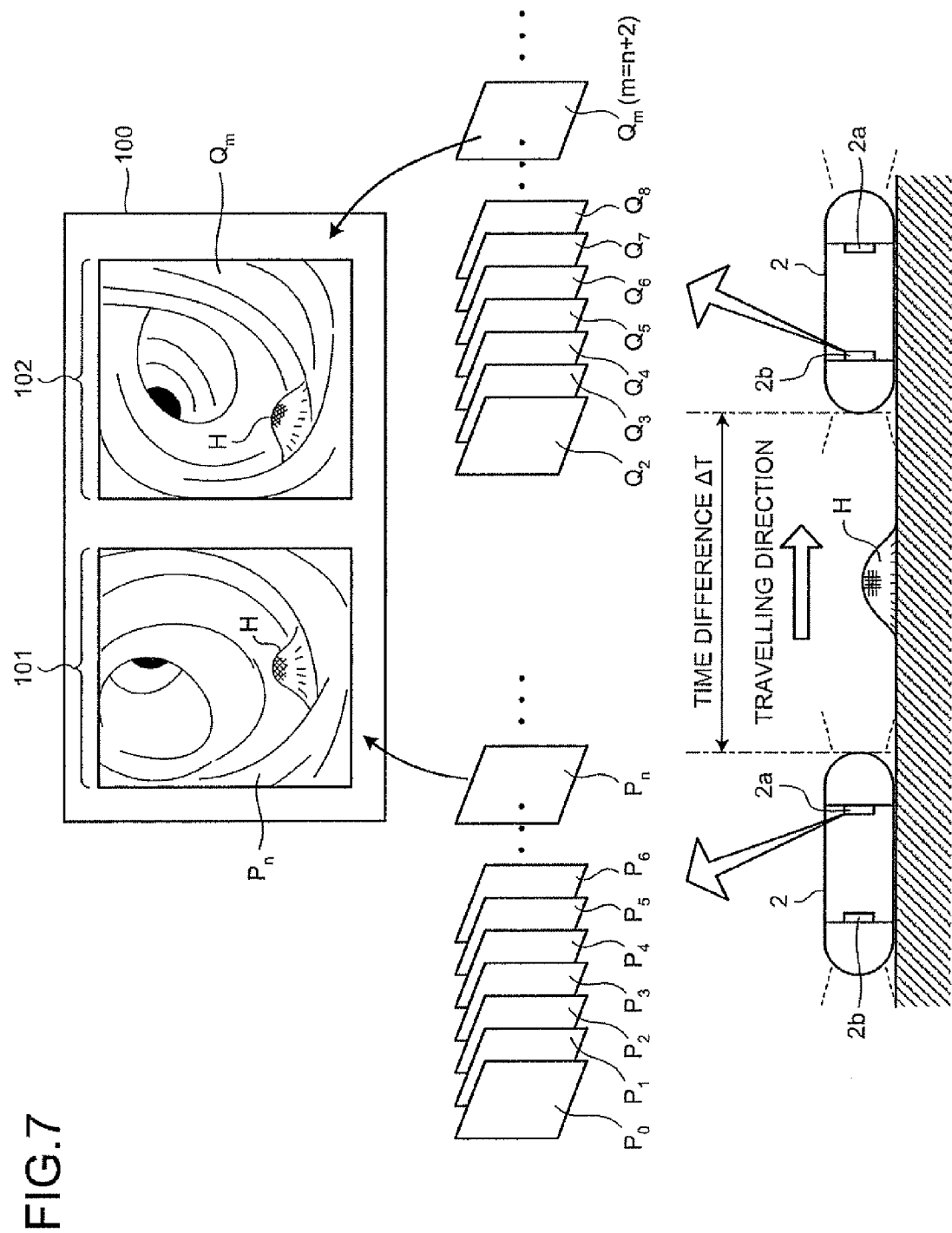
FIG. 7 is a schematic diagram illustrating a relationship between images synchronously displayed in respective display areas in a synchronous display mode.

Next, the images $P_n$ and $Q_m$ synchronously displayed in the respective display areas 101 and 102 in the synchronous display mode will be described. FIG. 7 is a schematic diagram illustrating a relationship between the images $P_n$ and $Q_m$ synchronously displayed respectively in the display areas 101 and 102 in the synchronous display mode. As shown in FIG. 7, the images $P_n$ and $Q_m$ (for example, m=n+2) having the set time difference ΔT are synchronously displayed in the respective display areas 101 and 102 in the main image display area 100 based on control of the display controller 16a in the synchronous display mode.

When the images $P_n$ and $Q_m$ are synchronously displayed in the respective display areas 101 and 102, an object common to the image $P_n$ appears in the image $Q_m$. More specifically, the imaging device 2a picks up the image $P_n$ containing, for example, the lesion site H as an object positioned in the forward direction (that is, the traveling direction of the capsule endoscope 2 in the digestive tract of the subject 1) of the capsule endoscope 2. The imaging device 2b, on the other hand, picks up the image $Q_m$ containing as an object the lesion site H positioned in the reverse direction of the capsule endoscope 2 after the capsule endoscope 2 passes the position of the lesion site H.

Here, the elapsed time between the time when the image of the lesion site H is picked up by the imaging device 2a from one imaging direction and the time when the image of the lesion site H is picked up by the imaging device 2b from another imaging direction is approximately equal to the time difference ΔT of the images $P_n$ and $Q_m$ synchronously displayed in the respective display areas 101 and 102. That is, by setting the time difference ΔT approximately equal to such an elapsed time by using the data setting area 131 or the time sliders 132 and 133, the images $P_n$ and $Q_m$ having the time difference ΔT become images obtained by picking up the image of a common object (for example, the lesion site H) from different imaging directions.

The elapsed time is a time interval elapsed between the time when the imaging device 2a picks up the lesion site H positioned in a front direction from the capsule endoscope 2 and, after the capsule endoscope 2 passes the position of the lesion site H, the time when the imaging device 2b picks up the lesion site H positioned in a rear direction from the capsule endoscope 2.

Thus, by synchronously displaying the images $P_n$ and $Q_m$ in which a common object appears respectively in the display areas 101 and 102 sequentially, a user such as a physician or a nurse can not only observe images inside the subject 1 easily, but also observe, for example, characteristic sites such as the lesion site H and inner walls (for example, a puckered site) of the digestive tract, which are difficult to observe from only one direction, easily from a plurality of directions.

Figure 8:
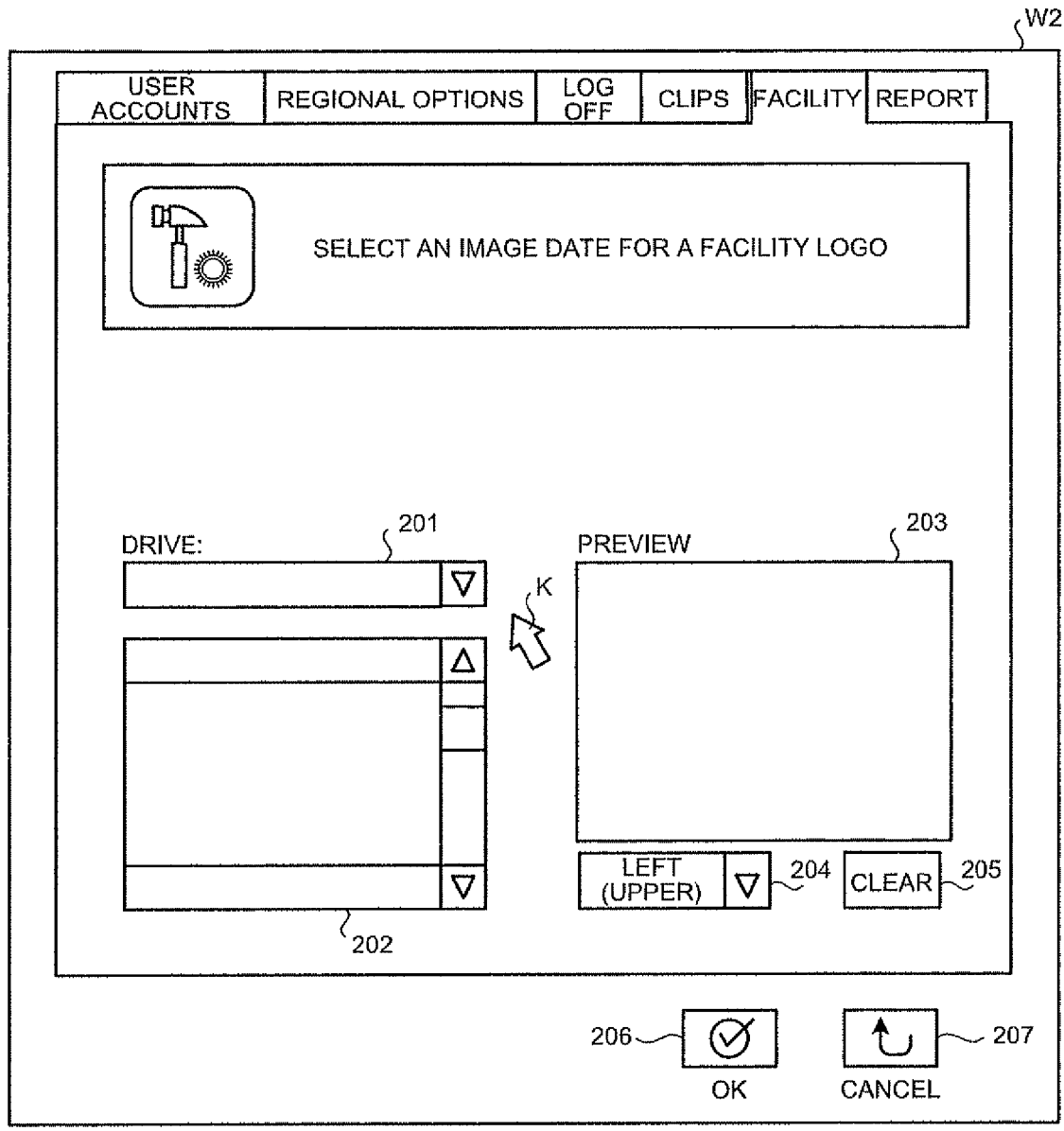
FIG. 8 is a schematic diagram showing a specific example of a window displaying setting GUIs for attaching a facility logo to a desired position in a report.

Next, the report maker 16c held by the control unit 16 will be described. As described above, the report maker 16c creates a report describing, for example, diagnosis results concerning the subject 1 using various kinds of information input by the input unit 11, images of the subject 1 and the like. In this case, the report maker 16c can insert a facility logo of the facility where the subject 1 is examined in a desired position of the report. FIG. 8 is a schematic diagram showing a specific example of a window displaying setting GUIs for attaching a facility logo to a desired position in a report.

As shown in FIG. 8, a window W2 has a drive setting unit 201 for setting a desired drive from drives of the input/output I/F 14 or the storage unit 15, a file display area 202 for listing files in the drive set by the drive setting unit 201, and a logo display area 203 for displaying a facility logo saved in a file selected from the file display area 202 formed therein. The window W2 also has a logo position setting unit 204 for setting the position of the facility logo to be inserted into a report, a Clear icon 205 for clearing the facility logo displayed in the logo display area 203, an OK icon 206 for deciding insertion of the facility logo into a report, and a Cancel icon 207 for canceling an insertion setting of the facility logo formed therein.

According to an operation of the input unit 11, the drive setting unit 201 displays a drop-down list of each drive of the input/output I/F 14 and the storage unit 15, from which a desired drive is set. The file display area 202 lists files in the drive set by the drive setting unit 201. A desired file from files listed in the file display area 202 is selected by a click operation of the input unit 11. The logo display area 203 displays an image of the facility logo saved in the file selected from the file display area 202.

According to an operation of the input unit 11, the logo position setting unit 204 displays a drop-down list of positions of the facility logo to be inserted into a report, from which a desired position is set. Such a drop-down list of the logo position setting unit 204 includes, for example, an upper left position, an upper right position, an upper center position, a lower left position, a lower right position, and a lower center position. The report maker 16c selects a desired position selected from among the drop-down list by a click operation of the input unit 11 as an insertion position of the facility logo in the report.

When instruction information corresponding to the OK icon 206 is input by the input unit 11, the report maker 16c inserts the facility logo displayed in the logo display area 203, that is, the facility logo in the file selected from the file display area 202 in a position in the report set by the logo position setting unit 204. In this manner, the report maker 16c can insert a facility logo of the facility where the subject 1 is examined into a report about the subject 1. If the insertion position of the facility logo is changed by the logo position setting unit 204, the report maker 16c changes the insertion position of the facility logo in the report in accordance with such a setting change.

Figure 9:
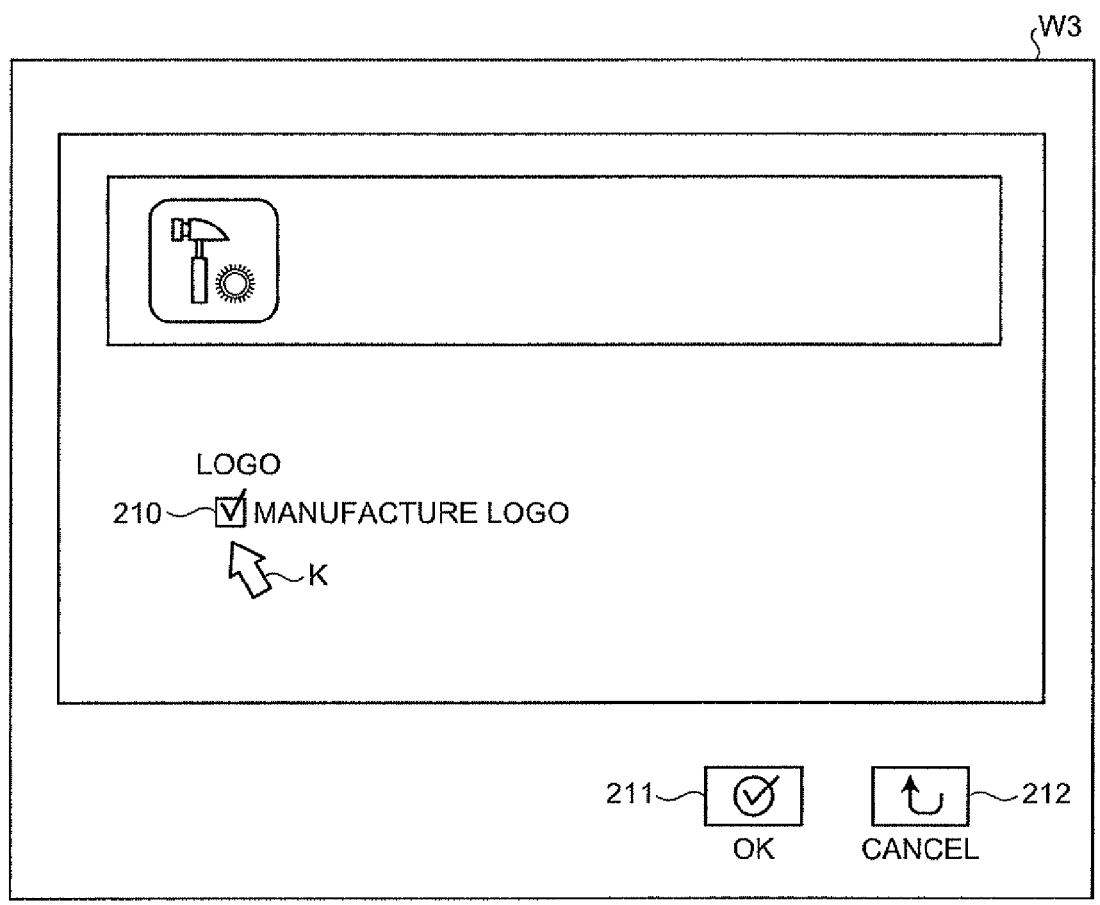
FIG. 9 is a schematic diagram showing a specific example of a window displaying setting GUIs for changing an insertion setting of a maker logo into a report.

Next, the insertion setting of a maker logo to a report of the subject 1 will be described. The report maker 16c places a maker logo at a predetermined position in a report of the subject 1 in a default setting, but by changing the insertion setting of the maker logo, a report can be created without the maker logo being placed. FIG. 9 is a schematic diagram showing a specific example of the window displaying setting GUIs for changing an insertion setting of a maker logo into a report.

As shown in FIG. 9, a window W3 has a check box 210 for setting whether or not to insert a maker logo (i.e., manufacture logo) in a predetermined position in a report, an OK icon 211, and a Cancel icon 212 formed therein. If insertion of a maker logo in a report is desired, the user operates the input unit 11 to set the check box 210 to a checked state (a state in which a check mark is displayed) and clicks the OK icon 211. In this case, setting information for setting insertion of a maker logo into a report is input by the input unit 11 and based on such setting information, the report maker 16c inserts a maker logo in a predetermined position (for example, at a footer) in a report.

If, on the other hand, insertion of a maker logo in a report is not desired, the user operates the input unit 11 to set the check box 210 to an unchecked state (a state in which no check mark is displayed) and clicks the OK icon 211. In this case, setting information for setting no insertion of a maker logo into a report is input by the input unit 11 and based on such setting information, the report maker 16c creates a report without inserting a maker logo. Switching of such a setting of presence/absence of a maker logo may be allowed only when logged in with service authorization.

Figure 10:
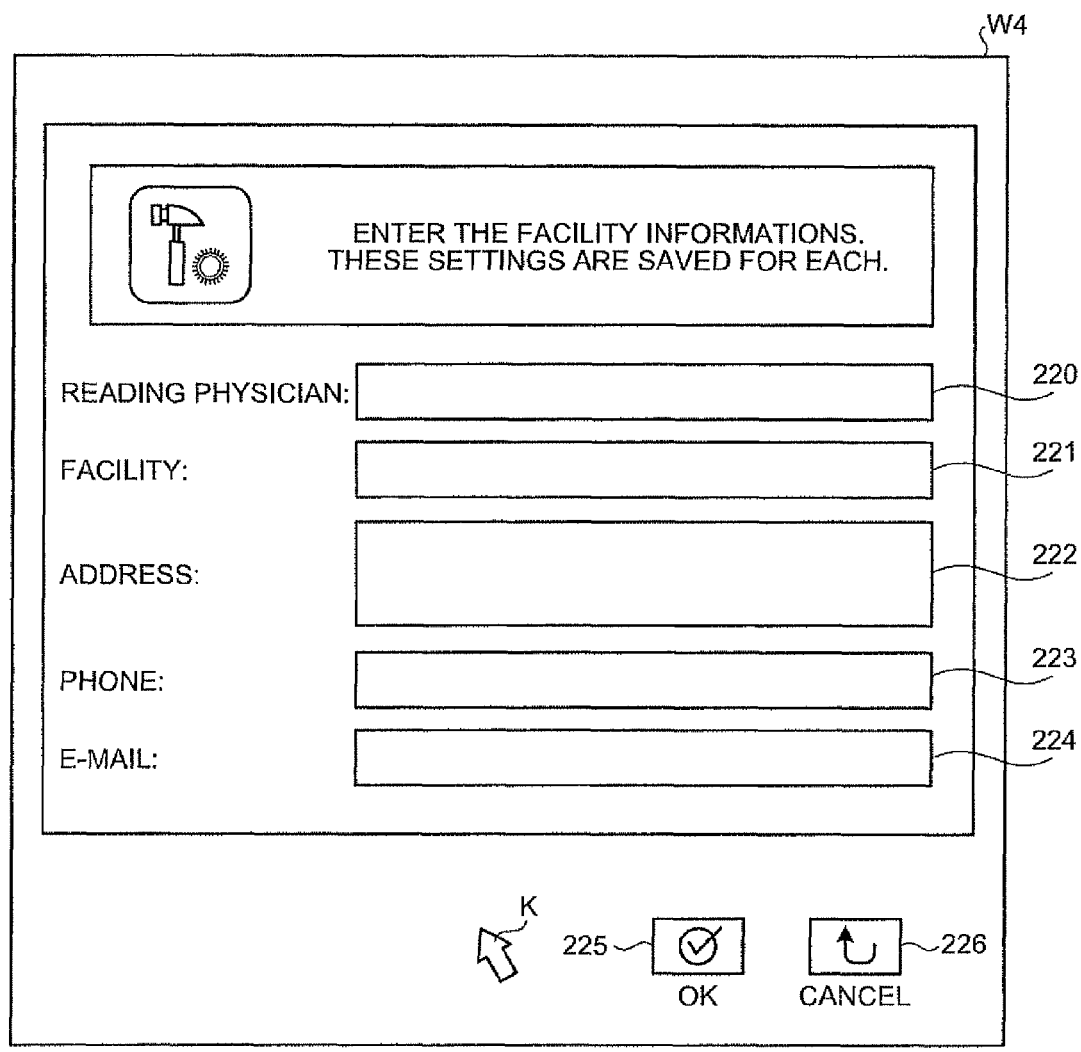
FIG. 10 is a schematic diagram showing a specific example of a window displaying setting GUIs for setting predetermined data to be written in a report.

Next, creation of a report about the subject 1 will be described. FIG. 10 is a schematic diagram showing a specific example of a window displaying setting GUIs for setting predetermined data to be written in a report. As shown in FIG. 10, a window W4 has a physician name text box 220 for setting the physician name to be described in the report, a facility name text box 221 for setting the facility name to be described in the report, an address text box 222 for setting the address to be described in the report, a phone number text box 223 for setting the phone number to be described in the report, a mail address text box 224 for setting the E-mail address to be described in the report, an OK icon 225, and a Cancel icon 226 formed therein.

The name of, for example, a physician who diagnoses the subject 1 is entered in the physician name text box 220 by operating the input unit 11. The name of, for example, a facility such as a hospital where the subject 1 is diagnosed is entered in the facility name text box 221 by operating the input unit 11. The address of, for example, a facility where the subject 1 is diagnosed is entered in the address text box 222 by operating the input unit 11. The phone number of, for example, a facility where the subject 1 is diagnosed is entered in the phone number text box 223 by operating the input unit 11. The E-mail address of, for example, a physician who diagnoses the subject 1 or a facility where the subject 1 is diagnosed is entered in the mail address text box 224 by operating the input unit 11.

If a click operation of the OK icon 225 is performed, the input unit 11 inputs text data such as characters and numbers entered in each of the physician name text box 220, the facility name text box 221, the address text box 222, the phone number text box 223, and the mail address text box 224 to the control unit 16. In this case, based on the text data input by the input unit 11, the report maker 16c grasps the physician name, facility name, address, phone number, and E-mail address to be described in the report. In this manner, the physician name, facility name, address, phone number, and E-mail address to be described in the report are set. When creating a report about the subject 1, the report maker 16c automatically inserts the he physician name, facility name, address, phone number, and E-mail address set as described above in predetermined positions in the report.

Figure 11:
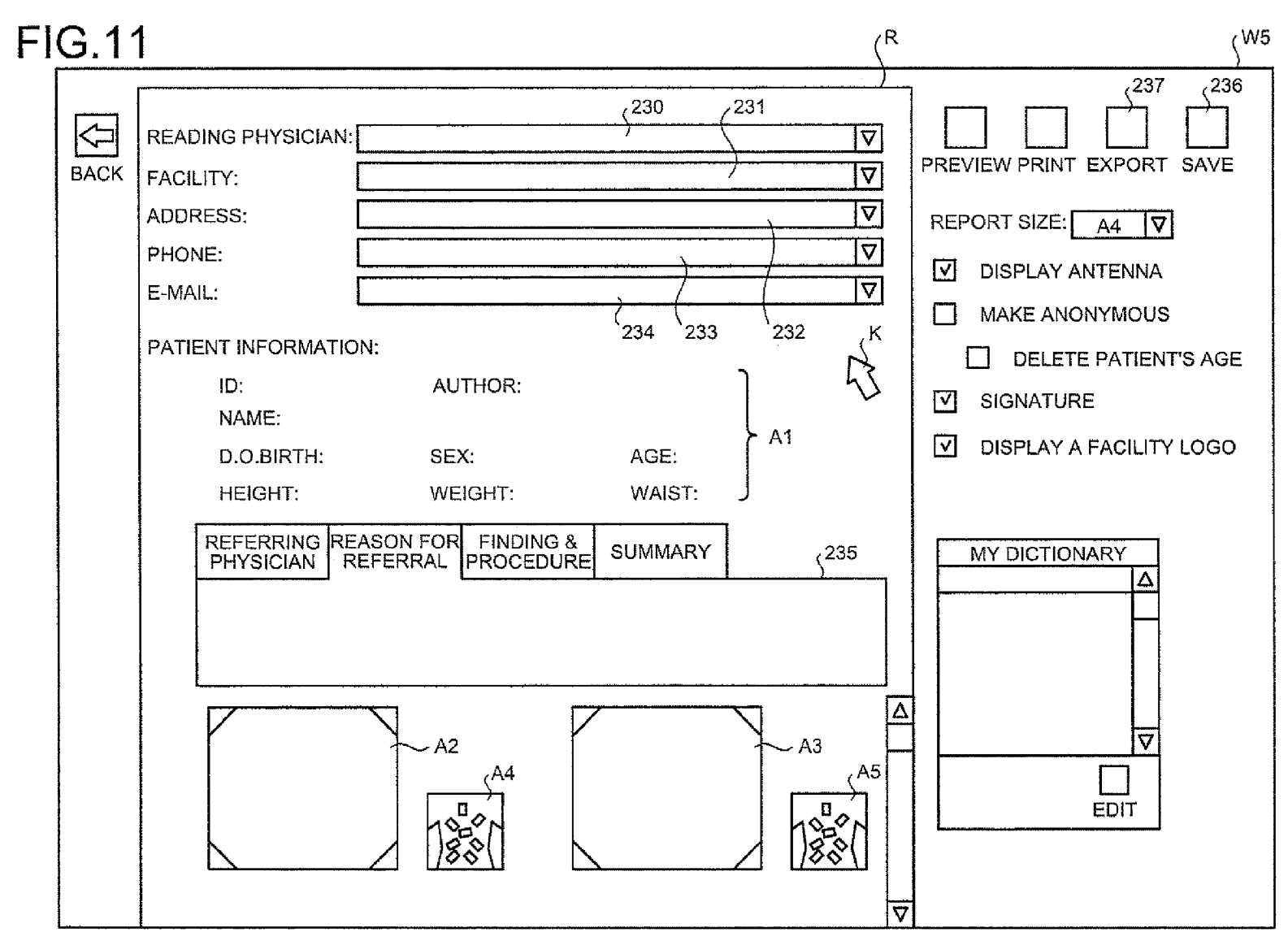

FIG. 11 is a schematic diagram showing a specific example of a window displaying GUIs for creating a report of the subject 1. As shown in FIG. 11, a window W5 has a format R of a report of the subject 1 to be created formed therein and has a physician name setting unit 230 for setting the physician name to be described at a predetermined position in the format R of the report, a facility name setting unit 231 for setting the facility name to be described at a predetermined position in the report, an address setting unit 232 for setting the address to be described at a predetermined position in the report, a phone number setting unit 233 for setting the phone number to be described at a predetermined position in the report, and a mail address setting unit 234 for setting the E-mail address to be described at a predetermined position in the report formed in the format R of the report. The window W5 also has a diagnostic information text box 235 for entry of diagnostic information such as findings and summary of diagnosis results of the subject 1 formed in the format R of the report and also a Save icon 236 and an Export icon 237 are formed near the format R of the report.

The report maker 16c inserts patient information A1 of the subject 1 saved in the examination folder 15a of the storage unit 15, images A2 and A3 inside the subject 1, and antenna arrangement plans A4 and A5 for estimating sites of the images A2 and A3 respectively into the format R of the report.

The physician name entered in the physician name text box 220 when a new report is created is automatically inserted into the physician name setting unit 230. According to an operation of the input unit 11, the physician name setting unit 230 displays a drop-down list of physician names and a desired physician name is set from among the drop-down list of physician names. In this case, the physician name setting unit 230 displays a drop-down list including the physician name entered first in the physician name text box 220 and reentered physician names. The report maker 16c can insert a desired physician name selected from among the drop-down list of physician names into a report.

The facility name entered in the facility name text box 221 when a new report is created is automatically inserted into the facility name setting unit 231. According to an operation of the input unit 11, the facility name setting unit 231 displays a drop-down list of facility names and a desired facility name is set from among the drop-down list of facility names. In this case, the facility name setting unit 231 displays a drop-down list including the facility name entered first in the facility name text box 221 and reentered facility names. The report maker 16c can insert a desired facility name selected from among the drop-down list of facility names into a report.

The address entered in the address text box 222 when a new report is created is automatically inserted into the address setting unit 232. According to an operation of the input unit 11, the address setting unit 232 displays a drop-down list of addresses and a desired address is set from among the drop-down list of addresses. In this case, the address setting unit 232 displays a drop-down list including the address entered first in the address text box 222 and reentered addresses. The report maker 16c can insert a desired address selected from among the drop-down list of addresses into a report.

The phone number entered in the phone number text box 223 when a new report is created is automatically inserted into the phone number setting unit 233. According to an operation of the input unit 11, the phone number setting unit 233 displays a drop-down list of phone numbers and a desired phone number is set from among the drop-down list of phone numbers. In this case, the phone number setting unit 233 displays a drop-down list including the phone number entered first in the phone number text box 223 and reentered phone numbers. The report maker 16c can insert a desired phone number selected from among the drop-down list of phone numbers into a report.

The E-mail address entered in the mail address text box 224 when a new report is created is automatically inserted into the mail address setting unit 234. According to an operation of the input unit 11, the mail address setting unit 234 displays a drop-down list of E-mail addresses and a desired E-mail address is set from among the drop-down list of E-mail addresses. In this case, the mail address setting unit 234 displays a drop-down list including the E-mail address entered first in the mail address text box 224 and reentered E-mail addresses. The report maker 16c can insert a desired E-mail address selected from among the drop-down list of E-mail addresses into a report.

The report maker 16c creates a report in which the physician name, facility name, address, phone number, and E-mail address set as described above, the patient information A1 of the subject 1, diagnostic information of the subject 1 entered in the diagnostic information text box 235, the images A2 and A3 inside the subject 1, and the antenna arrangement plans A4 and A5 are inserted in predetermined positions.

If a click operation of the Save icon 236 is performed using the input unit 11, a report file (report data) of the subject 1 created by the report maker 16c is saved in the management folder 15b of the storage unit 15 based on control of the control unit 16. If a click operation of the Export icon 237 is performed using the input unit 11, the report file (report data) of the subject 1 is output (recorded) to (in) a portable recording medium (such as FD, CD, and DVD) inserted in a drive of the input/output I/F 14 based on control of the control unit 16.

Next, the image file maker 16d of the control unit 16 will be described. As described above, the image file maker 16d creates an image file of desired static images or dynamic images based on image groups (for example, the first image group PG1 and the second image group PG2) contained in examination files saved in the examination folder 15a.

More specifically, the image file maker 16d extracts, based on instruction information input by the input unit 11, for example, one or more desired images from the first image group PG1 or the second image group PG2 and create a static image file or a dynamic image file based on the extracted one or more desired images. In this case, the control unit 16 saves the static image file or dynamic image file created by the image file maker 16d in the management folder 15b of the storage unit 15.

A static image file created by the image file maker 16d is an image file that can be output in a general-purpose static image data format such as GIF, JPEG, and TIF. A dynamic image file created by the image file maker 16d is an image file that can be output in a general-purpose dynamic image data format such as WMV and MPEG.

Figure 12:
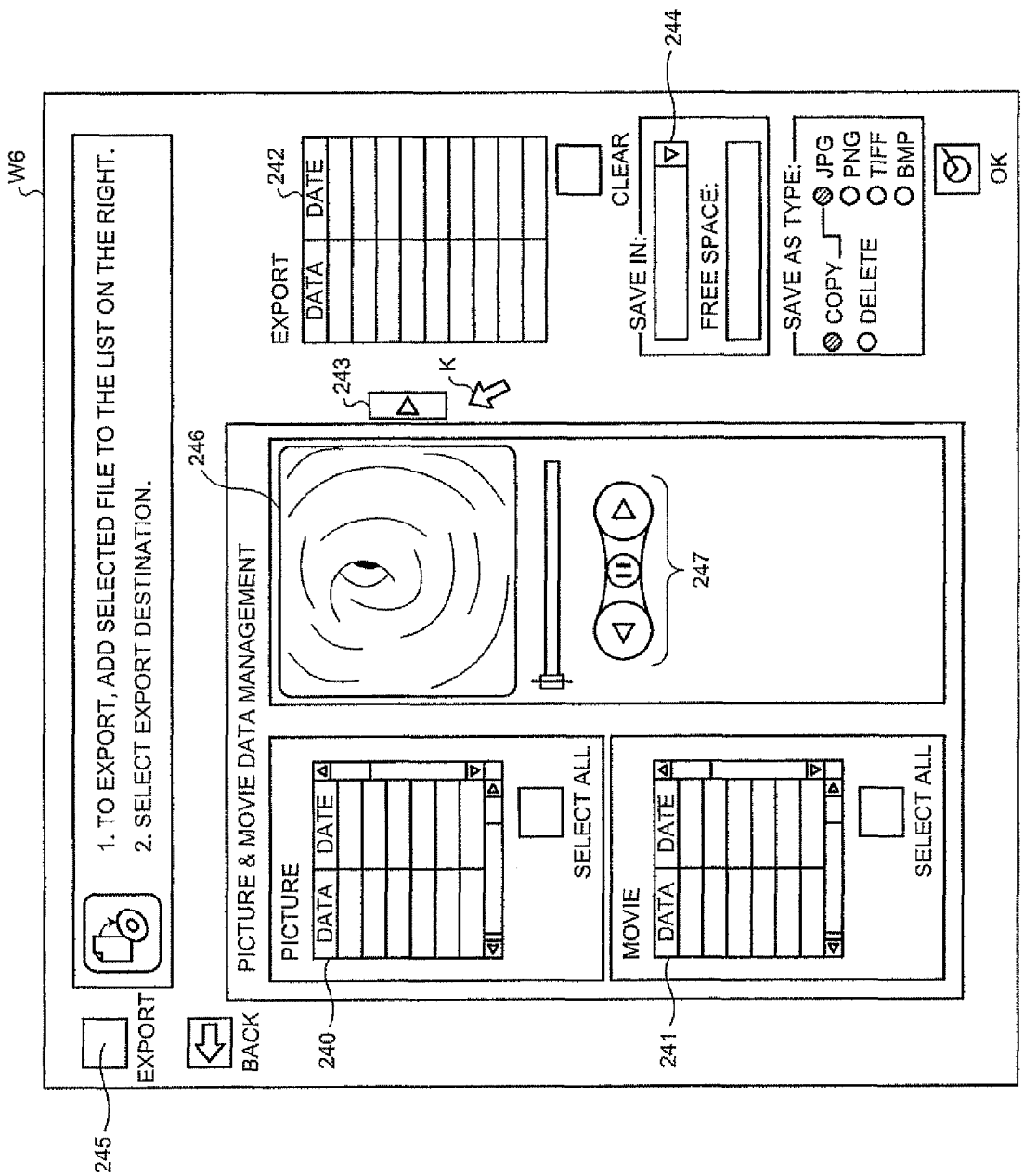
FIG. 12 is a schematic diagram showing a specific example of a window displaying GUIs for outputting a static image file or a dynamic image file to a desired drive.

FIG. 12 is a schematic diagram showing a specific example of a window displaying GUIs for outputting a static image file or a dynamic image file of the subject 1 created by the image file maker 16d to a desired drive. As shown in FIG. 12, a window W6 has a static image file display area 240 for listing static image files, a dynamic image file display area 241 for listing dynamic image files, an output file display area 242 for displaying static image files and dynamic image files to be output, and an Add icon 243 for adding a static image file or a dynamic image file to be output to the output file display area 242 formed therein. The window W6 also has a drive setting unit 244 for setting a drive as an output destination of static image files and dynamic image files to be output and an Export icon 245 for executing output of image files to the drive set by the drive setting unit 244. Further, the window W6 has an image display area 246 for displaying a static image file selected from the static image file display area 240 or a dynamic image file selected from the dynamic image file display area 241 and a display operation icon group 247 for performing a display operation of a static image or dynamic image displayed in the image display area 246.

The static image file display area 240 lists static image files created by the image file maker 16d. A desired static image file among static image files listed in the static image file display area 240 is selected by a click operation of the input unit 11. Then, if the Add icon 243 is clicked by the input unit 11, the desired static image file is added to the output file display area 242. The output file display area 242 displays such an added desired static image file as a file to be output.

The dynamic image file display area 241 lists dynamic image files created by the image file maker 16d. A desired dynamic image file among dynamic image files listed in the dynamic image file display area 241 is selected by a click operation of the input unit 11. Then, if the Add icon 243 is clicked by the input unit 11, the desired dynamic image file is added to the output file display area 242. The output file display area 242 displays such an added desired dynamic image file as a file to be output.

According to an operation of the input unit 11, the drive setting unit 244 displays a drop-down list of drives of the input/output I/F 14 and the storage unit 15 and a desired drive, that is, a drive as an output destination of static image files and dynamic image files to be output and displayed in the output file display area 242 is set from among the drop-down list. In this case, the drive setting unit 244 sets a recording medium for saving static image files and dynamic image files to be output and displayed in the output file display area 242 by setting the drive as an output destination. A recording medium for saving static image files and dynamic image files to be output can be a hard disk constituting the storage unit 15 and a portable recording medium (for example, FD, CD, and DVD) inserted in the input/output I/F 14.

If the Export icon 245 is clicked by the input unit 11, such static image files and dynamic image files to be output are output to the drive set by the drive setting unit 244 and recorded in the recording medium of the drive.

Based on a display operation using the display operation icon group 247, the image display area 246 plays or reversely plays a static image file selected from among the static image file display area 240 or a dynamic image file selected from among the dynamic image file display area 241.

Figure 13:
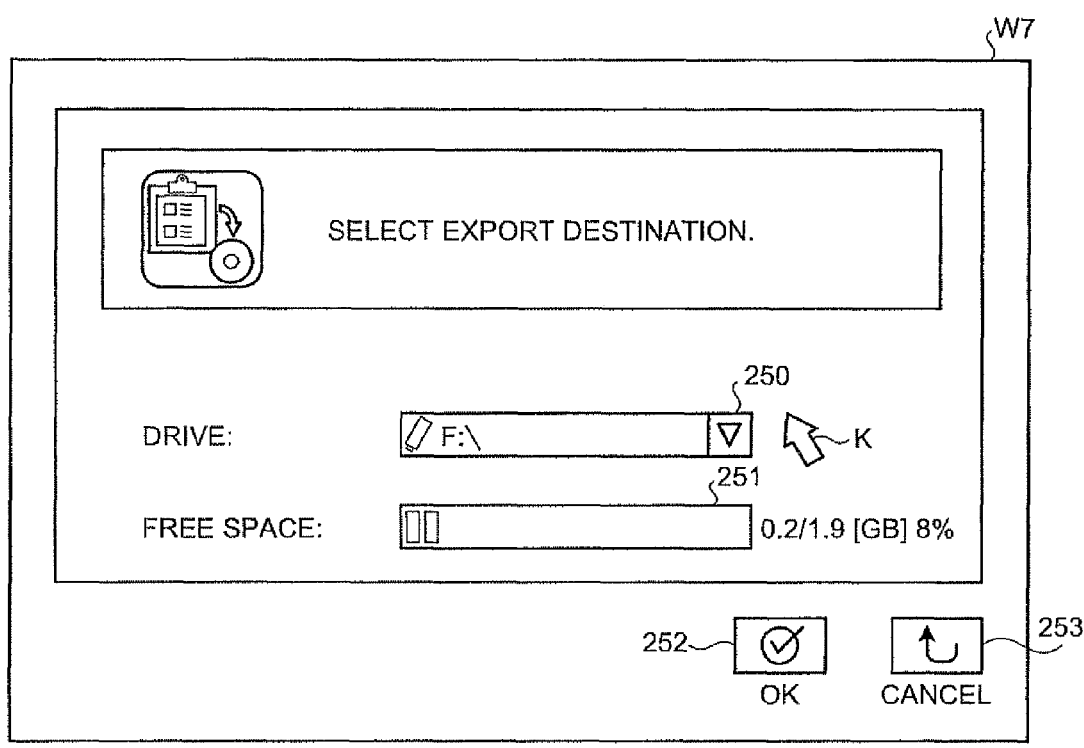
FIG. 13 is a schematic diagram showing a specific example of a window displaying GUIs for outputting a report file to a desired drive.

Approximately in the same manner as such a static image file or dynamic image file, a report file created by the report maker 16c is output to a set desired drive and recorded in the recording medium of the drive. FIG. 13 is a schematic diagram showing a specific example of the window displaying GUIs for outputting a report file of the subject 1 created by the report maker 16c to the desired drive As shown in FIG. 13, a window W7 has a drive setting unit 250 for setting a drive as an output destination of a report file to be output, a capacity display area 251 for showing a free capacity of the drive set by the drive setting unit 250, an OK icon 252, and a Cancel icon 253 formed therein. The window W7 is displayed when the Export icon 237 formed in the window W5 for report creation exemplified in FIG. 11 is clicked by the input unit 11.

According to an operation of the input unit 11, the drive setting unit 250 displays a drop-down list of drives of the input/output I/F 14 and the storage unit 15 and a desired drive, that is, a drive as an output destination of a report created by the report maker 16c is set from among the drop-down list. In this case, the drive setting unit 250 sets a recording medium (for example, a hard disk constituting the storage unit 15 and FD, CD, or DVD inserted in the input/output I/F 14) for saving a report file created by the report maker 16c by setting the drive as an output destination.

If the OK icon 252 is clicked by the input unit 11, such a report file to be output is output to the drive set by the drive setting unit 250 and recorded in the recording medium of the drive.

Next, user authorization settings of the image display apparatus 4 will be described. Depending on the method of examination of the subject 1 performed by a user (such as a physician and a nurse), the type of software processing licensed by user authorization set by default for the image display apparatus 4 may not match actual operation. In such a case, the type of software processing licensed by user authorization of the image display apparatus 4 may be made changeable.

Figure 14:
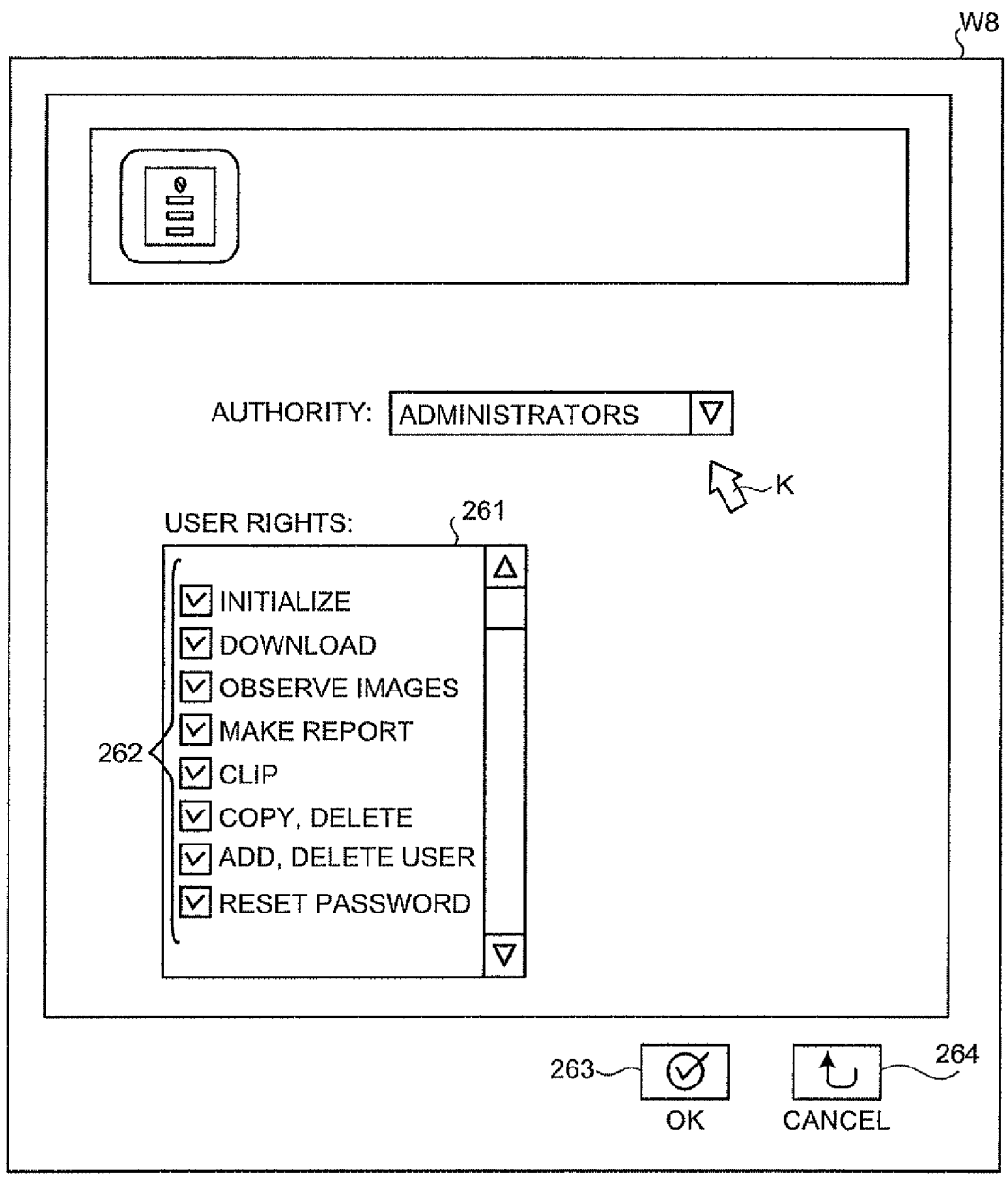
FIG. 14 is a schematic diagram showing a specific example of a window displaying setting GUIs for changing user authorization settings of an image display apparatus according to the present invention.

FIG. 14 is a schematic diagram showing a specific example of the window displaying setting GUIs for changing user authorization settings of the image display apparatus 4. As shown in FIG. 14, a window W8 has a user authorization display area 261 for listing software processing depending on user authorization of the image display apparatus 4, a check box group 262 for setting licensing or cancellation of licensing of software listed in the user authorization display area 261, an OK icon 263, and a Cancel icon 264 formed therein.

The user authorization display area 261 displays a list of software processing whose user authorization setting can be changed by changing the list in accordance with the type of user (for example, an administrator or a general user) who logs in to software in the image display apparatus 4. In this case, a check box of the check box group 262 is formed for each piece of software processing listed in the user authorization display area 261.

More specifically, a user (for example, an administrator) who logs in to software in the image display apparatus 4 operates the input unit 11, sets check boxes corresponding to software processing to be licensed to general users (for example, physicians or nurses) from among software processing listed in the user authorization display area 261 to a checked state (a state in which a check mark is displayed) and those corresponding to software processing whose licensing should be canceled to an unchecked state (a state in which no check mark is displayed), and then clicks the OK icon 263.

By setting each check box in the check box group 262 to a checked state or an unchecked state in this manner when needed, user authorization for general users can be reset so that types of software processing licensed by such user authorization can be adapted to those matching the operation of general users.

In the first embodiment of the present invention, as described above, the time difference $\Delta T$ between imaging times of first and second images contained in first and second image groups respectively of a plurality of image groups inside a subject picked up by a group of imaging devices mounted on a multiple-lens capsule endoscope is set through GUIs, and the first and second images having the time difference $\Delta T$ are synchronously displayed in respective display areas of a display unit sequentially so that the first image and the second image, in which an object common to the first images appears, are synchronously displayed in respective display areas sequentially. Thus, images obtained by picking up the same object common to the first and second images from a plurality of imaging directions can synchronously be displayed in respective display areas of the display unit sequentially. As a result, an image display apparatus capable of sequentially displaying each image contained in each of image groups picked up from multiple directions inside the subject by the group of imaging devices mounted on the multiple-lens capsule endoscope in a mode in which observations can be made easily can be realized.

By synchronously displaying image groups inside a subject from multiple directions using an image display apparatus according to the first embodiment of the present invention, a user such as a physician or a nurse can easily observe images inside the subject and can also observe characteristic sites such as a lesion site and inner walls (for example, a puckered site) of the digestive tract or the like, which are difficult to observe from only one direction, easily from a plurality of directions.

Next, the second embodiment of the present invention will be described. In an image display apparatus according to the first embodiment described above, the time difference $\Delta T$ between the images $P_n$ and $Q_m$ synchronously displayed respectively in the display areas 101 and 102 of the display unit 12 is set using GUIs. In an image display apparatus according to the second embodiment, default data of the time difference $\Delta T$ preset for each site inside a subject is stored in the storage unit 15 and the time difference $\Delta T$ between the images $P_n$ and $Q_m$ is set based on the default data.

Figure 15:
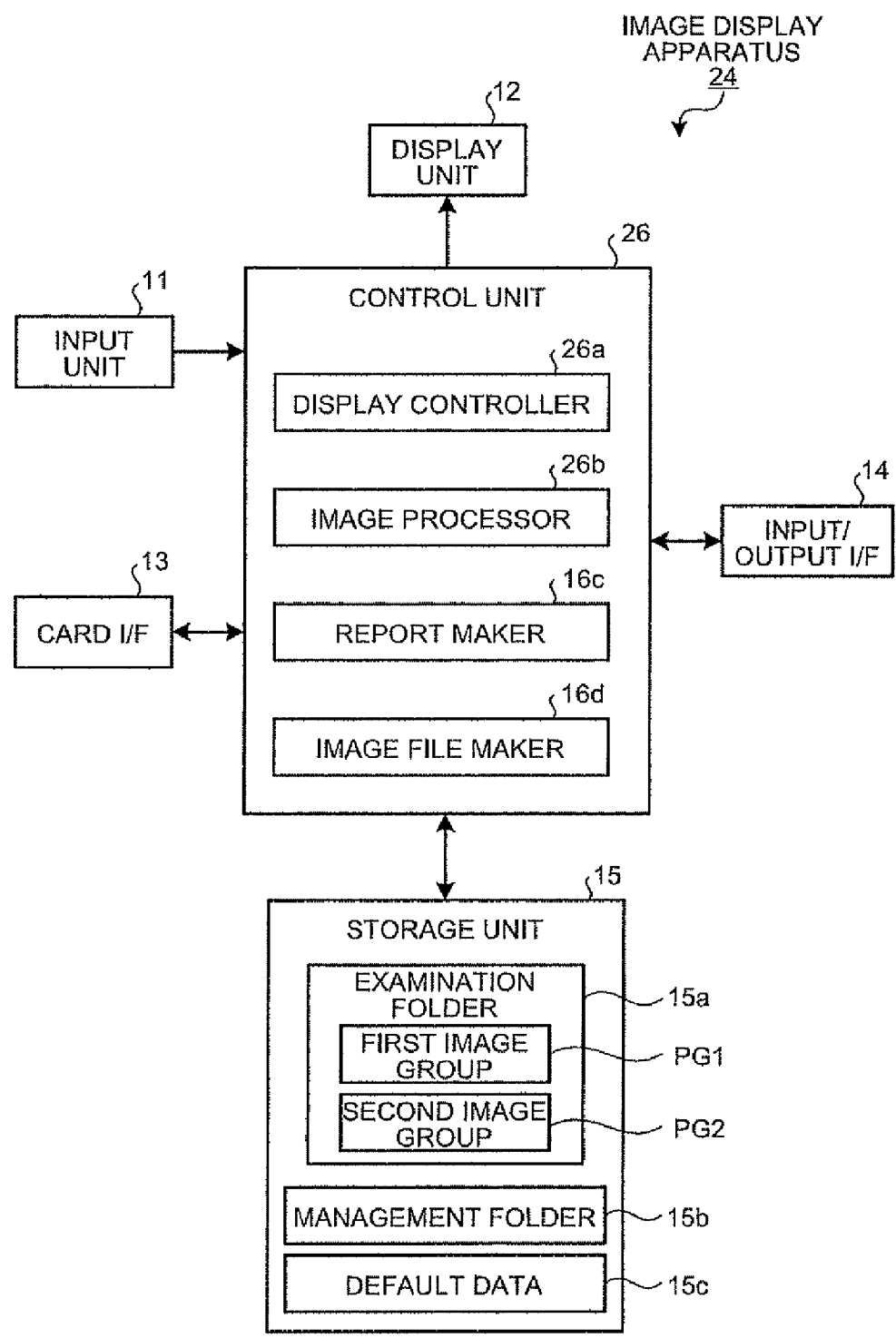
FIG. 15 is a block diagram exemplarily showing a configuration example of an image display apparatus according to a second embodiment of the present invention.

FIG. 15 is a block diagram exemplarily showing a configuration example of an image display apparatus according to the second embodiment of the present invention. As shown in FIG. 15, an image display apparatus 24 has a control unit 26 in place of the control unit 16 of the image display apparatus 4 according to the first embodiment. The control unit 26 has a display controller 26a in place of the display controller 16a of the control unit 16 of the image display apparatus 4 and an image processor 26b in place of the image processor 16b. Moreover, default data 15c of the time difference $\Delta T$ between the images $P_n$ and $Q_m$ in the synchronous display mode is saved in advance in the storage unit 15 of the image display apparatus 24 according to the second embodiment. Other components are the same as those in the first embodiment and the same reference numerals are attached to the same components.

An intra-subject information acquisition system using the image display apparatus 24 according to the second embodiment is realized by using the image display apparatus 24 in place of the image display apparatus 4 of the intra-subject information acquisition system according to the first embodiment exemplified in FIG. 1.

The control unit 26 has almost the same function as that of the control unit 16 of the image display apparatus 4 according to the first embodiment. In this case, the control unit 26 maintains and manages the default data 15c of the time difference $\Delta T$ saved in the storage unit 15 as data in which the time difference $\Delta T$ between the images $P_n$ and $Q_m$ to be synchronously displayed respectively in the display areas 101 and 102 in the synchronous display mode is preset for each site (for example, the esophagus, stomach, small intestine, large intestine) of the subject 1. The control unit 26 reads time difference data for each site preset by the default data 15c when needed and sets the time difference $\Delta T$ between the images $P_n$ and $Q_m$ for each site of the subject 1 based on the read time difference data.

The display controller 26a has almost the same function as that of the display controller 16a of the image display apparatus 4 according to the first embodiment. In this case, the display controller 26a sets the time difference $\Delta T$ between the images $P_n$ and $Q_m$ in the synchronous display mode for each site of the subject 1 based on time difference data for each site of the subject 1 preset by the default data 15c. In the synchronous display mode, the display controller 26a performs control to synchronously display the images $P_n$ and $Q_m$ having the time difference ΔT set based on the default data 15c respectively in the display areas 101 and 102 sequentially.

The time difference ΔT set for each site of the subject 1 by the display controller 26a is displayed in the data setting area 131. Moreover, the time sliders 132 and 133 move in such a way that the interval between temporal positions corresponding to the time difference ΔT for each site is maintained.

The image processor 26b has almost the same function as that of the image processor 16b of the image display apparatus 4 according to the first embodiment. In this case, the image processor 26b detects color information (for example, the mean color) of each image contained in each of the first image group PG1 and the second image group PG2 and, based on the detected color information of each image, determines each site (for example, the esophagus, stomach, small intestine, large intestine) of the subject 1 picked in each image. That is, the image processor 26b detects color information of the image $P_n$ of the frame number n (n=0, 1, 2, 3, ...) and, based on the detected color information, determines the imaged site of image $P_n$. Moreover, the image processor 26b detects color information of the image $Q_m$ of the frame number m (m=0, 1, 2, 3, ...) and, based on the detected color information, determines the imaged site of the image $Q_m$.

Next, the default data 15c of the time difference ΔT saved in the storage unit 15 will be described. FIG. 16 is a schematic diagram showing a specific example of the default data 15c of the time difference ΔT set for each site of the subject 1. As shown in FIG. 16, the default data 15c is a data group in tabular form associating each preset time difference ΔT and each site of the subject 1. More specifically, the time differences ΔT contained in the default data 15c include, for example, a time difference ΔT1 associated with the esophagus of the subject 1, a time difference ΔT2 associated with the stomach of the subject 1, a time difference ΔT3 associated with the small intestine of the subject 1, and a time difference ΔT4 associated with the large intestine of the subject 1.

Such time differences ΔT1, ΔT2, ΔT3, and ΔT4 are set based on the mean transit time of the capsule endoscope 2 of each site of the subject 1 and the mean length of each site (organ). More specifically, the time difference ΔT1 is set based on the mean transit time of the capsule endoscope 2 of the esophagus of the subject 1 and the mean length of the esophagus, and the time difference ΔT2 is set based on the mean transit time of the capsule endoscope 2 of the stomach of the subject 1 and the mean length of the stomach. Further, the time difference ΔT3 is set based on the mean transit time of the capsule endoscope 2 of the small intestine of the subject 1 and the mean length of the small intestine, and the time difference ΔT4 is set based on the mean transit time of the capsule endoscope 2 of the large intestine of the subject 1 and the mean length of the large intestine. In this case, the magnitude correlation of time differences ΔT1, ΔT2, ΔT3, ΔT4 is normally ΔT1<ΔT2≦ΔT3<ΔT4.

Figure 17:
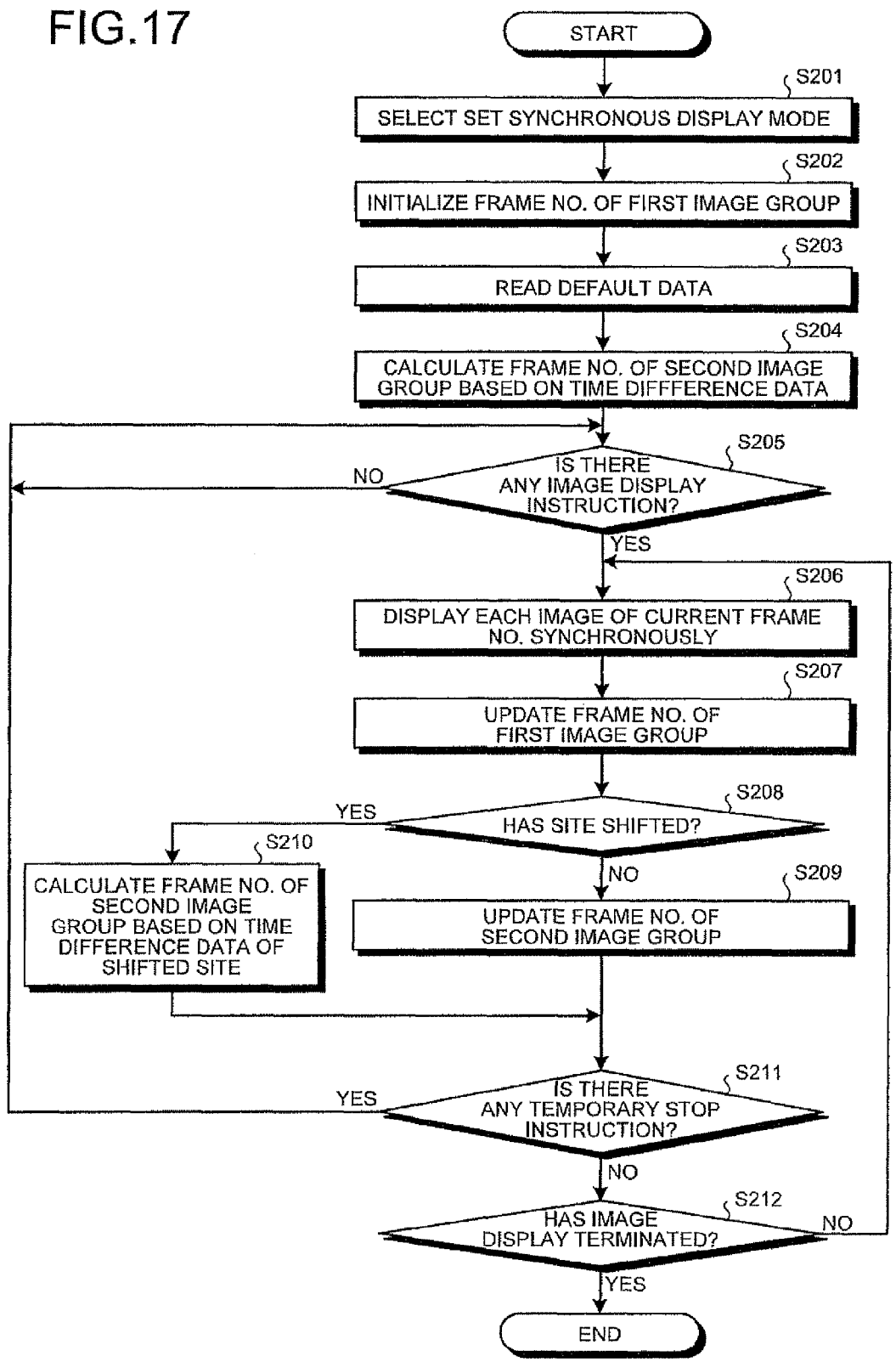
FIG. 17 is a flowchart illustrating a processing procedure by the control unit that makes images having a time difference based on the default data synchronously displayed in respective display areas.

Next, the operation of the control unit 26 controlling to make a synchronous display of the images $P_n$ and $Q_m$ in the respective display areas 101 and 102 in the synchronous display mode will be described. FIG. 17 is a flowchart illustrating the processing procedure by the control unit 26 that makes images $P_n$ and $Q_m$ having the time difference ΔT based on the default data 15c synchronously displayed in the respective display areas 101 and 102.

In FIG. 17, similarly to step S101 described above, the control unit 26 first selects the synchronous display mode set by the synchronization icon 130 as the image display mode (step S201). In this case, the display controller 26a selects the synchronous display mode from the plurality of image display modes based on setting information input from the input unit 11 by a click operation of the synchronization icon 130.

Next, similarly to step S103, the control unit 26 initializes the frame numbers of the first image group PG1 (step S202). In this case, the display controller 26a initializes the frame number n of the image to be processed for display from the first image group PG1 (for example, set n=0).

Then, the control unit 26 reads time difference data preset by the default data 15c from the storage unit 15 (step S203). In this case, the image processor 26b detects color information (for example, the mean color) of the image $P_0$ of the frame number n=0 initialized at step S202 and, based on the detected color information, determines the imaged site of the image $P_0$. The display controller 26a selects time difference data of the imaged site (that is, the site of the subject 1 picked up in the image $P_0$) determined by the image processor 26b from the default data 15c and, based on the selected time difference data, sets the time difference ΔT between the images $P_n$ and $Q_m$ of the imaged site.

Next, based on the time difference data selected from the default data 15c at step S203, the control unit 26 calculates the frame number m of the image to be processed for display from the second image group PG2 (step S204). In this case, the display controller 26a calculates the frame number m of the image $Q_m$ having the time difference ΔT with respect to the image $P_n$ (for example, n=0) based on the time difference data selected from the default data 15c at step S203.

Then, similarly to step S105, the control unit 26 determines whether or not any image display instruction of the images $P_n$ and $Q_m$ has been issued (step S205) More specifically, if no display instruction information corresponding to any icon in the display operation icon group 110 has been input from the input unit 11, the control unit 26 determines that no image display instruction of the images $P_n$ and $Q_m$ has been issued (step S205, No) and repeats step S205. That is, the control unit 26 repeats step S205 until such display instruction information is input by the input unit 11.

If, on the other hand, such display instruction information has been input from the input unit 11, the control unit 26 determines that an image display instruction of the images $P_n$ and $Q_m$ has been issued based on the input display instruction information (step S205, Yes) and, similarly to step S106, makes the images $P_n$ and $Q_m$ of the current frame numbers n and m synchronously displayed respectively in the display areas 101 and 102 (step S206). In this case, the display controller 26a extracts the image $P_n$ of the current frame number n (n=0, 1, 2, 3, ...) from among the first image group PG1 saved in the storage unit 15 and performs control to display the extracted image $P_n$ in the display area 101. In synchronization with the display of the image $P_n$ the display controller 26a extracts the image $Q_m$ of the current frame number m from among the second image group PG2 saved in the storage unit 15 and performs control to display the extracted image $Q_m$ in the display area 102. In this manner, the display controller 26a makes the images $P_n$ and $Q_m$ (m=n+α) having the time difference ΔT matching the imaged site synchronously displayed respectively in the display areas 101 and 102.

The current frame number n at step S206 is the frame number n (n=0) initialized at step S202 or a frame number n updated at step S207 described later.

Then, similarly to step S107, the control unit 26 updates the frame number n of the first image group PG1 (step S207). In this case, the display controller 26a updates (for example, adds +1) the frame number n of the first image group PG1 to read the image $P_n$ to be displayed in the display area 101 at next step S206 from the storage unit 15.

Next, the control unit 26 determines whether or not the imaged site (site of the subject 1) in the image $P_n$ displayed in the display area 101 shifts to a subsequent site (for example, the stomach for the esophagus) (step S208). In this case, the image processor 26b determines the imaged site of the image $P_n$ based on color information of the image $P_n$ currently displayed, and determines the imaged site of the image $P_{n+1}$ based on color information of the image $P_{n+1}$ of the frame number after being updated at step S207. If the imaged sites of the images $P_n$ and $P_{n+1}$ determined by the image processor 26b are the same, the control unit 26 determines that no shift of the imaged site (that is, the site of the subject 1) of the image $P_n$ has taken place (step S208, No) and, similarly to step S109 updates the frame number m of the second image group PG2 (step S209). In this case, the display controller 26a updates (for example, adds +1) the frame number m (m=n+α) of the second image group PG2 in accordance with the frame number n to read the image $Q_m$ to be displayed in the display area 102 in synchronization with the image $P_n$ at next step S206 from the storage unit 15.

If, on the other hand, the imaged sites of the images $P_n$ and $P_{n+1}$ determined by the image processor 26b are different, the control unit 26 determines that the imaged site (that is, the site of the subject 1) of the image $P_n$ has shifted (step S208, Yes) and selects time difference data of the imaged site after shifting from the default data 15c and updates the current time difference ΔT to that of the imaged site after shifting. Then, the control unit 26 calculates the frame number m of the second image group PG2 based on the time difference data of the imaged site after shifting (step S210). In this case, based on the time difference data of the imaged site after shifting, the display controller 26a calculates the frame number m (m=n+β) of the image $Q_m$ having the time difference ΔT of the imaged site after shifting with respect to the image $P_n$ to be synchronously displayed in the display area 101 at next step S206.

Then, similarly to step S111, the control unit 26 determines whether or not any temporary stop instruction to the control to display the images $P_n$ and $Q_m$ in the respective display areas 101 and 102 has been issued (step S211) and, if determined that a temporary stop instruction has been issued (step S211, Yes), returns to step S205 to repeat the processing procedure at step S205 and onward.

If determined, on the other hand, that no temporary stop instruction has been issued (step S211, No), similarly to step S112, the control unit 26 determines whether or not synchronous display processing of the images $P_n$ and $Q_m$ in the synchronous display mode has terminated (step S212). If the control unit 26 determines that synchronous display processing of the images $P_n$ and $Q_m$ in the synchronous display mode has terminated (step S212, Yes), the control unit 26 completes the synchronous display processing in the synchronous display mode. If, on the other hand, the control unit 26 determines that synchronous display processing of the images $P_n$ and $Q_m$ in the synchronous display mode has not terminated (step S212, No), the control unit 26 returns to step S206 to repeat the processing procedure at step S206 and onward.

Figure 18:
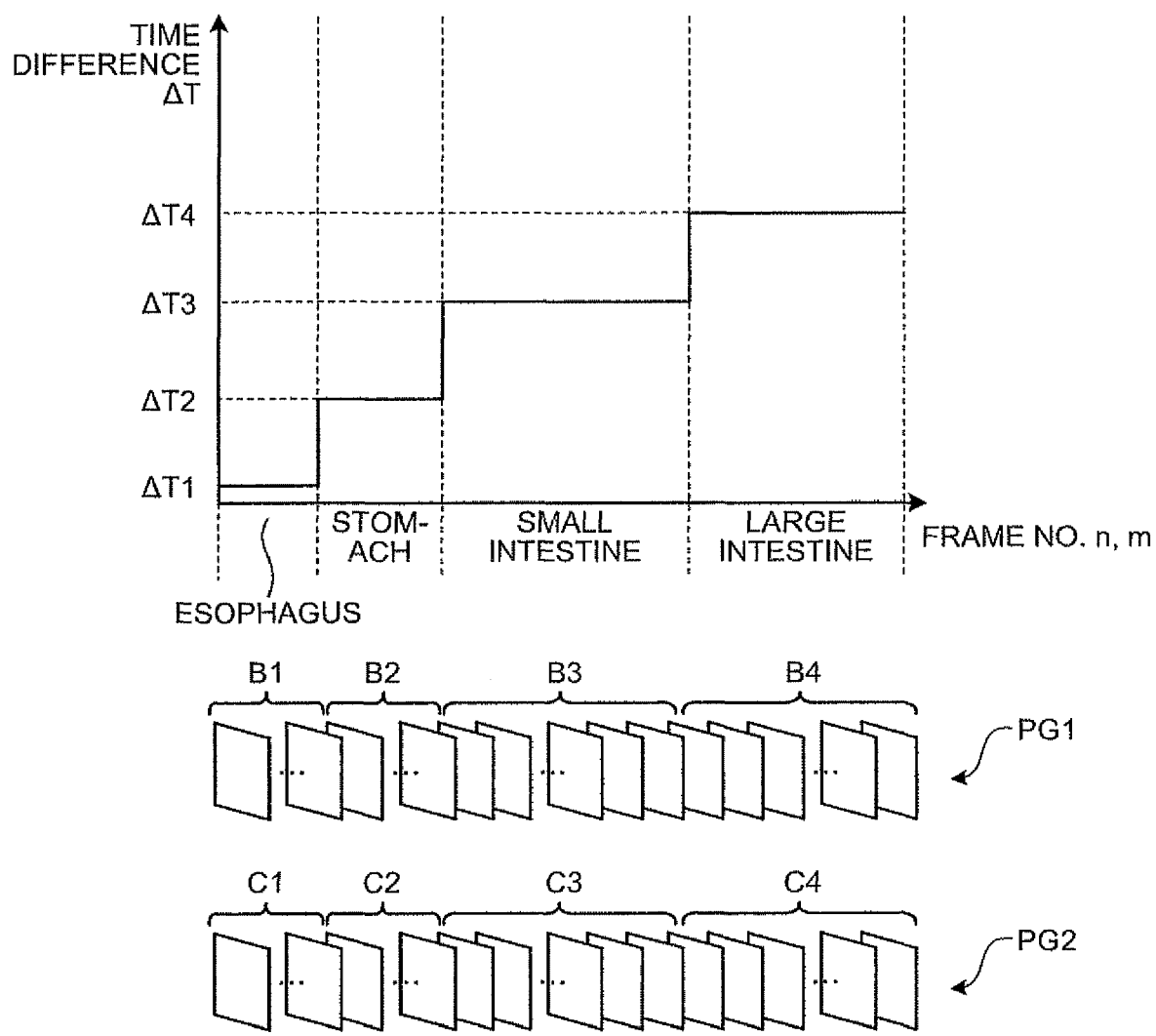
FIG. 18 is a schematic diagram illustrating a specific example of operation of the control unit that makes images having a time difference for each site based on the default data synchronously displayed in respective display areas sequentially.

Next, the operation of the control unit 26 controlling to synchronously display the images $P_n$ and $Q_m$ having the time difference ΔT for each site based on the default data 15c respectively in the display areas 101 and 102 will specifically be described by exemplifying, as shown in FIG. 16, a case in which the time difference ΔT1 is set to the esophagus, the time difference ΔT2 to the stomach, the time difference ΔT3 to the small intestine, and the time difference ΔT4 to the large intestine as the time differences ΔT for each site in the default data 15c. FIG. 18 is a schematic diagram illustrating a specific example of operation of the control unit 26 that makes images $P_n$ and $Q_m$ having the time difference ΔT for each site based on the default data 15c synchronously displayed respectively in the display areas 101 and 102 sequentially.

In FIG. 18, image groups B1, B2, B3, and B4 are image groups of each site contained in the first image group PG1 and are image groups in which the esophagus, stomach, small intestine, and large intestine of the subject 1 appear, respectively. Image groups C1, C2, C3, and C4 are image groups of each site contained in the second image group PG2 and are image groups in which the esophagus, stomach, small intestine, and large intestine of the subject 1 appear, respectively. In this case, the image $P_n$ (n=0, 1, 2, 3, . . . ) is contained in one of the image groups B1, B2, B3, and B4 and the image $Q_m$ (m=0, 1, 2, 3, . . . ) is contained in one of the image groups C1, C2, C3, and C4.

If images of the image groups B1 and C1 in which the esophagus of the subject 1 appears should be synchronously displayed, the control unit 26 sets the time difference ΔT1 of the default data 15c and, if images of the image groups B2 and C2 in which the stomach of the subject 1 appears should be synchronously displayed, the control unit 26 sets the time difference ΔT2 of the default data 15c. Further, if images of the image groups B3 and C3 in which the small intestine of the subject 1 appears should be synchronously displayed, the control unit 26 sets the time difference ΔT3 of the default data 15c and, if images of the image groups B4 and C4 in which the large intestine of the subject 1 appears should be synchronously displayed, the control unit 26 sets the time difference ΔT4 of the default data 15c.

More specifically, the image processor 26b determines the imaged site (esophagus) in the first image (that is, the image $P_0$) based on color information of the first image in the image group B1. In this case, the display controller 26a sets the time difference ΔT1 corresponding to the esophagus of the default data 15c and calculates the frame number m of the image group C1 of the esophagus having the time difference ΔT1 with respect to the first image of the image group B1. The image of the frame number m is an image of the esophagus contained in the image group C1 and an image in which an object common to the first image of the image group B1 appears.

Until, for example, the imaged site of the image $P_n$ displayed in the display area 101 shifts from the esophagus to the stomach, the display controller 26a maintains the setting of the time difference ΔT1, and makes the images $P_n$ and $Q_m$ (that is, each image of the image groups B1 and C1) of the esophagus having the time difference ΔT1 synchronously displayed respectively in the display areas 101 and 102. The images $P_n$ and $Q_m$ of the esophagus synchronously displayed in this manner are images in which an object common to each other appears.

Then, when an end image of the image group B1 of the esophagus is displayed in the display area 101, the image processor 26b determines that the imaged site of the image $P_n$ shifts from the esophagus to the stomach based on color information of the end image of the image group B1 and that of the first image of the image group B2. In this case, the display controller 26a sets the time difference ΔT2 corresponding to the stomach of the default data 15c in place of the time difference ΔT1 and calculates the frame number m of the image group C2 of the stomach having the time difference ΔT2 with respect to the first image of the image group B2 of the stomach. The image of the frame number m is an image of the stomach contained in the image group C2 and an image in which an object common to the first image of the image group B2 appears.

Until, for example, the imaged site of the image $P_n$ displayed in the display area 101 shifts from the stomach to the small intestine, the display controller 26a maintains the setting of the time difference ΔT2, and makes the images $P_n$ and $Q_m$ (that is, each image of the image groups B2 and C2) of the stomach having the time difference ΔT2 synchronously displayed respectively in the display areas 101 and 102. The images $P_n$ and $Q_m$ of the stomach synchronously displayed in this manner are images in which an object common to each other appears.

Then, when an end image of the image group B2 of the stomach is displayed in the display area 101, the image processor 26b determines that the imaged site of the image $P_n$ shifts from the stomach to the small intestine based on color information of the end image of the image group B2 and that of the first image of the image group B3. In this case, the display controller 26a sets the time difference ΔT3 corresponding to the small intestine of the default data 15c in place of the time difference ΔT2 and calculates the frame number m of the image group C3 of the small intestine having the time difference ΔT3 with respect to the first image of the image group B3 of the small intestine. The image of the frame number m is an image of the small intestine contained in the image group C3 and an image in which an object common to the first image of the image group B3 appears.

Until, for example, the imaged site of the image $P_n$ displayed in the display area 101 shifts from the small intestine to the large intestine, the display controller 26a maintains the setting of the time difference ΔT3, and makes the images $P_n$ and $Q_m$ (that is, each image of the image groups B3 and C3) of the small intestine having the time difference ΔT3 synchronously displayed respectively in the display areas 101 and 102. The images $P_n$ and $Q_m$ of the small intestine synchronously displayed in this manner are images in which an object common to each other appears.

Then, when an end image of the image group B3 of the small intestine is displayed in the display area 101, the image processor 26b determines that the imaged site of the image $P_n$ shifts from the small intestine to the large intestine based on color information of the end image of the image group B3 and that of the first image of the image group B4. In this case, the display controller 26a sets the time difference ΔT4 corresponding to the large intestine of the default data 15c in place of the time difference ΔT3 and calculates the frame number m of the image group C4 of the large intestine having the time difference ΔT4 with respect to the first image of the image group B4 of the large intestine. The image of the frame number m is an image of the large intestine contained in the image group C4 and an image in which an object common to the first image of the image group B4 appears.

As long as the imaged site of the image $P_n$ displayed in the display area 101 is the large intestine, the display controller 26a maintains the setting of the time difference ΔT4, and makes the images $P_n$ and $Q_m$ (that is, each image of the image groups B4 and C4) of the large intestine having the time difference ΔT4 synchronously displayed respectively in the display areas 101 and 102. The images $P_n$ and $Q_m$ of the large intestine synchronously displayed in this manner are images in which an object common to each other appears.

In the second embodiment of the present invention, as described above, the time difference ΔT between imaging times of first and second images contained in first and second image groups respectively of a plurality of image groups picked up inside a subject by a group of imaging devices mounted on a multiple-lens capsule endoscope is saved in a storage unit as default data preset for each site of the subject, and the first and second images having the time difference ΔT set for each site of the subject are synchronously displayed respectively in display areas of a display unit sequentially so that the first image and the second image, in which an object common to the first image appears, are synchronously displayed respectively in the display areas sequentially. Thus, even if the site of the subject where the image is picked up sequentially shifts, images obtained by picking up the same object common to the first and second images from a plurality of imaging directions can synchronously be displayed in respective display areas of the display unit sequentially. As a result, almost the same operation effect as that of the first embodiment can be achieved and also an image display apparatus capable of sequentially displaying each image contained in each of image groups picked up inside the subject from multiple directions by the group of imaging devices mounted on the multiple-lens capsule endoscope in a mode in which observations can be made easily can be realized.

By synchronously displaying image groups inside a subject from multiple directions using an image display apparatus according to the second embodiment of the present invention, a user such as a physician or a nurse can synchronously display images obtained by picking up the same object from a plurality of directions by a simple operation sequentially, thereby enabling the user to observe a series of images, for example, from esophagus to large intestine inside the subject and also to observe characteristic sites such as a lesion site and inner walls (for example, a puckered site) of the digestive tract or the like, which are difficult to observe from only one direction, easily from a plurality of directions.

Next, the third embodiment of the present invention will be described. While the time difference ΔT between the images $P_n$ and $Q_m$ is set for each site based on default data preset for each site inside the subject in an image display apparatus according to the second embodiment, the default data of the time difference ΔT can further be updated by GUIs in an image display apparatus according to the third embodiment.

Figure 19:
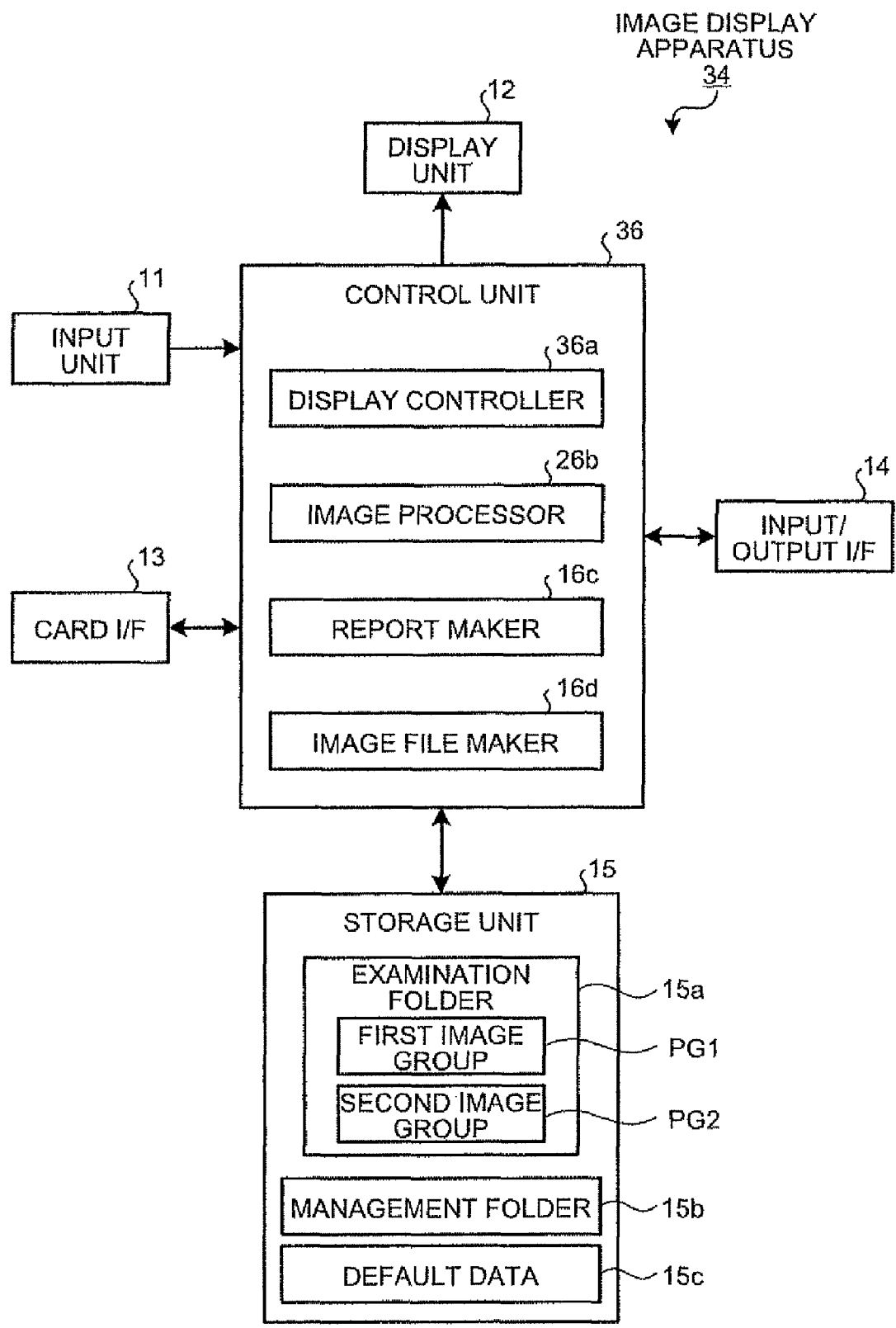
FIG. 19 is a block diagram exemplarily showing a configuration example of an image display apparatus according to a third embodiment of the present invention.

FIG. 19 is a block diagram exemplarily showing a configuration example of an image display apparatus according to the third embodiment of the present invention.

Figure 20:
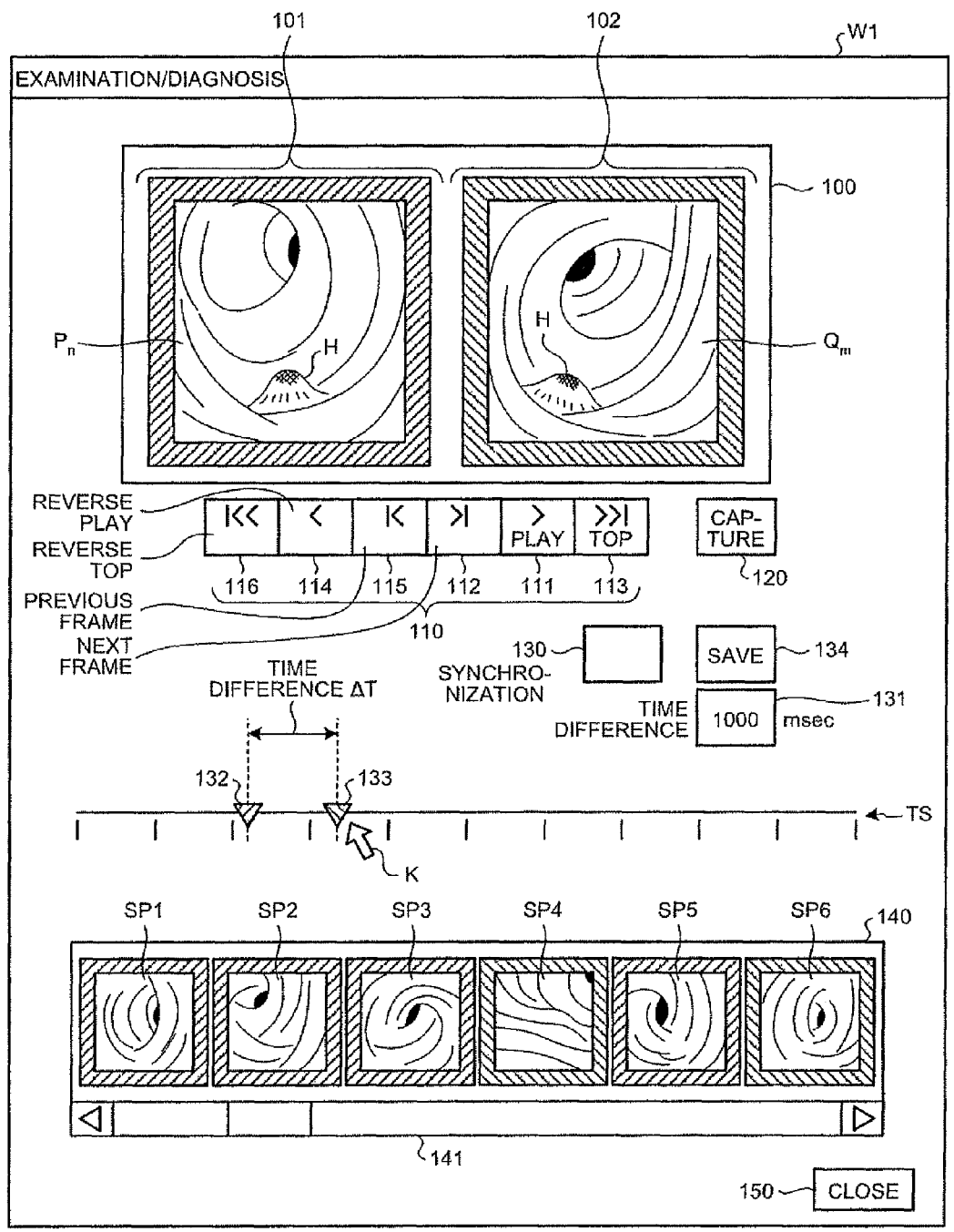
FIG. 20 is a schematic diagram exemplarily showing a specific example of various GUIs displayed in a display unit of the image display apparatus according to the third embodiment.

FIG. 20 is a schematic diagram exemplarily showing a configuration example of various GUIs displayed in the display unit of the image display apparatus according to the third embodiment. As shown in FIG. 19, an image display apparatus 34 has a control unit 36 in place of the control unit 26 of the image display apparatus 24 according to the second embodiment. The control unit 36 has a display controller 36a in place of the display controller 26a of the control unit 26 of the image display apparatus 24. Further, as shown in FIG. 20, a Save icon 134, which is a GUI for updating the default data 15c in frames, is formed in the window W1 displayed in the display unit 12. Other components are the same as those in the second embodiment and the same reference numerals are attached to the same components.

An intra-subject information acquisition system using the image display apparatus 34 according to the third embodiment is realized by using the image display apparatus 34 in place of the image display apparatus 4 of the intra-subject information acquisition system according to the first embodiment exemplified in FIG. 1.

The control unit 36 has almost the same function as that of the control unit 26 of the image display apparatus 24 according to the second embodiment. In this case, the control unit 36 updates the default data 15c in frames by partially overwriting the default data 15c with time difference data reset in frames by the data setting area 131 or the time sliders 132 and 133. If update instruction information has been input from the input unit 11 by a click operation of the Save icon 134, the control unit 36 each time performs update processing of the default data 15c. The control unit 36 as described above reads time difference data for each site reset by the default data 15c after being updated when needed and, based on the read time difference data after the reset, sets the time difference $\Delta T$ between the images $P_n$ and $Q_m$ for each site of the subject 1.

The display controller 36a has almost the same function as that of the display controller 26a of the image display apparatus 24 according to the second embodiment. In this case, the display controller 36a sets the time difference $\Delta T$ between the images $P_n$ and $Q_m$ in the synchronous display mode for each site of the subject 1 or for each frame based on the default data 15c updated by partial resetting (updating) in frames. In the synchronous display mode, the display controller 36a performs control to synchronously display the images $P_n$ and $Q_m$ having the time difference $\Delta T$ set for each site or each frame based on the updated default data 15c respectively in the display areas 101 and 102 sequentially.

Figure 21:
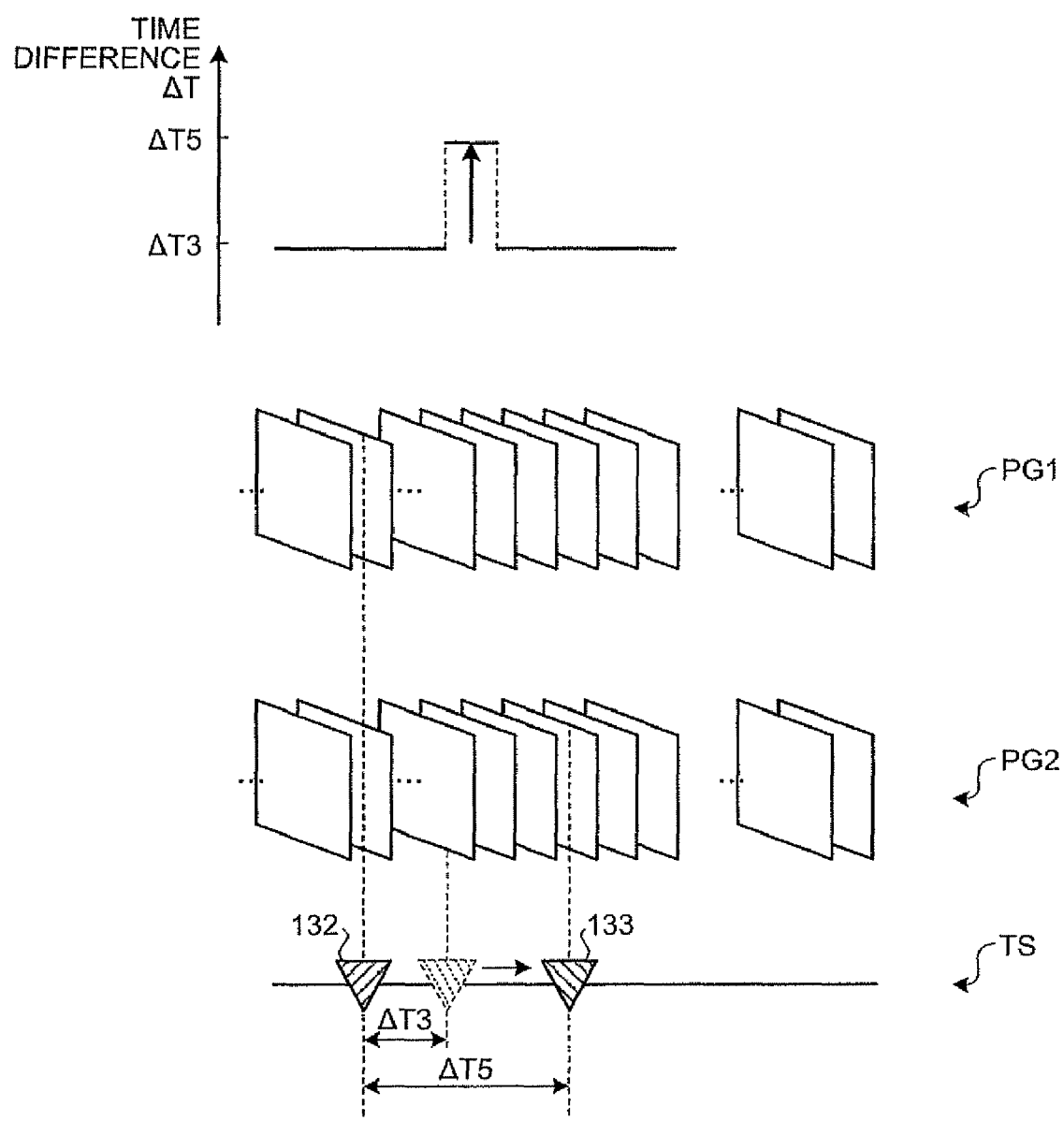
FIG. 21 is a schematic diagram illustrating operation of the control unit that partially updates the default data.

Next, the operation of the control unit 36 to partially update the default data 15c will be described by exemplifying a case in which the time difference $\Delta T3$ of the small intestine is partially updated to a time difference $\Delta T5$. FIG. 21 is a schematic diagram illustrating the operation of the control unit 36 that partially updates the default data 15c. In FIG. 21, first the time sliders 132 and 133 respectively indicate temporal positions of the images $P_n$ and $Q_m$ of the small intestine currently displayed in the display areas 101 and 102 respectively. In this case, the interval between the time sliders 132 and 133 corresponds to the time difference $\Delta T3$ of the small intestine based on the default data 15c before being updated. In this state, the display controller 36a sets the time difference $\Delta T3$.

Here, if the time difference $\Delta T3$ of the image $Q_m$ with respect to the image $P_n$ displayed in the current display area 101 should be changed (reset) to the time difference $\Delta T5$, the time slider 133 is moved by a drag operation using the input unit 11 to create an interval corresponding to the time difference $\Delta T5$ with respect to the time slider 132. Further, if a click operation of the Save icon 134 is performed, the input unit 11 inputs update instruction information to the control unit 36. Based on the update instruction information, the control unit 36 partially overwrites the default data 15c with the time difference $\Delta T5$ corresponding to the current interval between the time sliders 132 and 133 as time difference data of the small intestine. In this case, the time difference $\Delta T3$ between the images $P_n$ and $Q_m$ displayed currently in the respective display areas 101 and 102 will be replaced by the time difference $\Delta T5$. As a result, as shown in FIG. 21, the default data 15c is updated to one in which the time difference between the images $P_n$ and $Q_m$ of desired frame numbers of the image groups of the small intestine is partially reset from $\Delta T3$ to $\Delta T5$.

By repeating update processing of the default data 15c as described above, the control unit 36 can partially update the default data 15c by updating one or more desired frames of the first image group PG1 or the second image group PG2. In this case, the display controller 36a partially resets the time differences $\Delta T$ (for example, the time differences $\Delta T1$, $\Delta T2$, $\Delta T3$, and $\Delta T4$) set for each site of the subject 1 in frames based on the default data 15c after being updated.

Such resetting of the time differences $\Delta T$ can also be performed by directly entering a numeric value in the data setting area 131 using the input unit 11. In this case, the time sliders 132 and 133 move in such a way that the interval therebetween corresponds to the time difference $\Delta T$ entered in the data setting area 131.

Figure 22:
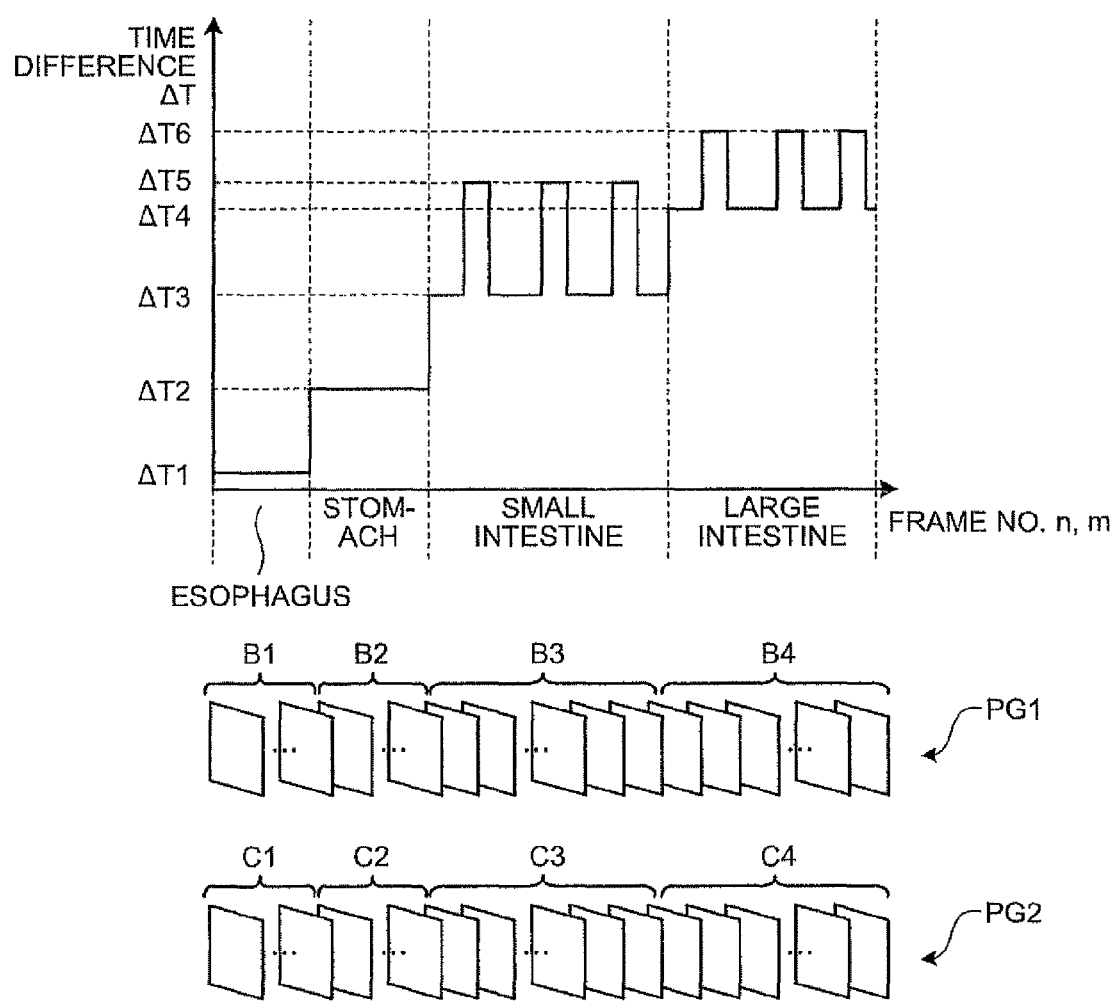
FIG. 22 is a schematic diagram illustrating a specific example of operation of the control unit that makes images having a time difference based on the default data after being updated synchronously displayed in respective display areas sequentially.

Next, the operation of the control unit 36 controlling to synchronously display the images $P_n$ and $Q_m$ having the time difference $\Delta T$ based on the default data 15c after being updated in the respective display areas 101 and 102 will specifically be described by exemplifying a case in which the time difference $\Delta T3$ of the small intestine of the default data 15c shown in FIG. 16 is partially reset to the time difference $\Delta T5$ and the time difference $\Delta T4$ of the large intestine is partially reset to a time difference $\Delta T6$. FIG. 22 is a schematic diagram illustrating a specific example of operation of the control unit 36 that makes the images $P_n$ and $Q_m$ having the time difference $\Delta T$ based on the default data 15c after being updated synchronously displayed respectively in the display areas 101 and 102.

In FIG. 22, the time difference $\Delta T3$ between images of the image groups B3 and C3 of the small intestine is partially updated to the time difference $\Delta T5$ ($>\Delta T3$) in accordance with peristaltic movement of the small intestine of the subject 1. More specifically, the time difference $\Delta T3$ is updated to the time difference $\Delta T5$ in portions of the image groups B3 and C3 of the small intestine corresponding to a frame period in which the capsule endoscope 2 retains in the small intestine. Moreover, the time difference $\Delta T4$ between images of the image groups B4 and C4 of the large intestine is partially updated to the time difference $\Delta T6$ ($>\Delta T4$) in accordance with peristaltic movement of the large intestine of the subject 1. More specifically, the time difference $\Delta T4$ is updated to the time difference $\Delta T6$ in portions of the image groups B4 and C4 of the large intestine corresponding to a frame period in which the capsule endoscope 2 retains in the large intestine.

The control unit 36 performs almost the same processing procedure as steps S201 to S212 described above. In this case, the control unit 36 determines at step S209 whether or not the time difference $\Delta T$ has been changed based on the default data 15c after being updated. If the control unit 36 determines that the time difference $\Delta T$ has been changed, the display controller 36a calculates the frame number m based on time difference data of the time difference $\Delta T$ after being changed (for example, the time difference $\Delta T$ reset in frames). If, on the other hand, the control unit 36 determines that the time difference $\Delta T$ has not been changed, the display controller 36a updates the frame number m as described above (for example, adds +1).

More specifically, if images of the image groups B3 and C3 in which the small intestine of the subject 1 appears should be synchronously displayed, the control unit 36 determines that the time difference $\Delta T$ has not been changed if the image of the frame number n after being updated is the one whose setting is made and maintained at the time difference $\Delta T3$ or time difference $\Delta T5$. In this case, the display controller 36a updates, similarly to step S209, the frame number m. If, on the other hand, the image of the frame number n after being updated is the one whose setting is reset from the time difference $\Delta T3$ to the time difference $\Delta T5$ and then maintained, the control unit 36 determines that the time difference $\Delta T$ has been changed. In this case, the display controller 36a calculates the frame number m from time difference data of the time difference $\Delta T5$ based on the default data 15c after being updated. Similarly, if the image of the frame number n after being updated is the one whose setting is brought back from the time difference $\Delta T5$ to the time difference $\Delta T3$, the control unit 36 determines that the time difference $\Delta T$ has been changed. In this case, the display controller 36a calculates the frame number m from time difference data of the time difference $\Delta T3$ based on the default data 15c after being updated.

The display controller 36a as described above performs control to synchronously display the images $P_n$ and $Q_m$ having the original time difference $\Delta T3$ in each of the display areas 101 and 102 for image groups of the image groups B3 and C3 picked up while the capsule endoscope 2 moves through the small intestine, and performs control to synchronously display the images $P_n$ and $Q_m$ having the reset time difference $\Delta T5$ in each of the display areas 101 and 102 for image groups of the image groups B3 and C3 picked up while the capsule endoscope 2 retains in the small intestine.

Moreover, if each image of the image groups B4 and C4 in which the larger intestine of the subject 1 is picked up should be synchronously displayed, the control unit 36 determines that the time difference $\Delta T$ has not been changed if the image of the frame number n after being updated is the one whose setting is made and maintained at the time difference $\Delta T4$ or time difference $\Delta T6$. In this case, the display controller 36a updates, as same in step S209, the frame number m. If, on the other hand, the image of the frame number n after being updated is the one whose setting is reset from the time difference $\Delta T4$ to the time difference $\Delta T6$ and then maintained, the control unit 36 determines that the time difference $\Delta T$ has been changed. In this case, the display controller 36a calculates the frame number m from time difference data of the time difference $\Delta T6$ based on the default data 15c after being updated. Similarly, if the image of the frame number n after being updated is the one whose setting is brought back from the time difference $\Delta T6$ to the time difference $\Delta T4$, the control unit 36 determines that the time difference $\Delta T$ has been changed. In this case, the display controller 36a calculates the frame number m from time difference data of the time difference $\Delta T4$ based on the default data 15c after being updated.

The display controller 36a as described above performs control to synchronously display the images $P_n$ and $Q_m$ having the original time difference $\Delta T4$ in each of the display areas 101 and 102 for image groups of the image groups B4 and C4 picked up while the capsule endoscope 2 moves through the large intestine, and performs control to synchronously display the images $P_n$ and $Q_m$ having the reset time difference $\Delta T6$ in each of the display areas 101 and 102 for image groups of the image groups B4 and C4 picked up while the capsule endoscope 2 retains in the large intestine.

The image display apparatus 34 having the control unit 36 described above can partially switch settings of the time difference $\Delta T$ in accordance with peristaltic movement of the subject 1 and even if image groups are picked up in organs (such as the stomach, small intestine, and large intestine) in which the capsule endoscope 2 is in a retained state and a movement state repeatedly in the digestive tract, images in which an object common to both are picked up can reliably be displayed synchronously in each of the display areas 101 and 102.

The third embodiment of the present invention has, as described above, a configuration similar to one in the second embodiment. Further, the third embodiment is configured in such a way that default data of the time difference $\Delta T$ is updated (reset) by using GUIs and first and second images having the time difference $\Delta T$ set based on the default data after being updated are made to be synchronously displayed in each display area of a display unit sequentially so that the first images and the second images in which an object common to the first images are picked up are synchronously displayed in each display area sequentially. Thus, the setting of the time difference $\Delta T$ can further be switched in accordance with image groups picked up while a multiple-lens capsule endoscope moves through the digestive tract or those picked up while the multiple-lens capsule endoscope retains therein. As a result, the operation effect of the second embodiment can be achieved and also an image display apparatus capable of reliably displaying images in which an object common to each other is picked up synchronously in each display area of the display unit can be realized even if the images are picked up in organs (such as the stomach, small intestine, and large intestine) in which the multiple-lens capsule endoscope is in a retained state and a movement state repeatedly in the digestive tract.

Next, the fourth embodiment of the present invention will be described. In an image apparatus according to the fourth embodiment, a plurality of thumbnail images additionally displayed in the sub-image display area 140 can be associated in a desired combination.

Figure 23:
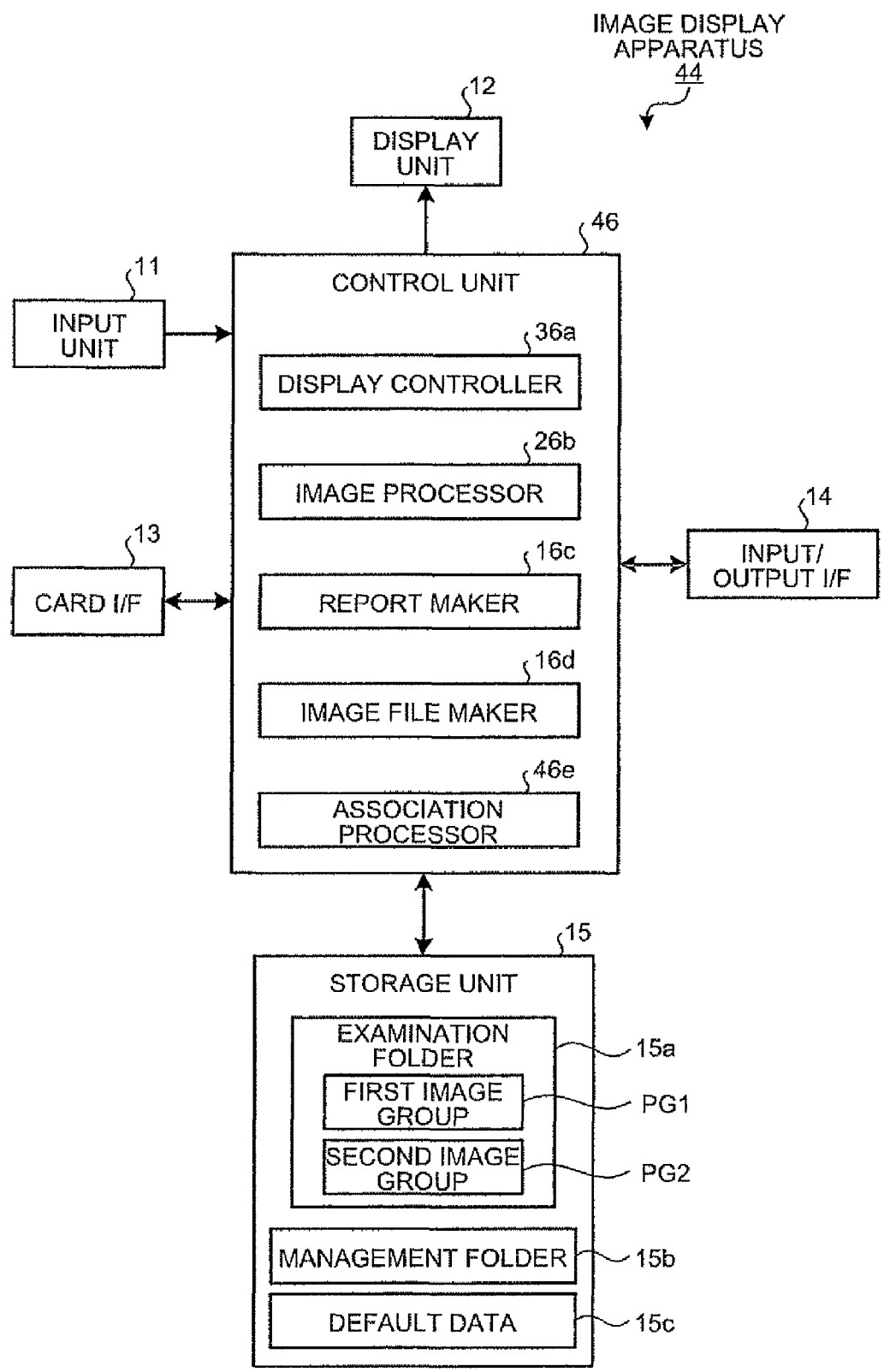
FIG. 23 is a block diagram exemplarily showing a configuration example of an image display apparatus according to a fourth embodiment of the present invention.

FIG. 23 is a block diagram exemplarily showing a configuration example of an image display apparatus according to the fourth embodiment of the present invention.

Figure 24:
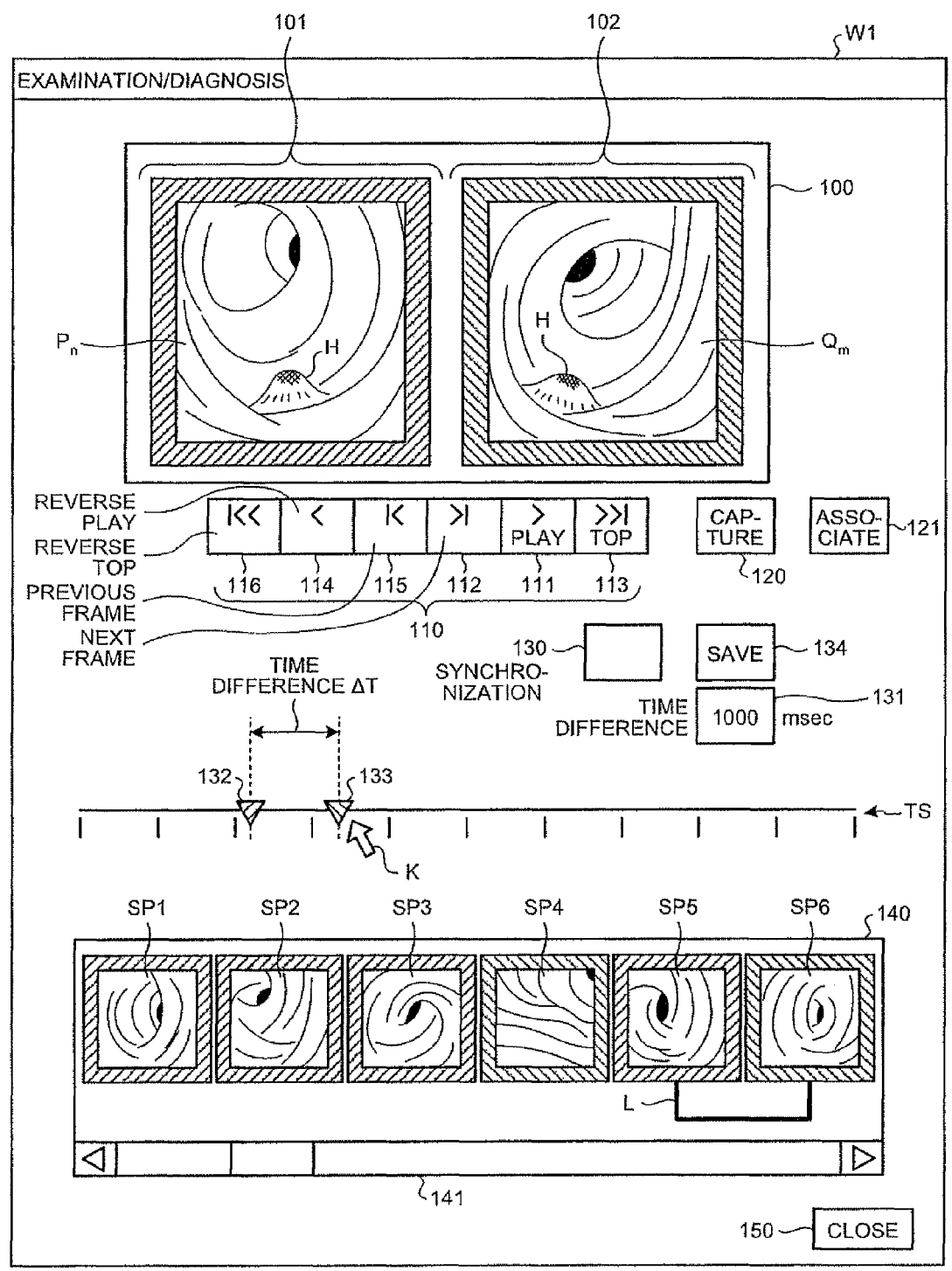
FIG. 24 is a schematic diagram exemplarily showing a specific example of various GUIs displayed in a display unit of the image display apparatus according to the fourth embodiment.

FIG. 24 is a schematic diagram exemplarily showing a configuration example of various GUIs displayed in the display unit of the image display apparatus according to the fourth embodiment. As shown in FIG. 23, an image display apparatus 44 has a control unit 46 in place of the control unit 36 of the image display apparatus 34 according to the third embodiment. The control unit 46 has a configuration obtained by adding an association processor 46e to the control unit 36 of the image display apparatus 34. Also, as shown in FIG. 24, an Associate icon 121, which is a GUI for associating the plurality of thumbnail images displayed in the sub-image display area 140 in a desired combination, is further formed in the window W1 displayed in the display unit 12. Other components are the same as those in the third embodiment and the same reference numerals are attached to the same components.

An intra-subject information acquisition system using the image display apparatus 44 according to the fourth embodiment is realized by using the image display apparatus 44 in place of the image display apparatus 4 of the intra-subject information acquisition system according to the first embodiment exemplified in FIG. 1.

The control unit 46 has functions similar to those of the control unit 36 of the image display apparatus 34 according to the third embodiment and further an association function to associate the plurality of thumbnail images in a desired combination. As described above, the control unit 46 has the association processor 46e.

The association processor 46e performs association processing to associate the plurality of thumbnail images displayed in the sub-image display area 140 in a desired combination. More specifically, the association processor 46e associates, based on instruction information input by the input unit 11, a desired thumbnail image group selected from among the plurality of thumbnail images displayed in the sub-image display area 140. In this case, the control unit 46 performs control to display an indicator indicating a thumbnail image group associated by the association processor 46e, for example, a line L (See FIG. 24) connecting the associated thumbnail images inside the window W1.

Figure 25:
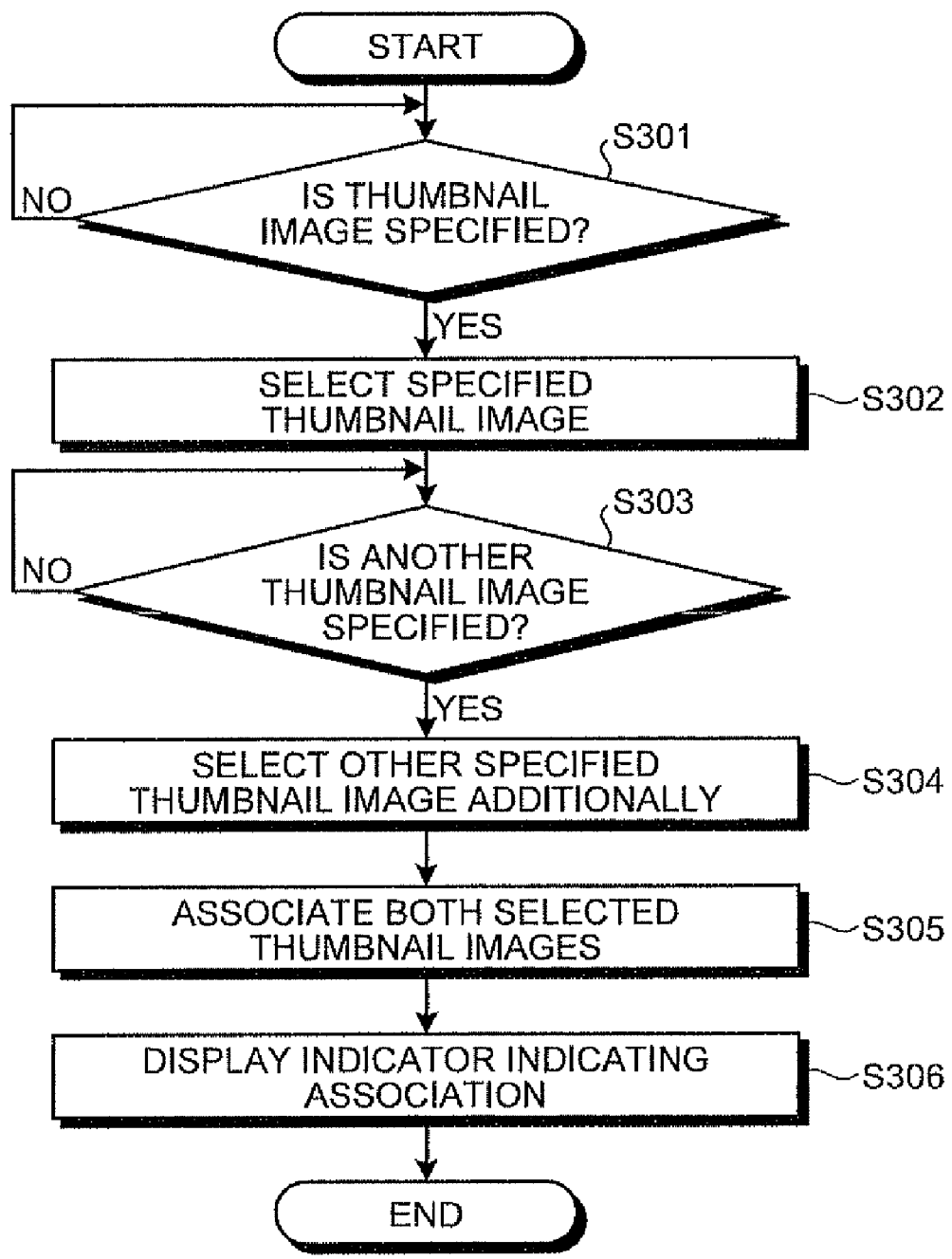
FIG. 25 is a flowchart illustrating a processing procedure by the control unit when a plurality of thumbnail images is associated in a desired combination.

Next, the operation of the control unit 46 when associating the plurality of thumbnail images in a desired combination will be described. FIG. 25 is a flowchart illustrating the processing procedure by the control unit 46 when a plurality of thumbnail images is associated in a desired combination In FIG. 25, the control unit 46 first determines whether or not any desired thumbnail image is specified from a plurality of thumbnail images displayed in the sub-image display area 140 (step S301). More specifically, if a desired thumbnail image is clicked from the plurality of thumbnail images displayed in the sub-image display area 140, the input unit 11 inputs instruction information specifying the desired thumbnail image as one image of a desired combination to the control unit 46. If no such instruction information has been input by the input unit 11, the control unit 46 determines that no desired thumbnail image is specified (step S301, No) and repeats step S301. That is, the control unit 46 repeats step S301 until a desired thumbnail image is specified from among the sub-image display area 140.

If, on the other hand, such instruction information has been input by the input unit 11, the control unit 46 determines that a desired thumbnail image has been specified (step S301, Yes) and, based on the input instruction information, selects a desired thumbnail image specified from among the sub-image display area 140 (step S302).

Next, the control unit 46 determines whether or not another desired thumbnail image is specified from the plurality of thumbnail images displayed in the sub-image display area 140 (step S303). More specifically, if another desired thumbnail image is further clicked from the plurality of thumbnail images displayed in the sub-image display area 140, the input unit 11 inputs instruction information additionally specifying the other thumbnail image as another image of a desired combination to the control unit 46. If no such instruction information has been input by the input unit 11, the control unit 46 determines that no other thumbnail image is specified (step S303, No) and repeats step S303. That is, the control unit 46 repeats step S303 until another desired thumbnail image is additionally specified from among the sub-image display area 140.

If, on the other hand, such additional instruction information has been input by the input unit 11, the control unit 46 determines that another thumbnail image has additionally been specified (step S303, Yes) and, based on the additional input instruction information, additionally selects a desired thumbnail image (that is, a thumbnail image different from the desired thumbnail image selected at step S302 described above) additionally specified from among the sub-image display area 140 (step S304).

Next, the control unit 46 associates the two thumbnail images selected as described above (step S305). In this case, the association processor 46e associates the thumbnail image selected at step S302 and the other thumbnail image additionally selected at step S304. In this manner, the association processor 46e associates the plurality of thumbnail images displayed in the sub-image display area 140 in a desired combination. The control unit 46 saves the combination of desired thumbnail images associated by the association processor 46e in the storage unit 15 and maintains and manages the saved desired combination as one combination of thumbnail images.

Then, the control unit 46 makes the display unit 12 display an indicator indicating association of such desired thumbnail images (step S306). More specifically, the control unit 46 performs control to display a line connecting desired thumbnail images associated by the association processor 46e as an indicator of association.

Here, association of such thumbnail images will be described specifically with reference to FIG. 24. As shown in FIG. 24, a plurality of thumbnail images SP1 to SP6 is displayed in the sub-image display area 140. Among the plurality of thumbnail images, the thumbnail images SP1, SP2, SP3, and SP5 are reduced images of images selected from an image group displayed in the display area 101 and the thumbnail images SP4 and SP6 are reduced images of images selected from an image group displayed in the display area 102.

First, according to a click operation of the thumbnail image SP5, the input unit 11 inputs instruction information specifying the thumbnail image SP5 to the control unit 46. In this case, the control unit 46 selects the specified thumbnail image SP5 as the first thumbnail image forming a desired combination. Next, according to a click operation of the thumbnail image SP6, the input unit 11 inputs instruction information additionally specifying the thumbnail image SP6 to the control unit 46. In this case, the control unit 46 selects the additionally specified thumbnail image SP6 as a remaining thumbnail image to form a desired combination.

If the control unit 46 selects the combination of the desired thumbnail images SP5 and SP6 from the plurality of thumbnail images SP1 to SP6 in this manner, the association processor 46e associates the two thumbnail images SP5 and SP6. The control unit 46 also makes the display unit 12 display the line L connecting the thumbnail image SP5 and the thumbnail image SP6 associated by the association processor 46e as an indicator of association.

By visually recognizing such the line L, a user can easily understand that the thumbnail images SP5 and SP6 are associated. In this case, the associated thumbnail images SP5 and SP6 are, for example, thumbnail images in which an object common to both is picked up or those in which a characteristic portion such as a lesion site and hemorrhagic site is picked up.

When instruction information is input from the input unit 11 to the control unit 46 according to the clicking of one of the thumbnail images SP5 and SP6 associated as described above, the control unit 46 makes, based on the instruction information, an image $P_n$ corresponding to the thumbnail image SP5 displayed in the display area 101 and an image $Q_m$ corresponding to the thumbnail image SP6 displayed in the display area 102. The image display apparatus 44 having the control unit 46 described above can easily display images in which a characteristic portion such as a lesion site and hemorrhagic site is picked up from a plurality of directions in each of the display areas 101 and 102 by specifying one of associated thumbnail images (specifically, by clicking).

The fourth embodiment of the present invention has, as described above, the configuration of the third embodiment. Further, the fourth embodiment is configured in such a way that a plurality of thumbnail images displayed in a sub-image display area is associated in a desired combination and an indicator indicating association of such desired thumbnail images is displayed. Thus, the operation effect of the third embodiment can be achieved and also an image display apparatus enabling a user to easily understand a combination of mutually associated thumbnail images among the plurality of thumbnail images can be realized.

By using an image display apparatus according to the fourth embodiment, images in which a characteristic portion such as a lesion site and hemorrhagic site is picked up can be retrieved from image groups from multiple directions of a subject and also images in which such a characteristic site is picked up from a plurality of directions can easily be synchronously displayed in each display area of a display unit.

Next, the fifth embodiment of the present invention will be described. In an image display apparatus according to the fifth embodiment, in addition to the synchronous display function of the images $P_n$ and $Q_m$ described above, display operations of the images $P_n$ and $Q_m$ can further be performed separately in normal display mode.

Figure 26:
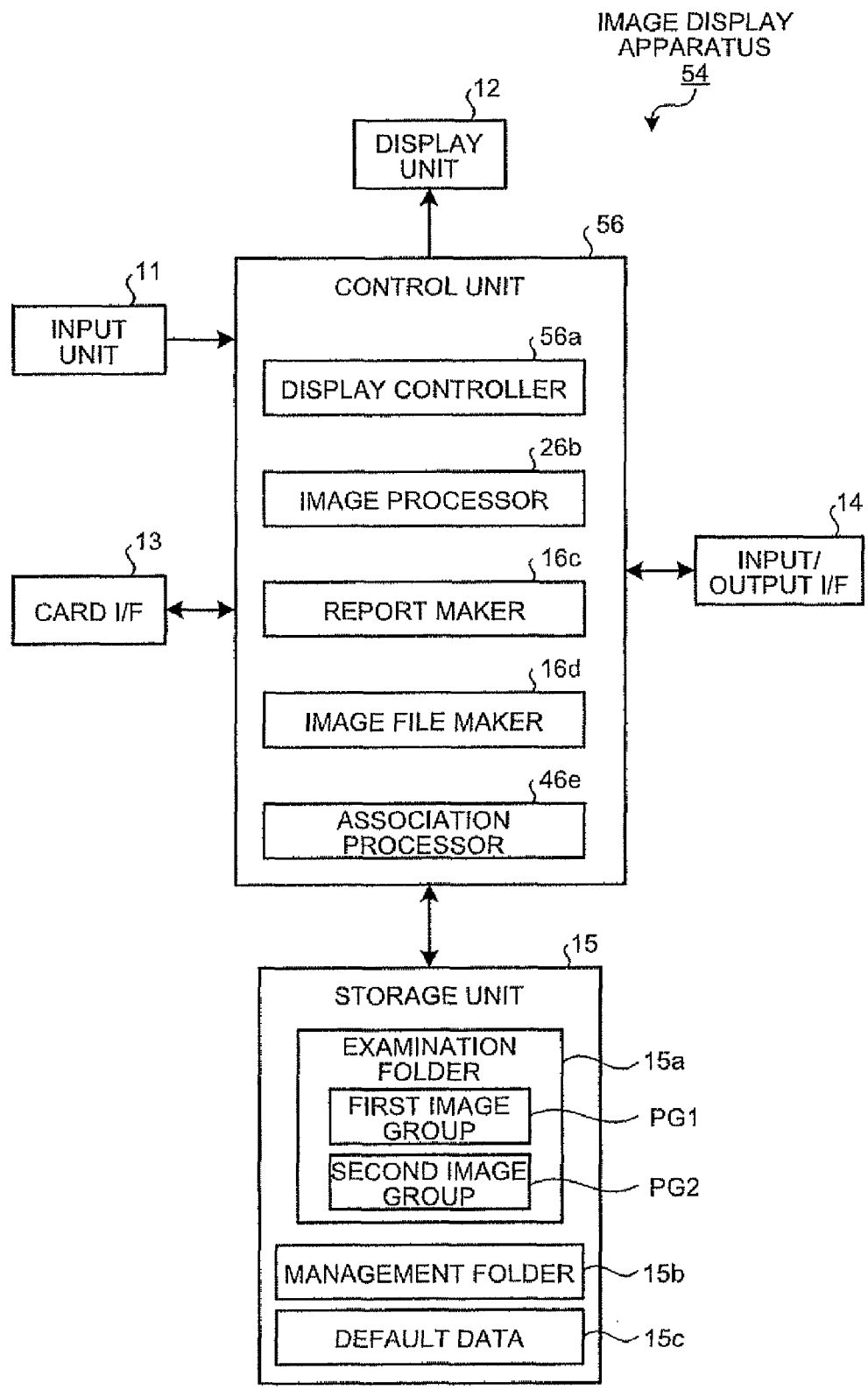
FIG. 26 is a block diagram exemplarily showing a configuration example of an image display apparatus according to a fifth embodiment of the present invention.
Figure 27:
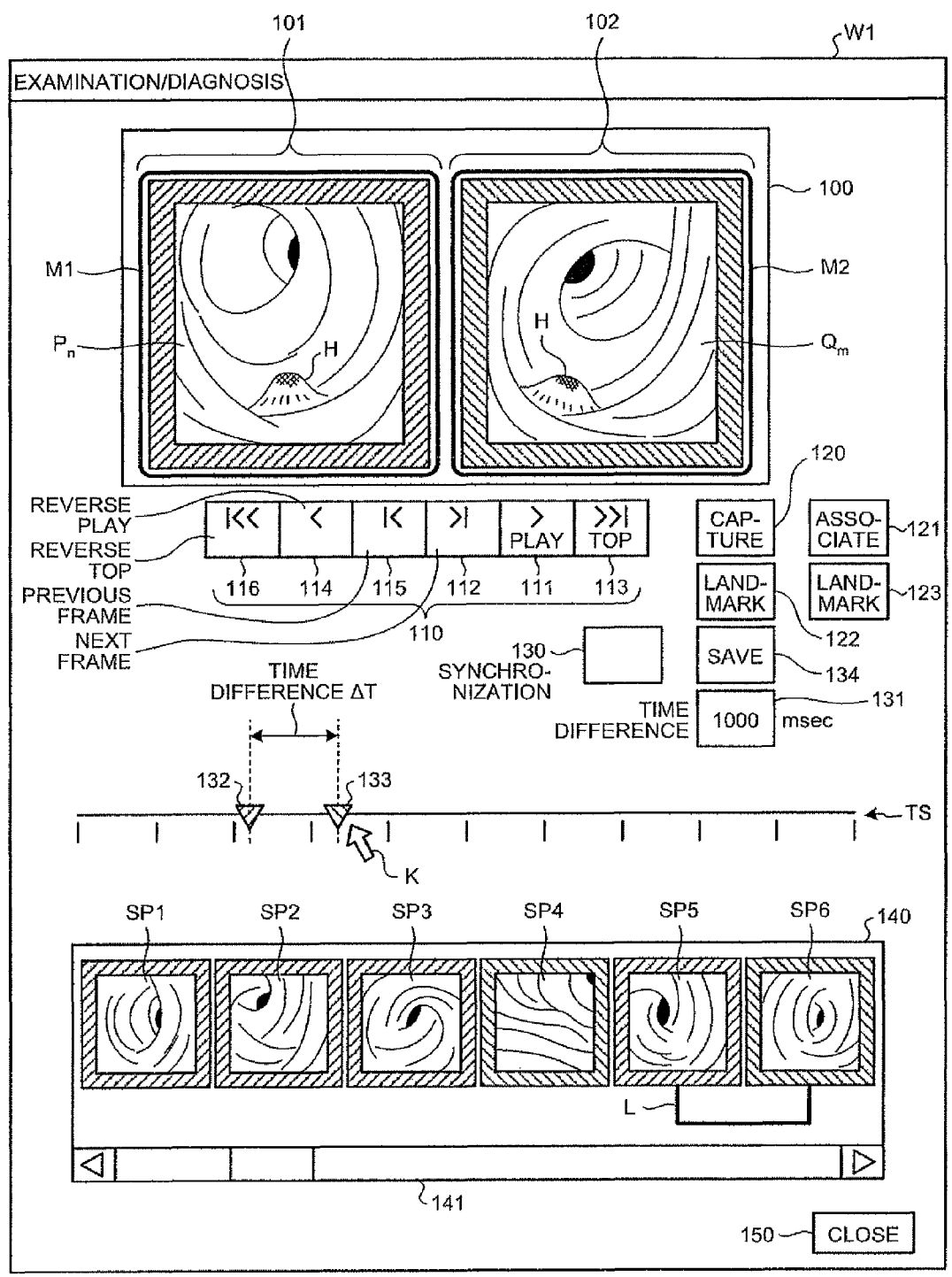
FIG. 27 is a schematic diagram exemplarily showing a specific example of various GUIs displayed in a display unit of the image display apparatus according to the fifth embodiment.

FIG. 26 is a block diagram exemplarily showing a configuration example of an image display apparatus according to the fifth embodiment of the present invention. FIG. 27 is a schematic diagram exemplarily showing a specific example of various GUIs displayed in the display unit of the image display apparatus according to the fifth embodiment. As shown in FIG. 26, an image display apparatus 54 has a control unit 56 in place of the control unit 46 of the image display apparatus 44 according to the fourth embodiment. The control unit 56 has a display controller 56a in place of the display controller 36a of the control unit 46 of the image display apparatus 44. Also, as shown in FIG. 27, further a landmark icon 122, which is a GUI for characterizing the image $P_n$ displayed in the display area 101, and a landmark icon 123, which is a GUI for characterizing the image $Q_m$ displayed in the display area 102, are formed in the window W1 displayed in the display unit 12. In the fifth embodiment, a selected state of the display area 101 is made switchable in normal display mode by a click operation of the display area 101 to enable image display operations of the display area 101 in the selected state. Also, a selected state of the display area 102 is made switchable in normal display mode by a click operation of the display area 102 to enable image display operations of the display area 102 in the selected state. Other components are the same as those in the fourth embodiment and the same reference numerals are attached to the same components.

An intra-subject information acquisition system using the image display apparatus 54 according to the fifth embodiment is realized by using the image display apparatus 54 in place of the image display apparatus 4 of the intra-subject information acquisition system according to the first embodiment exemplified in FIG. 1.

The control unit 56 has almost the same function as that of the control unit 46 of the image display apparatus 44 according to the fourth embodiment. In this case, the control unit 56 selects in normal display mode one of enable and disable of image display operations for the display area 101 to display the image $P_n$ and also selects in normal display mode one of enable and disable of image display operations for the display area 102 to display the image $Q_m$.

The display controller 56a has almost the same function as that of the display controller 36a of the image display apparatus 44 according to the fourth embodiment. In this case, the display controller 56a can perform image display control of the display areas 101 and 102 of the main image display area 100 separately. More specifically, if the display area 101 is set to the selected state in normal display mode by a click operation of the display area 101 using the input unit 11, the display controller 56a enables image display operations of the display area 101 in the selected state and, if the display area 101 is set to the non-selected state by a click operation of the display area 101 using the input unit 11, the display controller 56a disables image display operations of the display area 101 in the non-selected state. In this case, the display area 101 functions as a setting GUI for setting the selected state or non-selected state by a click operation using the input unit 11.

Similarly, if the display area 102 is set to the selected state in normal display mode by a click operation of the display area 102 using the input unit 11, the display controller 56a enables image display operations of the display area 101 in the selected state and, if the display area 102 is set to the non-selected state by a click operation of the display area 102 using the input unit 11, the display controller 56a disables image display operations of the display area 102 in the non-selected state. In this case, the display area 102 functions as a setting GUI for setting the selected state or non-selected state by a click operation using the input unit 11.

According to a click operation of the landmark icon 122, the display controller 56a also performs control to display a landmark M1 characterizing the desired image $P_n$ displayed in the display area 101, for example, around the display area 101 based on instruction information input from the input unit 11 by a click operation of the landmark icon 122. In this case, the landmark icon 122 functions as a setting GUI for setting the landmark M1 characterizing the desired image $P_n$. The landmark icon 122 is enabled when the display area 101 is set to the selected state (that is, image display operations are enabled) and disabled when the display area 101 is set to the non-selected state (that is, image display operations are disabled).

Further, according to a click operation of the landmark icon 123, the display controller 56a performs control to display a landmark M2 characterizing the desired image $Q_m$ displayed in the display area 102, for example, around the display area 102 based on instruction information input from the input unit 11 by a click operation of the landmark icon 123. In this case, the landmark icon 123 functions as a setting GUI for setting the landmark M2 characterizing the desired image $Q_m$. The landmark icon 123 is enabled when the display area 102 is set to the selected state (that is, image display operations are enabled) and disabled when the display area 102 is set to the non-selected state (that is, image display operations are disabled).

The images $P_n$ and $Q_m$ characterized by the landmarks M1 and M2 may be, for example, images of the stomach or small intestine, or those in which a characteristic portion such as a lesion site and hemorrhagic site is picked up.

Figure 28:
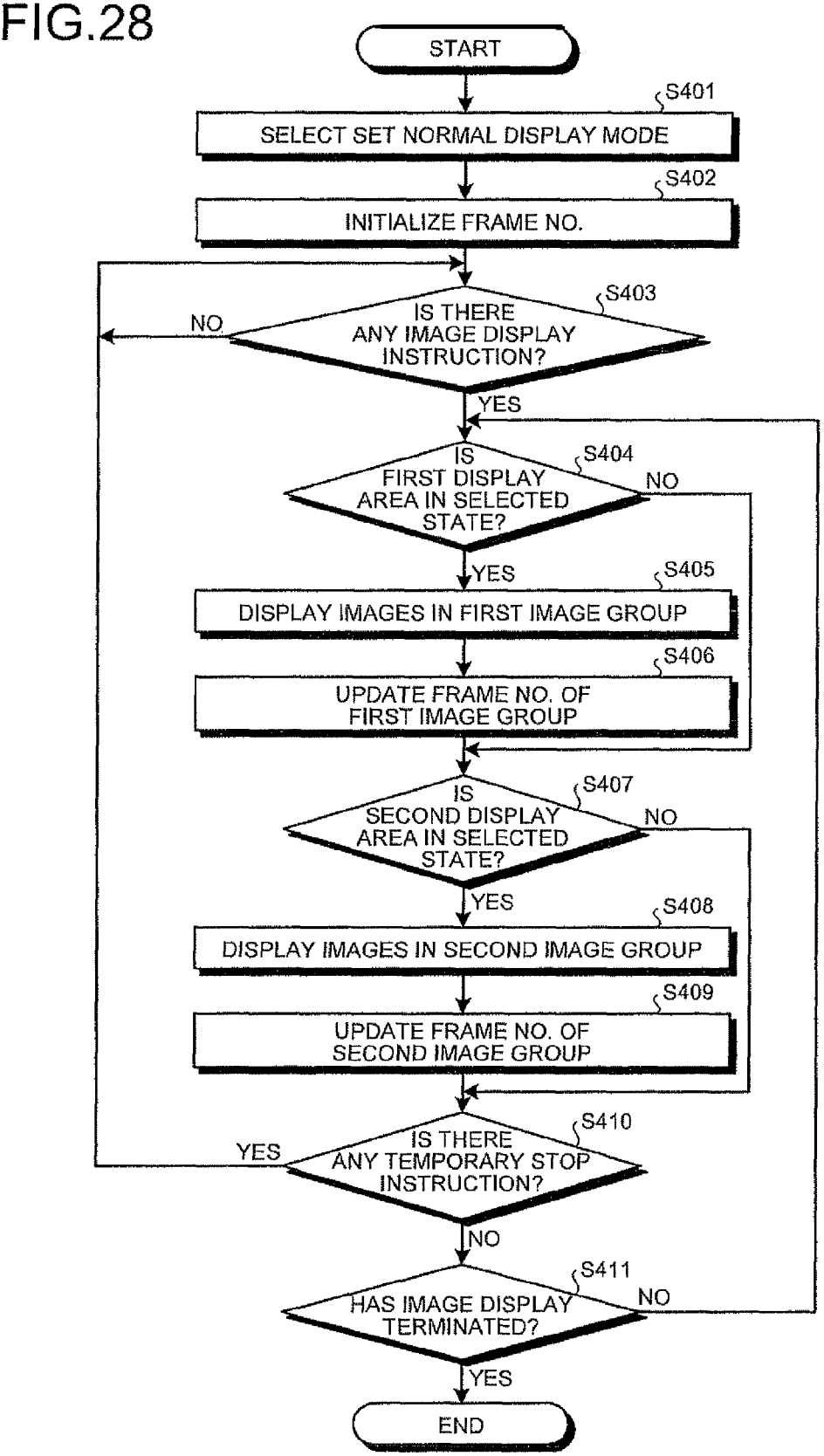
FIG. 28 is a flowchart illustrating a processing procedure by the control unit that make an image displayed in each display area in a selected state in a normal display mode.

Next, the operation of the control unit 56 controlling to display the images $P_n$ and $Q_m$ in the display areas 101 and 102 in the selected state in normal display mode respectively will be described. FIG. 28 is a flowchart illustrating the processing procedure by the control unit 56 that makes the images $P_n$ and $Q_m$ respectively displayed in the display areas 101 and 102 in the selected state in the normal display mode.

In FIG. 28, the control unit 56 first selects the normal display mode set by another click operation of the synchronization icon 130 as the image display mode (step S401). In this case, the display controller 56a selects the normal display mode from among a plurality of image display modes based on setting information input from the input unit 11 by another click operation of the synchronization icon 130.

Next, the control unit 56 initializes both the frame number n of the first image group PG1 and the frame number m of the second image group PG2 (step S402). In this case, the display controller 56a initializes the frame number n of the image to be processed for display from the first image group PG1 (for example, n=0). The display controller 56a also initializes the frame number m of the image to be processed for display from the second image group PG2 (for example, m=0).

Then, approximately as same in step S205, the control unit 56 determines whether or not any image display instruction corresponding to any one of the display operation icon group 110 has been issued (step S403) More specifically, if no display instruction information corresponding to the display operation icon group 110 has been input from the input unit 11, the control unit 56 determines that there is no image display instruction of the images $P_n$ and $Q_m$ (step S403, No) and repeats step S403. That is, the control unit 56 repeats step S403 until such display instruction information is input by the input unit 11.

If, on the other hand, such display instruction information has been input by the input unit 11, the control unit 56 determines that there is an image display instruction of the images $P_n$ and $Q_m$ based on the input display instruction information (step S403, Yes) and determines whether or not the display area 101 (first display area) for displaying the image $P_n$ is set at the selected state (step S404). More specifically, the display area 101 sets the selected state when a click operation is performed by the input unit 11 and sets the non-selected state when another click operation is performed by the input unit 11. That is, the control unit 56 determines that the display area 101 is in the selected state if setting information of the selected state is input by the input unit 11 by one click operation to the display area 101 and that the display area 101 is not in the selected state (that is, in the non-selected state) if setting information of the non-selected state is input by the input unit 11 by another click operation to the display area 101.

If the display area 101 is determined to be in the selected state (step S404, Yes), the display controller 56*a* enables image display operations to the display area 101 and also makes the image P$_n$ of the current frame number n displayed in the display area 101 based on display instruction information input by the input unit 11 (step S405). In this case, the display controller 56*a* performs control to extract the image P$_n$ of the current frame number n (n=0, 1, 2, 3, . . . ) from the first image group PG1 saved in the storage unit 15 and to display the extracted image P$_n$ in the display area 101.

The current frame number n at step S405 is the frame number n (n=0) initialized at step S402 or a frame number n updated at step S406 described later.

Then, as same in step S207, the controller 56 updates the frame number n of the first image group PG1 (step S406). In this case, the display controller 56*a* updates (for example, addition of +1) the frame number n of the first image group PG1 to read the image P$_n$ to be displayed in the display area 101 at next step S405 from the storage unit 15.

Next, the control unit 56 determines whether or not the display area 102 (second display area) for displaying the image Q$_m$ is set at the selected state (step S407). More specifically, the display area 102 sets the selected state when a click operation is performed by the input unit 11 and sets the non-selected state when another click operation is performed by the input unit 11. That is, the control unit 56 determines that the display area 102 is in the selected state if setting information of the selected state is input by the input unit 11 by one click operation to the display area 102 and that the display area 102 is not in the selected state (that is, in the non-selected state) if setting information of the non-selected state is input by the input unit 11 by another click operation to the display area 102.

If the display area 102 is determined to be in the selected state (step S407, Yes), the display controller 56*a* enables image display operations to the display area 102 and also makes the image Q$_m$ of the current frame number m displayed in the display area 102 based on display instruction information input by the input unit 11 (step S408). In this case, the display controller 56*a* performs control to extract the image Q$_m$ of the current frame number m (m=0, 1, 2, 3, . . . ) from the second image group PG2 saved in the storage unit 15 and to display the extracted image Q$_m$ in the display area 102.

The current frame number m at step S408 is the frame number m (m=0) initialized at step S402 or a frame number m updated at step S409 described later.

Then, as same in step S209, the controller 56 updates the frame number m of the second image group PG2 (step S409). In this case, the display controller 56*a* updates (for example, addition of +1) the frame number m of the second image group PG2 to read the image Q$_m$ to be displayed in the display area 102 at next step S408 from the storage unit 15.

Next, the control unit 56 determines whether or not any temporary stop instruction to the control to display the images P$_n$ and Q$_m$ in the display areas 101 and 102 in the selected state has been issued (step S410). More specifically, if display instruction information corresponding to one of the frame advance icon 112, the top search icon 113, the previous frame icon 115, and the review search icon 116 is input from the input unit 11 at step S403, the control unit 56 determines that a temporary stop instruction has been issued (step S410, Yes). In this case, the control unit 56 returns to step S403 to repeat the processing procedure of step S403 and onward.

If, on the other hand, display instruction information corresponding to one of the play icon 111 and the reverse play icon 114 is input from the input unit 11 at step S403, the control unit 56 determines that no temporary stop instruction has been issued (step S410, No). In this case, the control unit 56 determines whether or not image display processing of the images P$_n$ and Q$_m$ in normal display mode has terminated (step S411).

More specifically, if the frame number n updated at step S406 is equal to or greater than the number of frames in the first image group PG1, the control unit 56 determines that image display processing of the display area 101 in the selected has terminated (step 8411, Yes) and completes the image display processing of the display area 101. Also, if the frame number m updated at step S409 is equal to or greater than the number of frames in the second image group PG2, the control unit 56 determines that image display processing of the display area 102 in the selected has terminated (step S411, Yes) and completes the image display processing of the display area 102.

If, on the other hand, the frame number n updated at step S406 is less than the number of frames in the first image group P01, the control unit 56 determines that image display processing of the display area 101 in the selected state has not terminated (step S411, No) and returns to step S404. Also, if the frame number m updated at step S409 is less than the number of frames in the second image group PG2, the control unit 56 determines that image display processing of the display area 102 in the selected state has not terminated (step S411, No) and returns to step S404. Then, the control unit 56 repeats the processing procedure of step S404 and onward.

If the display area 101 is determined not to be in the selected state at step S404 (step 404, No), the display controller 56*a* proceeds to step S407 by skipping the processing procedure at step S405 and step S406. Then, the control unit 56 repeats the processing procedure at step S407 and onward. If the display area 102 is determined not to be in the selected state at step S407 (step 407, No), the display controller 56*a* proceeds to step S410 by skipping the processing procedure at step S408 and step S409. Then, the control unit 56 repeats the processing procedure at step S410 and onward.

Figure 29:
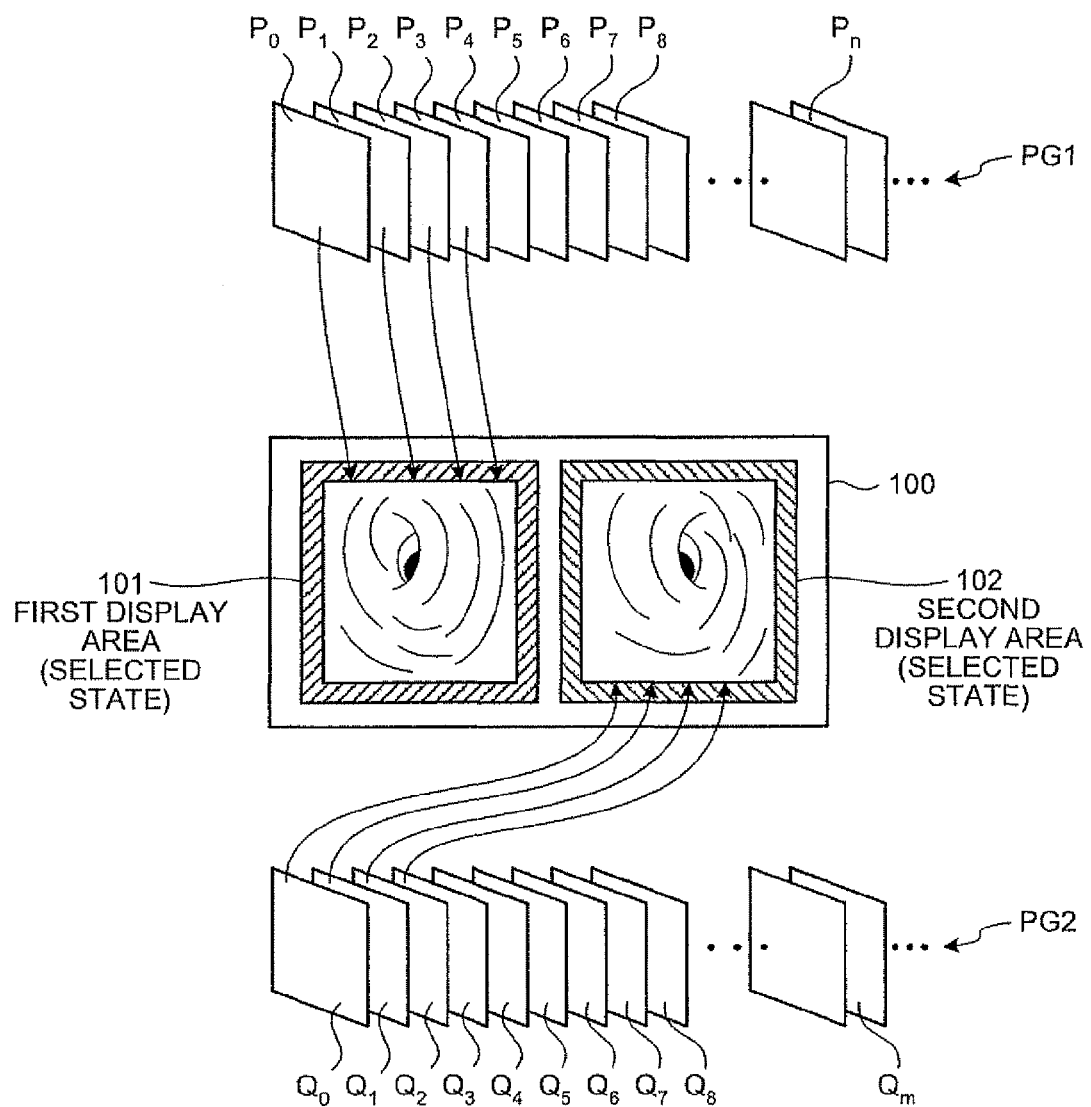
FIG. 29 is a schematic diagram illustrating operation of the control unit controlling image display processing when both display areas are set in a selected state in the normal display mode.
Figure 30:
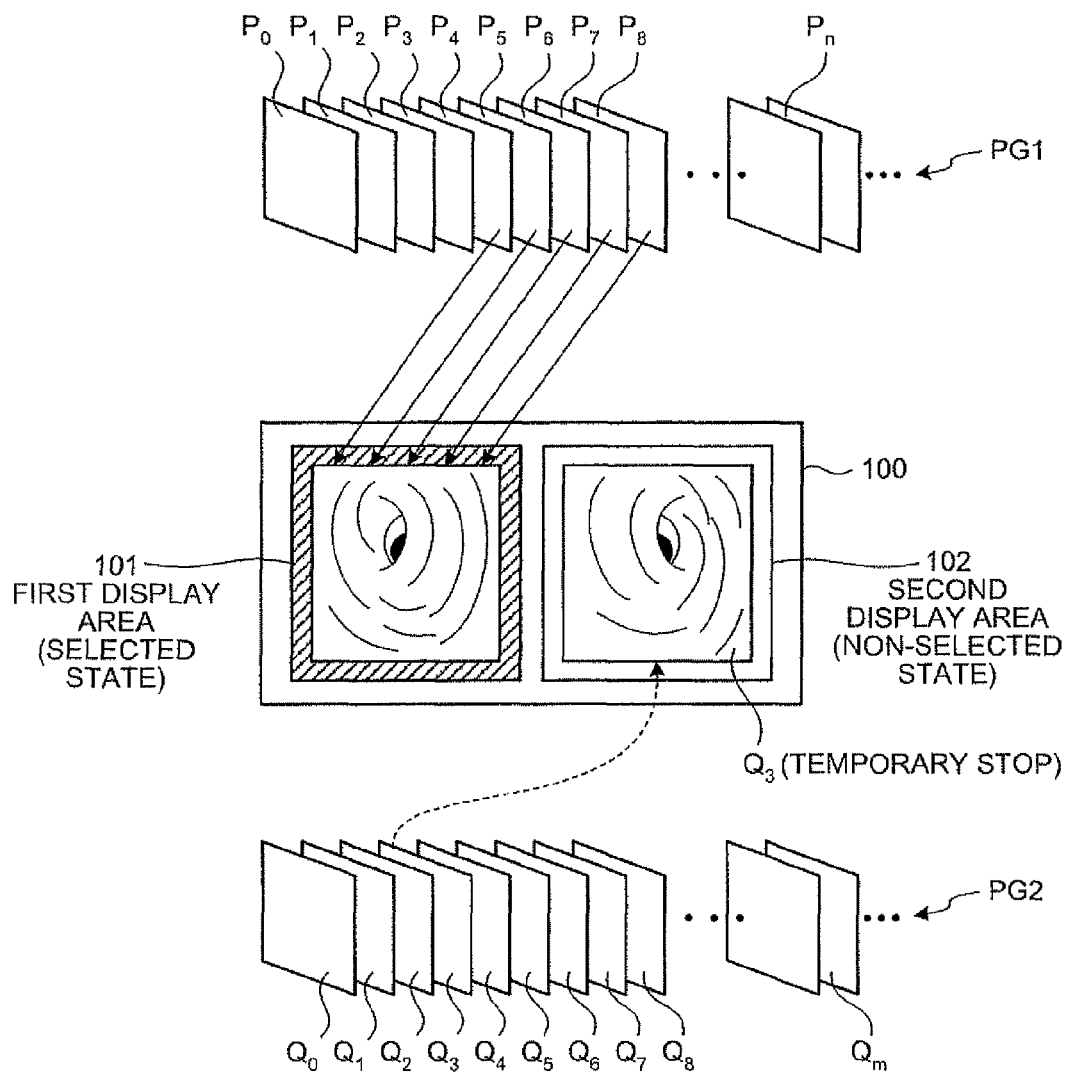
FIG. 30 is a schematic diagram illustrating operation of the control unit controlling image display processing separately when only one display area is set in the selected state in the normal display mode.
Figure 31:
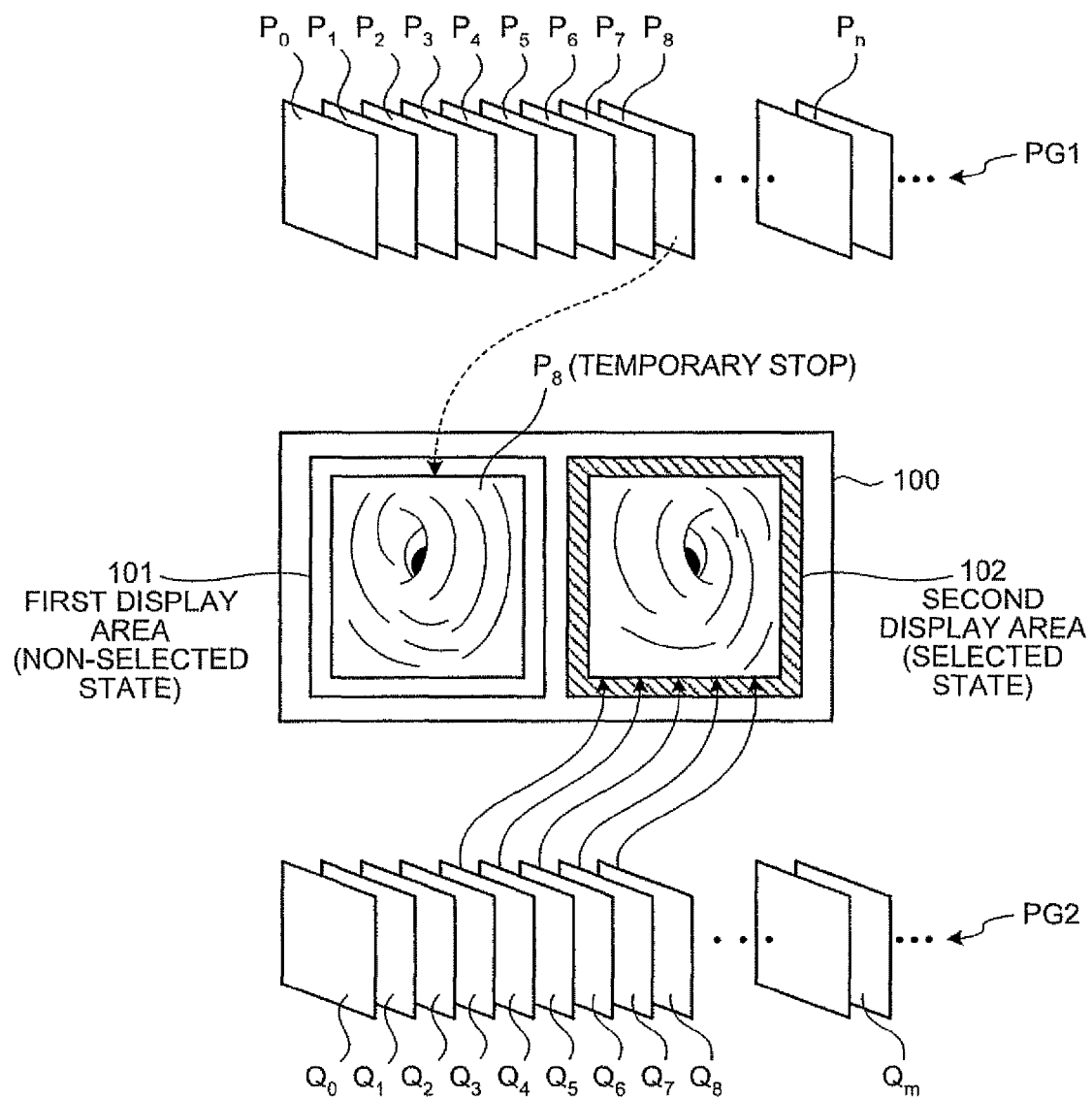
FIG. 31 is a schematic diagram illustrating operation of the control unit controlling image display processing separately when only the other display area is set in the selected state in the normal display mode.

Next, the operation of the control unit 56 controlling to display the images P$_n$ and Q$_m$ in the display areas 101 and 102 in the selected state in normal display mode respectively will be specifically described. FIG. 29 is a schematic diagram illustrating the operation of the control unit 56 controlling image display processing when both the display areas 101 and 102 are set at the selected state in normal display mode. FIG. 30 is a schematic diagram illustrating the operation of the control unit 56 controlling image display processing individually when only the display area 101 is set at the selected state in normal display mode. FIG. 31 is a schematic diagram illustrating the operation of the control unit 56 controlling image display processing individually when only the display area 102 is set at the selected state in normal display mode.

As shown in FIG. 29, when both the display areas 101 and 102 are set at the selected state, the control unit 56 enables image display operations for both the display areas 101 and 102 in the selected state and controls display processing of the images P$_n$ and Q$_m$ based on display instruction information corresponding to one of the display operation icon group 110. More specifically, the display controller 56*a* highlights the display area 101 (first display area) in the selected state to indicate that the display area 101 is in the selected state and also makes the image P$_n$ (n=0, 1, 2, 3, . . . ) in the first image group PG1 sequentially displayed in the display area 101 in the selected state. In this case, based on control of the display controller 56*a*, for example, the images $P_0$, $P_1$, $P_2$, and $P_3$, are sequentially displayed in the display area 101 in the selected state.

The display controller 56*a* also highlights the display area 102 (second display area) in the selected state to indicate that the display area 102 is in the selected state and makes the image $Q_m$ (m=0, 1, 2, 3, . . . ) in the second image group PG2 sequentially displayed in the display area 102 in the selected state. In this case, based on control of the display controller 56*a*, for example, the images $Q_0$, $Q_1$, $Q_2$, and $Q_3$ are sequentially displayed in the display area 102 in the selected state in synchronization with the images $P_0$, $P_1$, $P_2$, and $P_3$ respectively.

Then, if only the display area 101 is set to the selected state, as shown in FIG. 30, the control unit 56 enables image display operations only for the display area 101 in the selected state and individually controls display processing of the image $P_n$ based on display instruction information corresponding to one of the display operation icon group 110. More specifically, the display controller 56*a* highlights only the display area 101 in the selected state to indicate that the display area 101 is in the selected state and makes only the image $P_n$ in the first image group PG1 sequentially displayed in the display area 101 in the selected state. In this case, based on control of the display controller 56*a*, for example, the images $P_4$, $P_5$, $P_6$, $P_7$, and $P_8$, are sequentially displayed in the display area 101 in the selected state.

Here, the control unit 56 disables image display operations for the display area 102 set at the non-selected state to set the display area 102 in the non-selected state to a temporary stop state of image display processing or an image non-display state. In this case, the display controller 56*a* performs control to display the image (for example, the image $Q_3$) displayed in the display area 102 immediately before being set to the non-selected state in the temporary stop state. Or, the display controller 56*a* may perform control to perform deletion processing of the image in the display area 102 in the non-selected state to set the display area 102 in the non-selected state to the image non-display state.

Then, if only the display area 102 is set to the selected state, as shown in FIG. 31, the control unit 56 enables image display operations only for the display area 102 in the selected state and individually controls display processing of the image $Q_m$ based on display instruction information corresponding to one of the display operation icon group 110. More specifically, the display controller 56*a* highlights only the display area 102 in the selected state to indicate that the display area 102 is in the selected state and also makes only the image $Q_m$ (m=0, 1, 2, 3, . . . ) in the second image group PG2 sequentially displayed in the display area 102 in the selected state. In this case, based on control of the display controller 56*a*, for example, the images $Q_4$, $Q_5$, $Q_6$, $Q_7$, and $Q_8$, are sequentially displayed in the display area 102 in the selected state.

Here, the control unit 56 disables image display operations for the display area 101 set at the non-selected state to set the display area 101 in the non-selected state to a temporary stop state of image display processing or an image non-display state. In this case, the display controller 56*a* performs control to display the image (for example, the image $P_8$) displayed in the display area 101 immediately before being set to the non-selected state in the temporary stop state. Or, the display controller 56*a* may perform control to perform deletion processing of the image in the display area 101 in the non-selected state to set the display area 101 in the non-selected state to the image non-display state.

If a click operation of the capture icon 120 is performed by the input unit 11 in the image display apparatus 54 according to the fifth embodiment, a thumbnail image (or thumbnail images) of an image (or images) displayed in the displayed area(s) of the display area 101 and 100 set at the selected state of the main image display area 100 is (are) created, and the created thumbnail image (thumbnail images) is (are) added to the sub-image display area 140 before being displayed. In this case, based on instruction information input from the input unit 11 by a click operation of the capture icon 120, the image processor 26*b* creates a thumbnail image (or thumbnail images) of an image (or images) displayed in the displayed area(s) of the display areas 101 and 102 in the selected state. That is, if the display area 101 is set at the selected state, the image processor 26*b* creates a thumbnail image of the image $P_n$ displayed in the display area 101 in the selected state, if the display area 102 is set at the selected state, the image processor 26*b* creates a thumbnail image of the image $Q_m$ displayed in the display area 102 in the selected state, and if both the display areas 101 and 102 are set at the selected state, the image processor 26*b* creates each thumbnail image of the images $P_n$ and $Q_m$ displayed in the display areas 101 and 102 in the selected state respectively.

The fifth embodiment of the present invention has, as described above, the configuration of the fourth embodiment. Further, the fifth embodiment is configured in such a way that enable or disable of image display operations is individually set for a plurality of display areas formed in a display unit so that images contained in desired image groups among a plurality of image groups inside a subject picked up by a group of imaging devices mounted on a multiple-lens capsule endoscope are sequentially displayed in enabled display areas. Thus, the operation effect of the fourth embodiment can be achieved and also an image display apparatus capable of sequentially displaying each image contained in desired image groups in display areas while stopping display processing of unnecessary image groups can be realized.

By using an image display apparatus according to the fifth embodiment of the present invention, a user can concentrate his (her) consciousness on desired image groups without being distracted by unnecessary image groups among a plurality of image groups picked up by a group of imaging devices mounted on a multiple-lens capsule endoscope and, as a result, can easily observe images inside a subject.

Figure 37:
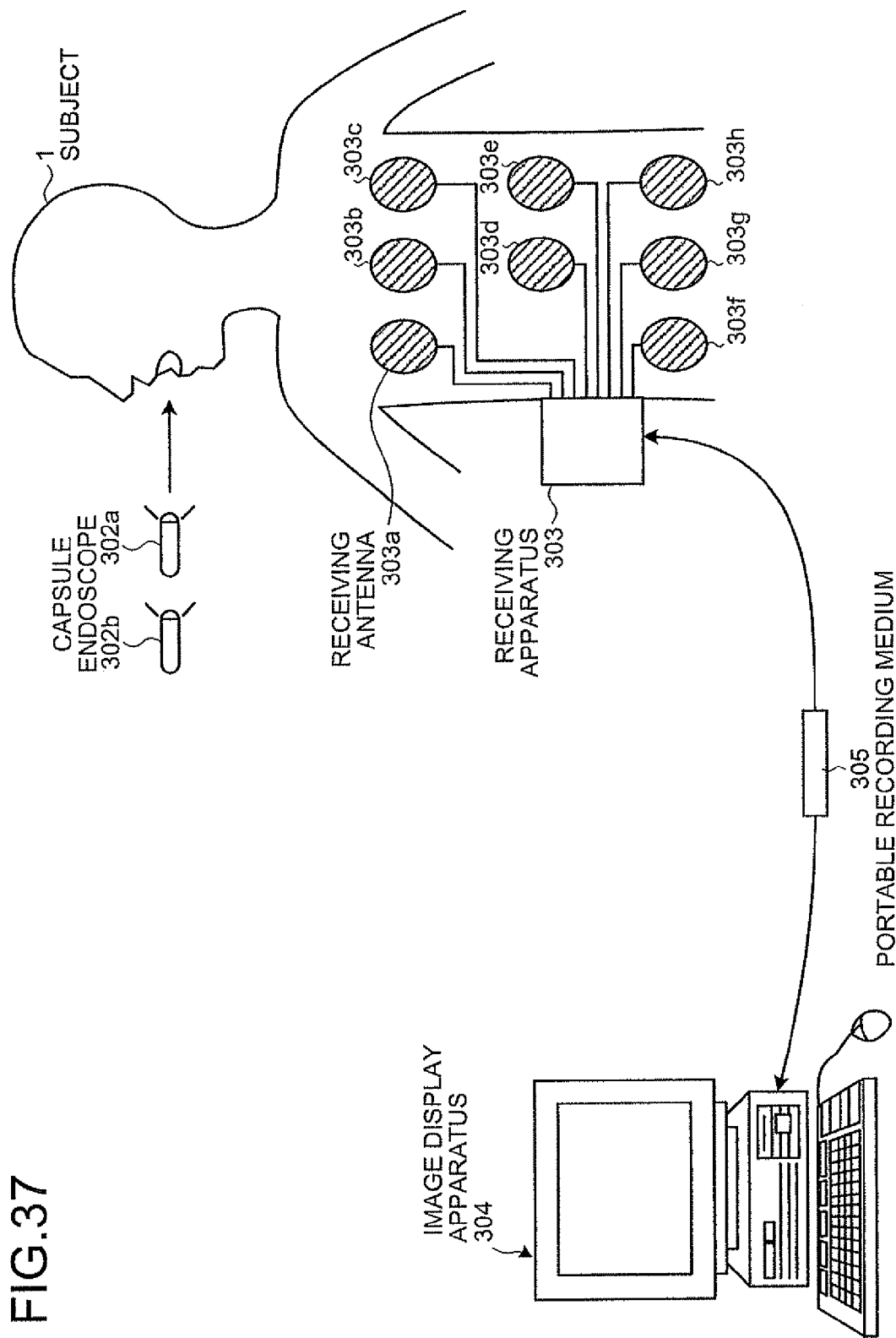
FIG. 37 is a schematic diagram showing a configuration example of the intra-subject information acquisition system having an image display apparatus according to a sixth embodiment of the present invention.

Next, the sixth embodiment of the present invention will be described. FIG. 37 is a schematic diagram showing a configuration example of an intra-subject information acquisition system having an image display apparatus according to the sixth embodiment of the present invention. As shown in FIG. 37, the intra-subject information acquisition system includes capsule endoscopes 302*a* and 302*b* that move through organs of the subject 1 and pick up images inside the subject 1, a receiving apparatus 303 for receiving a radio signal transmitted by the capsule endoscopes 302*a* and 302*b* to accumulate image groups inside the subject 1 contained in the received radio signal, an image display apparatus 304 for displaying images of the subject 1 contained in image groups accumulated in the receiving apparatus 303, and a portable recording medium 305 for passing data between the receiving apparatus 303 and the image display apparatus 304.

The capsule endoscopes 302*a* and 302*b* have an imaging function to sequentially pick up images inside the subject 1 (more specifically, images inside organs) and a radio communication function to transmit an image group picked up inside the subject 1 to the external receiving apparatus 303 by radio. More specifically, the capsule endoscopes 302*a* and 302*b* are sequentially introduced into the subject 1 by leaving a predetermined interval (for example, several hours or longer) between the capsule endoscopes 302*a* and 302*b* to move through organs of the subject 1 by peristaltic movement and also to pick up images inside organs of the subject 1. In this case, each imaging device such as CCD mounted in each of the capsule endoscopes 302a and 302b sequentially picks up images inside the subject 1, for example, at the same frame rate. Each of the capsule endoscopes 302a and 302b sequentially transmits a radio signal including images inside the subject 1 picked up by the imaging device and ID information specific to each imaging device to the external receiving apparatus 303.

The receiving apparatus 303 is connected, for example, to a plurality of receiving antennas 303a to 303h arranged over the body surface of the subject 1 and receives a radio signal from each of the capsule endoscopes 302a and 302b via any of the plurality of receiving antennas 303a to 303h. Based on the radio signal received from the capsule endoscope 302a, the receiving apparatus 303 acquires images inside the subject 1 picked up by the imaging device of the capsule endoscope 302a and ID information of the imaging device. Likewise, based on the radio signal received from the capsule endoscope 302b, the receiving apparatus 303 acquires images inside the subject 1 picked up by the imaging device of the capsule endoscope 302b and ID information of the imaging device.

The receiving apparatus 303 has the portable recording medium 305 detachably inserted therein. The receiving apparatus 303 sequentially stores images inside the subject 1 picked up by the imaging device of the capsule endoscope 302a, the receiving number showing the reception sequence of images inside the subject 1, and ID information of the imaging device of the capsule endoscope 302a in the portable recording medium 305. Thus, the receiving apparatus 303 accumulates image groups inside the subject 1 picked up along time series by the imaging device of the capsule endoscope 302a in the portable recording medium 305 by associating with the receiving number of each image and ID information of the imaging device of the capsule endoscope 302a. Likewise, the receiving apparatus 303 accumulates image groups inside the subject 1 picked up along time series by the imaging device of the capsule endoscope 302b in the portable recording medium 305 by associating with the receiving number of each image and ID information of the imaging device of the capsule endoscope 302b.

The receiving antennas 303a to 303h are realized by using, for example, a loop antenna and receive each radio signal transmitted by each of the capsule endoscopes 302a and 302b. As shown in FIG. 37, the receiving antennas 303a to 303h are arranged at predetermined positions over the body surface of the subject 1, for example, at positions corresponding to the passing route (that is, the digestive tract) of the capsule endoscopes 302a and 302b inside the subject 1. The receiving antennas 303a to 303h may also be arranged at predetermined positions of a jacket to be worn by the subject 1. In this case, the receiving antennas 303a to 303h are arranged at predetermined positions over the body surface of the subject 1 corresponding to the passing route of the capsule endoscope 302a, 302b inside the subject 1 by the jacket being worn by the subject 1. Only one or more such receiving antennas need to be arranged for the subject 1 and the number of arranged antennas is not limited to eight.

The portable recording medium 305 is a recording medium that can be carried such as CompactFlash (registered trademark). The portable recording medium 305 is detachable from the receiving apparatus 303 and the image display apparatus 304 and has a structure enabling output and recording of data when inserted in the receiving apparatus 303 or the image display apparatus 304. More specifically, when inserted in the receiving apparatus 303, the portable recording medium 305 sequentially stores a plurality of image groups inside the subject 1 acquired by the receiving apparatus 303, ID information of each imaging device of the capsule endoscopes 302a and 302b associated with each image contained in the plurality of image groups and receiving numbers. When inserted in the image display apparatus 304, on the other hand, the portable recording medium 305 outputs saved data such as the plurality of image groups inside the subject 1, ID information of each imaging device, and the receiving number of each image to the image display apparatus 304. In this manner, the saved data in the portable recording medium 305 is taken into the image display apparatus 304. Information such as a patient ID and examination date of the subject 1 is written into the portable recording medium 305 by the image display apparatus 304.

The image display apparatus 304 is used to display images inside organs of the subject 1 picked up by the capsule endoscopes 302a and 302b. More specifically, the image display apparatus 304 has a configuration such a workstation that acquires various kinds of data such as image groups inside the subject 1 by capturing various kinds of data accumulated in the portable recording medium 305 by the receiving apparatus 303 and displays images inside the subject 1 contained in the acquired data groups. In this case, the image display apparatus 304 classifies the acquired image groups inside the subject 1 by imaging device of the capsule endoscopes 302a and 302b and then saves a plurality of image groups classified by imaging device in the storage unit. The image display apparatus 304 has an image display function to display each image similar to one another among the plurality of image groups classified as described above (for example, each image in which a mutually neighboring site inside the subject 1 is picked up) by switching such images, Further, the image display apparatus 304 has a processing function allowing a user such as physician or a nurse to diagnose the subject 1 by observing (examining) images inside the subject 1. In this case, the user sequentially makes the image display apparatus 304 display images inside the subject 1 to observe (examine) sites inside the subject 1, for example, the esophagus, stomach, small intestine, and large intestine and can diagnose the subject 1 based on the observation (examination).

Figure 38:
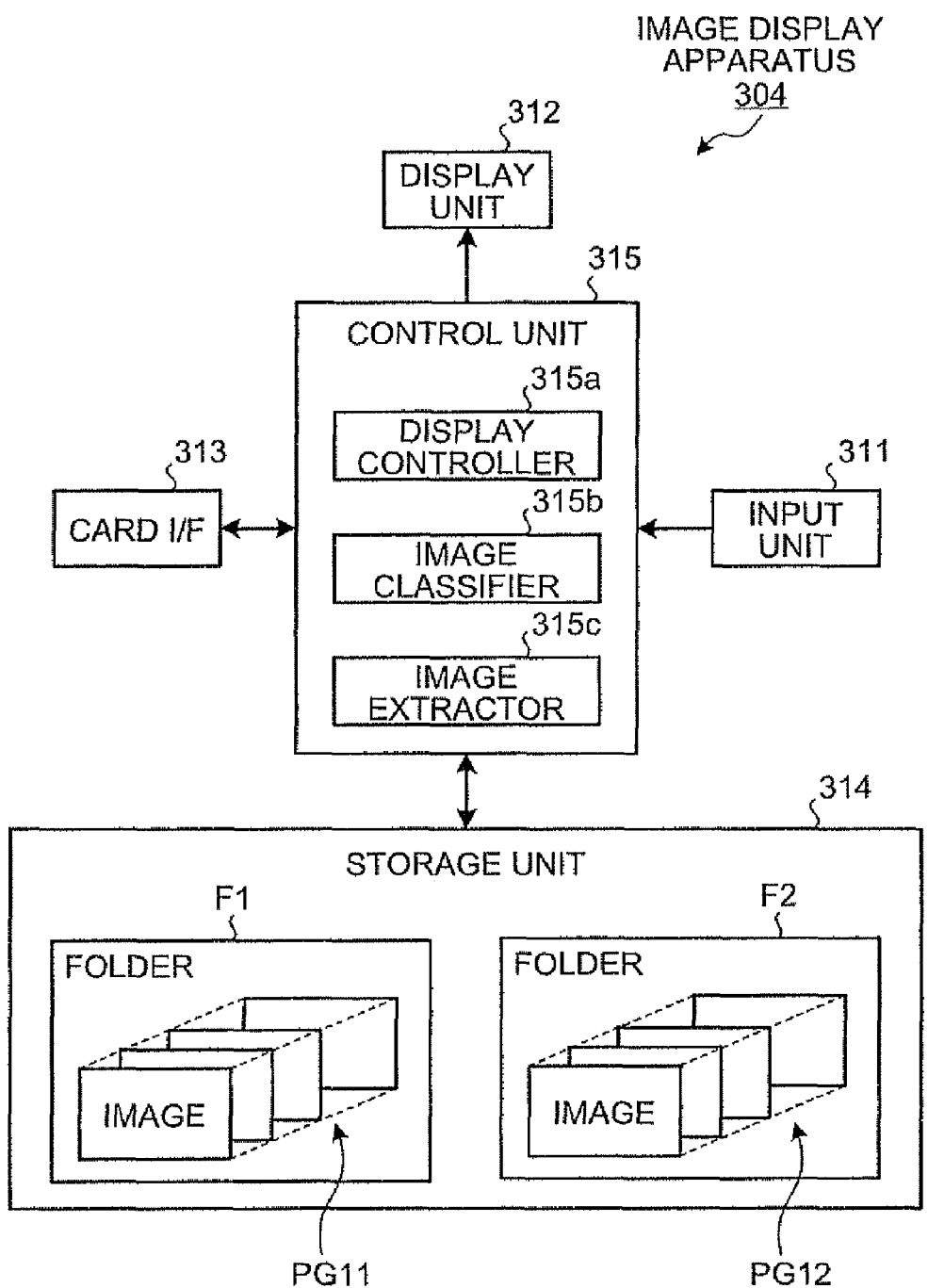
FIG. 38 is a block diagram exemplarily showing a configuration example of the image display apparatus according to the sixth embodiment of the present invention.

Next, the configuration of the image display apparatus 304 according to the sixth embodiment of the present invention will be described. FIG. 38 is a block diagram exemplarily showing a configuration example of the image display apparatus 304 according to the sixth embodiment of the present invention. As shown in FIG. 38, the image display apparatus 304 according to the embodiment 6 has an input unit 311 for inputting various kinds of information, a display unit 312 for displaying images inside the subject 1, GUIs (Graphical User Interface) and the like in a screen, and a card interface (I/F) 313 for capturing saved data such as images inside the subject 1 from the portable recording medium 305. The image display apparatus 304 also has a storage unit 314 for storing the plurality of image groups of the subject 1 classified by imaging device of the capsule endoscopes 302a and 302b and a control unit 315 for controlling each component of the image display apparatus 304.

The input unit 311 is realized by using an input device such as a keyboard or a mouse and various kinds of information are input to the control unit 315 by user's input operations. Information input to the control unit 315 by the input unit 311 includes instruction information instructing the control unit 315, patient information about the subject 1, and selection information selecting an image group of the subject 1 from a plurality of image groups to be displayed in the display unit 312.

The display unit 312 is realized by using various kinds of displays such as a CRT display and liquid crystal display and displays various kinds of information instructed to display by the control unit 315. More specifically, the display unit 312 displays various kinds of information needed for observation and diagnosis of the subject 1, for example, images inside the subject 1 contained in a plurality of image groups picked up by each imaging device of the capsule endoscopes 302a and 302b. The display unit 312 also displays selection GUIs for selecting an image group to be displayed from the plurality of image groups and display operation GUIs for performing display operations of the image group selected by the selection GUIs.

The card I/F 313 is used to take in saved data of the portable recording medium 305. More specifically, when the portable recording medium 305 is detachably inserted, the card I/F 313 reads saved data accumulated in the portable recording medium 305 and also transfers the acquired saved data to the control unit 315. The card I/F 313 also writes information instructed by the control unit 315 to write, for example, patient information of the subject 1 to the portable recording medium 305.

The storage unit 314 is realized by a RAM, EEPROM, hard disk or the like and saves data instructed to write by the control unit 315 and transmits saved data instructed to read by the control unit 315. The storage unit 314 as described above functions as a storage unit for storing a plurality of image groups inside the subject 1 classified by imaging device of the capsule endoscopes 302a and 302b and identification information for identifying each image contained in the plurality of image groups. More specifically, the storage unit 314 saves an image group PG11 inside the subject 1 picked by the imaging device of the capsule endoscope 302a and identification information of each image contained in the image group PG11 in a folder F1 and an image group PG12 inside the subject 1 picked by the imaging device of the capsule endoscope 302b and identification information of each image contained in the image group PG12 in a folder F2. In this case, the storage unit 314 stores identification information of each image of the image group PG11 by associating with each image contained in the image group PG11 and identification information of each image of the image group PG12 by associating with each image contained in the image group PG12.

Here, identification information of each image saved in the storage unit 314 is, for example, a combination of ID information of an imaging device mounted on one of the capsule endoscopes 302a and 302b and number information (an input number described later) indicating the frame sequence of images inside an image group picked up by the imaging device identified by the ID information. That is, each image contained in the image groups PG11 and PG12 inside the subject 1 is identified by identification information, which is a combination of ID information of the imaging device and the input number indicating the frame sequence.

The control unit 315 controls each component of the image display apparatus 304. More specifically, the control unit 315 controls each of the input unit 311, the display unit 312, the card I/F 313, and the storage unit 314 and also controls input/output of information among these components. In this case, the control unit 315 acquires image groups inside the subject 1, ID information of the imaging device associated with each image contained in the image groups inside the subject 1, and the receiving number of each image from the portable recording medium 305 inserted in the card I/F 313.

The control unit 315 associates the image groups inside the subject 1 (for example, the above image groups PG11 and PG12), ID information of the imaging device, and the receiving number of an image for each image before saving them in the storage unit 314. The control unit 315 maintains and manages each image contained in the image groups inside the subject 1 saved in the storage unit 314 by identification information described above. Based on instruction information input by the input unit 311, the control unit 315 makes the display unit 312 display each image contained in the image groups inside the subject 1.

The control unit 315 has a display controller 315a, an image classifier 315b, and an image extractor 315c. The display controller 315a performs control to display each image contained in the image groups PG11 and PG12 inside the subject saved in the storage unit 314. Also, when selection information of an image group is input by the input unit 311, the display controller 315a performs control to switch the image currently displayed in the display unit 312 to an image in the image group selected based on the selection information before displaying the image.

The image classifier 315b classifies image groups inside the subject 1 acquired via the portable recording medium 305 inserted in the card I/F 313 by imaging device. In this case, the image classifier 315b checks ID information of the imaging device associated with each image contained in the image groups inside the subject 1 and classifies the image groups inside the subject 1 by ID information of the imaging device. In this manner, the image classifier 315b classifies the image groups inside the subject 1, for example, into a plurality of image groups PG11 and PG12. Moreover, the image classifier 315b attaches the input number to each image in the image group PG11 in ascending order of receiving number associated with each image in the image group PG11 classified as described above. The input number attached to each image inside the image group PG11 is number information indicating the frame sequence of images in the image group PG11. Likewise, the image classifier 315b attaches the input number indicating the frame sequence of images in the image group PG12 to each image inside the image group PG12.

The image extractor 315c extracts a related image most similar to the image (current displayed image) currently displayed in the display unit 312 from an image group (for example, from one of the image groups PG11 and PG12) selected based on selection information input by the input unit 311. In this case, the image extractor 315c determines from an image group selected based on the selection information a related image having ID information of the imaging device that picked up the image group and the input number of the currently displayed image as identification information and extracts the related image. The related image extracted by the image extractor 315c is displayed in the display unit 312 in place of the currently displayed image. The related image here is an image most similar to the currently displayed image, that is, an image in which a neighborhood of the site inside the subject shown by the currently displayed image is picked up and an image deeply related to the currently displayed image.

The control unit 315 having the configuration described above functions as a control unit for performing control to determine, based on identification information of each image in an image group selected based on such selection information and that of the currently displayed image, a related image most similar to the currently displayed image from the selected image group and to display the related image by switching the current display image to the related image.

Figure 39:
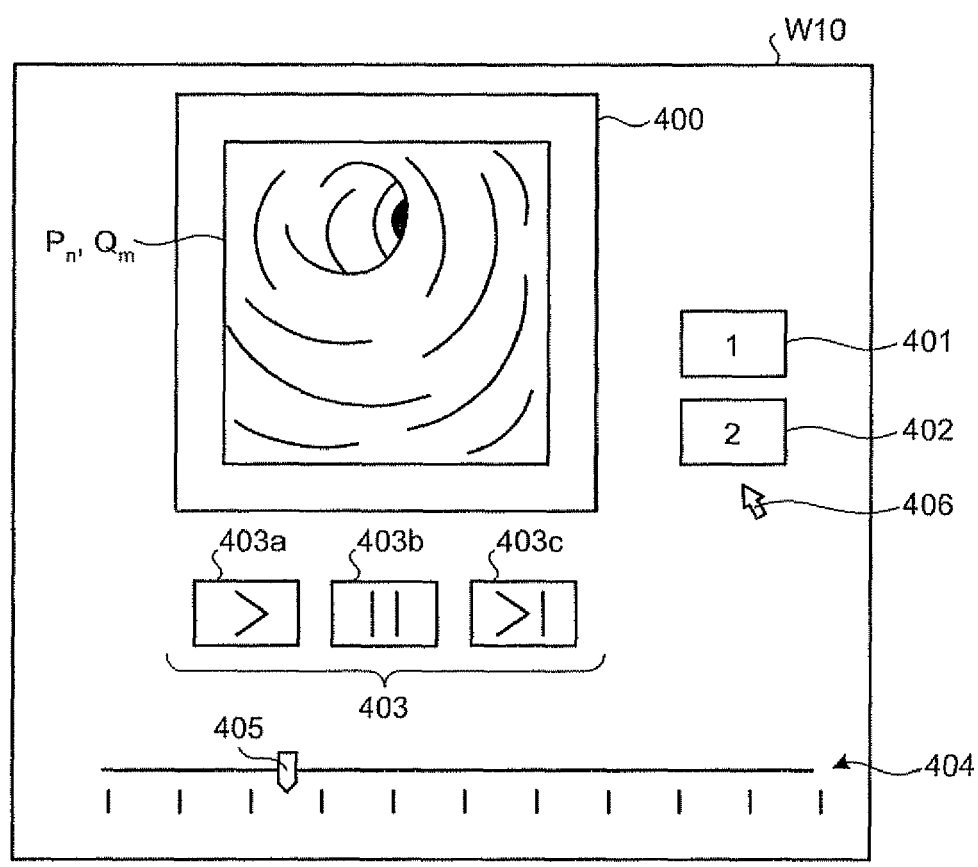
FIG. 39 is a schematic diagram exemplarily showing a specific example of various GUIs displayed in the display unit.

Next, a specific example of a display screen of the display unit 312 is shown to describe various kinds of GUIs displayed in the display unit 312 and the operation of the display controller 315a controlling the display operation of the display unit 312. FIG. 39 is a schematic diagram exemplarily showing a specific example of various GUIs displayed in the display unit 312. When predetermined login processing is performed by the control unit 315, the display controller 315a makes the display unit 312 display a window W10 as shown in FIG. 39.

The window W10 has a main-display area 400 for displaying each image contained in the image groups PG11 and PG12 inside the subject 1 picked up by each imaging device of the capsule endoscopes 302a and 302b formed therein. Also, image group selection icons 401 and 402 for selecting an image group to be displayed in the main-display area 400, a display operation icon group 403 for performing various display operations of an image to be displayed in the main-display area 400, a time bar 404 indicating the temporal length (for example, an elapsed time after starting to pick up the displayed image group) of the image group displayed in the main-display area 400, a slider 405 indicating the temporal position (that is, the position on the time bar 404 temporally corresponding to the currently displayed image) of the image (current displayed image) currently displayed in the main-display area 400, and a cursor 406 are displayed in the window W10.

The main-display area 400 functions as a display unit for displaying each image contained in a plurality of image groups picked up inside the subject 1 by each imaging device of the capsule endoscopes 302a and 302b. More specifically, the main-display area 400 displays, based on control of the display controller 315a, each image in an image group selected from the plurality of image groups PG1 and PG2 inside the subject 1 saved in the folders F1 and F2 of the storage unit 314 respectively. In this case, the display controller 315a controls the display unit 312 to sequentially display the image $P_n$ (frame number n=1, 2, 3, . . . ) contained in the image group PG11 or the image $Q_m$ (frame number m=1, 2, 3, . . . ) contained in the image group PG12 along time series.

The image group selection icons 401 and 402 function as a selection unit for selecting an image group to be displayed in the main-display area 400 from the plurality of image groups PG11 and PG12 inside the subject 1. More specifically, the image group selection icon 401 is a selection GUI for selecting the image group PG11 picked up by one imaging device from among a plurality of imaging devices picking up images inside the subject 1, for example, the imaging device of the capsule endoscope 302a. The image group selection icon 402 is a selection GUI for selecting the image group PG12 picked up by one imaging device from among a plurality of imaging devices picking up images inside the subject 1, for example, the imaging device of the capsule endoscope 302b.

If a click operation is performed after placing the cursor 406 on the image group selection icon 401, the input unit 311 inputs selection information corresponding to the image group PG11 of the plurality of image groups PG11 and PG12, for example, ID information of the imaging device that picked up the image group PG11 to the control unit 315.

In this case, the control unit 315 selects the image group PG11 from the plurality of image groups PG11 and PG12 based on the selection information of the image group PG11 and, based on identification information of each image in the image group PG11 and that of the currently displayed image in the main-display area 400, determines a related image similar to the currently displayed image inside the image group PG11 before performing control to switch the currently displayed image to the related image in the image group PG11. If, on the other hand, a click operation is performed after placing the cursor 406 on the image group selection icon 402, the input unit 311 inputs selection information corresponding to the image group PG12 of the plurality of image groups PG11 and PG12, for example, ID information of the imaging device that picked up the image group PG12 to the control unit 315. In this case, the control unit 315 selects the image group PG12 from the plurality of image groups PG11 and PG12 based on the selection information of the image group PG12 and, based on identification information of each image in the image group PG12 and that of the currently displayed image in the main-display area 400, determines a related image similar to the currently displayed image inside the image group PG12 before performing control to switch the currently displayed image to the related image in the image group PG12.

The display operation icon group 403 contains display operation GUIs for performing display operations of an image to be displayed in the main-display area 400. More specifically, the display operation icon group 403 functions, for example, as a display operation unit for performing various display operations making the main-display area 400 to display each image in the image group selected from the plurality of image groups PG11 and PG12 by the image group selection icons 401 and 402. The display operation icon group 403 contains, as shown, for example, in FIG. 39, a play icon 403a, a stop search icon 403b and a frame advance icon 403c.

If, for example, a click operation is performed by placing the cursor 406 on the play icon 403a, the input unit 311 inputs display instruction information corresponding to the play icon 403a to the control unit 315. In this case, based on the display instruction information corresponding to the play icon 403a, the display controller 315a performs control to sequentially display images (that is, images inside the image group selected from the plurality of image groups PG11 and PG12 by the image group selection icons 401 and 402) inside the subject 1 in the main-display area 400 along time series. If a click operation is performed by placing the cursor 406 on the stop search icon 403b, the input unit 311 inputs display instruction information corresponding to the stop search icon 403b to the control unit 315. In this case, based on the display instruction information corresponding to the stop search icon 403b, the display controller 315a performs control to set the currently displayed image in the main-display area 400 to a temporary stop state. If a click operation is performed by placing the cursor 406 on the frame advance icon 403c, the input unit 311 each time inputs display instruction information corresponding to the frame advance icon 403c to the control unit 315. In this case, based on the display instruction information corresponding to the frame advance icon 403c, the display controller 315a performs control to display the next frame of the image inside the subject 1 in the main-display area 400.

The slider 405 indicates the temporal position of the currently displayed image (for example, one of the images $P_n$ and $Q_m$) in the main-display area 400 and moves, based on control of the display controller 315a, on the time bar 404 in synchronization with switching of the currently displayed image in the main-display area 400. In this case, the display controller 315a makes the image inside the subject 1 corresponding to the current temporal position indicated by the slider 405 displayed in the main-display area 400 in synchronization with movement of the slider 405. By moving the slider 405 to a desired position on the time bar 404, the image inside the subject 1 corresponding to the temporal position indicated by the slider 405 is displayed in the main-display area 400.

The temporal length indicated by the time bar 404, that is, an elapsed time after starting picking up image groups displayed in the main-display area 400 is calculated from the frame rate of the imaging device that picked up the image group displayed in the main-display area 400 and number information (the above input number) indicating the frame sequence of each image.

Figure 40:
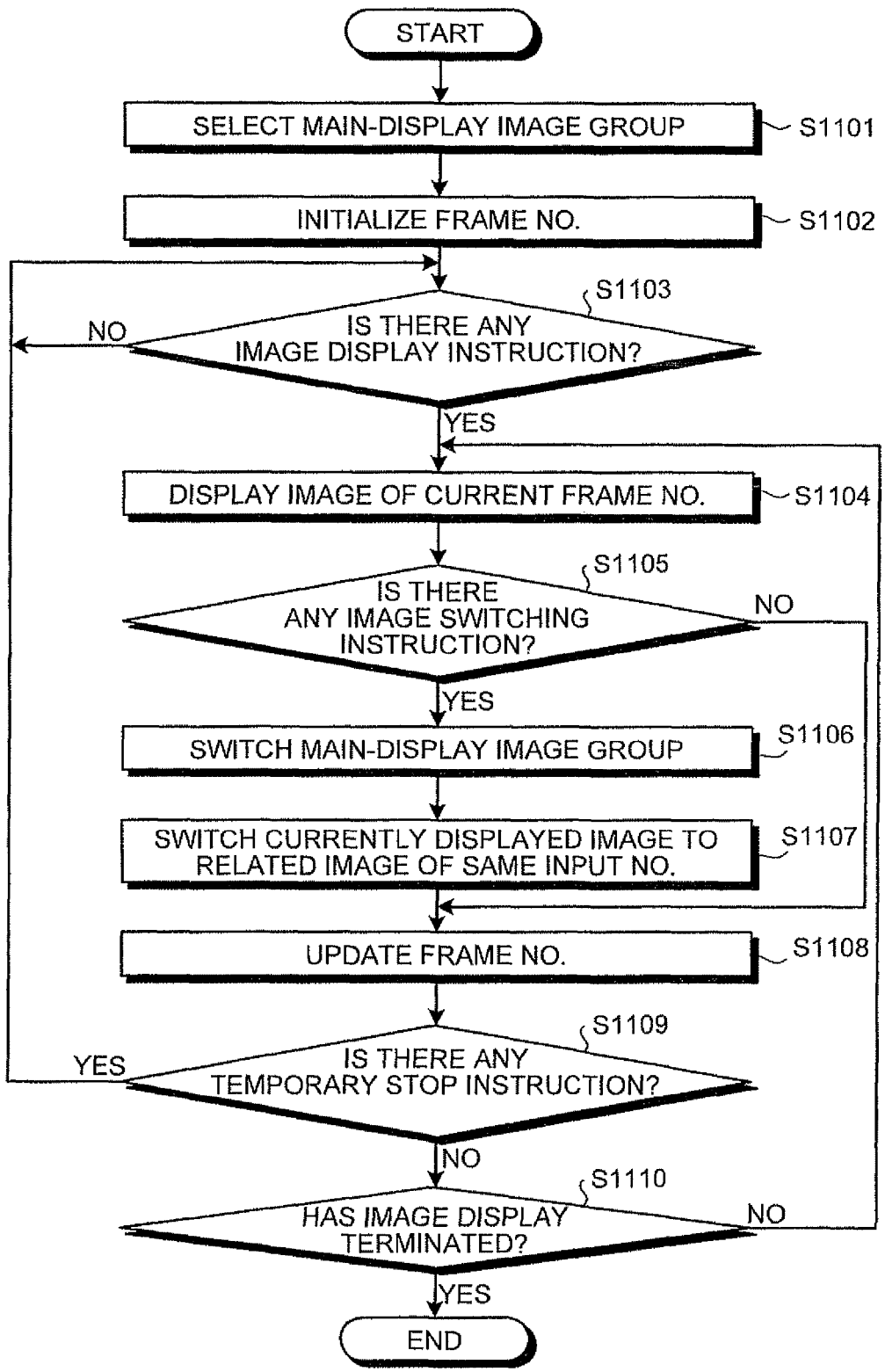
FIG. 40 is a flowchart illustrating a processing procedure by the control unit of the image display apparatus according to the sixth embodiment.

Next, the operation of the control unit 315 controlling to switch the currently displayed image in the main-display area 400 to a related image contained in the image group inside the subject 1 selected from the plurality of image groups PG11 and PG12 will be described. FIG. 40 is a flowchart illustrating the processing procedure by the control unit 315 of the image display apparatus 304 according to the sixth embodiment.

As shown in FIG. 40, the control unit 315 first selects the image group (main-display image group) made to be displayed in the main-display area 400 of the window W10 (See FIG. 39) while the display unit 312 is made to display the W10 (step S1101). In this case, after displaying the window W10, the display controller 335a, which has a pre-programmed default setting for selecting an image group inside a subject made first to be displayed in the main-display area 400, initially selects a main-display image group from a plurality of image groups saved in the storage unit 314 based on the default setting.

Next, the control unit 315 initializes the frame number of the main-display image group selected as described above (step S1102). In this case, the display controller 315a initializes the frame number indicating the image to be processed for display contained in the selected main-display image group (for example, one of the image groups PG11 and PG12), for example, to "1".

Then, the control unit 315 determines whether or not any image display instruction to the main-display area 400 has been issued (step S1103). More specifically, the input unit 311 inputs display instruction information corresponding to any icon (for example, the play icon 403a or the frame advance icon 403c) contained in the display operation icon group 403 to the control unit 315. If no such display instruction information has been input by the input unit 311, the display controller 315a determines that no image display instruction has been issued to the main-display area 400 (step S1103, No) and repeats step S1103. That is, the display controller 315a repeats step S1103 until such display instruction information is input by the input unit 311.

If, on the other hand, such display instruction information has been input by the input unit 311, the control unit 315 determines that an image display instruction has been issued to the main-display area 400 (step S1103, Yes) and performs control to display the image of the current frame number in the main-display area 400 (step S1104). In this case, based on the display instruction information (the play instruction or frame advance instruction) input by the input unit 311, the display controller 315a extracts the image of the current frame number contained in the main-display image group of the plurality of image groups inside the storage unit 314 and performs control to display the image of the current frame number in the main-display area 400.

The frame number of the image displayed in the main-display area 400 (that is, the current frame number) at step S1104 is the frame number initialized at step S1102 or a frame number updated at step S1108 described later.

Next, the control unit 315 determines whether or not any image switching instruction of the image currently displayed in the main-display area 400 (the currently displayed image in the main-display area 400) has been issued (step S1105). More specifically, the image group selection icons 401 and 402 select the image group inside the subject to be displayed in the main-display area 400 (main-display image group) from the plurality of image groups inside the storage unit 314 by a click operation using the input unit 311. In this case, the input unit 311 inputs selection information of the image group corresponding to the click-operated image group selection icon of the image group selection icons 401 and 402 to the control unit 315. If such selection information of the image group corresponding to an image group selection icon is input, the control unit 315 determines, based on the input selection information, that an image switching instruction of the currently displayed image has been issued.

If the control unit 315 determines that an image switching instruction has been issued (step S1105, Yes), the control unit 315 switches the main-display image group based on the selection information input at step S1105 (step S1106). In this case, the display controller 315a selects the image group identified by the selection information from the plurality of image groups inside the subject saved in the storage unit 314 and switches the main-display image group to the selected image group. The image group inside the subject corresponding to the selection information is thereby switched to the image group to be displayed in the main-display area 400.

Subsequently, based on identification information of each image in the image group corresponding to the selection information and that of the currently displayed image in the main-display area 400, the control unit 315 performs control to switch the currently displayed image to the related image of the same input number (step S1107). In this case, the image extractor 315c checks the input number contained in the identification information of the current display image in the main-display area 400 and that of each image in the image group corresponding to the selection information to extract the image containing the same input number as that of the currently displayed image as identification information from the image group corresponding to the selection information. The image extracted by the image extractor 315c is the related image most similar to the currently displayed image and contains ID information of the imaging device corresponding to the selection information and the input number matching the currently displayed image as identification information. In this manner, the image extractor 315c determines the related image most similar to the currently displayed image. The display controller 315a performs control to switch the currently displayed image to the related image extracted by the image extractor 315c. Thus, the related image is currently displayed in the main-display area 400.

Then, the control unit 315 updates the frame number of the image group inside the subject to be processed for display, that is, the main-display image group containing the image currently displayed in the main-display area 400 (such as a related image) (step S1108). In this case, the display controller 315a updates the frame number of the main-display image group by, for example, adding +1 to the frame number of the image currently displayed in the main-display area 400.

Next, the control unit 315 determines whether or not any temporary stop instruction to the image inside the subject currently displayed in the main-display area 400 has been issued (step S1109). More specifically, if display instruction information corresponding to the stop search icon 403b or that corresponding to the frame advance icon 403c has been input from the input unit 311, the control unit 315 determines that a temporary stop instruction has been issued (step S1109, Yes). In this case, the control unit 315 returns to step S1103 to repeat the processing procedure of step S1103 and onward.

If, on the other hand, display instruction information corresponding to the stop search icon 403b or that corresponding to the frame advance icon 403c has not been input, the control unit 315 determines that a temporary stop instruction has not been issued (step S1109, No) and determines whether or not image display processing to display images inside the subject in the main-display area 400 has terminated (step S1110).

More specifically, the control unit 315 determines that image display processing to display images inside the subject has terminated (step S1110, Yes) if the frame number updated at step S1108 exceeds the number of frames of the main-display image group and completes the image display processing to display images inside the subject. If, on the other hand, the control unit 315 determines that image display processing to display images inside the subject has not terminated (step S1110, No) if the frame number updated at step S1108 is equal to or less than the number of frames of the main-display image group and returns to step S1104 to repeat the processing procedure at step S1104 and onward.

If, at step S1105, no selection information of an image group corresponding to one of the image group selection icons 401 and 402 is input, the control unit 315 determines no image switching instruction of the currently displayed image has been issued (step S1105, No) and proceeds to step S1108 to repeat the processing procedure at S1108 and onward.

Next, a case in which a plurality of the capsule endoscopes 302a and 302b is introduced into organs of the subject 1 and image groups picked up inside the subject 1 by each imaging device of the capsule endoscopes 302a and 302b are classified into the two image groups PG11 and PG12 for each imaging device is exemplified to specifically describe processing of the image classifier 315b to attach the input number to each image in the image groups PG11 and PG12. FIG. 41 is a schematic diagram illustrating processing by the image classifier 315b to attach the input number to each image contained in each of a plurality of image groups inside the subject 1.

The image classifier 315b classifies, as shown in FIG. 41, image groups inside the subject 1 into a plurality of the image groups PG11 and PG12 for each imaging device of the capsule endoscopes 302a and 302b by checking ID information of the imaging device associated with each image inside the subject 1 and separating each image inside the subject 1 by ID information of the imaging device.

Here, if receiving numbers "1", "2", "3", "6", "8", and "10" are associated with images $P_1$ to $P_6$ inside the image group PG11 and receiving numbers "4", "5", "7", "9", "11", and "12" are associated with images $Q_1$ to $Q_6$ inside the image group PG12 respectively, each of the images $P_1$ to $P_6$ and $Q_1$ to $Q_6$ inside the subject 1 has been received by the receiving apparatus 303 in ascending order of receiving number, that is, in the order of image $P_1$, image $P_2$, image $P_3$, image $Q_1$, image $Q_2$, image $P_4$, image $Q_3$, image $P_5$, image $Q_4$, image $P_6$, image $Q_5$, and image $Q_6$. The image classifier 315b checks the receiving number of each image $P_n$ (frame number n=1, 2, 3, . . . ) inside the image group PG11 and attaches the consecutive input number (1, 2, 3, . . . ) beginning with "1" in ascending order of receiving number of each image $P_n$ in the image group PG11. In this case, the image classifier 315b attaches, for example, the input numbers "1", "2", "3", "4", "5", and "6" to the images $P_1$ to $P_6$ respectively. Such input numbers show the frame sequence of the images $P_1$ to $P_6$.

Likewise, the image classifier 315b checks the receiving number of each image $Q_m$ (frame number m=1, 2, 3, . . . ) inside the image group PG12 and attaches the consecutive input number (1, 2, 3, . . . ) beginning with "1" in ascending order of receiving number of each image $Q_m$ in the image group PG12. In this case, the image classifier 315b attaches, for example, the input numbers "1", "2", "3", "4", "5", and "6" to the images $Q_1$ to $Q_6$ respectively. Such input numbers show the frame sequence of the images $Q_1$ to $Q_6$.

Each image $P_n$ to which the input number indicating the frame sequence of the image group PG11 is associated is identified by the input number and ID information of the imaging device of the capsule endoscope 302a. Also, each image $Q_m$ to which the input number indicating the frame sequence of the image group PG12 is associated is identified by the input number and ID information of the imaging device of the capsule endoscope 302b.

Figure 42:
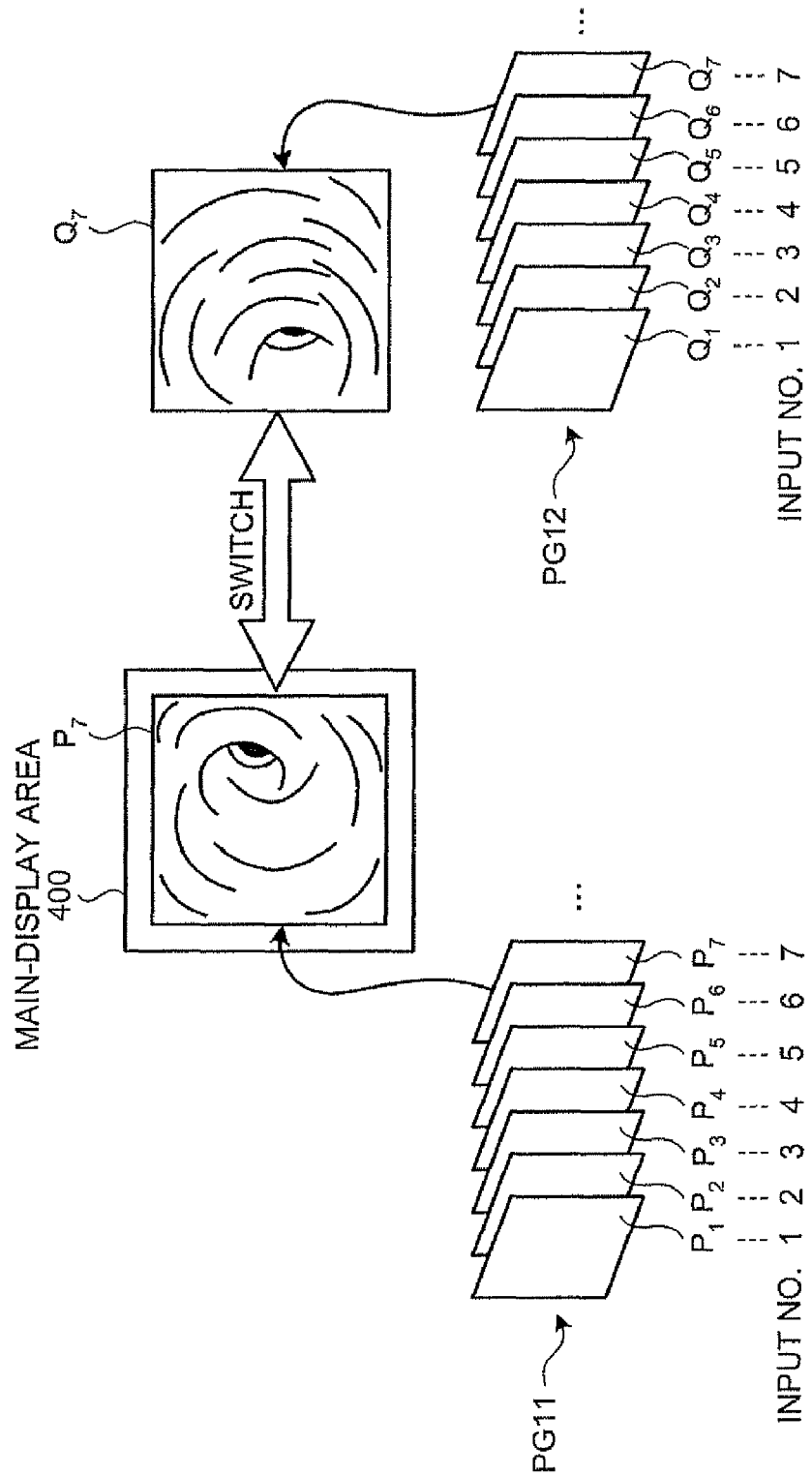
FIG. 42 is a schematic diagram illustrating operation of the control unit to switch a currently displayed image in a main-display area to a related image in another image group based on identification information of an image including an input number.

Next, a case in which an image inside the subject 1 contained in the plurality of image groups PG11 and PG12 picked up by the capsule endoscopes 302a and 302b is displayed in the main-display area 400 of the display unit 312 is exemplified to specifically describe the operation of the control unit 315 to switch the currently displayed image currently displayed in the main-display area 400 to a related image in another image group (an image group selected by a selection GUI). FIG. 42 is a schematic diagram illustrating the operation of the control unit 315 to switch the currently displayed image in the main-display area 400 to a related image in another image group based on identification information of the image including the input number As shown in FIG. 42, an image inside the subject 1 contained in the image group PG11 picked up by the imaging device of the capsule endoscope 302a, for example, an image $P_7$ is currently displayed in the main-display area 400 of the display unit 312. In this case, the image group PG11 containing the image $P_7$, which is the currently displayed image of the main-display area 400, is the image group to be processed for being displayed in the main-display area 400 (that is, the main-display image group). Moreover, the image $P_7$ in the main-display area 400 is associated with ID information of the imaging device of the capsule endoscope 302a and the input number "7" as identification information.

If a click operation of the image group selection icon 402 is performed and the input unit 311 inputs selection information corresponding to the image group PG12 to the control unit 315 in this state, the control unit 315 switches, based on the selection information corresponding to the image group PG12, the main-display image group from the currently displayed image group PG11 to the image group PG12. More specifically, the selection information corresponding to the image group PG12 is, for example, ID information of the imaging device of the capsule endoscope 302b and the display controller 315a selects the image group PG12 picked up by the imaging device of the capsule endoscope 302b identified by the selection information from the plurality of image groups P211 and PG12 saved in the storage unit 314. In this manner, the display controller 315a switches the main-display image group from the currently displayed image group P211 to the image group PG12.

Next, the control unit 315 determines a related image inside the image group PG12 most similar to the image $P_7$, which is the currently displayed image, based on identification information of each image inside the image group PG12 selected by the image group selection icon 402 and that of the image $P_7$ currently displayed in the main-display area 400 and performs control to switch the currently displayed image to the related image. In this case, the image extractor 315c checks the input number of each image ($Q_1$, $Q_2$, $Q_3$, $Q_4$, $Q_5$, $Q_6$, . . . ) inside the selected image group PG12 and that of the currently displayed image or the image $P_7$ before determining the image $Q_7$ having the same input number "7" as the image $P_7$ as the related image most similar to the image $P_7$. Then, the image extractor 315c extracts the image $Q_7$ determined to be the related image to the image $P_7$ from the image group PG12. In this case, the display controller 315a performs control to switch the currently displayed image in the main-display area 400 from the image $P_7$ to the image $Q_7$ (that is, the related image to the image $P_7$).

Here, the images $P_7$ and $Q_7$ related as the currently displayed image and a related image are mutually similar images and are, for example, images in which substantially the same site inside the same organ of the subject 1 is picked up or images in which neighboring sites mutually related as front and rear or opposite to each other are picked up. By displaying the currently displayed image and a related image in the main-display area 400 by switching them in this manner, images mutually similar to each other among the plurality of image groups inside the subject 1 can easily be observed and, as a result, images inside organs of the subject 1 can minutely be observed.

In the sixth embodiment of the present invention, as described above, if image groups inside a subject picked up by a plurality of imaging devices are classified by imaging device, a plurality of image groups inside the subject and identification information for identifying each image inside the plurality of image groups are saved in a storage unit, and an image group to be displayed in a main-display area of a display unit is selected by a selection GUI from the plurality of image groups, a related image most similar to a currently displayed image is determined from the selected image group based on the input number contained in identification information of each image inside the selected image group and that contained in identification information of the currently displayed image currently displayed in the main-display area and the currently displayed image is switched to the related image. Thus, by an easy operation using the selection GUI, images mutually similar to each other among the plurality of image groups, for example, images in which neighboring sites inside a subject are picked up can be displayed in the main-display area by switching them. As a result, images similar to each other among the plurality of image groups inside the subject can easily be observed so that an image display apparatus allowing minute observations inside organs of the subject can be realized.

Next, the seventh embodiment of the present invention will be described. While an image in an image group selected by a selection GUI from a plurality of image groups in a subject whose input number matches that of a currently displayed image in the main-display area 400 is selected as a related image of the currently displayed image in the sixth embodiment, in the seventh embodiment, identification information includes time information of an image indicating an elapsed time after starting picking up images in an image group instead of the input number of an image and an image in the selected image group having time information closest to that of the currently displayed image is determined as the related image of the currently displayed image.

Figure 43:
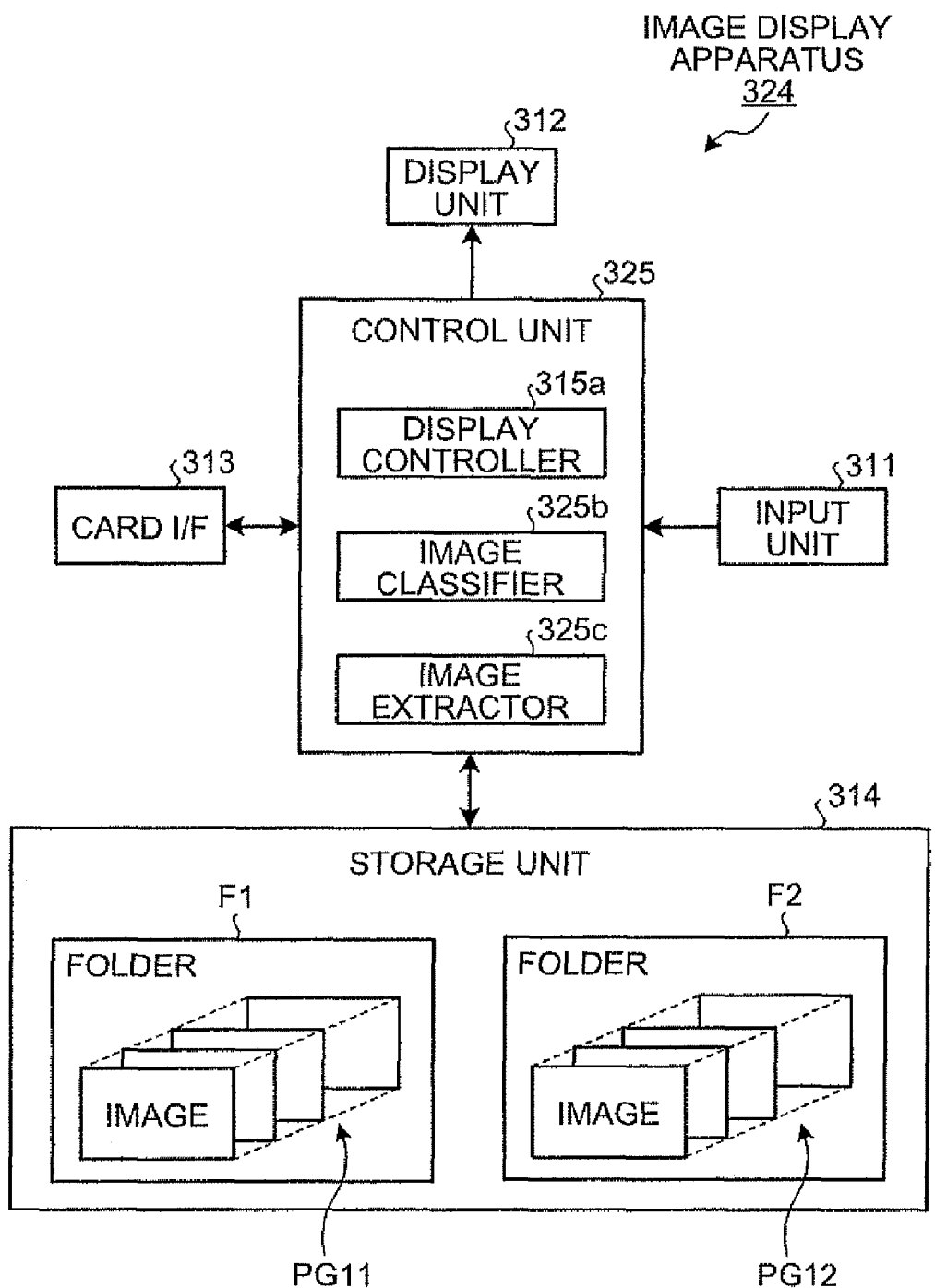
FIG. 43 is a block diagram exemplarily showing a configuration example of an image display apparatus according to a seventh embodiment of the present invention.

FIG. 43 is a block diagram exemplarily showing a configuration example of an image display apparatus according to the seventh embodiment of the present invention. As shown in FIG. 43, an image display apparatus 324 according to the seventh embodiment has a control unit 325 in place of the control unit 315 of the image display apparatus 304 according to the sixth embodiment. Also, an intra-subject information acquisition system according to the seventh embodiment of the present invention has the image display apparatus 324 in place of the image display apparatus 304 of the intra-subject information acquisition system according to the sixth embodiment (See FIG. 37). In this case, the receiving apparatus 303 sequentially accumulates a receiving time when an image inside the subject 1 is received in the portable recording medium 305 in place of the receiving number of an image. That is, in the seventh embodiment, an image inside the subject 1, ID information of the imaging device that picked up the image inside the subject 1, and the receiving time of the image inside the subject 1 are mutually associated. Other components are the same as those in the sixth embodiment and the same reference numerals are attached to the same components.

Substantially like the control unit 315 of the image display apparatus 304 according to the sixth embodiment, the control unit 325 controls each of the input unit 311, the display unit 312, the card I/F 313, and the storage unit 314 and also controls input/output of information among these components. In this case, the control unit 325 acquires image groups inside the subject 1, ID information of the imaging device associated with each image contained in the image groups inside the subject 1, and the receiving time of each image from the portable recording medium 305 inserted in the card I/F 313. The control unit 325 associates the image groups inside the subject 1 (for example, the above image groups PG11 and PG12), ID information of the imaging device, and the receiving time of an image for each image before saving them in the storage unit 314.

The control unit 325 as described above has the display controller 315a, an image classifier 325b in place of the image classifier 315b of the control unit 315 of the image display apparatus 304, and an image extractor 325c in place of the image extractor 315c.

Like the image classifier 315b of the control unit 315, the image classifier 325b classifies image groups inside the subject 1 into a plurality of image groups (for example, the image groups PG11 and PG12) by ID information of the imaging device associated with each image. Based on the receiving time of each image in the image group PG11 classified as described above, the image classifier 325b calculates the input time of each image in the image group PG11 and associates the calculated input time with each image in the image group PG11. Here, the input time associated with each image in the image group PG11 is time information indicating an elapsed time after starting picking up each image $P_n$ (frame number n=1, 2, 3, ... ) and is calculated as a relative time of each image to the receiving time of the first image $P_1$ in the image group PG11. Likewise, the image classifier 325b calculates the input time of each image in the image group PG12 and associates the calculated input time with each image in the image group PG12.

The control unit 325 saves the image groups PG11 and PG12 classified for each imaging device by the image classifier 325b in the folders F1 and F2 of the storage unit 314 respectively. In this case, the each image in the image groups PG11 and PG12 saved in the storage unit 314 is associated with the input time calculated by the image classifier 325b and the ID information of the imaging device. Therefore, identification information of each image in the image groups PG11 and PG12 is a combination of the ID information of the imaging device and the input time of the image.

Substantially like the image extractor 315c of the control unit 315, the image extractor 325c extracts a related image most similar to the currently displayed image in the main-display area 400 of the display unit 312 from an image group (for example, from one of the image groups PG11 and PG12 selected by the image group selection icons 401 and 402) inside a subject corresponding to selection information of an image group input by the input unit 311. In this case, the image extractor 325c determines from an image group selected based on the selection information a related image having ID information of the imaging device that picked up the image group and the input time closest to that of the currently displayed image as identification information and extracts the related image. The related image extracted by the image extractor 325c is displayed in the main-display area 400 of the display unit 312 in place of the currently displayed image.

Figure 44:
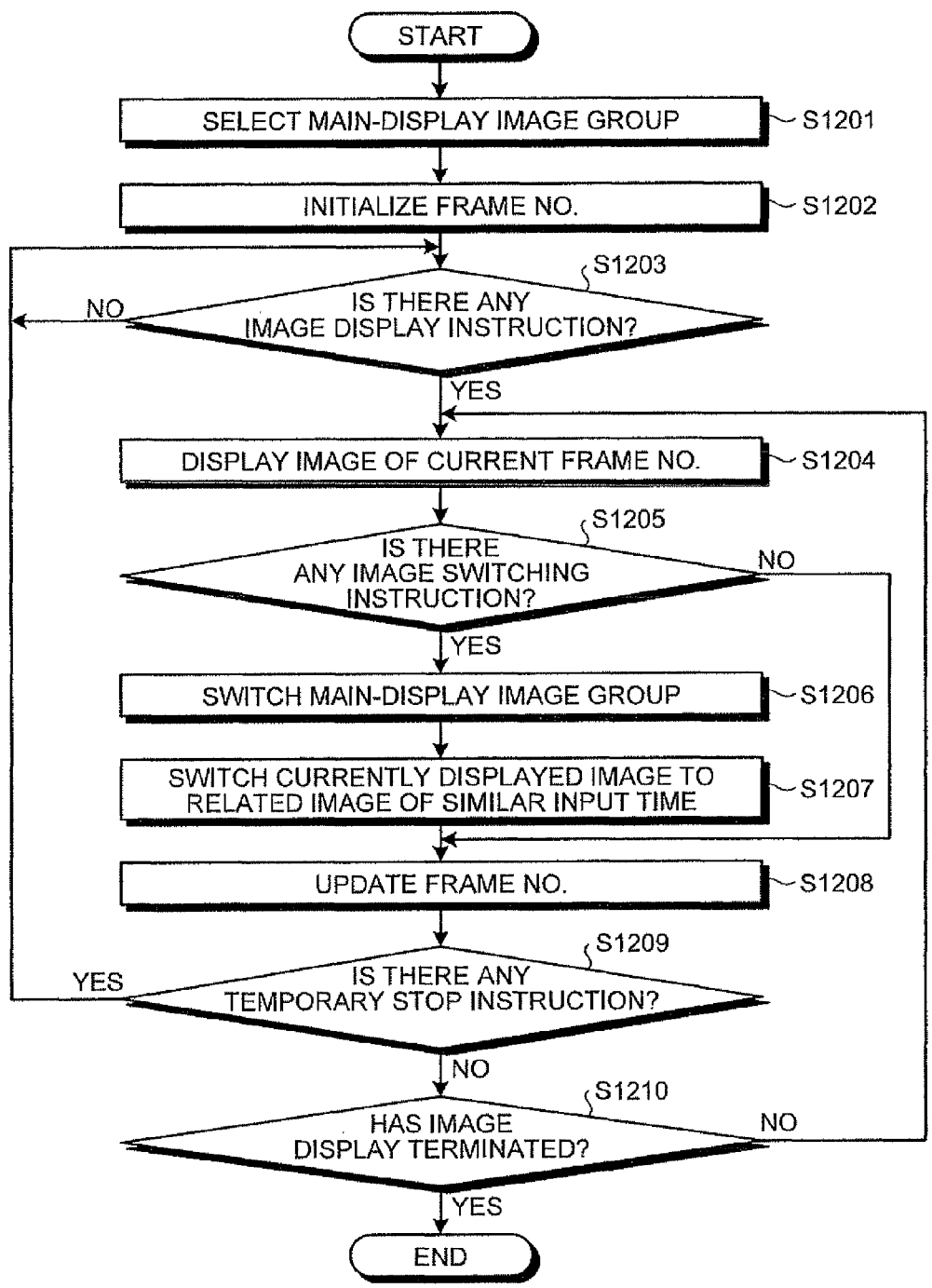
FIG. 44 is a flowchart illustrating the processing procedure by the control unit of the image display apparatus according to the seventh embodiment.

Next, the operation of the control unit 325 controlling to switch the currently displayed image in the main-display area 400 to a related image contained in an image group inside the subject 1 selected from the plurality of image groups PG11 and PG12 will be described. FIG. 44 is a flowchart illustrating the processing procedure by the control unit 325 of the image display apparatus 324 according to the seventh embodiment.

Substantially like the control unit 315 of the image display apparatus 304 according to the sixth embodiment, the control unit 325 performs control to display each image in the image groups PG11 and PG12 inside the subject 1 in the main-display area 400 of the display unit 312 and if the image group to be displayed in the main-display area 400 (main-display image group) is selected by the image group selection icons 401 and 402, performs control to switch the currently displayed image in the main-display area 400 to a related image in the selected image group. In this case, the control unit 325 determines the related image most similar to the currently displayed image from the selected image group based on the input time of an image in place of the input number of an image.

That is, as shown in FIG. 44, the control unit 325 performs the processing procedure similar to steps S1101 to S1104 (See FIG. 40) to select the main-display image group from a plurality of image groups (for example, the image groups PG11 and PG12) inside the subject 1 and if an image display instruction is issued, performs control to display images inside the subject contained in the main-display image group in the main-display area 400 (steps S1201 to S1204). Next, the control unit 325 performs the processing procedure similar to steps S1105 and S1106 to determine whether or not any image switching instruction to switch the currently displayed image main-display area 400 has been issued (step S1205) and, if an image switching instruction has been issued (step S1205, Yes), switches the main-display image group to an image group identified by selection information of an image group input by the input unit 311 (step S1206).

Subsequently, based on identification information of each image in the image group corresponding to the selection information and that of the currently displayed image in the main-display area 400, the control unit 325 performs control to switch the currently displayed image to a related image having the closest input time to that of the currently displayed image (step S1207). In this case, the image extractor 325c checks the input time contained in the identification information of the current display image in the main-display area 400 and that of each image in the image group corresponding to the selection information to extract an image containing the input time closest to that of the currently displayed image as identification information from the image group corresponding to the selection information. The image extracted by the image extractor 325c is the related image most similar to the currently displayed image and contains ID information of the imaging device corresponding to the selection information and the input time closest to that of the currently displayed image as identification information. In this manner, the image extractor 325c determines the related image most similar to the currently displayed image. The display controller 315a performs control to switch the currently displayed image to the related image extracted by the image extractor 325c. Thus, the related image is currently displayed in the main-display area 400.

Then, as same in step S1108 the control unit 325 updates the frame number of the main-display image group containing the image currently displayed in the main-display area 400 (such as a related image) (step S1208). Then, as same in step S1209, the control unit 325 determines whether or not any temporary stop instruction of the image in the main-display area 400 has been issued (step S1209) and if a temporary stop instruction has been issued (step S1209, Yes), returns to step S1203 to repeat the processing procedure at step S1203 and onward.

If, on the other hand, no temporary stop instruction has been issued (step S1209, No), as same in step S1110, the control unit 325 determines whether or not image display processing to display images inside the subject in the main-display area 400 has terminated (step S1210). If the control unit 325 determines that image display processing has not terminated (step S1210, No), the control unit 325 returns to step S1204 to repeat the processing procedure at step S1204 and onward. If the control unit 325 determines that image display processing has terminated (step S1210, Yes), the control unit 325 completes the image display processing of images inside the subject.

If the control unit 325 determines at step S1205 that no image switching instruction has been issued (step S1205, No), the control unit 325 proceeds to step S1208 to repeat the processing procedure at step S1208 and onward.

Next, a case in which a plurality of the capsule endoscopes 302a and 302b is introduced into organs of the subject 1 and image groups inside the subject 1 picked up by each imaging device of the capsule endoscopes 302a and 302b are classified into the two image groups PG11 and PG12 for each imaging device is exemplified to specifically describe processing of the image classifier 325b to associate the input time with each image contained in the plurality of image groups inside the subject 1 in the image groups PG11 and PG12. FIG. 45 is a schematic diagram illustrating processing by the image classifier 325b to associate the input time with each image contained in each of the plurality of image groups inside the subject 1.

The image classifier 325b classifies, as shown in FIG. 45, image groups inside the subject 1 into the plurality of the image groups PG11 and PG12 for each imaging device of the capsule endoscopes 302a and 302b by checking ID information of the imaging device associated with each image inside the subject 1 and separating each image inside the subject 1 by ID information of the imaging device.

Here, if receiving times $T_1$, $T_2$, $T_3$, $T_6$, $T_8$, and $T_{10}$ are associated with images $P_1$ to $P_6$ inside the image group PG11 and receiving times $T_4$, $T_5$, $T_7$, $T_9$, $T_{11}$, and $T_{12}$ are associated with images $Q_1$ to $Q_6$ inside the image group PG12 respectively, each of the images $P_1$ to $P_6$ and $Q_1$ to $Q_6$ inside the subject 1 has been received by the receiving apparatus 303 in ascending order of receiving time, that is, in the order of image $P_1$, image $P_2$, image $P_3$, image $Q_1$, image $Q_2$, image $P_4$, image $Q_3$, image $P_5$, image $Q_4$, image $P_6$, image $Q_5$, and image $Q_6$.

The image classifier 325b checks the receiving time of each image $P_n$ (frame number n=1, 2, 3, ... ) inside the image group PG11 and calculates a relative time (that is, an input time) of each image $P_n$ to the receiving time $T_1$ of the first image $P_1$ in the image group PG11. In this case, the image classifier 325b sets, for example, the receiving time $T_1$ of the first image $P_1$ as the reference time and calculates an elapsed time from the receiving time $T_1$ (that is, the start time of picking up the image group PG11) as the input time of an image. More specifically, the image classifier 325b calculates an input time $U_1$ of the image $P_1$, which is an elapsed time from the receiving time $T_1$ (that is, 0 (h)/0 (min)/0 (sec)) and then calculates each of input times $U_2$, $U_3$, $U_4$, $U_5$, and $U_6$ of the images $P_2$ to $P_6$, which is each of elapsed times until the receiving times $T_2$, $T_3$, $T_6$, $T_8$, and $T_{10}$ pass from the receiving time $T_1$. The image classifier 325b associates each input time ($U_1$, $U_2$, $U_3$, ...) calculated in this manner with each image $P_n$ in the image group PG11.

Likewise, the image classifier 325b checks the receiving time of each image $Q_m$ (frame number m=1, 2, 3, ...) inside the image group PG12 and calculates a relative time (that is, an input time) of each image $Q_m$ to the receiving time $T_4$ of the first image $Q_1$ in the image group PG12. In this case, the image classifier 325b calculates an input time $V_1$ of the image $Q_1$, which is an elapsed time from the receiving time $T_4$ (that is, 0 (h)/0 (min)/0 (sec)) and then calculates each of input times $V_2$, $V_3$, $V_4$, $V_5$, and $V_6$ of the images $Q_2$ to $Q_6$, which is each of elapsed times until the receiving times $T_5$, $T_7$, $T_9$, $T_{11}$, and $T_{12}$ pass from the receiving time $T_4$. The image classifier 325b associates each input time ($V_1$, $V_2$, $V_3$, ...) calculated in this manner with each image $Q_m$ in the image group PG12.

Each $P_n$ in the image group PG11 with which the input time ($U_1$, $U_2$, $U_3$, ...) is associated in this manner is identified by the input time and ID information of the imaging device of the capsule endoscope 302a. Also, each $Q_m$ in the image group PG12 with which the input time ($V_1$, $V_2$, $V_3$, ...) is associated in this manner is identified by the input time and ID information of the imaging device of the capsule endoscope 302b.

Figure 46:
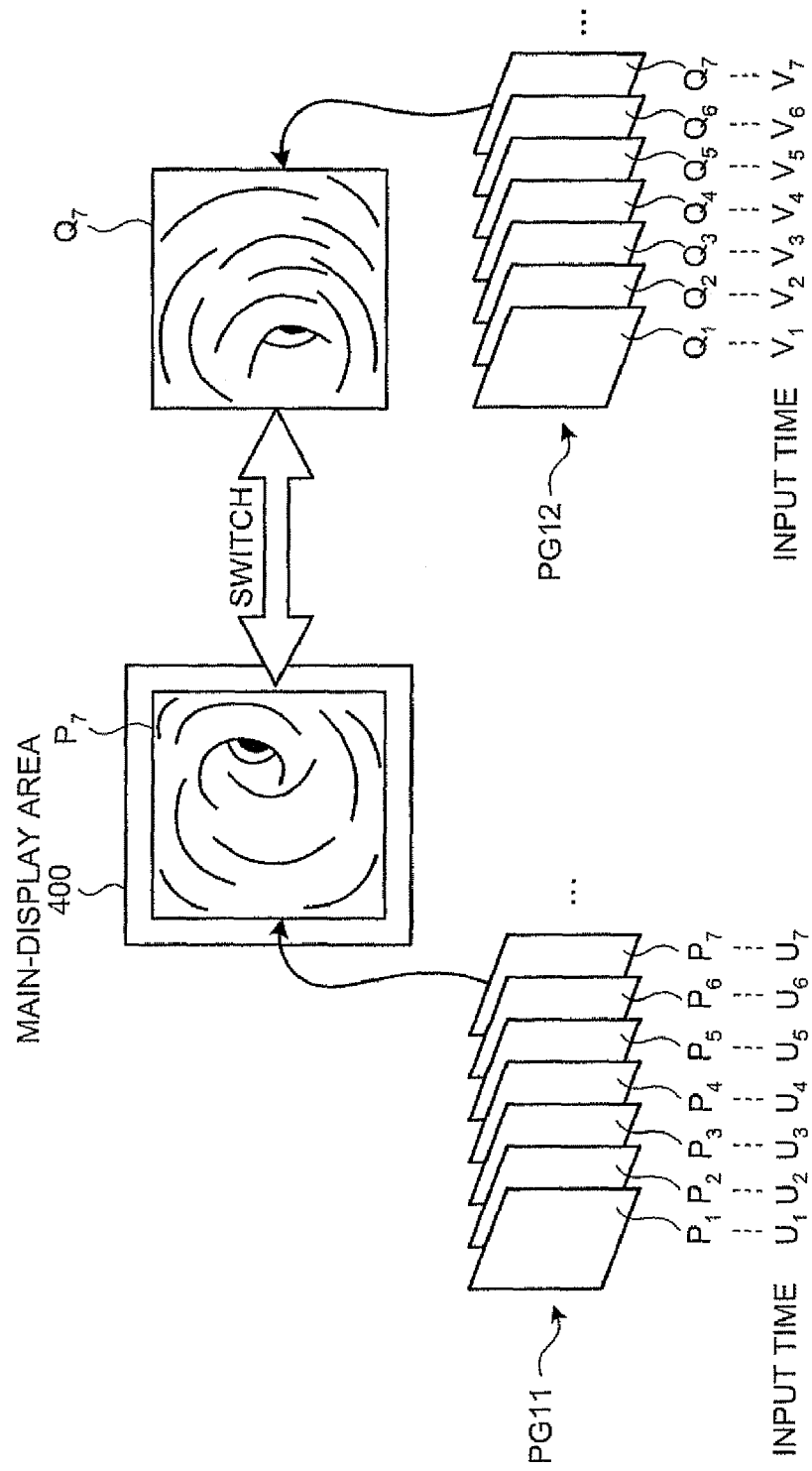
FIG. 46 is a schematic diagram illustrating operation of the control unit to switch the currently displayed image in the main-display area to a related image in another image group based on identification information of an image including an input time.

Next, a case in which an image inside the subject 1 contained in the plurality of image groups PG11 and PG12 picked up by the capsule endoscopes 302a and 302b is displayed in the main-display area 400 of the display unit 312 is exemplified to specifically describe the operation of the control unit 325 to switch the currently displayed image currently displayed in the main-display area 400 to a related image in another image group (an image group selected by a selection GUI). FIG. 46 is a schematic diagram illustrating the operation of the control unit 325 to switch the currently displayed image in the main-display area 400 to a related image in another image group based on identification information of an image including the input time.

As shown in FIG. 46, an image inside the subject 1 contained in the image group PG11 picked up by the imaging device of the capsule endoscope 302a, for example, the image $P_7$ is currently displayed in the main-display area 400 of the display unit 312. In this case, the image group PG11 containing the image $P_7$, which is the currently displayed image of the main-display area 400, is the image group to be processed for being displayed in the main-display area 400 (that is, the main-display image group). Moreover, the image $P_7$ in the main-display area 400 is associated with ID information of the imaging device of the capsule endoscope 302a and the input time $U_7$ as identification information.

If a click operation of the image group selection icon 402 is performed and the input unit 311 inputs selection information corresponding to the image group PG12 to the control unit 325 in this state, the control unit 325 switches, based on the selection information corresponding to the image group PG12, the main-display image group from the currently displayed image group PG11 to the image group PG12. More specifically, the selection information corresponding to the image group PG12 is, for example, ID information of the imaging device of the capsule endoscope 302b and the display controller 315a selects the image group PG12 picked up by the imaging device of the capsule endoscope 302b identified by the selection information from the plurality of image groups PG11 and PG12 saved in the storage unit 314. In this manner, the display controller 315a switches the main-display image group from the currently displayed image group PG11 to the image group PG12.

Next, the control unit 325 determines a related image inside the image group PG12 most similar to the image $P_7$, which is the currently displayed image, based on identification information of each image inside the image group PG12 selected by the image group selection icon 402 and that of the image $P_7$ currently displayed in the main-display area 400 and performs control to switch the currently displayed image to the related image. In this case, the image extractor 325c checks input times ($V_1$, $V_2$, $V_3$, $V_4$, $V_5$, $V_6$, $V_7$, ...) of each image ($Q_1$, $Q_2$, $Q_3$, $Q_4$, $Q_5$, $Q_6$, $Q_7$, ...) inside the selected image group PG12 and the input time $U_7$ of the currently displayed image or the image $P_7$ before determining the image $Q_7$ having the input time $V_7$ closest to the input time $U_7$ of the image $P_7$ as the related image most similar to the image $P_7$. Then, the image extractor 325c extracts the image $Q_7$ determined to be the related image to the image $P_7$ from the image group P12. In this case, the display controller 315a performs control to switch the currently displayed image in the main-display area 400 from the image $P_7$ to the image $Q_7$ (that is, the related image to the image $P_7$).

Here, the images $P_7$ and $Q_7$ related as the currently displayed image and a related image are mutually similar images and are, for example, images in which substantially the same site inside the same organ of the subject 1 is picked up or images in which neighboring sites mutually related as front and rear or opposite to each other are picked up. By displaying the currently displayed image and a related image in the main-display area 400 by switching them in this manner, images mutually similar to each other among the plurality of image groups inside the subject 1 can easily be observed and, as a result, images inside organs of the subject 1 can minutely be observed.

In the seventh embodiment of the present invention, as described above, if image groups inside a subject picked up by a plurality of imaging devices are classified by imaging device, a plurality of image groups inside the subject and identification information for identifying each image inside the plurality of image groups are saved in a storage unit, and an image group to be displayed in a main-display area of a display unit is selected by a selection GUI from the plurality of image groups, a related image most similar to a currently displayed image is determined from the selected image group based on the input time contained in identification information of each image inside the selected image group and that contained in identification information of the currently displayed image currently displayed in the main-display area and the currently displayed image is switched to the related image. Thus, like the sixth embodiment described above, by an easy operation using the selection GUI, images mutually similar to each other among the plurality of image groups can be displayed in the main-display area by switching them. As a result, an image display apparatus achieving an operation effect similar to that in the sixth embodiment can be achieved.

Next, the eighth embodiment of the present invention will be described. While an image in an image group selected by a selection GUT from a plurality of image groups in a subject whose input time is closest to that of a currently displayed image in the main-display area 400 is selected as a related image of the currently displayed image in the seventh embodiment, in the eighth embodiment, a time difference of images mutually closest to each other among the plurality of image groups inside the subject can be set by a predetermined GUI so that images that are the currently displayed image and a related image having a receiving time difference closest to the set time difference are switched.

Figure 47:
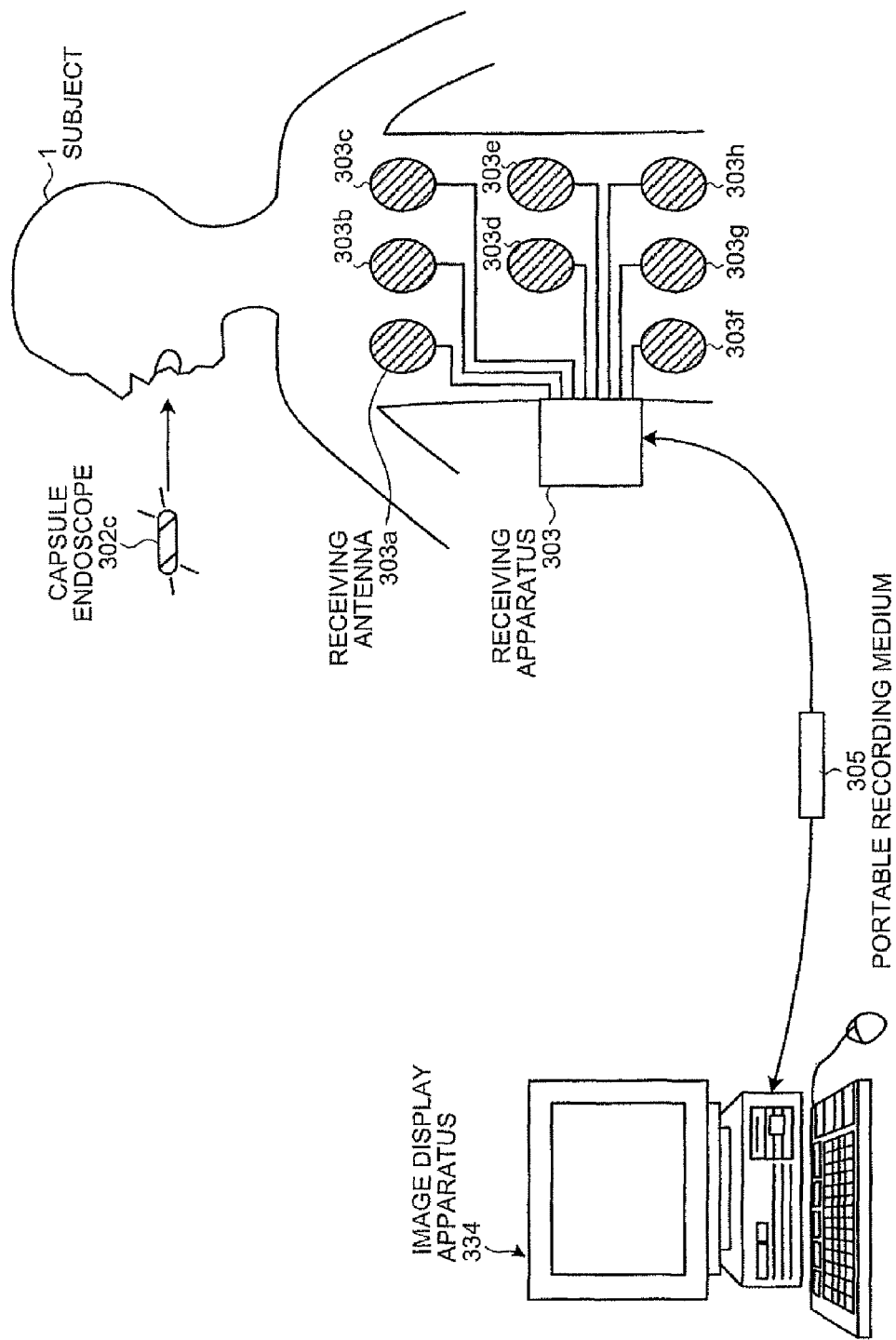
FIG. 47 is a schematic diagram showing a configuration example of the intra-subject information acquisition system having an image display apparatus according to an eighth embodiment of the present invention.

FIG. 47 is a schematic diagram showing a configuration example of an intra-subject information acquisition system having an image display apparatus according to the eighth embodiment of the present invention. As shown in FIG. 47, the intra-subject information acquisition system according to the eighth embodiment has a multiple-lens capsule endoscope 302c in place of the capsule endoscopes 302a and 302b of the intra-subject information acquisition system according to the seventh embodiment and an image display apparatus 334 in place of the image display apparatus 324. Other components are the same as those in the seventh embodiment and the same reference numerals are attached to the same components.

The capsule endoscope 302c is a multiple-lens capsule endoscope equipped with a plurality of imaging devices for picking up images from mutually different directions. The multiple-lens capsule endoscope 302c has an imaging function in multiple directions to sequentially pick up images from a plurality of directions inside the subject 1 along time series after being introduced into the subject 1 and a radio communication function to transmit image groups picked up from multiple directions to the external receiving apparatus 303 by radio. More specifically, the capsule endoscope 302c has, for example, an imaging device having a field of view diagonally to the front with respect to the traveling direction inside the subject 1 (hereinafter, referred to as a front imaging device) and an imaging device having a field of view diagonally to the rear (hereinafter, referred to as a rear imaging device). After being introduced into an organ of the subject 1, the capsule endoscope 302c passes through the organ of the subject 1 in accordance with peristaltic movement and sequentially picks up images inside the organ of the subject 1 diagonally to the front and diagonally to the rear with respect to the traveling direction. In this case, the front and rear imaging devices of the capsule endoscope 302c pick up images inside the subject 1, for example, alternately at the same frame rate. The capsule endoscope 302c sequentially transmits a radio signal including images inside the subject 1 picked up by the front and rear imaging devices and ID information of the imaging device that picked up each image to the external receiving apparatus 303.

Figure 48:
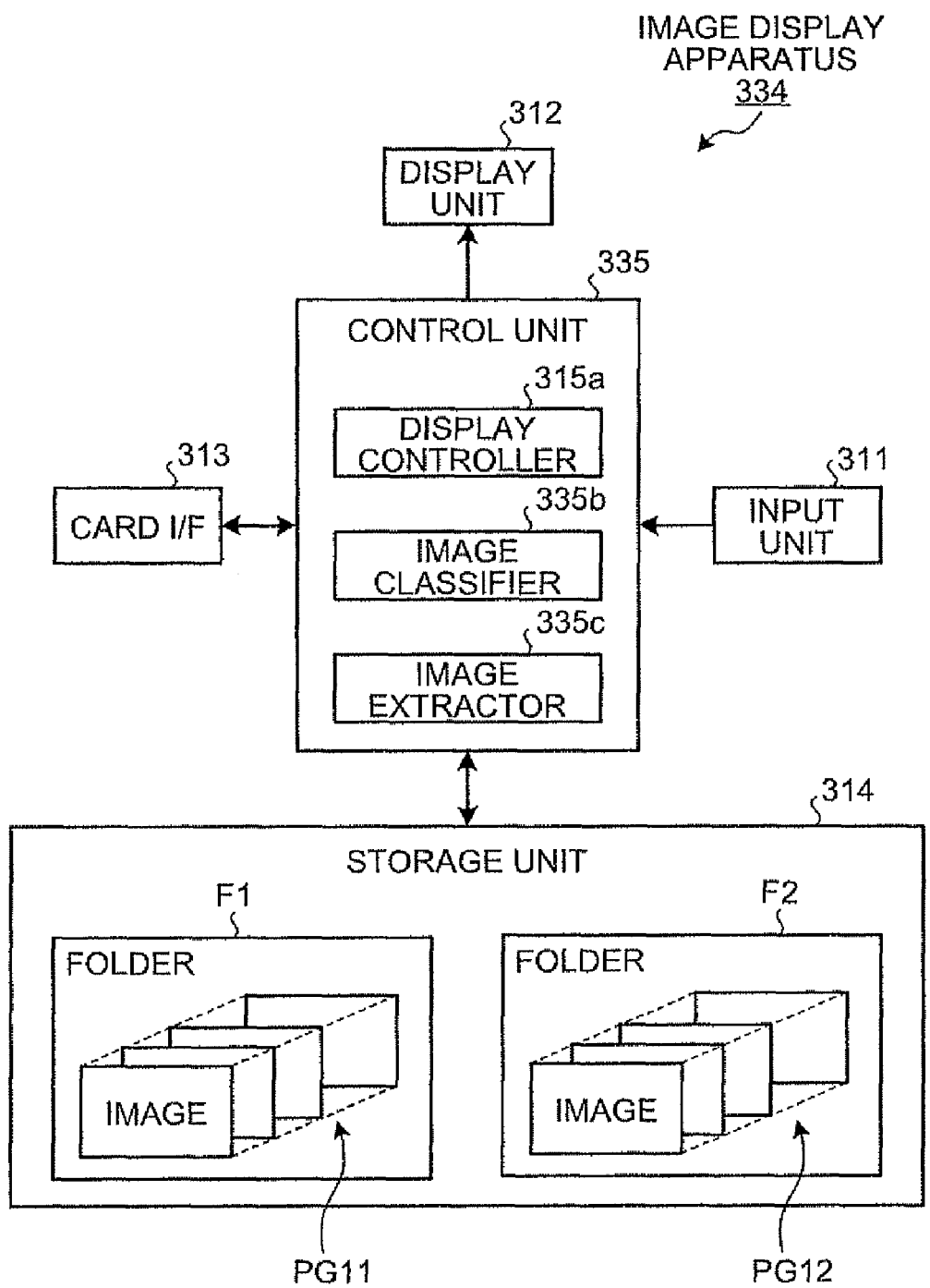
FIG. 48 is a block diagram exemplarily showing a configuration example of the image display apparatus according to the eighth embodiment of the present invention.

Next, the configuration of the image display apparatus 334 according to the eighth embodiment of the present invention will be described. FIG. 48 is a block diagram exemplarily showing a configuration example of the image display apparatus 334 according to the eighth embodiment of the present invention. As shown in FIG. 48, the image display apparatus 334 according to the eighth embodiment has a control unit 335 in place of the control unit 325 of the image display apparatus 324 according to the seventh embodiment. The display unit 312 of the image display apparatus 334 further displays a setting GUI for setting a time difference of images inside the window W10. The input unit 311 inputs time difference information set by the setting GUI displayed in the display unit 312 to the control unit 335. Other components are the same as those in the seventh embodiment and the same reference numerals are attached to the same components.

Substantially like the control unit 335 of the image display apparatus 324 according to the seventh embodiment, the control unit 335 controls each of the input unit 311, the display unit 312, the card I/F 313, and the storage unit 314 and also controls input/output of information among these components. In this case, the control unit 335 acquires image groups inside the subject 1 picked up by the multiple-lens capsule endoscope 302c, ID information of the imaging device associated with each image contained in the image groups inside the subject 1, and the receiving time of each image from the portable recording medium 305 inserted in the card I/F 313. The control unit 335 associates the image groups inside the subject 1, ID information of the imaging device, and the receiving time of an image for each image before saving them in the storage unit 314.

The control unit 335 as described above has the display controller 315a, an image classifier 335b in place of the image classifier 325b of the control unit 325 of the image display apparatus 324 according to the seventh embodiment, and an image extractor 335c in place of the image extractor 325c.

Like the image classifier 325b of the control unit 325, the image classifier 335b classifies image groups inside the subject 1 into a plurality of image groups (for example, the image groups PG11 and PG12) by ID information of the imaging device associated with each image. Each image in the image groups classified by the image classifier 335b is associated, for example, with ID information of the front imaging device or rear imaging device of the capsule endoscope 302c and the receiving time at which the image was received by the receiving apparatus 303.

The control unit 335 saves the image groups PG11 and PG12 classified for each imaging device by the image classifier 335b in the folders F1 and F2 of the storage unit 314 respectively. In this case, the each image in the image groups PG11 and PG12 saved in the storage unit 314 is associated with the ID information of the imaging device and the receiving time. Therefore, identification information of each image in the image groups PG11 and PG12 is a combination of the ID information of the imaging device and the receiving time of the image.

The image extractor 335c extracts, based on selection information of an image group input by the input unit 311 and time difference information between images, a related image most similar to the currently displayed image in the main-display area 400 of the display unit 312 from the image group (for example, from one of the image groups PG11 and PG12 selected by the image group selection icons 401 and 402) inside a subject corresponding to the selection information. Here, time difference information between images corresponds to a set time difference $\Delta t$ between images set by the setting GUI displayed in the display unit 312. The image extractor 335c determines from the image group selected based on the selection information a related image having ID information of the imaging device that picked up the image group and the receiving time whose subtraction from the receiving time of the currently displayed image yields a difference closest to the set time difference $\Delta t$ as identification information and extracts the related image. The related image extracted by the image extractor 335c is displayed in the main-display area 400 of the display unit 312 in place of the currently displayed image.

Figure 49:
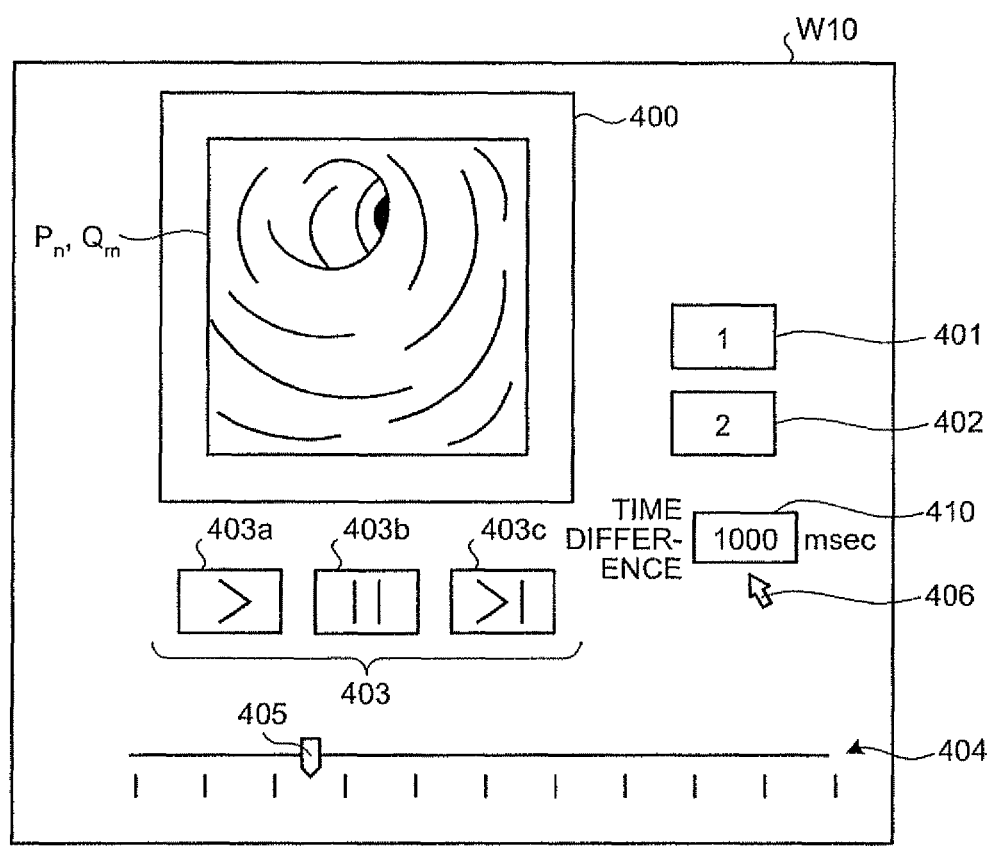
FIG. 49 is a schematic diagram illustrating a window of the display unit displaying setting GUIs for setting a set time difference of images.

Next, the setting GUI for setting the set time difference $\Delta t$ between images contained in an image group inside a subject will be described. FIG. 49 is a schematic diagram illustrating the window W10 of the display unit 312 displaying the setting GUI for setting a set time difference of images. As shown in FIG. 49, the main-display area 400 for displaying an image inside the subject is formed in the window W10 of the display unit 312, and the image group selection icons 401 and 402, the display operation icon group 403, the time bar 404, the slider 405, the cursor 406, and a time difference setting unit 410 are displayed.

The time difference setting unit 410 is a setting GUI functioning as a setting unit for setting a time difference between the receiving time of the currently displayed image in the main-display area 400 and that of a related image closest to the currently displayed image. More specifically, a numeric value indicating a desired time difference is input to the time difference setting unit 410 by an input operation of the input unit 311. The numeric value input to the time difference setting unit 410 indicates a set time difference Δt set as a difference between the receiving time of the currently displayed image in the main-display area 400 and that of the related image thereof. By inputting a desired time difference, as described above, the time difference setting unit 410 sets the set time difference Δt between the currently displayed image and related image. In this case, the input unit 311 inputs time difference information corresponding to the set time difference Δt to the control unit 335. The control unit 335 saves the time difference information corresponding to the set time difference Δt in the storage unit 314.

A numeric value (that is, the set time difference Δt) input to the time difference setting unit 410 may be positive or negative. If the set time difference Δt is a positive value, the time difference setting unit 410 sets a receiving time difference for images whose receiving time is in time series prior to that of the currently displayed image in the main-display area 400 (that is, images picked up before the currently displayed image was picked up). If, on the other hand, the set time difference Δt is a negative value, the time difference setting unit 410 sets a receiving time difference for images whose receiving time is in time series after that of the currently displayed image in the main-display area 400 (that is, images picked up after the currently displayed image was picked up).

Figure 50:
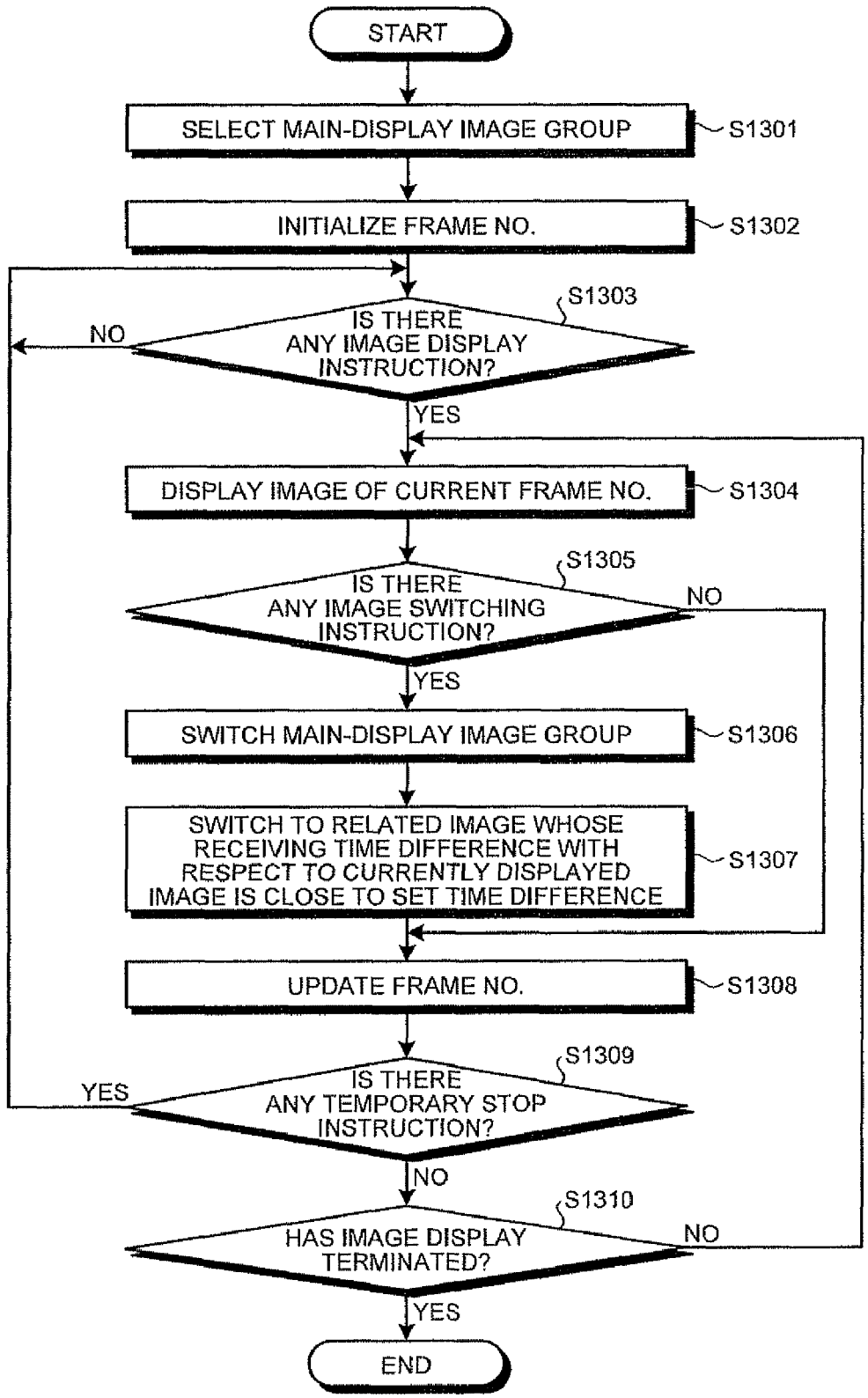
FIG. 50 is a flowchart illustrating a processing procedure by the control unit of the image display apparatus according to the eighth embodiment.

Next, the operation of the control unit 335 controlling to switch the currently displayed image in the main-display area 400 to a related image contained in an image group inside the subject 1 selected from the plurality of image groups PG11 and PG12 will be described. FIG. 50 is a flowchart illustrating the processing procedure by the control unit 335 of the image display apparatus 334 according to the eighth embodiment.

Substantially like the control unit 325 of the image display apparatus 324 according to the seventh embodiment, the control unit 335 performs control to display each image in the image groups PG11 and PG12 inside the subject 1 in the main-display area 400 of the display unit 312 and if the image group to be displayed in the main-display area 400 (main-display image group) is selected by the image group selection icons 401 and 402, performs control to switch the currently displayed image in the main-display area 400 to a related image in the selected image group. In this case, the control unit 335 determines the related image most similar to the currently displayed image from the selected image group based on a receiving time difference of images in place of the input time of an image.

That is, as shown in FIG. 50, the control unit 335 performs the processing procedure similar to steps S1201 to S1204 (See FIG. 44) to select the main-display image group from a plurality of image groups (for example, the image groups PG11 and PG12) inside the subject 1 and if an image display instruction is issued, performs control to display images inside the subject contained in the main-display image group in the main-display area 400 (steps S1301 to S1304). Next, the control unit 335 performs the processing procedure similar to steps S1205 and 31206 to determine whether or not any image switching instruction to switch the currently displayed image in the main-display area 400 has been issued (step S1305) and, if an image switching instruction has been issued (step S1305, Yes), switches the main-display image group to an image group identified by selection information of an image group input by the input unit 311 (step S1306).

Subsequently, based on identification information of each image in the image group corresponding to the selection information and that of the currently displayed image in the main-display area 400, the control unit 335 performs control to switch the currently displayed image to a related image having the receiving time whose subtraction from the receiving time of the currently displayed image yields a receiving time difference closest to the set time difference Δt (step S1307). In this case, the image extractor 335c checks the receiving time contained in the identification information of the current display image in the main-display area 400, that of each image in the image group corresponding to the selection information, and the set time difference Δt corresponding to time difference information input by the input unit 311 to extract an image containing the receiving time whose subtraction from the receiving time of the currently displayed image yields a receiving time difference closest to the set time difference Δt as identification information from the image group corresponding to the selection information. The image extracted by the image extractor 335c is the related image most similar to the currently displayed image and contains ID information of the imaging device corresponding to the selection information and the input time closest to that of the currently displayed image as identification information. In this manner, the image extractor 335c determines the related image most similar to the currently displayed image. The display controller 315a performs control to switch the currently displayed image to the related image extracted by the image extractor 335c. Thus, the related image is currently displayed in the main-display area 400.

Then, as same in step S1208, the control unit 335 updates the frame number of the main-display image group containing the image currently displayed in the main-display area 400 (such as a related image) (step S1308). Then, as same in step S1209, the control unit 335 determines whether or not any temporary stop instruction of the image in the main-display area 400 has been issued (step S1309) and if a temporary stop instruction has been issued (step S1309, Yes), returns to step S1303 to repeat the processing procedure at step S1303 and onward.

If, on the other hand, no temporary stop instruction has been issued (step S1309, No), as same in step S1210, the control unit 335 determines whether or not image display processing to display images inside the subject in the main-display area 400 has terminated (step S1310). If the control unit 335 determines that image display processing has not terminated (step S1310, No), the control unit 335 returns to step S1304 to repeat the processing procedure at step S1304 and onward. If the control unit 335 determines that image display processing has terminated (step S1310, Yes), the control unit 335 completes the image display processing of images inside the subject.

If the control unit 335 determines at step S1305 that no image switching instruction has been issued (step S1305, No), the control unit 335 proceeds to step S1308 to repeat the processing procedure at step S1308 and onward.

Figure 51:
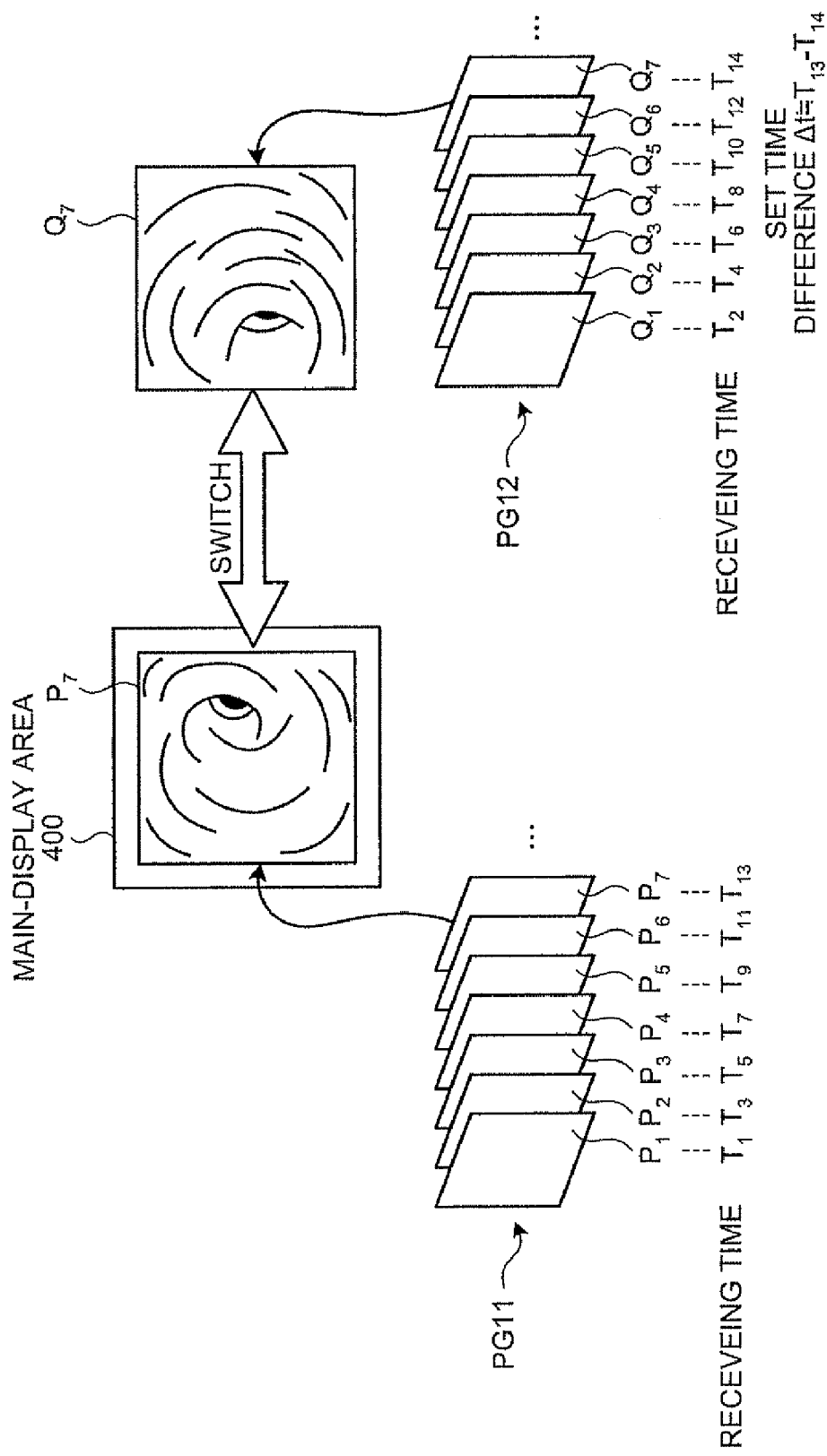
FIG. 51 is a schematic diagram illustrating operation of the control unit to switch the currently displayed image in the main-display area to a related image in another image group based on a receiving time difference of images.

Next, a case in which images inside the subject 1 contained in the plurality of image groups PG11 and PG12 picked up by the multiple-lens capsule endoscope 302c are displayed in the main-display area 400 of the display unit 312 is exemplified to specifically describe the operation of the control unit 335 to switch the currently displayed image currently displayed in the main-display area 400 to a related image in another image group (an image group selected by a selection GUI). FIG. 51 is a schematic diagram illustrating the operation of the control unit 335 to switch the currently displayed image in the main-display area 400 to a related image in another image group based on a receiving time difference of images.

As shown in FIG. 51, receiving times $T_1$, $T_3$, $T_5$, $T_7$, $T_9$, $T_{11}$, $T_{13}$, ... when received by the receiving apparatus 303 are associated with each image $P_n$ (frame number n=1, 2, 3, ...) inside the image group PG11 picked up by the front imaging device of the capsule endoscope 302c. On the other hand, receiving times $T_2$, $T_4$, $T_6$, $T_8$, $T_{10}$, $T_{12}$, $T_{14}$, ... when received by the receiving apparatus 303 are associated with each image $Q_m$ (frame number m=1, 2, 3, ...) inside the image group PG12 picked up by the rear imaging device of the capsule endoscope 302c. That is, each of the images $P_n$ and $Q_m$ inside the subject 1 has been received by the receiving apparatus 303 in order of time series of receiving time, that is, in the order of image $P_1$, image $Q_1$, image $P_2$, image $Q_2$, image $P_3$, image $Q_3$, image $P_4$, image $Q_4$, image $P_5$, image $Q_5$, image $P_6$, image $Q_6$ image $P_7$, and image $Q_7$.

Here, among images $P_n$ inside the subject 1 contained in the image group PG11, for example, the image $P_7$ is currently displayed in the main-display area 400 of the display unit 312. In this case, the image group PG11 containing the image $P_7$, which is the currently displayed image of the main-display area 400, is the image group to be processed for being displayed in the main-display area 400 (that is, the main-display image group). Moreover, the image $P_7$ in the main-display area 400 is associated with ID information of the front imaging device of the capsule endoscope 302c and the receiving time $T_{13}$ as identification information.

If a click operation of the image group selection icon 402 is performed and the input unit 311 inputs selection information corresponding to the image group PG12 to the control unit 335 in this state, the control unit 335 switches, based on the selection information corresponding to the image group PG12, the main-display image group from the currently displayed image group PG11 to the image group PG12. More specifically, the selection information corresponding to the image group PG12 is, for example, ID information of the rear imaging device of the capsule endoscope 302c and the display controller 315a selects the image group PG12 picked up by the rear imaging device of the capsule endoscope 302c identified by the selection information from the plurality of image groups PG11 and PG12 saved in the storage unit 314. In this manner, the display controller 315a switches the main-display image group from the currently displayed image group PG11 to the image group PG12.

Next, the control unit 335 determines a related image inside the image group PG12 most similar to the image $P_7$, which is the currently displayed image, based on identification information of each image inside the image group PG12 selected by the image group selection icon 402, that of the image $P_7$ currently displayed in the main-display area 400 and the set time difference Δt set by the time difference setting unit 410 and performs control to switch the currently displayed image to the related image. In this case, the image extractor 335c checks input times ($T_2$, $T_4$, $T_6$, $T_8$, $T_{10}$, $T_{12}$, $T_{14}$, ...) of each image ($Q_1$, $Q_2$, $Q_3$, $Q_4$, $Q_5$, $Q_6$, $Q_7$, ...) inside the selected image group PG12, the receiving time $T_{13}$ of the currently displayed image or the image $P_7$, and the set time difference Δt. Then, the image extractor 335c determines the image $Q_7$ having the receiving time $T_{14}$ whose subtraction from the receiving time $T_{13}$ of the image $P_7$ yields a receiving time difference closest to the set time difference Δt as the related image most similar to the image $P_7$. Then, the image extractor 335c extracts the image $Q_7$ determined to be the related image to the image $P_7$ from the image group PG12. In this case, the display controller 315a performs control to switch the currently displayed image in the main-display area 400 from the image $P_7$ to the image $Q_7$ (that is, the related image to the image $P_7$).

Here, the images $P_7$ and $Q_7$ related as the currently displayed image and a related image are mutually similar images and are, for example, images in which substantially the same site inside the same organ of the subject 1 is picked up or images in which neighboring sites mutually related as front and rear or opposite to each other are picked up. By displaying the currently displayed image and a related image in the main-display area 400 by switching them in this manner, images mutually similar to each other among the plurality of image groups inside the subject 1 can easily be observed and, as a result, images inside organs of the subject 1 can minutely be observed.

In the eighth embodiment of the present invention, as described above, if image groups inside a subject picked up by a plurality of imaging devices are classified by imaging device, a plurality of image groups inside the subject, identification information for identifying each image inside the plurality of image groups, and the set time difference Δt of images set by a setting GUS are saved in a storage unit, and an image group to be displayed in a main-display area of a display unit is selected by a selection GUI from the plurality of image groups, an image in the selected image group having the receiving time whose subtraction from that of a currently displayed image currently displayed in a main-display area yields a difference closest to the set time difference Δt as a related image most similar to the currently displayed image is determined and the currently displayed image is switched to the related image. Thus, like the seventh embodiment, by an easy operation using the selection GUT, images mutually similar to each other among the plurality of image groups can be displayed in the main-display area by switching them and also the receiving time difference between the currently displayed image in the main-display area and the related image can easily be adjusted. Therefore, even if there is a difference in traveling speed when moving inside an organ of the subject or in frame rate when picking up images inside the subject among the plurality of imaging devices sequentially picking up images inside the subject, a related image most similar to the currently displayed image can reliably be extracted from the selected image group. As a result, the operation effect of the seventh embodiment can be achieved and also an image display apparatus capable of reliably switching the currently displayed image to a related image thereof can be realized.

Next, the ninth embodiment of the present invention will be described. While an image whose input time is closest to that of the currently displayed image in the main-display area 400 is determined as a related image of the currently displayed image in the seventh embodiment, in the ninth embodiment, imaging position information of a capsule endoscope (that is, an imaging device) introduced into a subject is detected and a related image of the currently displayed image is determined based on the detected imaging position information.

Figure 52:
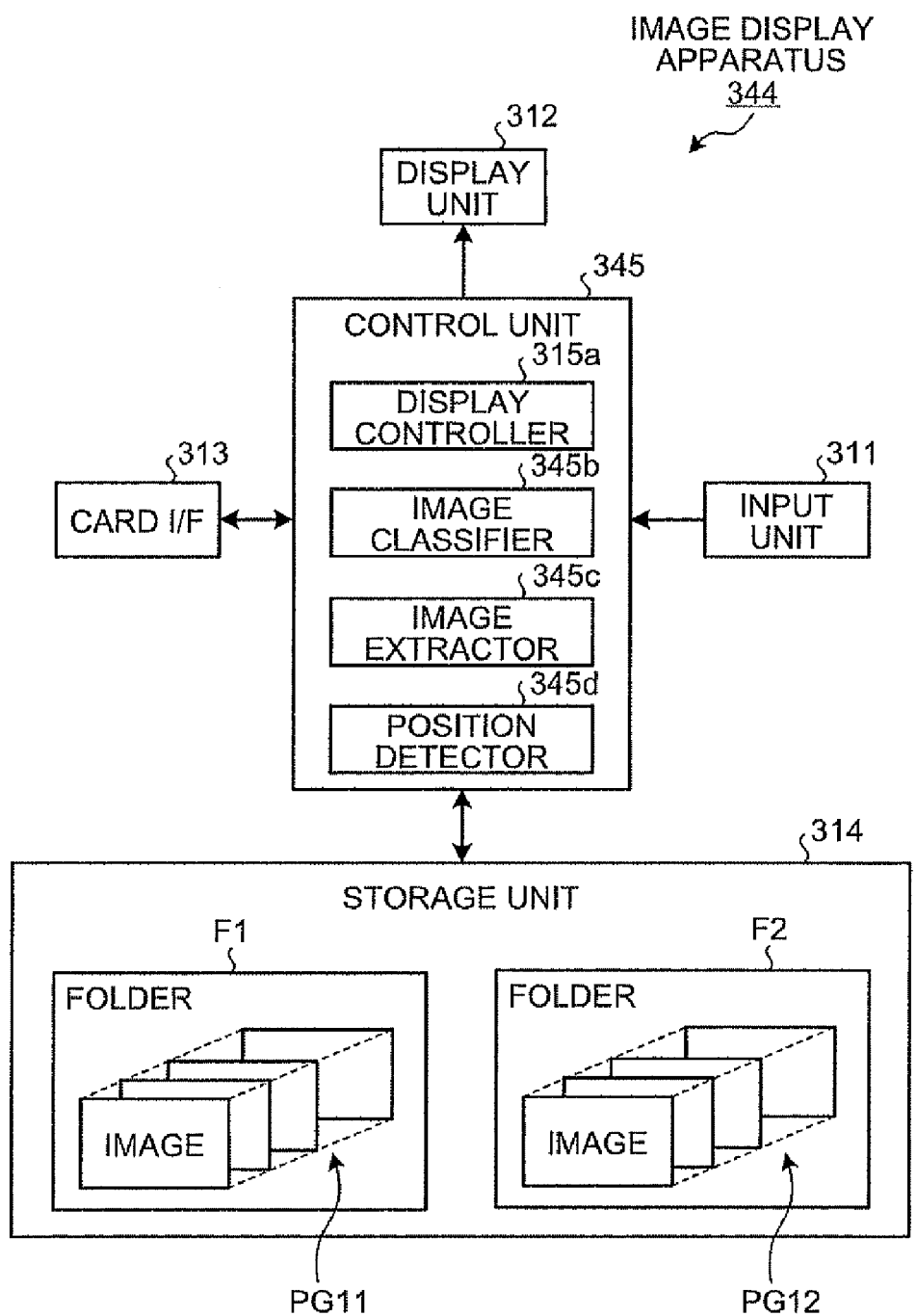
FIG. 52 is a block diagram exemplarily showing a configuration example of an image display apparatus according to a ninth embodiment of the present invention.

FIG. 52 is a block diagram exemplarily showing a configuration example of an image display apparatus according to the ninth embodiment of the present invention. As shown in FIG. 52, an image display apparatus 344 according to the ninth embodiment has a control unit 345 in place of the control unit 325 of the image display apparatus 324 according to the seventh embodiment. An intra-subject information acquisition system according to the ninth embodiment has an image display apparatus 344 in place of the image display apparatus 324 of the intra-subject information acquisition system according to the seventh embodiment. In this case, the receiving apparatus 303 sequentially accumulates receiving electric field strength in the portable recording medium 305 when an image inside the subject 1 is received in place of the receiving time of an image. That is, in the ninth embodiment, images inside the subject 1, ID information of the imaging device picking up images inside the subject 1, and receiving electric field strength of images inside the subject 1 are mutually associated. Other components are the same as those in the seventh embodiment and the same reference numerals are attached to the same components, Substantially like the control unit 325 of the image display apparatus 324 according to the seventh embodiment, the control unit 345 controls each of the input unit 311, the display unit 312, the card I/F 313, and the storage unit 314 and also controls input/output of information among these components. In this case, the control unit 345 acquires image groups inside the subject 1, ID information of the imaging device associated with each image contained in the image groups inside the subject 1, and receiving electric field strength of each image from the portable recording medium 305 inserted in the card I/F 313. The receiving electric field strength of an image includes, for example, three or more superior receiving electric field strengths when an image inside the subject is received by the receiving antennas 303a to 303h of the receiving apparatus 303. The control unit 345 saves image groups inside the subject 1, ID information of the imaging device, and receiving electric field strength of images in the storage unit 314 by associating them.

The control unit 345 as described above has the display controller 315a, an image classifier 345b in place of the image classifier 325b of the control unit 325 of the image display apparatus 324, and an image extractor 345c in place of the image extractor 325c. Further, the control unit 345 has a position detector 345d for detecting imaging position information of an imaging device inside the subject based on receiving electric field strength of an image.

Like the image classifier 325b of the control unit 325, the image classifier 345b classifies a plurality of image groups (for example, the image groups PG11 and PG12) inside the subject 1 by ID information of the imaging device associated with each image. Each image in the image groups classified by the image classifier 345b is associated, for example, with ID information of one of imaging devices of the capsule endoscopes 302a and 302b and three or more superior receiving electric field strengths when received by the receiving apparatus 303.

The image extractor 345c extracts, based on selection information of an image group input by the input unit 311 and imaging position information detected by the position detector 345d, a related image most similar to the currently displayed image in the main-display area 400 of the display unit 312 from the image group (for example, from one of the image groups PG11 and PG12 selected by the image group selection icons 401 and 402) inside a subject corresponding to the selection information, In this case, the image extractor 345c determines from the image group selected based on the selection information a related image having ID information of the imaging device that picked up the image group and imaging position information closest to that of the currently displayed image as identification information and extracts the related image. The related image extracted by the image extractor 345c is displayed in the main-display area 400 of the display unit 312 in place of the currently displayed image.

The position detector 345d functions as a position detection unit for detecting imaging position information of the capsule endoscopes 302a and 302b introduced into the subject. More specifically, the position detector 345d detects, based on receiving electric field strength associated with each image in the image group PG11, imaging position information of the imaging device of the capsule endoscopes 302a that picked up the image group PG11 for each image. The position detector 345d associates the imaging position information of the imaging device detected for each image in the image group PG11 with each image in the image group PG11. Similarly, the position detector 345d detects, based on receiving electric field strength associated with each image in the image group PG12, imaging position information of the imaging device of the capsule endoscopes 302b that picked up the image group PG12 for each image. The position detector 345d associates the imaging position information of the imaging device detected for each image in the image group PG12 with each image in the image group PG12.

The control unit 345 having the configuration described above saves the image groups PG11 and PG12 classified for each imaging device by the image classifier 345b in the folders F1 and F2 of the storage unit 314 respectively. In this case, the each image in the image groups PG11 and PG12 saved in the storage unit 314 is associated with the ID information of the imaging device and the imaging position information detected by the position detector 345d. Therefore, identification information of each image in the image groups PG11 and PG12 is a combination of the ID information of the imaging device and the imaging position information.

Figure 53:
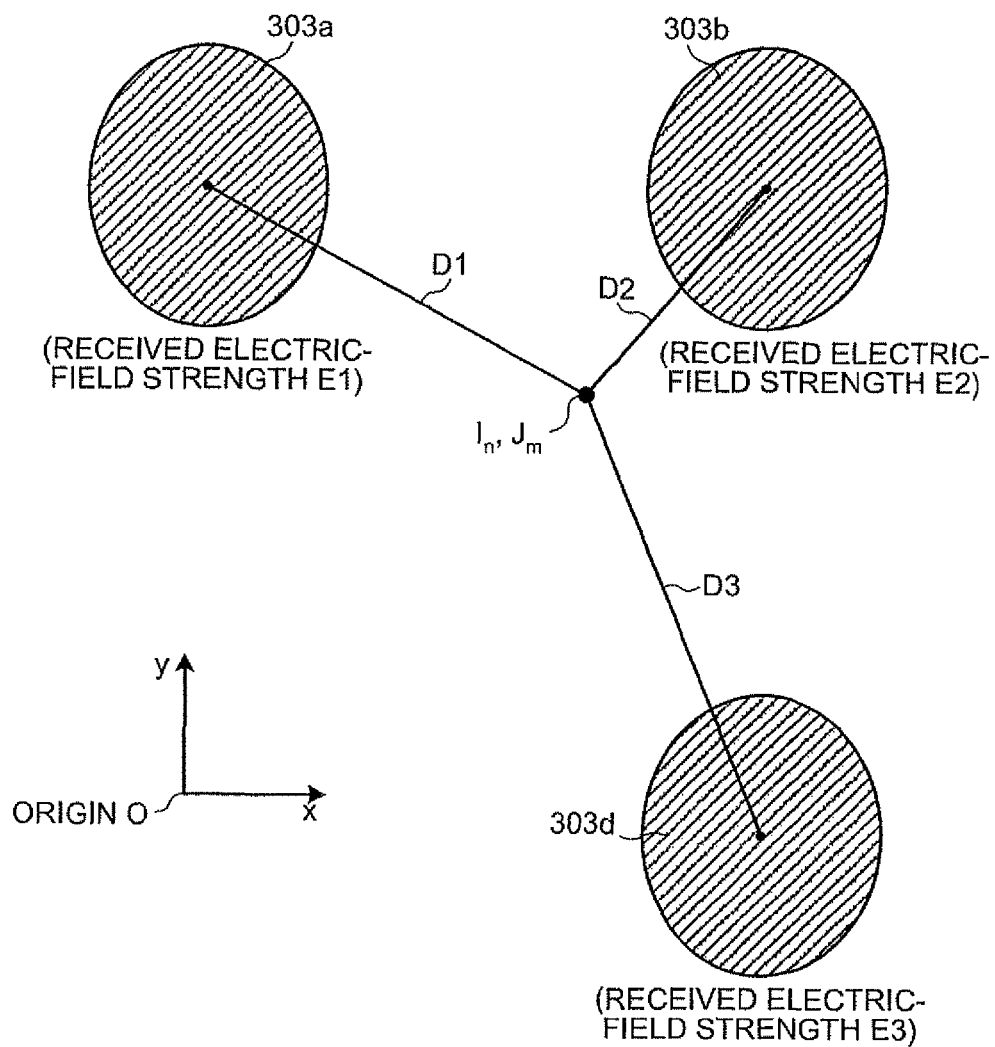
FIG. 53 is a schematic diagram illustrating processing of a position detector to detect imaging position information of an image inside the subject.

Next, processing of the position detector 345d to detect imaging position information of each image based on receiving electric field strength associated with each image contained in an image group inside a subject will be described. FIG. 53 is a schematic diagram illustrating processing of the position detector 345d for detecting imaging position information of an image inside the subject. Processing of the position detector 345d will be described below with reference to FIG. 53.

The position detector 345d has, for example, an xy coordinate system with an origin O specifying position coordinates inside an organ of the subject 1 and each position coordinate of the receiving antennas 303a to 303h arranged over the body surface of the subject 1. Based on three or more superior receiving electric field strengths associated with each image in the image groups PG11 and PG12, the position detector 345d calculates the distances between receiving antennas of three or more superior receiving electric field strengths and an imaging device of the capsule endoscopes 302a and 302b to detect imaging position information of each image based on trigonometry using the distances between the receiving antennas of three or more superior receiving electric field strengths and the imaging device.

More specifically, the position detector 345d checks, for example, three highest receiving electric field strengths E1, E2, and E3 associated with an image $P_n$ inside the image group PG11. Here, if the three highest receiving electric field strengths E1, E2, and E3 are receiving electric field strengths of radio signals from the capsule endoscope 302a received from the receiving antennas 303a, 303b, and 303d respectively, the position detector 345d calculates a distance D1 between the receiving antenna 303a and the capsule endoscope 302a based on the receiving electric field strength E1, a distance D2 between the receiving antenna 303b and the capsule endoscope 302a based on the receiving electric field strength E2, and a distance D3 between the receiving antenna 303d and the capsule endoscope 302a based on the receiving electric field strength E3.

The distance D1 between the receiving antenna 303a and the capsule endoscope 302a decreases with an increase in receiving electric field strength E1 and increases with a decrease in receiving electric field strength E1. Such a relation between receiving electric field strength and the distance from a receiving antenna to the capsule endoscope 302a also applies to between the receiving electric field strength E2 and the distance D2, and between the receiving electric field strength E3 and the distance D3.

The position detector 345d calculates position coordinates $I_n$ (x, y) in the xy coordinate system positioned at the distances D1, D2, and D3 from the receiving antennas 303a, 303b, and 303d respectively based on trigonometry using the distances D1, D2, and D3 calculated as described above. The position coordinate $I_n$ in the xy coordinate system indicates the position of the imaging device of the capsule endoscope 302a when an image $P_n$ inside an organ of the subject 1 is picked up and is imaging position information of the image $P_n$. The position detector 345d detects the position coordinate $I_n$ as imaging position information of the image $P_n$. The imaging position information of the image $P_n$ is saved in the storage unit 314 by associating with the image $P_n$.

Similarly, the position detector 345d calculates position coordinates $J_m$ (x, y) of the imaging device of the capsule endoscope 302b when an image $Q_m$ inside an organ of the subject 1 is picked up based on trigonometry using distances between receiving antennas of the three highest receiving electric field strengths and the capsule endoscope 302b and detects the position coordinate $J_m$ as imaging position information of the image $Q_m$. The imaging position information of the image $Q_m$ is saved in the storage unit 314 by associating with the image $Q_m$.

Figure 54:
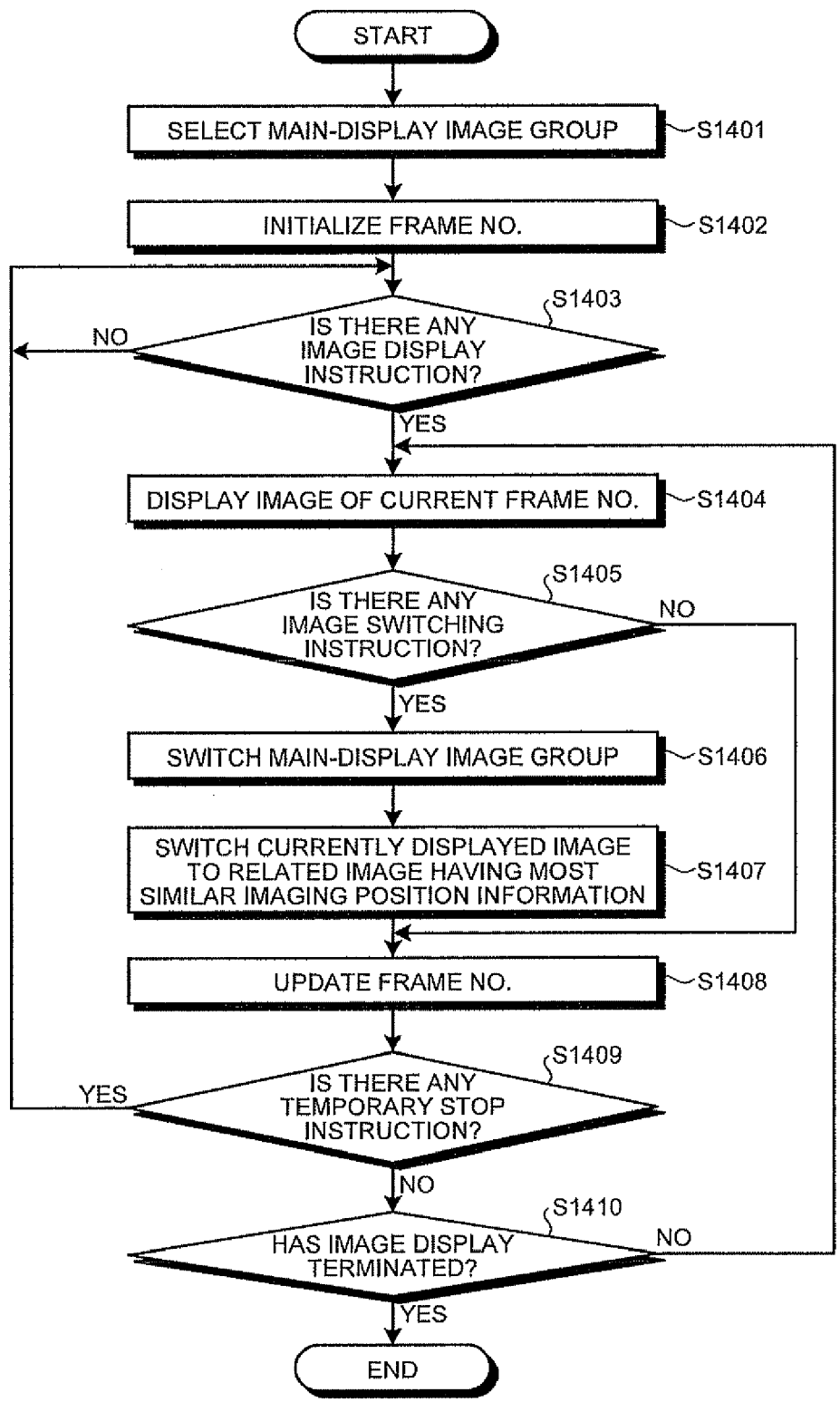
FIG. 54 is a flowchart illustrating processing procedure by the control unit of the image display apparatus according to the ninth embodiment.

Next, the operation of the control unit 345 controlling to switch the currently displayed image in the main-display area 400 to a related image contained in an image group inside the subject 1 selected from the plurality of image groups PG11 and PG12 will be described. FIG. 54 is a flowchart illustrating the processing procedure by the control unit 345 of the image display apparatus 344 according to the ninth embodiment.

Substantially like the control unit 325 of the image display apparatus 324 according to the seventh embodiment, the control unit 345 performs control to display each image in the image groups PG11 and PG12 inside the subject 1 in the main-display area 400 of the display unit 312 and if the image group to be displayed in the main-display area 400 (main-display image group) is selected by the image group selection icons 401 and 402, performs control to switch the currently displayed image in the main-display area 400 to a related image in the selected image group. In this case, the control unit 345 determines the related image most similar to the currently displayed image from the selected image group based on imaging position information of images in place of the input time of an image.

That is, as shown in FIG. 54, the control unit 345 performs the processing procedure similar to steps S1201 to S1204 (See FIG. 44) to select the main-display image group from a plurality of image groups (for example, the image groups PG11 and PG12) inside the subject 1 and if an image display instruction is issued, performs control to display images inside the subject contained in the main-display image group in the main-display area 400 (steps S1401 to S1404). Next, the control unit 345 performs the processing procedure similar to steps S1205 and S1206 to determine whether or not any image switching instruction to switch the currently displayed image in the main-display area 400 has been issued (step S1405) and, if an image switching instruction has been issued (step S1405, Yes), switches the main-display image group to an image group identified by selection information of an image group input by the input unit 311 (step S1406).

Subsequently, based on identification information of each image in the image group corresponding to the selection information and that of the currently displayed image in the main-display area 400, the control unit 345 performs control to switch the currently displayed image to a related image having the closest imaging position information to that of the currently displayed image (step S1407). In this case, the image extractor 345c checks imaging position information contained in the identification information of the current display image in the main-display area 400 and that of each image in the image group corresponding to the selection information to extract an image containing imaging position information closest to that of the currently displayed image as identification information from the image group corresponding to the selection information. The image extracted by the image extractor 345c is the related image most similar to the currently displayed image and contains ID information of the imaging device corresponding to the selection information and imaging position information closest to that of the currently displayed image as identification information. In this manner, the image extractor 345c determines the related image most similar to the currently displayed image. The display controller 315a performs control to switch the currently displayed image to the related image extracted by the image extractor 345c. Thus, the related image is currently displayed in the main-display area 400.

Then, as same in step S1208, the control unit 345 updates the frame number of the main-display image group containing the image currently displayed in the main-display area 400 (such as a related image) (step S1408). Then, as same in step S1209, the control unit 345 determines whether or not any temporary stop instruction of the image in the main-display area 400 has been issued (step S1409) and if a temporary stop instruction has been issued (step S1409, Yes), returns to step S1403 to repeat the processing procedure at step S1403 and onward.

If, on the other hand, no temporary stop instruction has been issued (step S1409, No), as same in step S1210, the control unit 345 determines whether or not image display processing to display images inside the subject in the main-display area 400 has terminated (step S1410). If the control unit 345 determines that image display processing has not terminated (step S1410, No), the control unit 345 returns to step S1404 to repeat the processing procedure at step S1404 and onward. If the control unit 345 determines that image display processing has terminated (step S1410, Yes), the control unit 345 completes the image display processing of images inside the subject.

If the control unit 345 determines at step S1405 that no image switching instruction has been issued (step S1405, No), the control unit 345 proceeds to step S1408 to repeat the processing procedure at step S1408 and onward.

Figure 55:
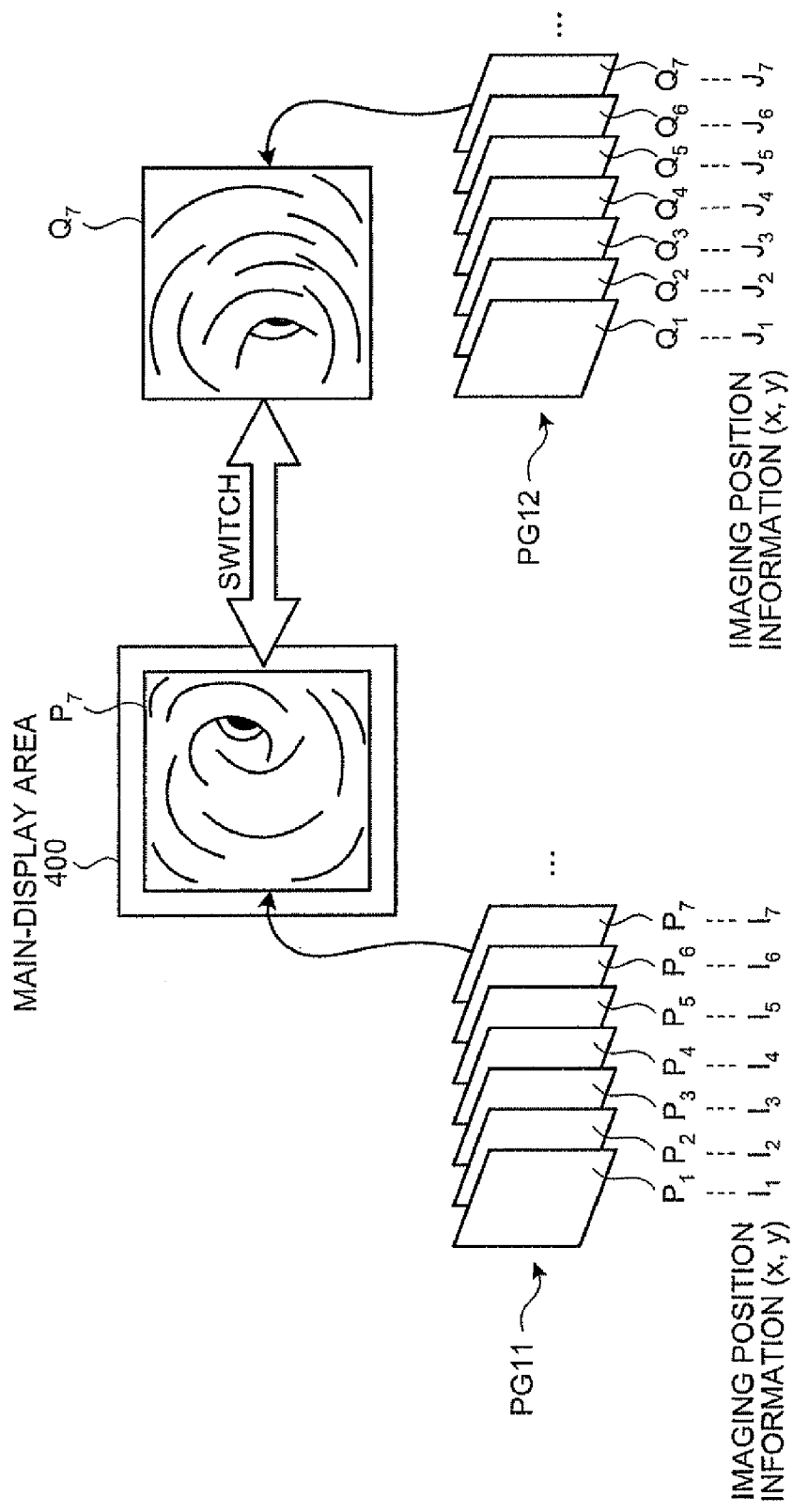
FIG. 55 is a schematic diagram illustrating operation of the control unit to switch the currently displayed image in the main-display area to a related image in another image group based on identification information of an image including imaging position information.

Next, a case in which images inside the subject 1 contained in the plurality of image groups PG11 and PG12 picked up by the capsule endoscopes 302a and 302b are displayed in the main-display area 400 of the display unit 312 is exemplified to specifically describe the operation of the control unit 345 to switch the currently displayed image currently displayed in the main-display area 400 to a related image in another image group (an image group selected by a selection GUI). FIG. 55 is a schematic diagram illustrating the operation of the control unit 345 to switch the currently displayed image in the main-display area 400 to a related image in another image group based on identification information of the image including imaging position information.

As shown in FIG. 55, position coordinates $I_1$, $I_2$, $I_3$, $I_4$, $I_5$, $I_6$, $I_7$, ..., $I_n$, which are imaging position information detected by the position detector 345d, are associated with each image $P_n$ (frame number n=1, 2, 3, ...) inside the image group PG11 picked up by the imaging device of the capsule endoscope 302a. On the other hand, position coordinates $J_1$, $J_2$, $J_3$, $J_4$, $J_5$, $J_6$, $J_7$, . . . , $J_m$, which are imaging position information detected by the position detector 345d, are associated with each image $Q_m$ (frame number m=1, 2, 3, . . . ) inside the image group PG12 picked up by the imaging device of the capsule endoscope 302b.

Here, among images $P_n$ inside the subject 1 contained in the image group PG11, for example, the image $P_7$ is currently displayed in the main-display area 400 of the display unit 312. In this case, the image group PG11 containing the image $P_7$, which is the currently displayed image of the main-display area 400, is the image group to be processed for being displayed in the main-display area 400 (that is, the main-display image group). Moreover, the image $P_7$ in the main-display area 400 is associated with ID information of the imaging device of the capsule endoscope 302a and the position coordinate $I_7$, which is imaging position information, as identification information.

If a click operation of the image group selection icon. 402 is performed and the input unit 311 inputs selection information corresponding to the image group PG12 to the control unit 345 in this state, the control unit 345 switches, based on the selection information corresponding to the image group PG12, the main-display image group from the currently displayed image group PG11 to the image group PG12. More specifically, the selection information corresponding to the image group PG12 is, for example, ID information of the imaging device of the capsule endoscope 302b and the display controller 315a selects the image group PG12 picked up by the imaging device of the capsule endoscope 302b identified by the selection information from the plurality of image groups PG11 and PG12 saved in the storage unit 314. In this manner, the display controller 315a switches the main-display image group from the currently displayed image group PG11 to the image group PG12.

Next, the control unit 345 determines a related image inside the image group PG12 most similar to the image $P_7$, which is the currently displayed image, based on identification information of each image inside the image group PG12 selected by the image group selection icon 402 and that of the image $P_7$ currently displayed in the main-display area 400 and performs control to switch the currently displayed image to the related image. In this case, the image extractor 345c checks imaging position information (position coordinates $J_1$, $J_2$, $J_3$, $J_4$, $J_5$, $J_6$, $J_7$, . . . , $J_m$) of each image ($Q_1$, $Q_2$, $Q_3$, $Q_4$, $Q_5$, $Q_6$, $Q_7$, . . . , $Q_m$) inside the selected image group PG12 and imaging position information (position coordinate $I_7$) of the currently displayed image or the image $P_7$. Then, the image extractor 345c determines the image $Q_7$ having the position coordinate $J_7$ as imaging position information closest to the position coordinate $I_7$, which is the imaging position information of the image $P_7$ as the related image most similar to the image $P_7$. The image extractor 345c extracts the image $Q_7$ determined to be the related image to the image $P_7$ from the image group PG12. In this case, the display controller 315a performs control to switch the currently displayed image in the main-display area 400 from the image $P_7$ to the image $Q_7$ (that is, the related image to the image $P_7$).

Here, the images $P_7$ and $Q_7$ related as the currently displayed image and a related image are mutually similar images and are, for example, images in which substantially the same site inside the same organ of the subject 1 is picked up or images in which neighboring sites mutually related as front and rear or opposite to each other are picked up. By displaying the currently displayed image and a related image in the main-display area 400 by switching them in this manner, images mutually similar to each other among the plurality of image groups inside the subject 1 can easily be observed and, as a result, images inside organs of the subject 1 can minutely be observed.

In the ninth embodiment of the present invention, as described above, if imaging position information of each image contained in image groups inside a subject picked up by a plurality of imaging devices, a plurality of image groups inside the subject classified by imaging device and identification information of each image including the imaging position information are saved in a storage unit, and an image group to be displayed in a main-display area of a display unit is selected by a selection GUI from the plurality of image groups, an image in the selected image group having imaging position information closest to that of the currently displayed image currently displayed in the main-display area is determined as a related image most similar to the currently displayed image and the currently displayed image is switched to the related image. Thus, like the seventh embodiment described above, by an easy operation using the selection GUI, images mutually similar to each other among the plurality of image groups can be displayed in the main-display area by switching them and even if there is a difference in traveling speed when moving inside an organ of the subject or in frame rate when picking up images inside the subject among the plurality of imaging devices sequentially picking up images inside the subject, a related image most similar to the currently displayed image can reliably be extracted from the selected image group. As a result, the operation effect of the seventh embodiment can be achieved and also an image display apparatus capable of reliably switching the currently displayed image to a related image thereof can be realized.

Next, the tenth embodiment of the present invention will be described. While the currently displayed image in the main-display area 400 is switched to a related image most similar to the currently displayed image in the sixth embodiment, the tenth embodiment is configured so that a plurality of main-display areas is formed in the window W10 of the display unit 312 to simultaneously display related images most similar to each other among a plurality of image groups inside a subject in the plurality of main-display areas.

Figure 56:
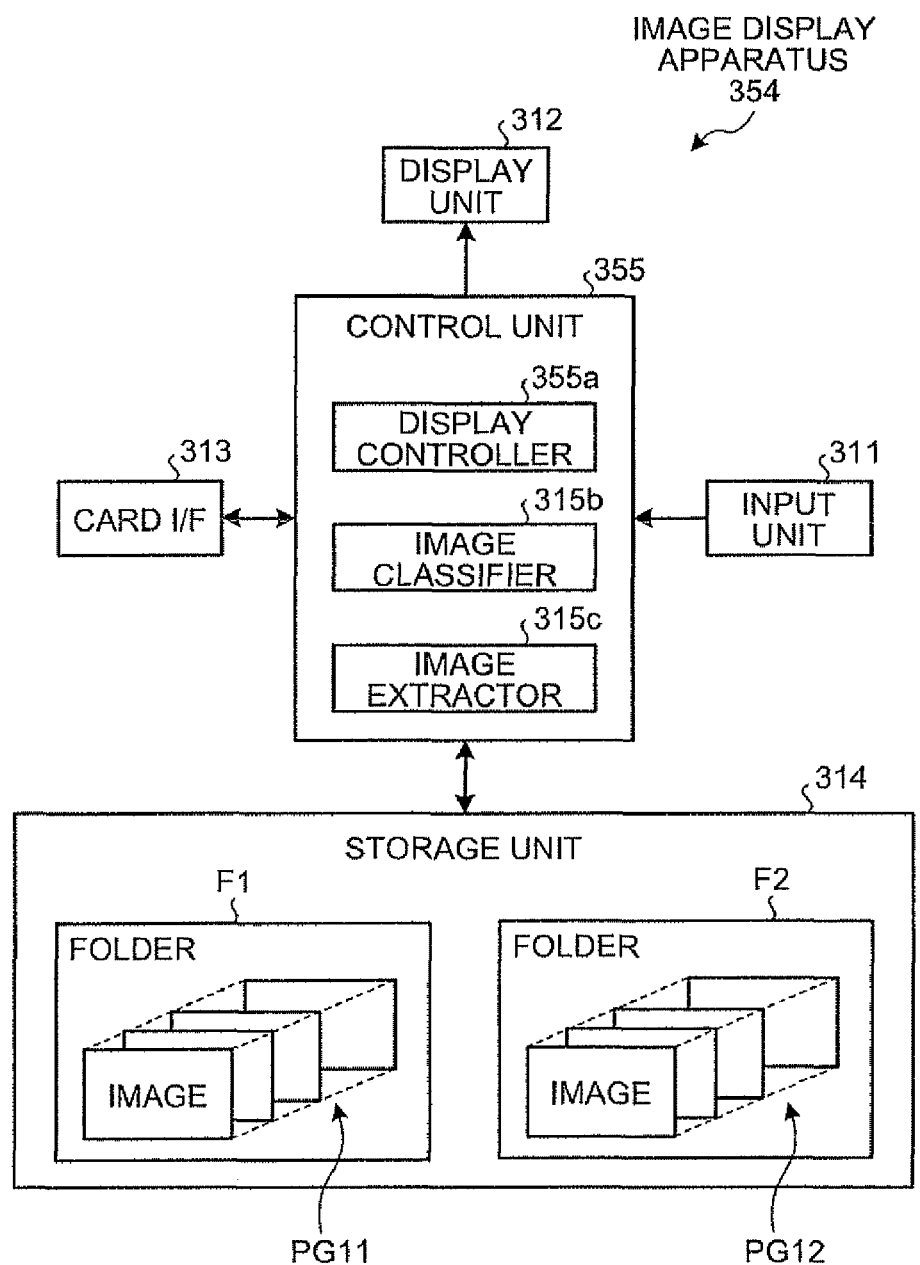
FIG. 56 is a block diagram exemplarily showing a configuration example of an image display apparatus according to a tenth embodiment of the present invention.

FIG. 56 is a block diagram exemplarily showing a configuration example of an image display apparatus according to the tenth embodiment of the present invention. As shown in FIG. 56, an image display apparatus 354 according to the tenth embodiment has a control unit 355 in place of the control unit 315 of the image display apparatus 304 according to the sixth embodiment. Also, an intra-subject information acquisition system according to the tenth embodiment of the present invention has the image display apparatus 354 in place of the image display apparatus 304 of the intra-subject information acquisition system according to the sixth embodiment (See FIG. 37). Other components are the same as those in the sixth embodiment and the same reference numerals are attached to the same components.

Substantially like the control unit 315 of the image display apparatus 304 according to the sixth embodiment, the control unit 355 controls each of the input unit 311, the display unit 312, the card I/F 313, and the storage unit 314 and also controls input/output of information among these components. In this case, the control unit 355 performs control to form a plurality of main-display areas in the window W10 of the display unit 312 for displaying each image contained in a plurality of image groups (for example, the above image groups PG11 and PG12) inside the subject 1 by image group and to simultaneously display related images most similar to each other (that is, a plurality of related images) among the plurality of image groups inside the subject 1 in the plurality of main-display areas. The control unit 355 has the image classifier 315*b* and the image extractor 315*c*, and a display controller 355*a* in place of the display controller 315*a* of the control unit 315 of the image display apparatus 304 according to the sixth embodiment.

The display controller 355*a* forms the plurality of main-display areas (main-display areas 400*a* and 400*b* described later) in the window W10 of the display unit 312 for displaying each image contained in the plurality of image groups inside the subject 1 by image group. The display controller 355*a* performs control to sequentially display each image contained in the plurality of image groups inside the subject 1 side by side by image group. In this case, the display controller 355*a* performs control to simultaneously display images most similar to each other among the plurality of image groups, that is, each related image extracted from each of the plurality of image groups in each of the plurality of main-display areas.

Next, a specific display mode of the display unit 312 is exemplified to describe the plurality of main-display areas for displaying each image contained in the image groups PG11 and PG12 inside the subject 1 side by side.

Figure 57:
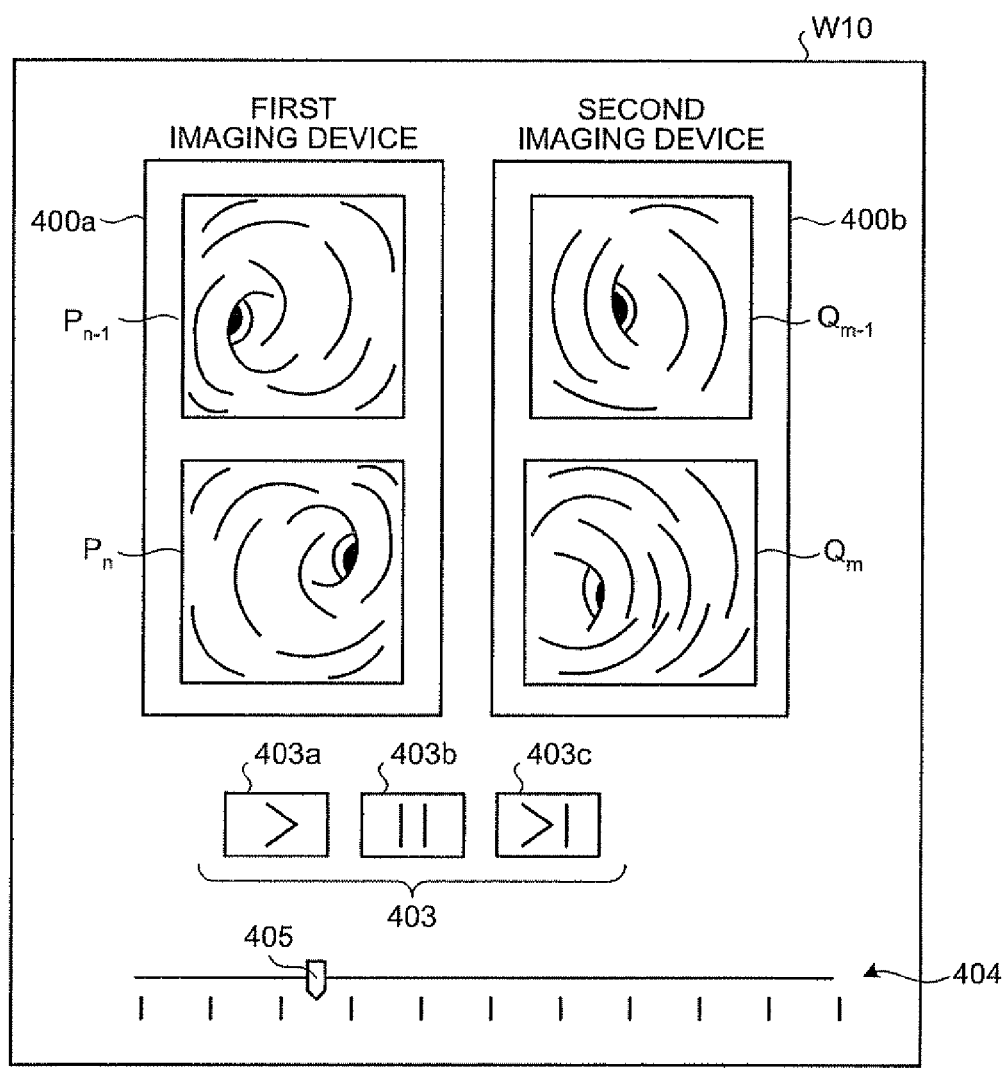
FIG. 57 is a schematic diagram illustrating a window of the display unit in which a plurality of main-display areas displaying images inside the subject by image group side by side is formed.

FIG. 57 is a schematic diagram illustrating the window W10 of the display unit 312 in which a plurality of main-display areas displaying images inside the subject by image group side by side is formed. As shown in FIG. 57, the plurality of main-display areas 400*a* and 400*b* is formed in the window W10 displayed in the display unit 312 of the image display apparatus 354 according to the tenth embodiment in place of the main-display are 400 in the sixth embodiment and thus, the image group selection icons 401 and 402 are not formed. Other components are the same as those in the sixth embodiment and the same reference numerals are attached to the same components.

The plurality of main-display areas 400*a* and 400*b* functions as a display unit for displaying each image contained in the plurality of image groups PG11 and PG12 inside the subject 1 side by side by image group. More specifically, the main-display area 400*a* displays each image in the image group PG11 of the plurality of image groups. In this case, as shown, for example, in FIG. 57, the main-display area 400*a* sequentially displays a plurality of images $P_{n-1}$ and $P_n$ that are consecutive in the image group PG11. In the vicinity of the main-display area 400*a*, information (for example, "First imaging device") indicating the imaging device (the imaging device of the capsule endoscope 302*a*) that picked up the image group PG11 to be displayed is displayed.

The main-display area 400*b* displays each image in the image group PG12 of the plurality of image groups. In this case, as shown, for example, in FIG. 57, the main-display area 400*b* sequentially displays a plurality of images $Q_{m-1}$ and $Q_m$ that are consecutive in the image group PG12. In the vicinity of the main-display area 400*b*, information (for example, "Second imaging device") indicating the imaging device (the imaging device of the capsule endoscope 302*b*) that picked up the image group PG12 to be displayed is displayed.

Based on control of the display controller 355*a*, the plurality of main-display areas 400*a* and 400*b* synchronously displays related images most similar to each other between the plurality of image groups PG11 and PG12 side by side. If, as shown, for example, in FIG. 57, the images $P_{n-1}$ and $P_n$ in the image group PG11 are displayed in the main-display area 400*a* and the images $Q_{m-1}$ and $Q_m$ in the image group PG12 are displayed in the main-display area 400*b*, the image $P_n$, which is the currently displayed image in the main-display area 400*a*, and the image $Q_m$, which is the current image synchronously displayed in the main-display area 400*b* side by side with the image $P_n$, are related images most similar to each other between the image groups PG11 and PG12. Similarly, the image $P_n$, which is the currently displayed image in the main-display area 400*a*, and the image $Q_{m-1}$, which is the current image synchronously displayed in the main-display area 400*b* side by side with the image $P_{n-1}$, are related images most similar to each other between the image groups PG11 and PG12.

Figure 58:
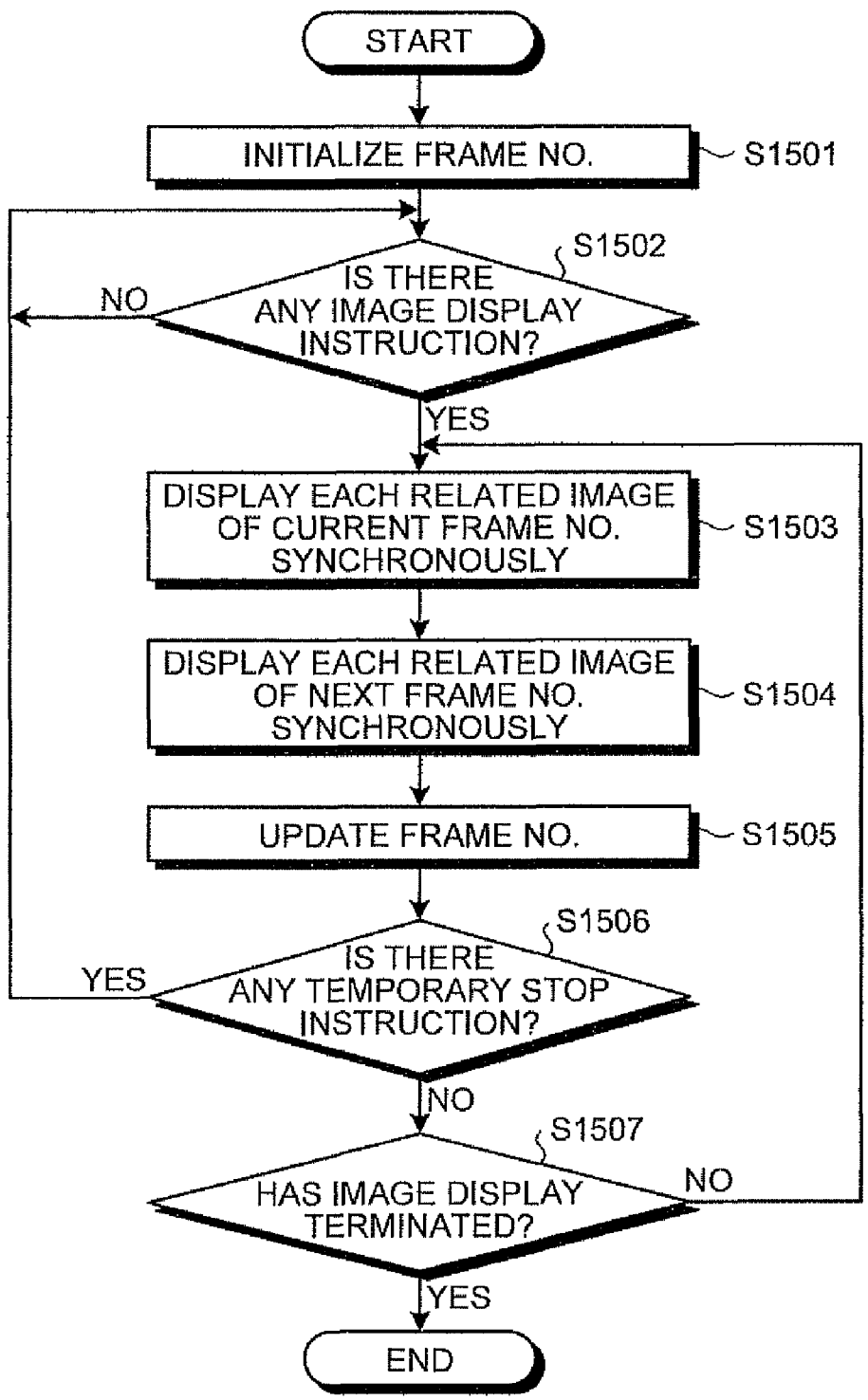
FIG. 58 is a flowchart illustrating a processing procedure by the control unit of the image display apparatus according to the tenth embodiment.

Next, the operation of the control unit 355 controlling to synchronously display related images most similar to each other between the plurality of image groups PG11 and PG12 in the main-display areas 400*a* and 400*b* by image group side by side. FIG. 58 is a flowchart illustrating the processing procedure by the control unit 355 of the image display apparatus 354 according to the tenth embodiment.

As shown in FIG. 58, the control unit 355 first initializes each frame number of the image groups PG11 and PG12 of the subject 1 to be displayed in the main-display areas 400*a* and 400*b* (step S1501). In this case, the display controller 355*a* initializes the frame number n of the image group PG11 of the subject 1 to be displayed in the main-display area 400*a*, for example, to "1" and the frame number m of the image group PG12 of the subject 1 to be displayed in the main-display area 400*b*, for example, to "1".

Next, as same in step S1103, the control unit 355 determines whether or not any image display instruction to the main-display areas 400*a* and 400*b* has been issued (step S1502). In this case, if no image display instruction to the main-display areas 400*a* and 400*b* has been input by the input unit 311, the display controller 355*a* determines that no image display instruction to the main-display areas 400*a* and 400*b* has been issued and, if any image display instruction to the main-display areas 400*a* and 400*b* has been input by the input unit 311, the display controller 355*a* determines that an image display instruction to the main-display areas 400*a* and 400*b* has been issued. If it is determined that no image display instruction to the main-display areas 400*a* and 400*b* is determined to have been issued (step S1502, No), the control unit 355 repeats step S1502.

If an image display instruction to the main-display areas 400*a* and 400*b* is determined to have been issued (step S1502, Yes), the control unit performs control to synchronously display each related image of the current frame numbers of the image groups PG11 and PG12 in the main-display areas 400*a* and 400*b* (step S1503). In this case, the image extractor 315*c* extracts a related image most similar to the image of the current frame number of the image group PG11 from the image group PG12 based on the input number of an image. Based on display instruction information (a play instruction or a frame advance instruction) input by the input unit 311, the display controller 355*a* performs control to display the image of the current frame number of the image group PG11 in the main-display area 400*a* and also performs control to display the related image (that is, the related image most similar to the image of the current frame number of the image group PG11) in the main-display area 400*b*. In this manner, related images (each related image of the current frame numbers) most similar to each other between the image groups PG11 and PG12 are synchronously displayed in the main-display areas 400*a* and 400*b* side by side.

Subsequently, the control unit 355 performs control to synchronously display each related image of the next frame numbers of the image groups PG11 and PG12 in the main-display areas 400*a* and 400*b* (step S1504). In this case, the image extractor 315*c* extracts a related image most similar to the image of the next frame number of the image group PG11 from the image group PG12 based on the input number of an image. The display controller 355a performs control to display the image of the next frame number of the image group PG11 in the main-display area 400a and also performs control to display the related image (that is, the related image most similar to the image of the next frame number of the image group PG11) in the image group PG12 extracted by the image extractor 315c in the main-display area 400b. In this manner, related images (each related image of the next frame numbers) most similar to each other between the image groups PG11 and PG12 are synchronously displayed in the main-display areas 400a and 400b side by side.

Next, the control unit 355 updates each frame number of the image groups PG11 and PG12 to be displayed in the main-display areas 400a and 400b (step S1505). In this case, the display controller 355a updates the frame number of the image group P11 by adding +1 to the frame number of the image in the currently displayed image group PG11 in the main-display area 400a. Similarly, the display controller 355a updates the frame number of the image group P12 by adding +1 to the frame number of the image in the image group PG12 currently displayed in the main-display area 400b.

Then, as same in step S1109, the control unit 355 determines whether or not any temporary stop instruction to each image in the main-display areas 400a and 400b has been issued (step S1506) and, if a temporary stop instruction has been issued (step S1506, Yes), returns to step S1502 to repeat the processing procedure at step S1502 and onward.

If, on the other hand, no temporary stop instruction has been issued (step S1506, No), the control unit 355 determines whether or not image display processing to synchronously display images inside the subject in the main-display areas 400a and 400b has terminated (step S1507). More specifically, the control unit 355 determines that image display processing has terminated (step S1507, Yes) if the frame number of the image group PG11 updated at step S1505 exceeds the number of frames of the image group PG11 or the frame number of the image group PG12 updated at step S1505 exceeds the number of frames of the image group PG12, and completes the image display processing for the main-display areas 400a and 400b. If, on the other hand, the frame number of the image group PG11 updated at step S1505 is equal to or less than the number of frames of the image group PG11 and the frame number of the image group PG12 updated at step S1505 is equal to or less than the number of frames of the image group PG12, the control unit 355 determines that image display processing has not terminated (step S1507, No) and returns to step S1503 to repeat the processing procedure at step S1503 and onward.

Figure 59:
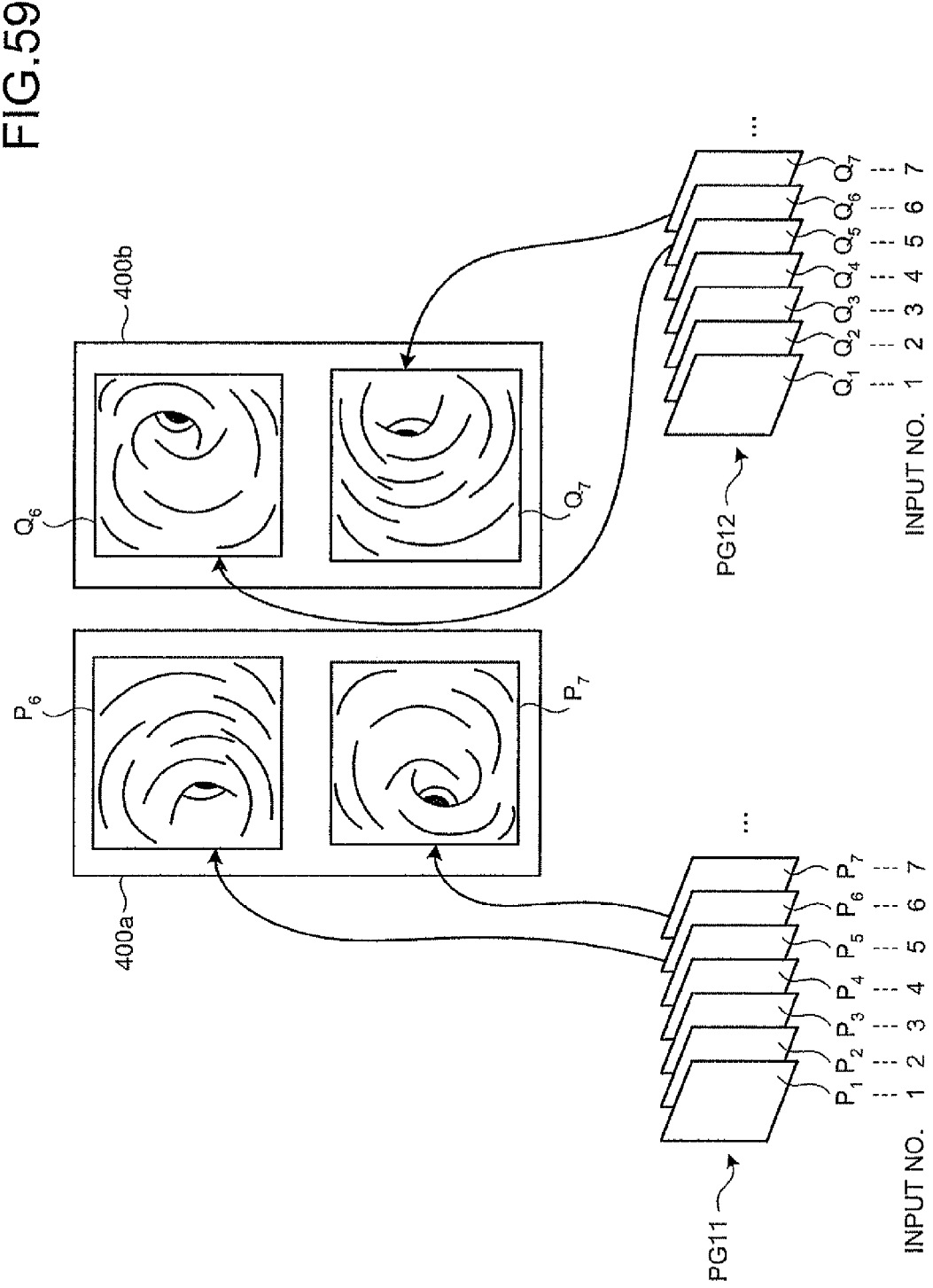
FIG. 59 is a schematic diagram illustrating operation of the control unit to synchronously display images mutually most similar to each other between the plurality of image groups in the plurality of main-display areas side by side.

Next, a case in which each image inside the subject 1 contained in the plurality of image groups picked up by the capsule endoscopes 302a and 302b is displayed in the main-display areas 400a and 400b by image group is exemplified to specifically described the operation of the control unit 355 controlling to synchronously display related images most similar to each other between the image groups PG11 and PG12 in the main-display areas 400a and 400b side by side. FIG. 59 is a schematic diagram illustrating the operation of the control unit 355 to synchronously display images mutually most similar to each other between the plurality of image groups PG11 and PG12 in the plurality of main-display areas 400a and 400b side by side.

The control unit 355 performs control to sequentially display the images $P_1, P_2, P_3, \ldots$ in the image group PG11 in the main-display area 400a and at the same time, performs control to sequentially display the images $Q_1, Q_2, Q_3, \ldots$ in the image group PG12 in the main-display area 400b. Here, if the image $P_6$ in the image group PG11 is displayed in the main-display area 400a as an image of the current frame number, the image extractor 315c extracts, based on the input number of the image, the image $Q_6$ that is most similar to the image $P_6$ of the current frame number from the image group PG12. The display controller 355a performs control to display the image $P_6$ of the current frame number in the main-display area 400a and also performs control to display the image $Q_6$ (that is, the related image to the image $P_6$) extracted by the image extractor 315c in the main-display area 400b. The images $P_6$ and $Q_6$, which are an example of related images most similar to each other between the image groups PG11 and PG12, are synchronously displayed side by side in the main-display areas 400a and 400b by the control of the display controller 355a.

Further, if the image $P_7$ in the image group PG11 is added to be displayed in the main-display area 400a as an image of the next frame number, the image extractor 315c extracts, based on the input number of an image, the image $Q_7$ that is most similar to the image $P_7$ of the next frame of the image $P_6$ of the current frame number from the image group PG12. The display controller 355a performs control to additionally display the image $P_7$ in the main-display area 400a and also performs control to additionally display the image $Q_7$ (that is, the related image to the image $P_7$) extracted by the image extractor 315c in the main-display area 400b. The images $P_7$ and $Q_7$, which are an example of related images most similar to each other between the image groups PG11 and PG12, are synchronously displayed side by side, in addition to the images $P_6$ and $Q_6$, in the main-display areas 400a and 400b by the control of the display controller 355a.

As described above, the images $P_6$ and $Q_6$ synchronously displayed in the main-display areas 400a and 400b side by side are, as described above, related images similar to each other. Likewise, the images $P_7$ and $Q_7$ synchronously displayed in the main-display areas 400a and 400b side by side are, as described above, related images similar to each other. Such related images are, for example, images in which substantially the same site inside the same organ of the subject 1 is picked up or images in which neighboring sites mutually related as front and rear or opposite to each other are picked up. By synchronously displaying related images most similar to each other between the image groups PG11 and PG12 in the main-display areas 400a and 400b in this manner, images mutually similar to each other among the plurality of image groups inside the subject 1 can easily be observed and, as a result, images inside organs of the subject 1 can minutely be observed.

In the tenth embodiment, as described above, image groups inside a subject picked up by a plurality of imaging devices are classified by imaging device, identification information for identifying a plurality of image groups inside the subject and each image in the plurality of image groups is saved in a storage unit, and related images most similar to each other among the plurality of image groups are sequentially displayed in a plurality of main-display areas formed in a display unit. Thus, by an easy operation using a display operation icon group, images similar to each other among the plurality of image groups, for example, images in which mutually neighboring sites in the subject are picked up can synchronously be displayed in the plurality of main-display areas side by side. As a result, related images similar to each other among the plurality of image groups inside the subject can easily be observed while comparing them so that an image display apparatus allowing a user to observe images inside organs of the subject minutely can be realized.

In the first to fifth embodiments of the present invention, the time sliders 132 and 133 move along the common time scale TS, but the present invention is not limited to this and two time scales, each representing the temporal length of the first image group PG1 and the second image group PG2 respectively, may be formed in neighboring positions to allow the time sliders 132 and 133 to move on each time scale. More specifically, as shown, for example, in FIG. 32, a TS1 indicating the temporal length of the first image group PG1 and a TS2 indicating the temporal length of the second image group PG2 may be arranged vertically in the vicinity of the sub-image display area 140 so that the time slider 132 moves on the TS1 and the time slider 133 moves on the TS2.

Figure 32:
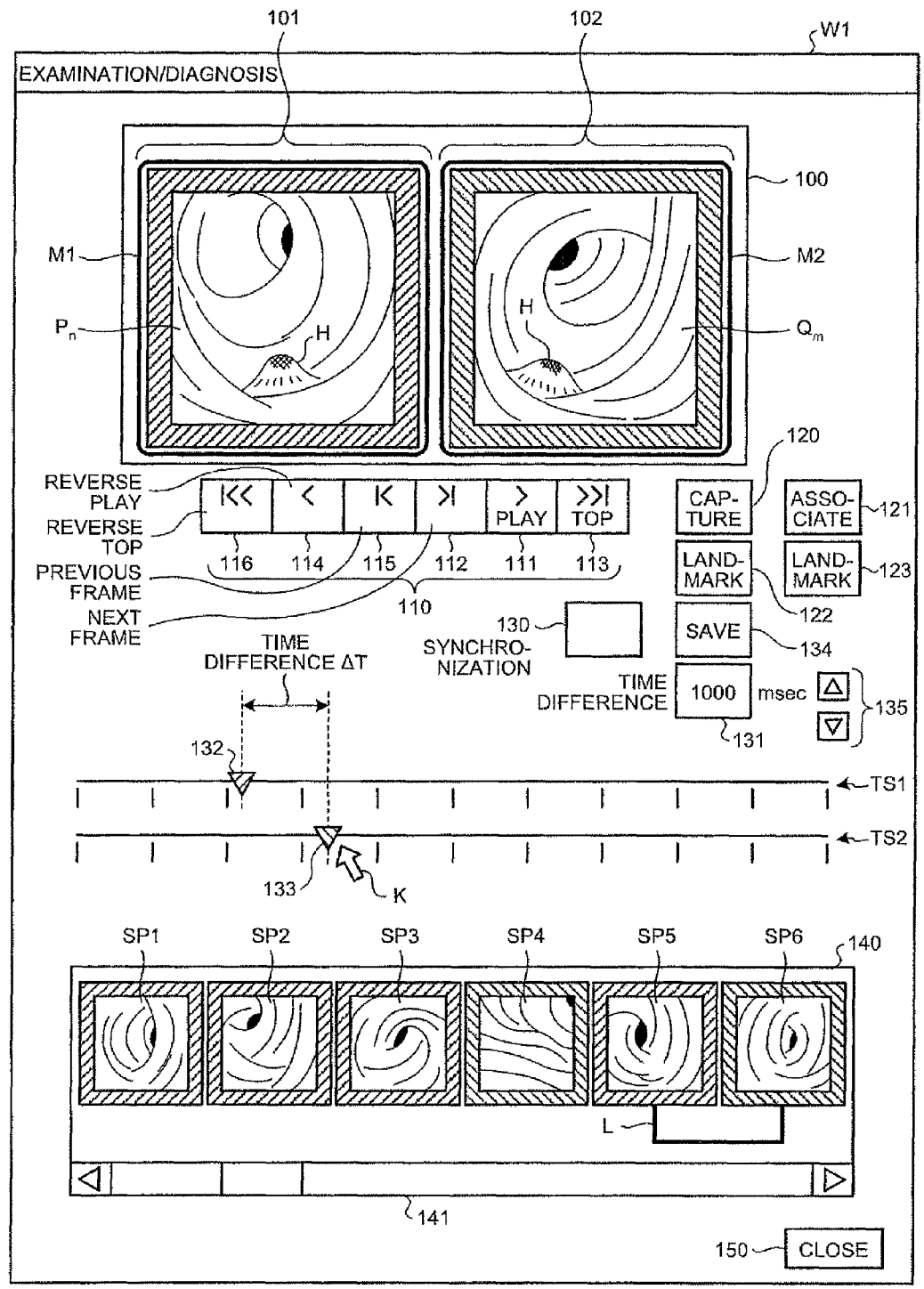
FIG. 32 is a schematic diagram showing a first modification of the various GUIs displayed in the display unit.

Also, in the first to fifth embodiments of the present invention, time difference data is directly input into the data setting area 131 by operating the input unit 11, but the present invention is not limited to this and, as shown, for example, in FIG. 32, a numeric value increment/decrement icon 135 for incrementing/decrementing time difference data (numeric data) in the data setting area 131 may be formed to adjust the time difference data in the data setting area 131 using the numeric value increment/decrement icon 135. Or, a jog dial may be provided to the input unit 11 so that the time difference data in the data setting area 131 is incremented/decremented by operating the jog dial of the input unit 11.

Figure 33:
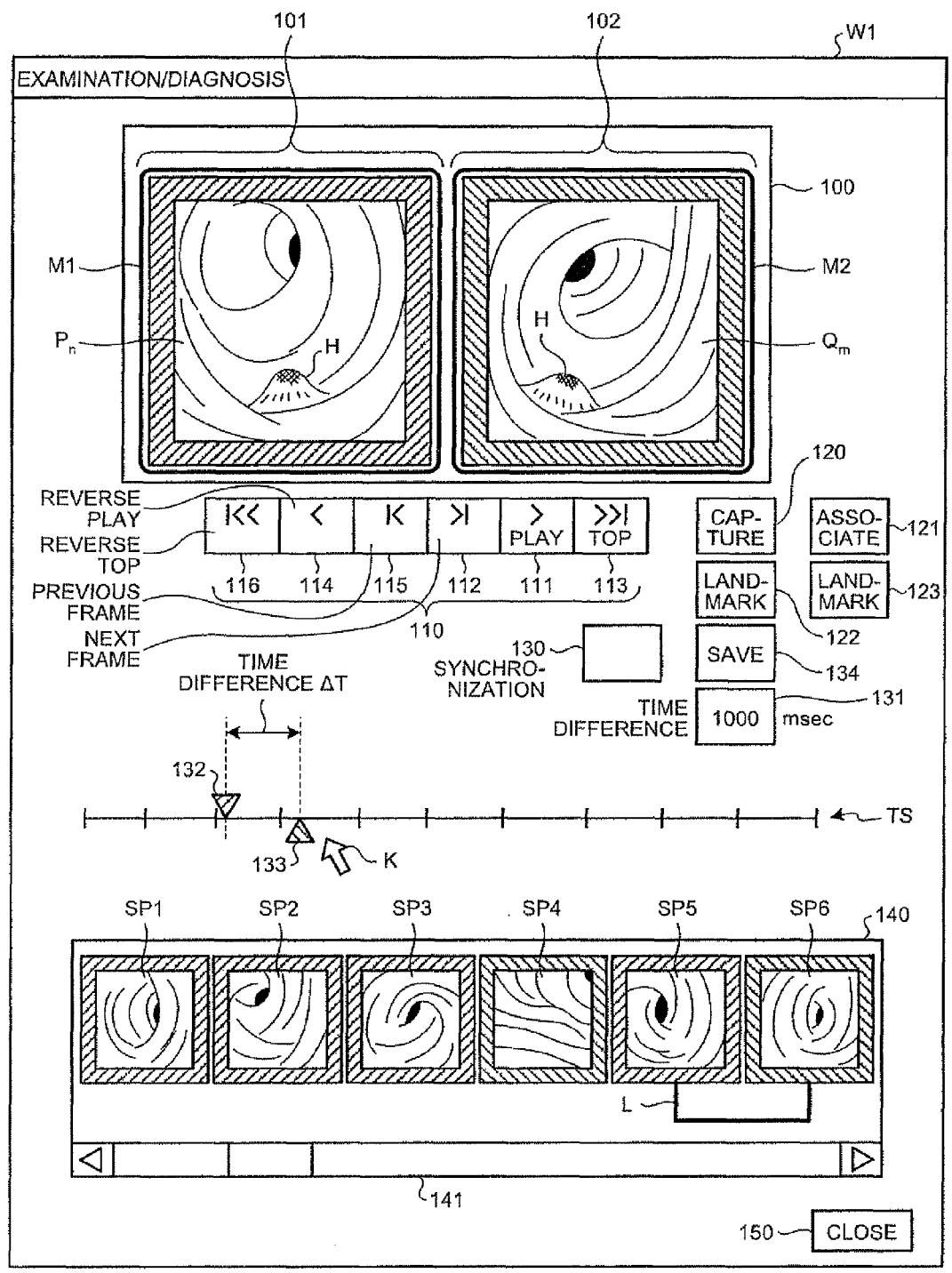
FIG. 33 is a schematic diagram showing a second modification of the various GUIs displayed in the display unit.

Further, in the first to fifth embodiments of the present invention, the time sliders 132 and 133 move on the same path along the time scale TS, but the present invention is not limited to this and the time sliders 132 and 133 may move on different paths along the time scale TS. More specifically, as shown, for example, in FIG. 33, the time slider 132 may move on the upper path of the time scale TS while the time slider 133 moves on the lower path of the time scale TS.

Figure 34:
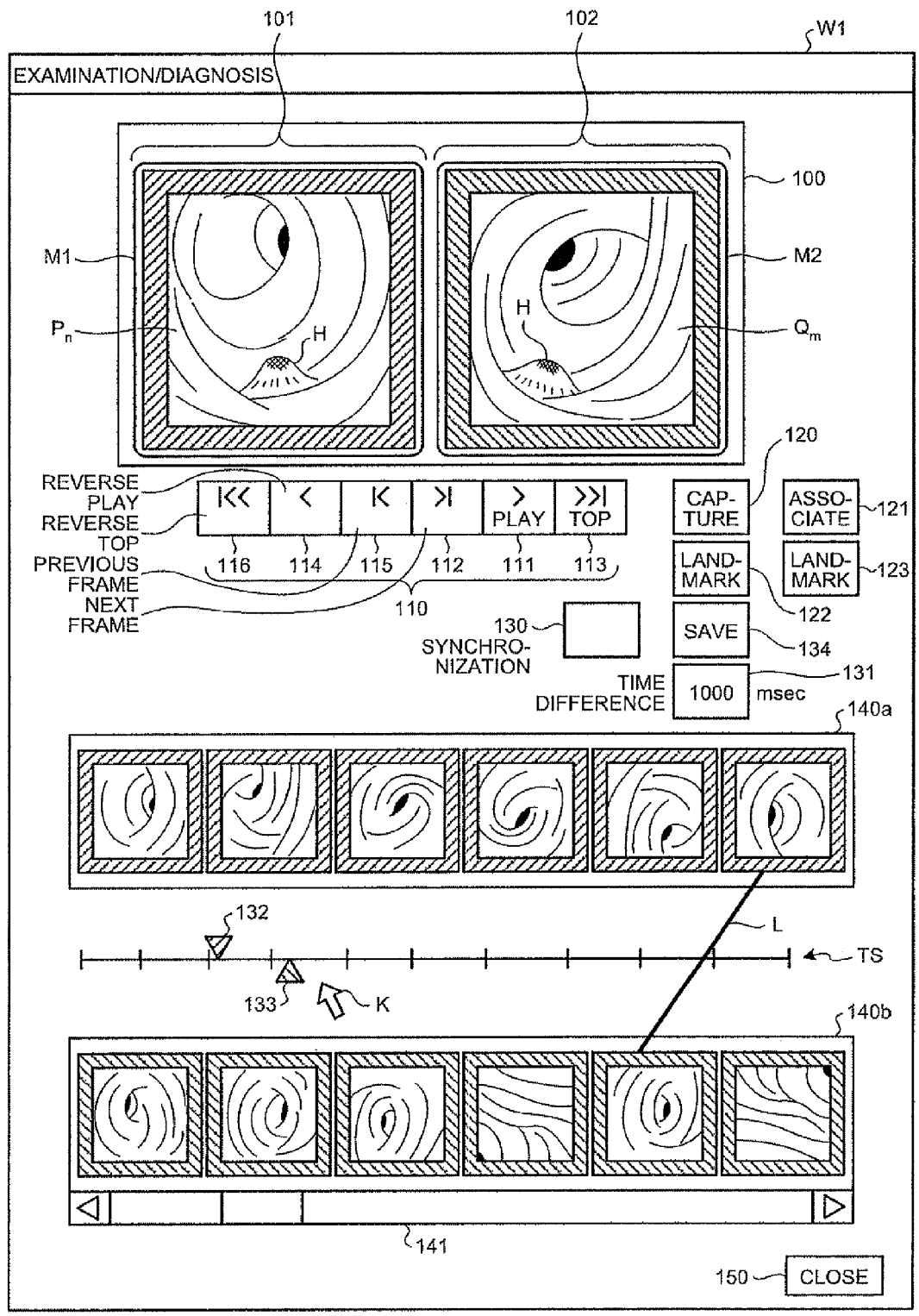
FIG. 34 is a schematic diagram showing a third modification of the various GUIs displayed in the display unit.

Also, in the first to fifth embodiments of the present invention, each thumbnail image of the images $P_n$ and $Q_m$ displayed in the display areas 101 and 102 respectively is added to the common sub-image display area 140 to be displayed, but the present invention is not limited to this and a plurality of sub-image display areas may be formed so that thumbnail images of the images $P_n$ and those of the images $Q_m$ are classified to be added to each of the plurality of sub-image display areas to be displayed. More specifically, as shown, for example, in FIG. 34, a plurality of sub-image display areas 140a and 140b may be formed so that thumbnail images of the images $P_n$ are added to sub-image display area 140a to be displayed and those of the images $P_n$ are added to sub-image display area 140b to be displayed. In this case, the line L indicating association between thumbnail images of the images $P_n$ and those of the images $Q_m$ is formed to connect associated thumbnail images.

Figure 35:
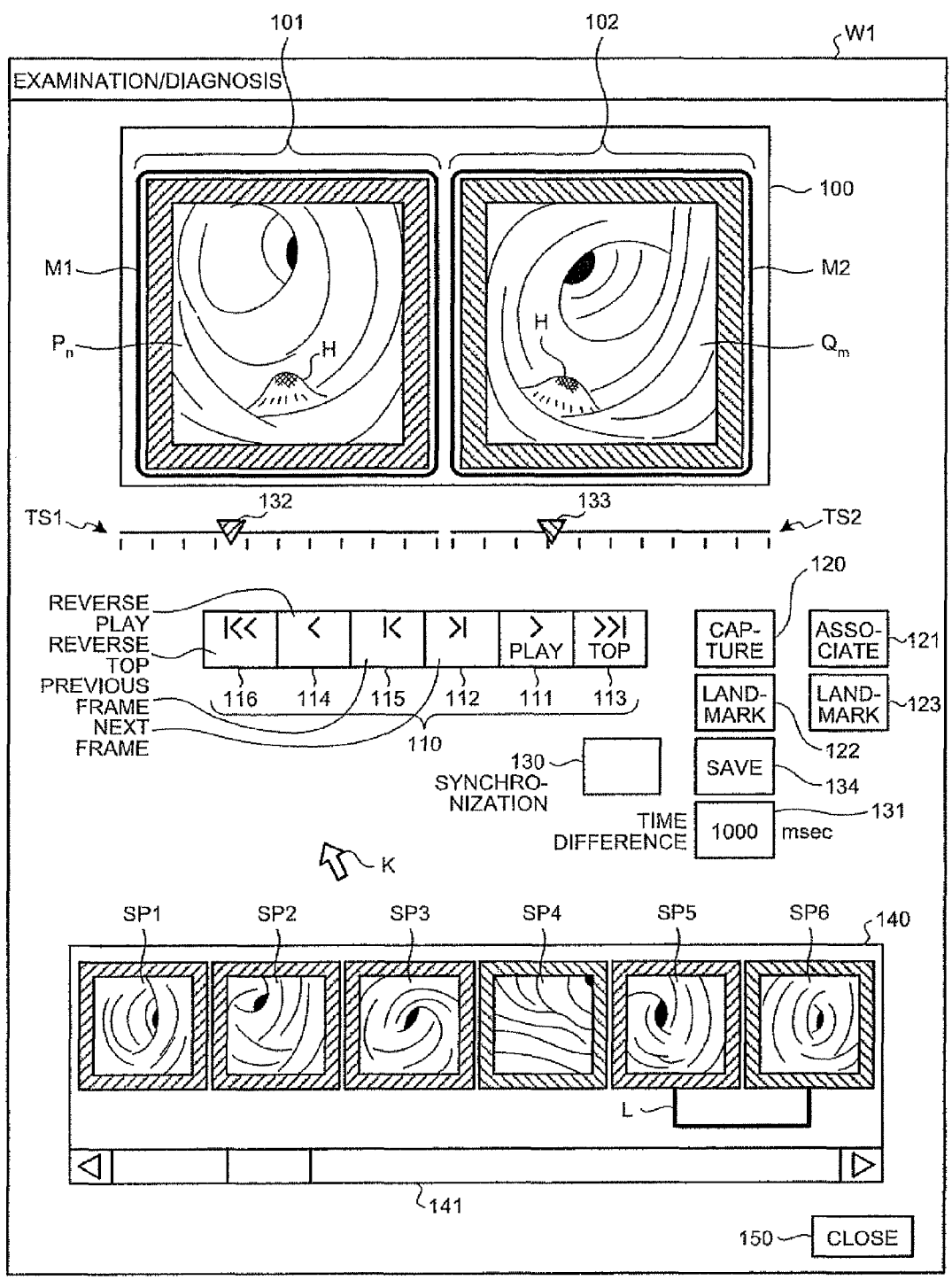
FIG. 35 is a schematic diagram showing a fourth modification of the various GUIs displayed in the display unit.

Further, in the first to fifth embodiments of the present invention, the time scale TS is formed in an area between the display operation icon group 110 and the sub-image display area 140, but the present invention is not limited to this and two time scales, each representing the temporal length of the first image group PG1 and the second image group PG2 respectively, may be formed near the display areas 101 and 102 respectively so that the time sliders 132 and 133 move on each of the two time scales. More specifically, as shown, for example, in FIG. 35, the time scale TS1 may be formed in the vicinity below the display area 101 so that the time slider 132 moves on the time scale TS1 and the time scale TS2 may be formed in the vicinity below the display area 102 so that the time slider 133 moves on the time scale TS2.

Also, in the first to fifth embodiments of the present invention, the time difference $\Delta T$ between imaging times of the images $P_n$ and $Q_m$ synchronously displayed in the display areas 101 and 102 respectively is set in synchronous display mode, but the present invention is not limited to this and a frame number difference between the images $P_n$ and $Q_m$ may be set using a GUI in place of the time difference $\Delta T$. More specifically, as shown, for example, in FIG. 36, the data setting area 131 and the time sliders 132 and 133 may be formed as a setting GUI of the frame number difference between the images $P_n$ and $Q_m$ so that the frame number difference input to the data setting area 131 is set as the frame number difference between the images $P_n$ and $Q_m$ synchronously displayed in the display areas 101 and 102 in synchronous display mode. Also, by using the time sliders 132 and 133 in the same manner as for setting the time difference $\Delta T$ as described above, the frame number difference between the images $P_n$ and $Q_m$ synchronously displayed in the display areas 101 and 102 in synchronous display mode may be set.

Figure 36:
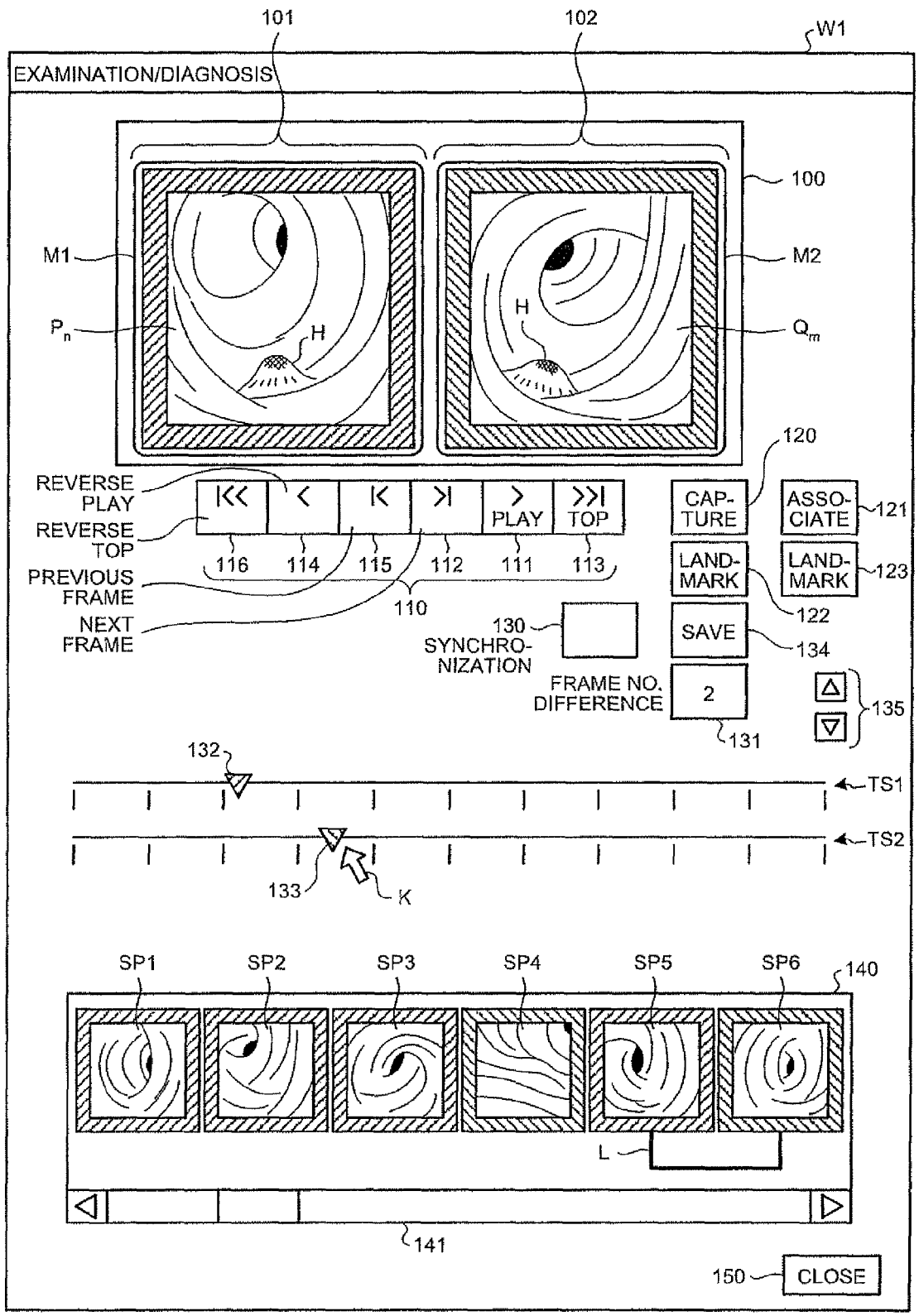
FIG. 36 is a schematic diagram showing a fifth modification of the various GUIs displayed in the display unit.

Further, as shown in FIG. 36, the numeric value increment/decrement icon 135 may be used to increment/decrement the frame number difference in the data setting area 131. Or, a jog dial may be provided to the input unit 11 so that the frame number difference is incremented/decremented using the jog dial.

Also, the setting of the frame number difference is not limited to the setting GUI such as the data setting area 131 or the time sliders 132 and 133 and default data in which the frame number difference between the images $P_n$ and $Q_m$ is preset for each site of the subject 1 may be saved in the storage unit 15 in place of the default data 15c so that the frame number difference is between the images $P_n$ and $Q_m$ is set for each site of the subject 1 based on the default data of the frame number difference. In this case, the setting GUI such as data setting area 131 or the time sliders 132 and 133 may be used to partially update default data of the frame number difference for each frame.

If the frame number difference between the images $P_n$ and $Q_m$ in synchronous display mode is set in this manner, a control unit of an image display apparatus according to the present invention performs control to synchronously display the images $P_n$ and $Q_m$ in each of the display areas 101 and 102 in synchronous display mode. Also in this case, like that of the time difference $\Delta T$ as described above, images in which the same object common to each other is picked up from a plurality of directions can synchronously be displayed in each of the display areas 101 and 102.

Also, in the first to fifth embodiments of the present invention, each image of the first image group PG1 and that of the second image group PG2 picked up by the two imaging devices 2a and 2b mounted on the multiple-lens capsule endoscope 2 are displayed in the display areas 101 and 102 respectively, but the present invention is not limited to this and each image contained in each of two image groups among three or more image groups acquired from three or more imaging devices mounted on a multiple-lens capsule endoscope may be displayed in each of the display areas 101 and 102. Or, three or more display areas for displaying images inside the subject may be formed so that each image contained in each of three or more image groups picked up by three or more imaging devices mounted on a multiple-lens capsule endoscope is displayed in the three or more display areas.

Further, in the first to fifth embodiments of the present invention, when a click operation of a single capture icon is performed, a thumbnail image (thumbnail images) of an image (images) in a display area (display areas) for which an image display operation is enabled is (are) added to a sub-image display area to be displayed, but the present invention is not limited to this and a capture icon may be formed for each display area so that when a click operation of the capture icon is performed, a thumbnail image of an image displayed in the display area corresponding to the clicked capture icon is added to the sub-image display area to be displayed.

Also, in the fourth and fifth embodiments of the present invention, desired two thumbnail images among a plurality of thumbnail images displayed in a sub-image display area are associated, but the present invention is not limited to this and three or more thumbnail images displayed in the sub-image display area may be associated. In this case, an indicator (for example, the line L) is formed to mutually connect three or more associated thumbnail images.

Further, in the fourth and fifth embodiments of the present invention, a line connecting associated thumbnail images is formed as an indicator of association of desired thumbnail images, but the present invention is not limited to this and the indicator indicating association of desired thumbnail images may be a desired mark such as a symbol, character, number, and graphic. In this case, the same type of mark can be attached to each of a plurality of associated thumbnail images.

Also, in the sixth to ninth embodiments of the present invention, the image group selection icons 401 and 402 for selecting an image group inside a subject to be displayed in the main-display area 400 are displayed in a mode of push button as exemplified in FIGS. 39 and 49, but the present invention is not limited to this and a reduced image (for example, a thumbnail image) formed by reducing a related image most similar to the currently displayed image of the main-display area 400 may be displayed on the selection GUI of image groups.

Figure 60:
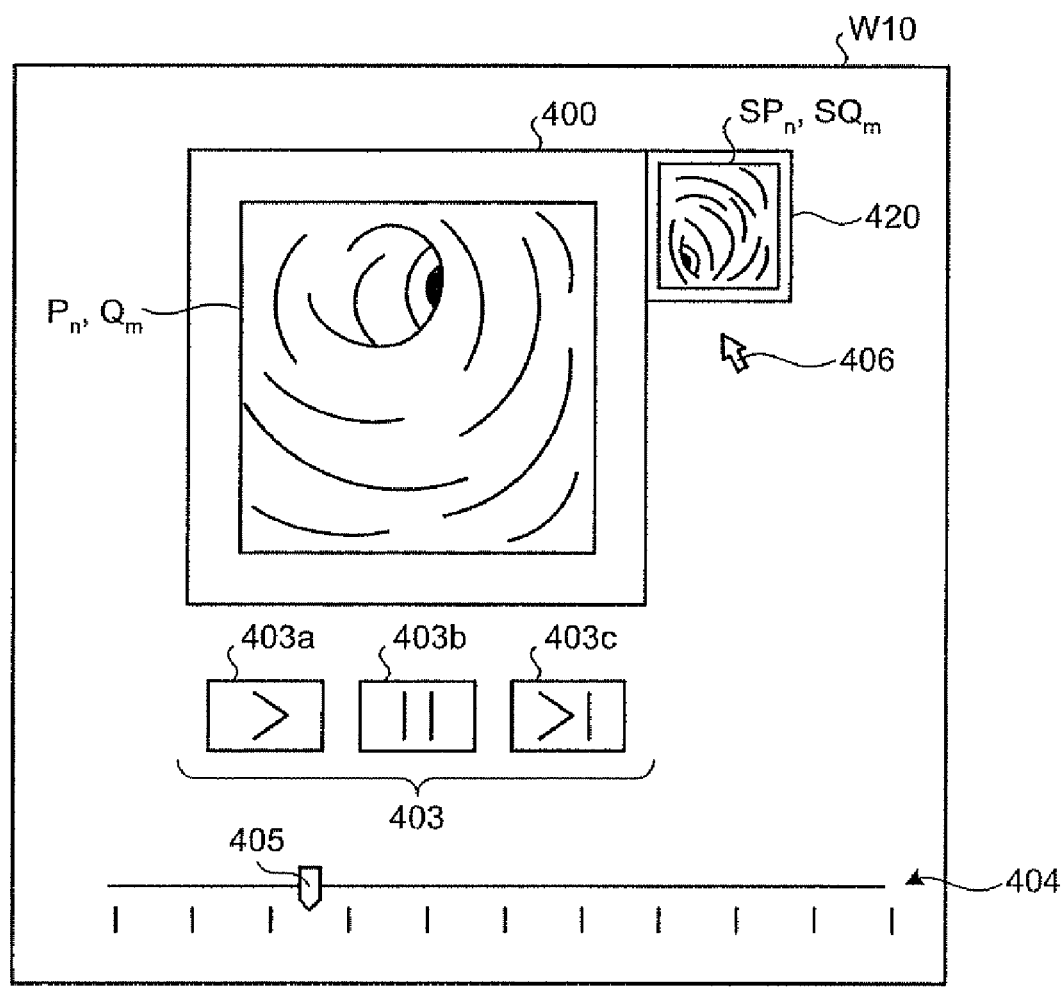
FIG. 60 is a schematic diagram illustrating another mode of selection GUIs for selecting an image group to be displayed in the main-display area.

More specifically, as shown, for example, in FIG. 60, a sub-display area 420 for displaying a reduced image of the related image is additionally formed near the main-display area 400 and a selection GUI for selecting the main-display image group is formed inside the sub-display area 420. A reduced image of the related image most similar to the currently displayed image in the main-display area 400 is displayed on the selection GUI. In this case, if the image $P_n$ in the image group PG11 is the currently displayed image, the display controller 315a additionally displays a reduced image $SQ_m$ of the related image in the image group PG12 most similar to the image $P_n$ on the selection GUI in the sub-display area 420. By performing a click operation of the selection GUI on which the reduced image $SQ_m$ is displayed, the image group PG12 containing the related image corresponding to the reduced image $SQ_m$ is selected as the main-display image group and also the image $P_n$ which is the currently displayed image, is switched to the related image corresponding to the reduced image $SQ_m$.

If, on the other hand, the image $Q_m$ in the image group PG12 is the currently displayed image, the display controller 315a additionally displays a reduced image $SP_n$ of the related image in the image group PG11 most similar to the image $Q_m$ on the selection GUI in the sub-display area 420. By performing a click operation of the selection GUT on which the reduced image $SP_n$ is displayed, the image group PG11 containing the related image corresponding to the reduced image $SP_n$ is selected as the main-display image group and also the image $Q_m$, which is the currently displayed image, is switched to the related image corresponding to the reduced image $SP_n$.

Figure 61:
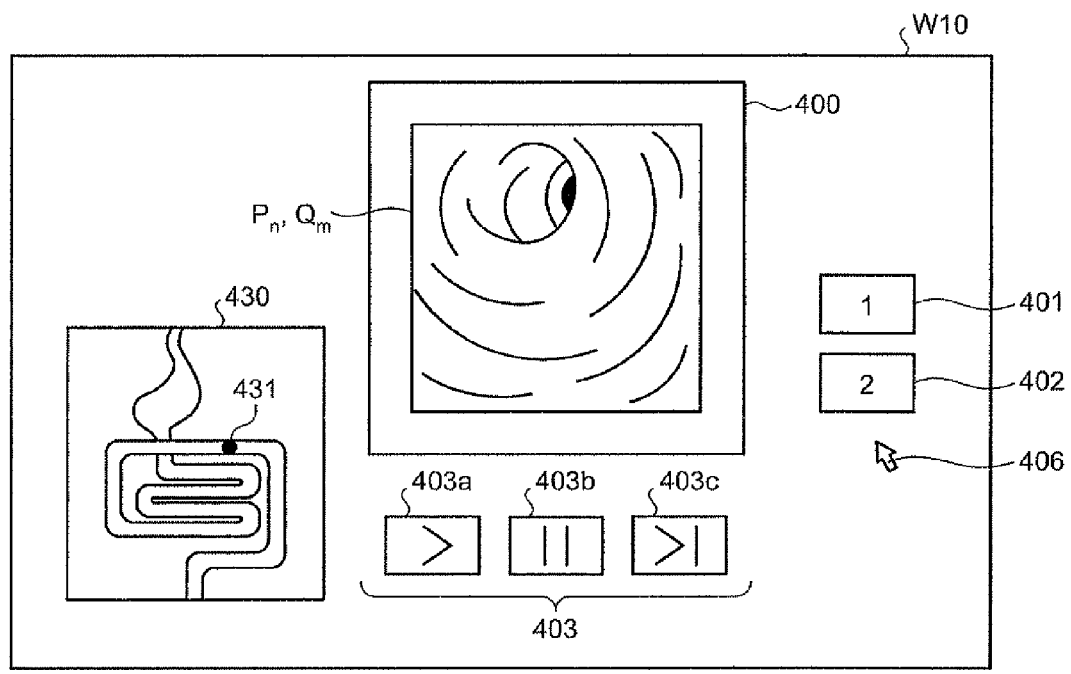
FIG. 61 is a schematic diagram illustrating an in-vivo exemplar image showing the imaging position of the currently displayed image of an inside of the subject.

Also, in the sixth to tenth embodiments of the present invention, the temporal position of the currently displayed image in the main-display area 400 is indicated by the time bar 404 and the slider 405, but the present invention is not limited to this and the imaging position of the currently displayed image in the main-display area 400 may be shown exemplarily. More specifically, as shown, for example, in FIG. 61, an intracorporeal exemplar image 430 exemplarily showing a movement route (that is, the digestive tract) of a capsule endoscope inside a subject and a slider 431 moving along the digestive tract shown in the intracorporeal exemplar image 430 may be displayed in the window W10 so that the imaging position of the currently displayed image in the main-display area 400 is indicated by the intracorporeal exemplar image 430 and the slider 431. In this case, the display controller 315a determines the position of each image in the digestive tract of the intracorporeal exemplar image 430 based on the receiving time or imaging position information of each image in the image groups PG11 and PG12. The display controller 315a may allow the slider 431b to move along the digestive tract of the intracorporeal exemplar image 430 to indicate the imaging position of the currently displayed image in the main-display area 400.

Further, in the seventh embodiment of the present invention, the input time is associated with each image contained in a plurality of image groups inside a subject, but the present invention is not limited to this and time information to be associated with each image in each image group may be time information indicating the imaging time of an imaging device of a capsule endoscope or time information indicating an elapsed time when images in a subject are sequentially picked up after a capsule endoscope is introduced into the subject. Time information showing the imaging time or an elapsed time after introduction is associated with each image in the subject by the capsule endoscope. The image display apparatus 324 may acquire time information associated with each image by the capsule endoscope together with image groups.

Also, in the seventh embodiment of the present invention, the input time of each image inside a subject is calculated based on the receiving time of each image inside the subject, but the present invention is not limited to this and time information (input time) of an image may be calculated based on the input number of an image and the frame rate of an imaging device exemplified in the sixth embodiment. In this case, like the image classifier 315b in the sixth embodiment, the image classifier 325b attaches the input number to each image inside the subject and can calculate time information of an image by dividing the input number by the frame rate of the imaging device that picked up the image.

Further, in the eighth embodiment of the present invention, the receiving time difference between the currently displayed image of the main-display area 400 and a related image thereof is set by a setting GUI, but the present invention is not limited to this and a setting GUI for setting an input number difference or frame number difference of images may be formed in the window W10 to set the input number difference or frame number difference between the currently displayed image of the main-display area 400 and a related image thereof using the setting GUI.

Also, in the ninth embodiment of the present invention, the position coordinates of a capsule endoscope (imaging device) that picked up an image within a subject are detected based on received electric field strength of a radio signal including the image within the subject, but the present invention is not limited to this and the position coordinates of a capsule endoscope within the subject may be detected based on an X ray image inside the subject that can be acquired by X ray imaging of the subject into which the capsule endoscope is introduced or the position coordinates of a capsule endoscope within the subject may be detected based on a magnetic field or supersonic wave generated to the subject.

Further, in the sixth, seventh, ninth, and tenth embodiments of the present invention, a case in which two capsule endoscopes, each having one imaging device mounted thereon, are introduced into a subject is exemplified, but the present invention is not limited to this and a plurality of capsule endoscopes, each having one or more imaging devices mounted thereon, may be introduced into the subject to acquire a plurality of image groups inside the subject picked up by the plurality of capsule endoscopes.

Also, in the eighth embodiment of the present invention, a case in which a multiple-lens capsule endoscope having two imaging devices mounted thereon is introduced into a subject is exemplified, but the present invention is not limited to this and one or more capsule endoscopes having one or more imaging devices mounted thereon may be introduced into the subject to acquire a plurality of image groups inside the subject picked up by one or more capsule endoscopes.

Further, in the tenth embodiment of the present invention, related images mutually similar to each other between the two image groups PG11 and PG12 inside the subject 1 are synchronously displayed in the plurality of main-display areas 400a and 400b respectively, but the present invention is not limited to this and related images mutually similar to one another among three or more image groups inside the subject 1 may synchronously be displayed in three or more main-display areas. In this case, three or more main-display areas corresponding to the number of the plurality of image groups inside the subject 1 can be formed in the window W10 of the display unit 312 to synchronously display three or more related images determined for each of three or more image groups in each of three or more main-display areas. One of the three or more related images can be determined as the currently displayed image in one image group of three or more image groups so that the remaining two or more related images can be determined as two or more images most similar to the currently displayed image for each image group of the remaining two or more image groups of these three or more image groups.

Also, in the tenth embodiment of the present invention, like the sixth embodiment, the related image is determined based on the input number of an image, but the present invention is not limited to this and the related image may be determined based on time information (such as the receiving time, input time and the like) of an image like the seventh embodiment, the related image may be determined based on the time difference or frame number difference of images like the eighth embodiment, or the related image may be determined based on imaging position information of an image like the ninth embodiment. In this case, the control unit 355 of the image display apparatus 354 according to the tenth embodiment only needs to have either of the image classifiers 325b and 335b in place of the image classifier 315b and one of the image extractors 325c and 335c in place of the image extractor 315c. Or, the control unit 355 only needs to have the image classifier 345b in place of the image classifier 315b, the image extractor 345c in place of the image extractor 315c, and further the position detector 345d.

Further, in the sixth to tenth embodiments of the present invention, ID information for identifying one or more imaging devices mounted on a capsule endoscope is attached to all images, but the present invention is not limited to this and if images inside a subject is picked up by two imaging devices, ID information may be attached to each image inside the subject picked up by one imaging device while attaching no ID information to each image inside the subject picked up by the other imaging device. In this case, an image group having ID information of the imaging device attached thereto may be classified as an image group picked up by one imaging device while classifying an image group having no ID information of the imaging device attached thereto as an image group picked up by the other imaging device.

Also, in the sixth to tenth embodiments of the present invention, when images inside a subject picked up by an imaging device of a capsule endoscope are received by the external receiving apparatus 303, ID information of the imaging device is attached to the images inside the subject, but the present invention is not limited to this and ID information of the imaging device may be attached to images inside the subject when the images inside the subject are saved in a storage unit of an image display apparatus according to the present invention. In this case, the imaging device that picked up an image may be determined based on an acquisition sequence of each image when the image display apparatus acquired image groups inside the subject picked by a plurality of imaging devices or the like before attaching the determined ID information of the imaging device to each image. The acquisition sequence of such an image may also be determined, for example, based on the input number, input time, receiving number, or receiving time.

Further, in the sixth to ninth embodiments of the present invention, the single main-display area 400 is formed in the display unit 312 and images and related images thereof are displayed in the main-display area 400 by switching them, but the present invention is not limited to this and a plurality of main-display areas may be formed in the display unit 312 so that images and related images thereof are displayed in the plurality of main-display areas by switching them. In this case, two or more image groups to be displayed in the plurality of main-display areas may be selected from three or more image groups picked up by three or more imaging devices so that images mutually similar to each other (that is, related images) among two or more image groups are displayed in the plurality of main-display areas by switching them.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An image display apparatus, comprising:
a display unit that displays a first image contained in a first image group of an inside of a subject and a second image contained in a second image group of the inside of the subject, the first image group and the second image group being picked up respectively by a first imaging device and a second imaging device that are included in a multiple-lens capsule endoscope;
a control unit that extracts a related image related to a currently displayed image currently displayed in the display unit from the first and second image groups to make the display unit display the related image extracted;
a storage unit that stores default data in which a time difference between an imaging time of the first image and an imaging time of the second image is set differently for each site inside the subject; and
a setting unit that obtains the default data from the storage unit and sets, for a site inside of the subject to be displayed, the time difference for the corresponding site of the default data;

wherein the control unit switches the time difference for each site inside the subject based on the default data and performs control to synchronously display the first image and the second image having the time difference set for each site inside the subject in respective display areas on the display unit.

2. The image display apparatus according to claim 1, wherein the display unit further displays a first reduced image corresponding to the first image and a second reduced image corresponding to the second image, and
the setting unit sets association between the first reduced image and the second reduced image.

3. The image display apparatus according to claim 2, wherein the display unit displays an indicator indicating the association between the first reduced image and the second reduced image.

4. The image display apparatus according to claim 1, wherein the display unit displays a first time slider indicating a temporal position of an image contained in the first image group and a second time slider indicating a temporal position of an image contained in the second image group, and
the first time slider and the second time slider are one of setting unit that sets the time difference of the first image and the second image.

5. The image display apparatus according to claim 1, wherein the second image is an image in which an object common to the first image is picked up from an imaging direction different from an imaging direction of the first image.

6. The image display apparatus according to claim 1, wherein the setting unit independently sets a display mode in which images contained in the first image group are displayed along time series, and a display mode in which images contained in the second image group are displayed along time series.

* * * * *